(12) United States Patent
Foltz et al.

(10) Patent No.: US 8,663,636 B2
(45) Date of Patent: Mar. 4, 2014

(54) METHOD OF TREATING A MALIGNANT TUMOR BY ADMINISTERING ANTIBODIES DIRECTED TO DLL4

(75) Inventors: Ian Foltz, British Columbia (CA); David Jenkins, Waltham, MA (US); Vahe Bedian, Waltham, MA (US)

(73) Assignee: MedImmune, LLC, Gaichersburg, MD (US)

( * ) Notice: Subject to any disclaimer, the term of this patent is extended or adjusted under 35 U.S.C. 154(b) by 0 days.

(21) Appl. No.: 13/446,637

(22) Filed: Apr. 13, 2012

(65) Prior Publication Data

US 2012/0195905 A1 Aug. 2, 2012

Related U.S. Application Data

(63) Continuation of application No. 12/562,268, filed on Sep. 18, 2009, now Pat. No. 8,192,738.

(60) Provisional application No. 61/098,673, filed on Sep. 19, 2008.

(51) Int. Cl.
*A61K 39/395* (2006.01)
*C07K 16/18* (2006.01)

(52) U.S. Cl.
USPC ............ 424/130.1; 424/141.1; 424/145.1; 530/387.1; 530/388.1; 530/388.23; 530/388.24; 514/13.3; 514/19.2

(58) Field of Classification Search
None
See application file for complete search history.

(56) References Cited

U.S. PATENT DOCUMENTS

| | | | |
|---|---|---|---|
| 7,488,806 B2* | 2/2009 | Papadopoulos et al. | 530/388.15 |
| 7,754,206 B2* | 7/2010 | Clarke et al. | 424/130.1 |
| 7,803,377 B2* | 9/2010 | Yan et al. | 424/145.1 |
| 2008/0014196 A1* | 1/2008 | Yan | 424/133.1 |
| 2008/0187532 A1* | 8/2008 | Gurney et al. | 424/133.1 |
| 2010/0119526 A1* | 5/2010 | Hellstrom | 424/172.1 |

FOREIGN PATENT DOCUMENTS

| | | |
|---|---|---|
| WO | 2007/143689 A2 | 12/2007 |
| WO | 2008/019144 A2 | 2/2008 |
| WO | 2008/042236 A2 | 4/2008 |
| WO | 2008/060705 A2 | 5/2008 |

OTHER PUBLICATIONS

Lobov et al. Delta-like ligand 4 (Dll4) is induced by VEGF as a negative regulator of angiogenic sprouting. Proc Natl Acad Sci USA 104(9): 3219-3224, 2007.*
Noguera-Troise et al. Blockade of Dll4 inhibits tumour growth by promoting non-productive angiogenesis. Nature 444: 1032-1037, 2006.*
Ridgway et al. Inhibition of Dll4 signalling inhibits tumour growth by deregulating angiogenesis. Nature 444: 1083-1087, 2006.*
Sainson et al. Amti-Dll4 therapy: can we block tumour growth by increasing angiogenesis? TRENDS Molec Med 13(9): 389-395, 2007.*
Jenkins et al. MEDI0639: a novel therapeutic antibody targeting Dll4 modulates endothelial cell function and angiogenesis in vivo. Mol Cancer Ther 11: 1650-1660, 2012.*
Patel et al. Up-regulation of endothelial delta-like 4 expression correlates with vessel maturation in bladder cancer. Clin Cancer Res 12: 4836-4844, 2006.*

* cited by examiner

*Primary Examiner* — Bridget E Bunner

(57) ABSTRACT

The invention relates to targeted binding agents against DLL4 and uses of such agents. More specifically, the invention relates to fully human monoclonal antibodies directed to DLL4. The described targeted binding agents are useful in the treatment of diseases associated with the activity and/or overproduction of DLL4 and as diagnostics.

5 Claims, 11 Drawing Sheets

US 8,663,636 B2

METHOD OF TREATING A MALIGNANT TUMOR BY ADMINISTERING ANTIBODIES DIRECTED TO DLL4

CROSS REFERENCE TO RELATED APPLICATIONS

This application claims priority to and is a continuation of U.S. patent application Ser. No. 12/562,268, filed Sep. 18, 2009, now U.S. Pat. No. 8,192,738 B2, which is a nonprovisional of U.S. Provisional Patent Application No. 61/098,673 filed on Sep. 19, 2008, the entire disclosure of each of which is incorporated by reference herein.

REFERENCE TO THE SEQUENCE LISTING

This application incorporates by reference a Sequence Listing submitted with this application as a text file entitled DLL4-100US2seqlist.txt created on Aug. 8, 2013 and having a size of 81,962 bytes.

FIELD OF THE INVENTION

The invention relates to targeted binding agents against DLL4 and uses of such agents. More specifically, the invention relates to fully human monoclonal antibodies directed to DLL4. The described targeted binding agents are useful in the treatment of diseases associated with the activity and/or overproduction of DLL4 and as diagnostics.

DESCRIPTION OF THE RELATED ART

The Notch signaling cascade is an evolutionarily conserved pathway that has been implicated in cell fate determination, stem cell maintenance and differentiation in many tissues during development. Thus far, four Notch receptor ligands (Notch1-4) and five ligands (Jagged-1/2 and Delta-like ligand (Dll) 1/3/4) have been identified in mammals. Notch receptors exist as heterodimers, comprised of two non-covalently associated extracellular and transmembrane subunits. Ligand binding to the extracellular subunit triggers proteolytic cleavages by enzymes such as TNFα converting enzyme (TACE) and gamma-secretase which results in the creation of Notch intracellular domains (NICD), which translocate to the nucleus and bind to transcription factors which ultimately results in the activation of downstream target genes (see Bray, 2006, Nat. Rev. Mol. Cell. Biol., 7, 678).

Emerging evidence suggests that multiple Notch pathway components are expressed in the vasculature and that aberrations in normal Notch signaling can result in vascular phenotypes. For example, mutations in Jagged 1 and Notch 3 result in Alagille syndrome and cerebral autosomal dominant arteriopathy with subcortical infarcts and leukoencephalopathy, respectively, two disorders that exhibit vascular defects. Furthermore, genetic deletion of Notch1 and DLL4 in mice all result in embryonic lethality with vascular abnormalities. In addition, deletion of a single allele of DLL4 in mice results in embryonic lethality with severe vascular defects in most genetic backgrounds (Duarte et al., 2004, Genes Dev., 18, 2474; Gale et al., 2004, Proc. Nat. Acad. Sci., 101, 15949). This phenotype has only previously been reported for VEGF-A and suggests that DLL4 may play an important role in vascular development.

DLL4 expression has also been reported on the vasculature of tumors from human clear-cell renal cell carcinomas, glioblastomas and cancers of the breast and bladder (Mailhos et al., 2001, Differentiation, 69, 135: Patel et al., 2005, Cancer Res., 65, 8690; Patel et al., 2006, Clin. Cancer Res., 12, 4836; Li et al., 2007, Cancer Res., 67, 11244). A recent study has also suggested that DLL4 may be expressed on a small proportion of tumor cells in human glioblastoma (Li et al., 2007, Cancer Res., 67, 11244). The effect of blocking DLL4 signaling on tumor growth has also been evaluated in several preclinical models of cancer in which tumor cell lines are grown subcutaneously in immunodeficient mice (Ridgway et al., 2006, Nature, 444, 1083; Noguera-Troise et al., Nature, 444, 1032). In these studies, reductions in tumor growth of have been reported. These anti-tumor effects were associated with an increase in the density of poorly functional vessels in the tumors concomitant with an increase in hypoxia. Taken together, these data suggest that, in addition to its role in vascular development, DLL4 may also play a role in development of the tumor vasculature.

In addition to effects on angiogenesis, Notch signaling has also been implicated in cancer stem cells from multiple tumor types (Dontu et al., 2004, Breast Can. Res., 6, R605; Wilson & Radtke, 2006, FEBS Lett., 580, 2860). Cancer stem cells have been isolated from a variety of heamtopoietic and solid tumors (Al-Hajj et al., 2003, Proc. Nat. Acad. Sci., 100, 3983; Lapidot et al., 1994. Nature, 17, 645; Tan et al., 2006, Laboratory Investigation, 86, 1203) and the presence of DLL4 on small populations of tumor cells further suggests that DLL4 may also be involved in cancer stem cell biology and that DLL4 antagonists may partially mediate anti-tumor effects through interactions with these cell types.

SUMMARY OF THE INVENTION

The present invention relates to targeted binding agents that specifically bind to DLL4 and inhibit the biological activity of DLL4. Embodiments of the invention relate to targeted binding agents that specifically bind to DLL4 and inhibit binding of DLL4 to a Notch receptor (e.g., Notch 1, 2, 3 or 4).

Embodiments of the invention relate to targeted binding agents that specifically bind to DLL4 and inhibit binding of DLL4 to a Notch receptor (e.g., Notch 1 or 4). In one embodiment of the invention the targeted binding agent specifically binds to DLL4 and inhibits binding to a Notch receptor, e.g., Notch 1. In one embodiment the targeted binding agent inhibits at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% of DLL4 binding to a Notch receptor, (e.g., Notch 1), compared to binding that would occur in the absence of the targeted binding agent.

In some embodiments of the invention, the targeted binding agent binds DLL4 with a binding affinity ($K_D$) of less than 5 nanomolar (nM). In other embodiments, the targeted binding agent binds with a $K_D$ of less than 4 nM, 3 nM, 2 nM or 1 nM. In some embodiments of the invention, the targeted binding agent binds DLL4 with a $K_D$ of less than 950 picomolar (pM). In some embodiments of the invention, the targeted binding agent binds DLL4 with a $K_D$ of less than 900 pM. In other embodiments, the targeted binding agent binds with a $K_D$ of less than 800 pM, 700 pM or 600 pM. In some embodiments of the invention, the targeted binding agent binds DLL4 with a $K_D$ of less than 500 pM. In other embodiments, the targeted binding agent binds with a $K_D$ of less than 400 pM. In still other embodiments, the targeted binding agent binds with a $K_D$ of less than 300 pM. In some other embodiments, the targeted binding agent binds with a $K_D$ of less than 200 pM. In some other embodiments, the targeted binding agent binds with a $K_D$ of less than 150 pM. In yet another embodiment, the targeted binding agent binds with a $K_o$ of less than 100 pM. In another embodiment, the targeted binding agent binds with a $K_D$ of less than 50 pM. In one specific embodiment, the targeted binding agent of the invention can bind human with an affinity $K_D$ of less than 10 pM. In another specific embodiment, the targeted binding agent of the invention can bind human DLL4 with an affinity $K_D$ of less than 1 pM. The $K_D$ may be assessed using a method described herein or known to one of skill in the art (e.g., a BIAcore assay, ELISA, FACS) (Biacore International AB, Uppsala, Sweden).

The binding properties of the targeted binding agent or antibody of the invention may also be measured by reference to the dissociation or association rates ($k_{off}$ and $k_{on}$ respectively).

In one embodiment of the invention, a targeted binding agent or an antibody may have an $k_{on}$ rate (antibody (Ab)+ antigen (Ag)$^{k_{on}} \rightarrow$Ab-Ag) of at least $10^4$ $M^{-1}$ $s^{-1}$, at least $5 \times 10^4$ $M^{-1}$ $s^{-1}$, at least $10^5$ $M^{-1}$ $s^{-1}$, at least $2 \times 10^5$ $M^{-1}$ $s^{-1}$, at least $5 \times 10^5$ $M^{-1}$ $s^{-1}$, at least $10^6$ $M^{-1}$ $s^{-1}$, at least $5 \times 10^5$ $M^{-1}$ $s^{-1}$, at least $10^7$ $M^{-1}$ $s^{-1}$, at least $5 \times 10^7$ $M^{-1}$ $s^{-1}$, or at least $10^8$ $M^{-1}$ $s^{-1}$.

In another embodiment of the invention, targeted binding agent or an antibody may have a $k_{off}$ rate ((Ab-Ag)$^{k_{off}} \rightarrow$antibody (Ab)+antigen (Ag)) of less than $5 \times 10^{-1}$ $s^{-1}$, less than $10^{-1}$ $s^{-1}$, less than $5 \times 10^{-2}$ $s^{-1}$, less than $10^{-2}$ $s^{-1}$, less than $5 \times 10^{-3}$ $s^{-1}$, less than $10^{-3}$ $s^{-1}$, less than $5 \times 10^{-4}$ $s^{-1}$, less than $4 \times 10^{-4}$ $s^{-1}$, less than $3 \times 10^{-4}$ $s^{-1}$, less than $2 \times 10^{-4}$ $s^{-1}$, less than $10^{-4}$ $s^{-1}$, less than $5 \times 10^{-5}$ $s^{-1}$, less than $10^{-5}$ $s^{-1}$, less than $5 \times 10^{-6}$ $s^{-1}$ less than $10^{-6}$ $s^{-1}$, less than $5 \times 10^{-7}$ $s^{-1}$, less than $10^{-7}$ $s^{-1}$, less than $5 \times 10^{-8}$ $s^{-1}$, less than $10^{-8}$ $s^{-1}$, less than $5 \times 10^{-9}$ $s^{-1}$, less than $10^{-9}$ $s^{-1}$, or less than $10^{-10}$ $s^{-1}$.

The targeted binding agent of the invention binds human DLL4. In some examples the targeted binding agent of the invention is cross-reactive with other DLL4 proteins from other species. In one embodiment, the targeted binding agent of the invention is cross-reactive with cynomolgus monkey DLL4. In another embodiment, the targeted binding agent of the invention is cross-reactive with cynomolgus monkey DLL4 but is only weakly cross-reactive with DLL4 proteins from other species, e.g., is only weakly cross-reactive with mouse DLL4, e.g., the targeted binding agent binds mouse DLL4 with a $K_D$ of more than 360 nM as assessed by BIAcore technology.

In another embodiment, the targeted binding agent of the invention has nearly equivalent affinity for DLL4 proteins from other species. In one specific example, the human DLL-4 targeted binding agent of the invention has nearly equivalent affinity for cynomolgus monkey DLL4. By equivalent level of affinity we mean that when the affinity with respect to human DLL4 is 1, the affinity of the antibody with respect to cynomolgus monkey DLL4 is between 0.2-5 or between 0.2-2.

In another embodiment, the targeted binding agent of the invention is specific for human DLL4 but does not bind other Notch ligands. In one example, the targeted binding agent of the invention is specific for human DLL4 but does not bind significantly to DLL1, e.g., the DLL1/mock ratio is less than 2.5 as determined by testing the ability of a targeted binding agent as described herein (15-300 μg/ml) to bind 293T cells transiently transfected with human DLL1 or HEK293 cells stably transfected with Dll1. In another example, the targeted binding agent of the invention is specific for human DLL4 but does not bind significantly to Jagged 1, e.g., the DLL1/mock ratio is less than 1.5 as determined by testing the ability of a targeted binding agent as described herein (5 μg/ml) to bind 293T cells transiently transfected with human Jagged 1 or HEK293 cells stably transfected with human Jagged 1.

In yet another embodiment, the targeted binding agent of the invention inhibits DLL4-Notch1 receptor-ligand binding. In one example, activity possessed by the targeted binding agent can be demonstrated at an $IC_{50}$ concentration (a concentration to achieve 50% inhibition of) below 10 μM. In another example, the targeted binding agent of the invention can have an $IC_{50}$ concentration of less than 50, 40, 30, 20, 10, 5, 4, 2, 1, 0.8, 0.7, 0.6, 0.5 or 0.4 nM.

In yet another embodiment, the targeted binding agent of the invention can have both in vitro and in vivo activity. In one specific example, the targeted binding agent reverses DLL4-stimulated inhibition of HUVEC cell proliferation in 2D culture. In one example, the antibodies of the invention can reverse DLL4 stimulated inhibition of HUVEC cell proliferation by 70% or over, e.g., 75%, 80%, 85%, 90%, or 95% compared to a control (using the assay of example 9 where no DLL4 is added).

In still yet another embodiment, the targeted binding agents, e.g., antibodies, of the invention can inhibit HUVEC tube formation in 2D culture. For example, the antibodies of the invention can exhibit greater than 50% inhibition, e.g., 50%, 60%, 70%, 80%, 90%, or 95% inhibition at a concentration of 0.08 μg/ml relative to a control (the control is the maximal inhibitory effect determined using 20 μg/ml of the same antibody).

In yet another embodiment, the targeted binding agents of the invention can exhibit less than 50%, e.g., 45%, 40%, 35%, 30%, 25%, 20%, 15%, 10% or 5 internalization at four hours relative to t=0 control. In another embodiment, the targeted binding agents of the invention can exhibit between 5-50%, 10-40% or 20-40% internalization at four hours relative to t=0 control (see example 15).

In one embodiment, the targeted binding agents of the invention that specifically binds to DLL4 can exhibit one or more of the following properties, including binds human DLL4 with a $K_D$ of less than 200 pM; cross-reacts with cynolmolgus monkey DLL4; weakly cross-reacts with mouse DLL4; binds cynomologus DLL4 with nearly equivalent affinity; does not hind significantly to DLL4 or Jagged 1; exhibits over 85% reverse DLL4-stimulated inhibition of HUVEC cell proliferation in 2D culture compared to a control; exhibits greater than 50% inhibition of HUVEC cell tube formation in 2D culture at a concentration of 0.08 μg/ml relative to a control; and exhibits less than 50% internalization relative at four hours relative to t=0 control.

In another embodiment, the targeted binding proteins disclosed herein possess beneficial efficacious, metabolic, and/or pharmacodynamic properties.

In another embodiment of the invention, the targeted binding agent competes with any one of fully human monoclonal antibodies of 4B4, 2H10, 21F7, 12A1, 17F3, 9G8, 20G8, 21H3, 1E4, 3A7, 4B3, 1D4 or 21H3RK for binding to Notch 1.

In some embodiments of the invention, the targeted binding agent inhibits tumor growth and/or metastasis in a mammal. In another embodiment, the targeted binding agent can treat a condition associated with angiogenesis.

In some embodiments of the invention, the targeted binding agent is an antibody. In some embodiments of the invention, the targeted binding agent is a monoclonal antibody. In one embodiment of the invention, the targeted binding agent is a fully human monoclonal antibody. In another embodiment of the invention, the targeted binding agent is a fully human monoclonal antibody of the IgG1, IgG2, IgG3 or IgG4 isotype. In another embodiment of the invention, the targeted binding agent is a fully human monoclonal antibody of the IgG2 isotype. This isotype has reduced potential to elicit effector function in comparison with other isotypes, which may lead to reduced toxicity. In another embodiment of the invention, the targeted binding agent is a fully human monoclonal antibody of the IgG1 isotype. The IgG1 isotype has increased potential to elicit ADCC in comparison with other isotypes, which may lead to improved efficacy. The IgG1 isotype has improved stability in comparison with other isotypes, e.g. IgG4, which may lead to improved bioavailability, or improved ease of manufacture or a longer half-life. In one embodiment, the fully human monoclonal antibody of the IgG1 isotype is of the z, za or f allotype.

A further embodiment is a targeted binding agent or an antibody that specifically binds to DLL4 and comprises a sequence comprising one of the complementarity determining regions (CDR) sequences shown in Table 2. Embodiments of the invention include a targeted binding agent or antibody comprising a sequence comprising: any one of a CDR1, a CDR2 or a CDR3 sequence as shown in Table 2. A further embodiment is a targeted binding agent or an antibody that specifically binds to DLL4 and comprises a sequence comprising two of the CDR sequences shown in Table 2. In another embodiment the targeted binding agent or antibody comprises a sequence comprising a CDR1, a CDR2 and a CDR3 sequence as shown in Table 2. In another embodiment the targeted binding agent or antibody comprises a sequence comprising one of the CDR sequences shown in Table 2. Embodiments of the invention include a targeted binding agent or antibody comprising a sequence comprising: any one of a CDR1, a CDR2 or a CDR3 sequence as shown in Table 2. In another embodiment the targeted binding agent or antibody comprises a sequence comprising two of the CDR sequences shown in Table 2. In another embodiment the targeted binding agent or antibody comprises a sequence comprising a CDR1, a CDR2 and a CDR3 sequence as shown in Table 2. In another embodiment the targeted binding agent or antibody may comprise a sequence comprising a CDR1, a CDR2 and a CDR3 sequence of a variable heavy chain sequence or a variable light chain sequence as shown in Table 2. In some embodiments, the targeted binding agent is an antibody. In certain embodiments, the targeted binding agent is a fully human monoclonal antibody. In certain other embodiments, the targeted binding agent is a binding fragment of a fully human monoclonal antibody.

In another embodiment, the targeted binding agent comprises a VH CDR1 as shown in Table 2, wherein the sequence of the VH CDR1 has an amino acid sequence identical to or comprising 1, 2, or 3 amino acid residue substitutions relative to the VH CDR1 as shown in Table 2; a VH CDR2 as shown in Table 2 having an amino acid sequence identical to or comprising 1, 2, or 3 amino acid residue substitutions relative to the VH CDR2 as shown in Table 2; a VH CDR3 as shown in Table 2 having an amino acid sequence identical to or comprising 1, 2, or 3 amino acid residue substitutions relative to the VH CDR3 as shown in Table 2; a VL CDR1 as shown in Table 2 having an amino acid sequence identical to or comprising 1, 2, or 3 amino acid residue substitutions relative to VL CDR1 as shown in Table 2; a VL CDR2 as shown in Table 2 having an amino acid sequence identical to or comprising 1, 2, or 3 amino acid residue substitutions relative to the VL CDR2 as shown in Table 2; and a VL CDR3 as shown in Table 2 having an amino acid sequence identical to or comprising 1, 2, or 3 amino acid residue substitutions relative to the VL CDR3 as shown in Table 2.

In one embodiment, the targeted binding agent comprises a VH CDR1, CDR2 and CDR3 as shown in Table 2 and a VL CDR1 CDR2 and CDR3 as shown in Table 2.

In yet another embodiment, the targeted binding agent immunospecifically binds DLL4 and comprises a heavy chain variable domain as shown in table 2 having at least 90% identity to the amino acid as shown in table 2 and comprises a light chain variable domain as shown in table 2 having at least 90% identity to the amino acid sequence as shown in table 2, wherein said antibody has the activity of binding to DLL4.

In another embodiment the targeted binding agent may comprise a sequence comprising any one of the CDR1, CDR2 or CDR3 of the variable heavy chain sequences encoded by a polynucleotide in a plasmid designated Mab2H10VHOP, Mab9G8VH, Mab21H3VH, and Mab4B4VH which were deposited at the American Type Culture Collection (ATCC) under number PTA-9502, PTA-9517, PTA-9501, or PTA-9508 on Sep. 17, 2008. In another embodiment the targeted binding agent may comprise a sequence comprising any one of the CDR1, CDR2 or CDR3 of the variable light chain sequences encoded by a polynucleotide in a plasmid designated Mab9G8VLOPT1, Mab21H3VLOP, and Mab4B4VL which were deposited at the American Type Culture Collection (ATCC) under number PTA-9516, PTA-9500 or PTA-9520 on Sep. 17, 2008 and Mab2H10VLOP which was deposited on Jul. 7, 2009 under number PTA-10181.

In one embodiment, a targeted binding agent or an antibody of the invention comprises a variable heavy chain amino acid sequence comprising a CDR3 encoded by the polynucleotide in plasmid designated Mab2H10VHOP which was deposited at the American Type Culture Collection (ATCC) under number PTA-9502 on Sep. 17, 2008.

In one embodiment, a targeted binding agent or an antibody of the invention comprises a variable heavy chain amino acid sequence comprising a CDR3 encoded by the polynucleotide in plasmid designated Mab2H10VHOP which was deposited at the American Type Culture Collection (ATCC) under number PTA-9502 on Sep. 17, 2008 and a variable light chain amino acid sequence comprising a CDR3 encoded by the polynucleotide in plasmid designated Mab2H10VLOP which was deposited at the American Type Culture Collection (ATCC) under number PTA-10181 on Jul. 7, 2009.

In another embodiment, a targeted binding agent or an antibody of the invention comprises a variable heavy chain amino acid sequence comprising at least one, at least two, or at least three of the CDRs of the antibody encoded by the polynucleotide in plasmid designated Mab2H10VHOP which was deposited at the American Type Culture Collection (ATCC) under number PTA-9502 on Sep. 17, 2008.

In another embodiment, a targeted binding agent or an antibody of the invention comprises a variable light chain amino acid sequence comprising at least one, at least two, or at least three of the CDRs of the antibody encoded by the polynucleotide in plasmid designated Mab2H10VLOP which was deposited at the American Type Culture Collection (ATCC) under number PTA-10181 on Jul. 7, 2009.

In another embodiment, a targeted binding agent or an antibody of the invention comprises a variable heavy chain amino acid sequence comprising at least one, at least two, or at least three of the CDRs of the antibody encoded by the polynucleotide in plasmid designated Mab2H10VLOP which was deposited at the American Type Culture Collection (ATCC) under number PTA-9502 on Sep. 17, 2008 and a variable light chain amino acid sequence comprising at least one, at least two, or at least three of the CDRs of the antibody encoded by the polynucleotide in plasmid designated Mab2H10VLOP which was deposited at the American Type Culture Collection (ATCC) under number PTA-10181 on Jul. 7, 2009.

In one embodiment, a targeted binding agent or an antibody of the invention comprises a variable heavy chain amino acid sequence comprising a CDR3 encoded by the polynucleotide in plasmid designated Mab9G8VH which was deposited at the American Type Culture Collection (ATCC) under number PTA-9517.

In one embodiment, a targeted binding agent or an antibody of the invention comprises a variable heavy chain amino acid sequence comprising a CDR3 encoded by the polynucleotide in plasmid designated Mab9G8VH which was deposited at the American Type Culture Collection (ATCC) under number PTA-9517 on Sep. 17, 2008 and a variable light chain amino acid sequence comprising a CDR3 encoded by the polynucleotide in plasmid designated Mab9G8VLOPT1 which was deposited at the American Type Culture Collection (ATCC) under number PTA-9516 on Sep. 17, 2008.

In another embodiment, a targeted binding agent or an antibody of the invention comprises a variable heavy chain amino acid sequence comprising at least one, at least two, or at least three of the CDRs of the antibody encoded by the polynucleotide in plasmid designated Mab9G8VH which was deposited at the American Type Culture Collection (ATCC) under number PTA-9517 on Sep. 17, 2008.

In another embodiment, a targeted binding agent or an antibody of the invention comprises a variable light chain amino acid sequence comprising at least one, at least two, or at least three of the CDRs of the antibody encoded by the polynucleotide in plasmid designated Mab9G8VLOPT1 which was deposited at the American Type Culture Collection (ATCC) under number PTA-9516 on Sep. 17, 2008.

In another embodiment, a targeted binding agent or an antibody of the invention comprises a variable heavy chain amino acid sequence comprising at least one, at least two, or at least three of the CDRs of the antibody encoded by the polynucleotide in plasmid designated Mab9G8VH which was deposited at the American Type Culture Collection (ATCC) under number PTA-9517 on Sep. 17, 2008 and a variable light chain amino acid sequence comprising at least one, at least two, or at least three of the CDRs of the antibody encoded by the polynucleotide in plasmid designated Mab9G8VLOPT1 which was deposited at the American Type Culture Collection (ATCC) under number PTA-9516 on Sep. 17, 2008.

In one embodiment, a targeted binding agent or an antibody of the invention comprises a variable heavy chain amino acid sequence comprising a CDR3 encoded by the polynucleotide in plasmid designated Mab21H3VH which was deposited at the American Type Culture Collection (ATCC) under number PTA-9501 on Sep. 17, 2008.

In one embodiment, a targeted binding agent or an antibody of the invention comprises a variable heavy chain amino acid sequence comprising a CDR3 encoded by the polynucleotide in plasmid designated Mab21H3VH which was deposited at the American Type Culture Collection (ATCC) under number PTA-9501 on Sep. 17, 2008 and a variable light chain amino acid sequence comprising a CDR3 encoded by the polynucleotide in plasmid designated Mab21H3VLOP which was deposited at the American Type Culture Collection (ATCC) under number PTA-9500 on Sep. 17, 2008.

In another embodiment, a targeted binding agent or an antibody of the invention comprises a variable heavy chain amino acid sequence comprising at least one, at least two, or at least three of the CDRs of the antibody encoded by the polynucleotide in plasmid designated Mab21H3VH which was deposited at the American Type Culture Collection (ATCC) under number PTA-9501 on Sep. 17, 2008.

In another embodiment, a targeted binding agent or an antibody of the invention comprises a variable light chain amino acid sequence comprising at least one, at least two, or at least three of the CDRs of the antibody encoded by the polynucleotide in plasmid designated Mab21H3VLOP which was deposited at the American Type Culture Collection (ATCC) under number PTA-9500 on Sep. 17, 2008.

In another embodiment, a targeted binding agent or an antibody of the invention comprises a variable heavy chain amino acid sequence comprising at least one, at least two, or at least three of the CDRs of the antibody encoded by the polynucleotide in plasmid designated Mab21H3VH which was deposited at the American Type Culture Collection (ATCC) under number PTA-9501 on Sep. 17, 2008 and a variable light chain amino acid sequence comprising at least one, at least two, or at least three of the CDRs of the antibody encoded by the polynucleotide in plasmid designated Mab21H3VLOP which was deposited at the American Type Culture Collection (ATCC) under number PTA-9500 on Sep. 17, 2008.

In one embodiment, a targeted binding agent or an antibody of the invention comprises a variable heavy chain amino acid sequence comprising a CDR3 encoded by the polynucleotide in plasmid designated Mab4B4VH which was deposited at the American Type Culture Collection (ATCC) under number PTA-9508 on Sep. 7, 2008.

In one embodiment, a targeted binding agent or an antibody of the invention comprises a variable heavy chain amino acid sequence comprising a CDR3 encoded by the polynucleotide in plasmid designated Mab4B4VH which was deposited at the American Type Culture Collection (ATCC) under number PTA-9508 on Sep. 17, 2008 and a variable light chain amino acid sequence comprising a CDR3 encoded by the polynucleotide in plasmid designated Mab4B4VL which was deposited at the American Type Culture Collection (ATCC) under number PTA-9520 on Sep. 17, 2008.

In another embodiment, a targeted binding agent or an antibody of the invention comprises a variable heavy chain amino acid sequence comprising at least one, at least two, or at least three of the CDRs of the antibody encoded by the polynucleotide in plasmid designated Mab4B4VH which was deposited at the American Type Culture Collection (ATCC) under number PTA-9508 on Sep. 17, 2008.

In another embodiment, a targeted binding agent or an antibody of the invention comprises a variable light chain amino acid sequence comprising at least one, at least two, or at least three of the CDRs of the antibody encoded by the polynucleotide in plasmid designated Mab4B4VL which was deposited at the American Type Culture Collection (ATCC) under number VIA-9520 on Sep. 17, 2008.

In another embodiment, a targeted binding agent or an antibody of the invention comprises a variable heavy chain amino acid sequence comprising at least one, at least two, or at least three of the CDRs of the antibody encoded by the polynucleotide in plasmid designated Mab4B4VH which was deposited at the American Type Culture Collection (ATCC) under number VIA-9508 on Sep. 17, 2008 and a variable light chain amino acid sequence comprising at least one, at least two, or at least three of the CDRs of the antibody encoded by the polynucleotide in plasmid designated Mab4B4VL which was deposited at the American Type Culture Collection (ATCC) under number PTA-9520 on Sep. 17, 2008.

In another embodiment, a targeted binding agent or an antibody of the invention comprises a variable heavy chain of an antibody encoded by the polynucleotide in plasmid designated Mab2H10VHOP which was deposited at the American Type Culture Collection (ATCC) under number PTA-9502 on Sep. 17, 2008.

In another embodiment, a targeted binding agent or an antibody of the invention comprises a variable heavy chain of an antibody encoded by the polynucleotide in plasmid designated Mab9G8VH which was deposited at the American Type Culture Collection (ATCC) under number PTA-9517 on Sep. 17, 2008.

In another embodiment, a targeted binding agent or an antibody of the invention comprises a variable heavy chain of an antibody encoded by the polynucleotide in plasmid designated Mab21H3VH which was deposited at the American Type Culture Collection (ATCC) under number PTA-9501 on Sep. 17, 2008.

In another embodiment, a targeted binding agent or an antibody of the invention comprises a variable heavy chain of an antibody encoded by the polynucleotide in plasmid designated Mab4B4VH which was deposited at the American Type Culture Collection (ATCC) under number PTA-9508 on Sep. 17, 2008.

In another embodiment, a targeted binding agent or an antibody of the invention comprises a variable light chain of an antibody encoded by the polynucleotide in plasmid designated Mab2H10VLOP which was deposited at the American Type Culture Collection (ATCC) under number PTA-10181 on Jul. 7, 2009.

In another embodiment, a targeted binding agent or an antibody of the invention comprises a variable light chain of an antibody encoded by the polynucleotide in plasmid designated Mab9G8VLOPT1 Which was deposited at the American Type Culture Collection (ATCC) under number PTA-9516 on Sep. 17, 2008.

In another embodiment, a targeted binding agent or an antibody of the invention comprises a variable light chain of an antibody encoded by the polynucleotide in plasmid designated Mab21H3VLOP which was deposited at the American Type Culture Collection (ATCC) under number VIA-9500 on Sep. 17, 2008.

In another embodiment, a targeted binding agent or an antibody of the invention comprises a variable light chain of an antibody encoded by the polynucleotide in plasmid designated Mab4B4VL which was deposited at the American Type Culture Collection (ATCC) under number PTA-9520 on Sep. 17, 2008.

In another embodiment, a targeted binding agent or an antibody of the invention comprises a variable heavy chain of an antibody encoded by the polynucleotide in plasmid designated Mab2H10VHOP which was deposited at the American Type Culture Collection (ATCC) under number PTA-9502 on Sep. 17, 2008 and a variable light chain of an antibody encoded by the polynucleotide in plasmid designated Mab2H10VLOP which was deposited at the American Type Culture Collection (ATCC) under number PTA-10181 on Jul. 7, 2009.

In another embodiment, a targeted binding agent or an antibody of the invention comprises a variable light chain of an antibody encoded by the polynucleotide in plasmid designated Mab9G8VLOPT1 which was deposited at the American Type Culture Collection (ATCC) under number PTA-9516 on Sep. 17, 2008 and a variable heavy chain of an antibody encoded by the polynucleotide in plasmid designated Mab9G8VH which was deposited at the American Type Culture Collection (ATCC) under number PTA-9517 on Sep. 17, 2008.

In another embodiment, a targeted binding agent or an antibody of the invention comprises a variable heavy chain of an antibody encoded by the polynucleotide in plasmid designated Mab21H3VH which was deposited at the American Type Culture Collection (ATCC) under number PTA-9501 on Sep. 17, 2008 and a variable light chain of an antibody encoded by the polynucleotide in plasmid designated Mab21H3VLOP which was deposited at the American Type Culture Collection (ATCC' under number PTA-9500 on Sep. 17, 2008.

In another embodiment, a targeted binding agent or an antibody of the invention comprises a variable light chain of an antibody encoded by the polynucleotide in plasmid designated Mab4B4VL which was deposited at the American Type Culture Collection (ATCC) under number PTA-9520 on Sep. 17, 2008 and a variable light chain of an antibody encoded by the polynucleotide in plasmid designated Mab4B4VL which was deposited at the American Type Culture Collection (ATCC) under number PTA-9520 on Sep. 17, 2008.

It is noted that those of ordinary skill in the art can readily accomplish CDR determinations. See for example, Kabat et al., *Sequences of Proteins of Immunological Interest*, Fifth Edition, NIH Publication 91-3242, Bethesda Md. (1991), vols. 1-3. Kabat provides multiple sequence alignments of immunoglobulin chains from numerous species antibody isotypes. The aligned sequences are numbered according to a single numbering system, the Kabat numbering system. The Kabat sequences have been updated since the 1991 publication and are available as an electronic sequence database (latest downloadable version 1997). Any immunoglobulin sequence can be numbered according to Kabat by performing an alignment with the Kabat reference sequence. Accordingly, the Kabat numbering system provides a uniform system for numbering immunoglobulin chains.

In one embodiment, the targeted binding agent or antibody comprises a sequence comprising any one of the heavy chain sequences shown in Table 2. In another embodiment, the targeted binding agent or antibody comprises a sequence comprising any one of the heavy chain sequences of antibodies 20G8, 21H3, 14B1, 18B7, 17B6, 17F3, 12A1, 17G12, 19G9, 21F7, 20D6, 1D4, 4B4, 2H10, or 21H3RK, or any optimized version of the heavy chain sequences of these antibodies as shown in Table 5, 7, 9, 11 or 13. Light-chain promiscuity is well established in the art, thus, a targeted binding agent or antibody comprising a sequence comprising any one of the light chain sequences of antibodies 4B4, 2H10, 21F7, 12A1, 17F3, 9G8, 20G8, 21H3, 1E4, 3A7, 4B3, 1D4, or 21H3RK, or any optimized version of the light chain sequences of these antibodies as shown in Table 6, 8, 10, 12 or 13, or any other antibody as disclosed herein. In one embodiment, the targeted binding agent or antibody comprises a sequence comprising any one of the heavy chain sequences shown in Table 2, or any optimized version of the heavy chain sequences of these antibodies as shown in Table 5, 7, 9, 11 or 13, and may further comprise any one of the light chain sequences shown in Table 6, 8, 10, 12 or 13 or another antibody as disclosed herein. In some embodiments, the antibody is a fully human monoclonal antibody.

In some embodiments, the targeting binding agent is a monoclonal antibody selected from the group consisting of: 4B4, 2H10, 21F7, 12A1, 17F3, 9G8, 20G8, 21H3, 1E4, 3A7, 4B3, 1D4, or 21H3RK. In one embodiment, the targeted binding agent comprises one or more of fully human monoclonal antibodies 4B4, 2H10, 21F7, 12A1, 17F3, 9G8, 20G8, 21H3, 1E4, 3A7, 4B3, 1D4, or 21H3RK. In certain embodiments, the targeting binding agent is monoclonal antibody 4B4. In certain embodiments, the targeting binding agent is monoclonal antibody 21H3. In certain embodiments, the targeting binding agent is monoclonal antibody 2H10. In certain embodiments, the targeting binding agent is monoclonal antibody 9G8. In certain other embodiments, the targeting binding agent is monoclonal antibody 21H3RK.

In one embodiment a targeted binding agent or an antibody may comprise a sequence comprising a heavy chain CDR1, CDR2 and CDR3 selected from any one of the sequences shown in Table 2

In one embodiment a targeted binding agent or an antibody may comprise a sequence comprising a light chain CDR1, CDR2 and CDR3 selected from any one of the sequences shown in Table 2. In one embodiment a targeted binding agent or an antibody may comprise a sequence comprising a heavy chain CDR1, CDR2 and CDR3 selected from any one of the CDRs of antibodies 4B4, 2H10, 21F7, 12A1, 17F3, 9G8, 20G8, 21H3, 1E4, 3A7, 4B3, 1D4, or 21H3RK. In one embodiment a targeted binding agent or an antibody may comprise a sequence comprising a light chain CDR1, CDR2 and CDR3 selected from any one of the CDRs of antibodies 4B4, 2H10, 21F7, 12A1, 17F3, 9G8, 20G8, 21H3, 1E4, 3A7, 4B3, 1D4, or 21H3RK.

In another embodiment the targeted binding agent or antibody may comprise a sequence comprising any one of a CDR1, a CDR2 or a CDR3 of a variable heavy chain sequence of any one of the fully human monoclonal antibodies 4B4 or 21H3, 21H10, 9G8, or 21H3RK, as shown in Table 2. In another embodiment the targeted binding agent or antibody may comprise a sequence comprising any one of a CDR1, a CDR2 or a CDR3 of a variable light chain sequence of any one of the fully human monoclonal antibodies 4B4 or 21H3, 2H10, 9G8, or 21H3RK, as shown in Table 2. In another embodiment the targeted binding agent or antibody may comprise a sequence comprising a CDR1, a CDR2 and a CDR3 of fully human monoclonal antibody 4B4 or 21H3, 2H10, 9G8, or 21H3RK, as shown in Table 2, and a CDR1, a CDR2 and a CDR3 sequence of fully human monoclonal antibody 4B4 or 21H3, 2H10, 9G8, or 21H3RK, as shown in Table 2. In some embodiments, the antibody is a fully human monoclonal antibody.

In another embodiment the targeted binding agent or antibody comprises a sequence comprising the CDR1, CDR2 and CDR3 sequence of fully human monoclonal antibody 4B4 as shown in Table 2 and the CDR1, CDR2 and CDR3 sequence of fully human monoclonal antibody 4B4 as shown in Table 2. In another embodiment the targeted binding agent or antibody comprises a sequence comprising the CDR1, CDR2 and CDR3 sequence of fully human monoclonal antibody 21H3 as shown in Table 2 and the CDR1, CDR2 and CDR3 sequence of fully human monoclonal antibody 21H3 as shown in Table 2. In another embodiment the targeted binding agent or antibody comprises a sequence comprising the CDR1, CDR2 and CDR3 sequence of fully human monoclonal antibody 2H10 as shown in Table 2 and the CDR1, CDR2 and CDR3 sequence of fully human monoclonal antibody 2H10 as shown in Table 2. In some embodiments, the antibody is a fully human monoclonal antibody.

A further embodiment of the invention is a targeted binding agent or antibody comprising a sequence comprising the contiguous sequence spanning the framework regions and CDRs, specifically from FR1 through FR4 or CDR1 through CDR3, of any one of the sequences as shown in Table 2 or Table 13. In one embodiment the targeted binding agent or antibody comprises a sequence comprising the contiguous sequences spanning the framework regions and CDRs, specifically from FR1 through FR4 or CDR1 through CDR3, of any one of the sequences of monoclonal antibodies 4B4 or 21H3, 2H10, 9G8, or 21H3RK, as shown in Table 2 or Table 13. In some embodiments, the antibody is a fully human monoclonal antibody.

In another embodiment the agent or antibody, or antigen-binding portion thereof, comprises a heavy chain polypeptide comprising the sequence of SEQ ID NO.:2. In one embodiment, the agent or antibody, or antigen-binding portion thereof, further comprises a light chain polypeptide comprising the sequence of SEQ ID NO.:4. In some embodiments, the antibody is a fully human monoclonal antibody.

One embodiment provides a targeted binding agent or antibody, or antigen-binding portion thereof, wherein the agent or antibody, or antigen-binding portion thereof, comprises a heavy chain polypeptide comprising the sequence of SEQ ID NO.:6. In one embodiment, the agent or antibody, or antigen-binding portion thereof, further comprises a light chain polypeptide comprising the sequence of SEQ ID NO.:8. In some embodiments, the antibody is a fully human monoclonal antibody.

In another embodiment the agent or antibody, or antigen-binding portion thereof, comprises a heavy chain polypeptide comprising the sequence of SEQ ID NO.:22. In another embodiment, the agent or antibody, or antigen-binding portion thereof, further comprises a light chain polypeptide comprising the sequence of SEQ ID NO.:24. In some embodiments, the antibody is a fully human monoclonal antibody.

In another embodiment the agent or antibody, or antigen-binding portion thereof, comprises a heavy chain polypeptide comprising the sequence of SEQ ID NO.:30. In another embodiment, the agent or antibody, or antigen-binding portion thereof, further comprises a light chain polypeptide comprising the sequence of SEQ ID NO.:32. In some embodiments, the antibody is a fully human monoclonal antibody.

In another embodiment the agent or antibody, or antigen-binding portion thereof, comprises a heavy chain polypeptide comprising the sequence of SEQ ID NO.:30. In another embodiment, the agent or antibody, or antigen-binding portion thereof, further comprises a light chain polypeptide comprising the sequence of SEQ ID NO.:50. In some embodiments, the antibody is a fully human monoclonal antibody.

In one embodiment the targeted binding agent or antibody comprises as many as twenty, sixteen, ten, nine or fewer, e.g. one, two, three, four or five, amino acid additions, substitutions, deletions, and/or insertions within the disclosed CDRs or heavy or light chain sequences. Such modifications may potentially be made at any residue within the CDRs. In some embodiments, the antibody is a fully human monoclonal antibody.

In one embodiment, the targeted binding agent or antibody comprises variants or derivatives of the CDRs disclosed herein, the contiguous sequences spanning the framework regions and CDRs (specifically from FR1 through FR4 or CDR1 through CDR3), the light or heavy chain sequences disclosed herein, or the antibodies disclosed herein. Variants include targeted binding agents or antibodies comprising sequences which have as many as twenty, sixteen, ten, nine or fewer, e.g. one, two, three, four, five or six amino acid additions, substitutions, deletions, and/or insertions in any of the CDR1, CDR2 or CDR3s as shown in Table 2 or Table 13, the contiguous sequences spanning the framework regions and CDRs (specifically from FR1 through FR4 or CDR1 through CDR3) as shown in Table 2 or Table 13, the light or heavy chain sequences disclosed herein, or with the monoclonal antibodies disclosed herein. Variants include targeted binding agents or antibodies comprising sequences which have at least about 60, 70, 80, 85, 90, 95, 98 or about 99% amino acid sequence identity with any of the CDR1, CDR2 or CDR3s as shown in Table 2 or Table 13, the contiguous sequences spanning the framework regions and CDRs (specifically from FR1 through FR4 or CDR1 through CDR3) as shown in Table 2 or Table 13, the light or heavy chain sequences disclosed herein, or with the monoclonal antibodies disclosed herein. The percent identity of two amino acid sequences can be determined by any method known to one skilled in the art, including, but not limited to, pairwise protein alignment. In one embodiment variants comprise changes in the CDR sequences or light or heavy chain polypeptides disclosed herein that are naturally occurring or are introduced by in vitro engineering of native sequences using recombinant DNA techniques or mutagenesis techniques. Naturally occurring variants include those which are generated in vivo in the corresponding germline nucleotide sequences during the generation of an antibody to a foreign antigen. In one embodiment the derivative may be a heteroantibody, that is an antibody in which two or more antibodies are linked together. Derivatives include antibodies which have been chemically modified. Examples include covalent attachment of one or more polymers, such as water-soluble polymers, N-linked, or O-linked carbohydrates, sugars, phosphates, and/or other such molecules. The derivatives are modified in a manner that is different from the naturally occurring or starting antibody, either in the type or location of the molecules attached. Derivatives further include deletion of one or more chemical groups which are naturally present on the antibody.

In one embodiment, the targeted binding agent is a bispecific antibody. A bispecific antibody is an antibody that has binding specificity for at least two different epitopes. Methods for making bispecific antibodies are known in the art. (See, for example, Millstein et al., *Nature,* 305:537-539 (1983); Traunecker et al., *EMBO J.,* 10:3655-3659 (1991); Suresh et al., *Methods in Enzymology,* 121:210 (1986); Kostelny et al., *J. Immunol.,* 148(5):1547-1553 (1992); Hollinger et al., *Proc. Natl. Acad. Sci.* USA, 90:6444-6448 (1993); Gruber et al., *J. Immunol.,* 152:5368 (1994); U.S. Pat. Nos. 4,474,893; 4,714,681; 4,925,648; 5,573,920; 5,601,81; 95,731,168; 4,676,980; and 4,676,980, WO 94/04690; WO 91/00360; WO 92/200373; WO 93/17715; WO 92/08802; and EP 03089.)

In some embodiments of the invention, the targeted binding agent or antibody has its sequence optimized by either mutating its non-germline residues to germline residues, and/or removing structural liabilities. In one embodiment, the invention includes a sequence comprising SEQ ID NO.: 6. In certain embodiments, SEQ ID NO.: 6 comprises any one of the combinations of germline and non-germline residues indicated by each row of Table 7. In some embodiments, SEQ ID NO: 6 comprises any one, any two, any three, any four, any five, any six or all six of the germline residues as indicated in Table 7. In certain embodiments, SEQ ID NO.: 6 comprises any one of the unique combinations of germline and non-germline residues indicated by each row of Table 7.

In other embodiments, the targeted binding agent or antibody is derived from a germline sequence with VH3-33, 6-13 and JH4 domains, wherein one or more residues has been mutated to yield the corresponding germline residue at that position. In certain embodiments, SEQ ID NO.: 24 can comprise further modifications that include removing structural liabilities. For example, in addition to germlining, the C33 can be mutated to a S. Thus, SEQ ID NO.: 24 can comprise any one of the unique combinations of germline and non-germline residues indicated by each row of Table 10 and further include the mutation of C33 to a S.

A further embodiment of the invention is a targeted binding agent or antibody which competes for binding to DLL4. In another embodiment, the invention is directed to a targeted binding agent or antibody which competes with native DLL4 for binding to the Notch 1 or Notch 4 receptor. In another embodiment the targeted binding agent or antibody competes for binding to Notch 1 with any one of fully human monoclonal antibodies 4B4 or 21H3, 2H10, 9G8, or 21H3RK, "Competes" indicates that the targeted binding agent or antibody competes for binding to Notch 1 with any one of fully human monoclonal antibodies 4B4, 2H10, 21F7, 12A1, 17F3, 9G8, 20G8, 21H3, 1E4, 3A7, 4B3, 1D4, or 21H3RK, i.e. competition is unidirectional.

Embodiments of the invention include a targeted binding agent or antibody which cross competes with any one of fully human monoclonal antibodies 4B4, 2H10, 21F7, 12A1, 17F3, 9G8, 20G8, 21H3, 1E4, 3A7, 4B3, 1D4, or 21H3RK for binding to DLL4. "Cross competes" indicates that the targeted binding agent or antibody competes for binding to Notch 1 with any one of fully human monoclonal antibodies 4B4, 2H10, 21F7, 12A1, 17F3, 9G8, 20G8, 21H3, 1E4, 3A7, 4B3, 1D4, or 21H3RK, and vice versa, i.e. competition is bidirectional.

A further embodiment of the invention is a targeted binding agent or antibody that binds to the same epitope on DLL4 as the targeted binding agent or antibodies of the invention. Embodiments of the invention also include a targeted binding agent or antibody that binds to the same epitope on DLL4 as any one of fully human monoclonal antibodies 4B4, 2H10, 21F7, 12A1, 17F3, 9G8, 20G8, 21H3, 1E4, 3A7, 4B3, 1D4, or 21H3RK. It is clear from the cross-competition analysis that the antibodies of the invention have different or partially overlapping epitopes. For example, 4B4 cross competes with 21H3RK and 21H3. Also 4B4 and 21H3 do not bind DLL4 under reducing and denaturating conditions while 9G8 and 21H10 do suggestive of binding to different epitopes.

In certain embodiments, the epitope is comprised of at least one extracellular, portion of the DLL4. The at least one specified epitope (for example, for 21H3 or 21H3RK or 4B4) can comprise any combination of at least one amino acid sequence of at least 3 amino acid residues to the entire specified portion of contiguous amino acids occurring in DLL4 between amino acids 147-224, i.e., ICSDNYYGDNCSRLCKKRNDHFGHYVCQPDGNLSCLPGWTGEYCQQPICLSGCH EQNGYCSKPAECLCRPGWQGRLC (SEQ ID NO:90). In one embodiment, the epitope is at least 4 amino acid residues, at least 5 amino acid residues, at least 6 amino acid residues, at least 7 amino acid residues, at least 8 amino acid residues or at least 9 amino acid residues, at least 10 amino acid residues, at least 15 amino acid residues, at least 20 amino acid residues, at least 25 amino acid residues, at least 30 amino acid residues, at least 40 amino acid residues or at least 50 amino acid residues, at least 60 amino acid residues, at least 70 amino acid residues, at least 75 amino acid residues, at least 76 amino acid residues, or 77 amino acid residues of SEQ ID NO:90. In another embodiment, the epitope occurs in amino acid 187-201 of human DLL4, TGEYCQQPICLSGCH (SEQ ID NO:91). In one embodiment, the epitope is at least 4 amino acid residues, at least 5 amino acid residues, at least 6 amino acid residues, at least 7 amino acid residues, at least 8 amino acid residues or at least 9 amino acid residues, at least 10 amino acid residues, at least 11 amino acid residues, at least 12 amino acid residues, at least 13 amino acid residues, at least 14 amino acid residues, or 15 amino acid residues of SEQ ID NO:91.

In one embodiment, the invention includes mouse cross-reactive antibodies of the antibodies disclosed herein. In one embodiment, the variable regions of the antibodies are altered such that the antibodies can hind mouse DLL4. Typically the mouse cross-reactive antibodies have similar properties to the antibodies disclosed herein, e.g., can hind DLL4 and can inhibit binding of DLL4 to a Notch receptor. In one example, the variable region of the 21H3RK antibody is altered such that it can bind mouse DLL4, e.g., the heavy chain has the following alternations: H31 Asn to Lys, H52a Ala to Pro, H97 Val to Thr, H100b Val to Trp and H100e Glu to Ala (see SEQ ID NO:84) and the light chain has the following alterations: L30 Ser to Asn and L93 Asp to Ser (see SEQ ID NO:85). In another embodiment, the heavy chain has the following alternations: H30Thr to Ile, H31Asn to Met, H52a Ala to Pro, H100b Val to Trp and H100e Glu to Ala (see SEQ ID NO:86) and the light chain has the following alterations: L93 Asp to Ser (see SEQ ID NO:87). In yet another embodiment, the heavy chain has the following alternations: H30 Thr to Ile, H31 Asn to His, H100b Val to Trp and H100e Glu to Ala (see SEQ ID NO:88). and the light chain has the following alterations: L30 Ser to Asn and L93 Asp to Ser. (see SEQ ID NO:89).

Other embodiments of the invention include isolated nucleic acid molecules encoding any of the targeted binding agents or antibodies described herein, vectors having isolated nucleic acid molecules encoding the targeted binding agents or antibodies described herein or a host cell transformed with any of such nucleic acid molecules. Embodiments of the invention include a nucleic acid molecule encoding a fully human isolated targeted binding agent that specifically bind to DLL4 and inhibit binding of DLL4 to a Notch receptor. The invention also encompasses polynucleotides that hybridize under stringent or lower stringency hybridization conditions, as defined herein, to polynucleotides that encode any of the targeted binding agents or antibodies described herein. Embodiments of the invention also include a vector comprising the nucleic acid molecule encoding the binding agent. Additional embodiments include a host cell comprising the vector of comprising the nucleic acid molecule.

As known in the art, antibodies can advantageously be, for example, polyclonal, oligoclonal, monoclonal, chimeric, humanised, and/or fully human antibodies.

It will be appreciated that embodiments of the invention are not limited to any particular form of an antibody or method of generation or production. In some embodiments of the invention, the targeted binding agent is a binding fragment of a fully human monoclonal antibody. For example, the targeted binding agent can be a full-length antibody (e.g., having an intact human Fc region) or an antibody binding fragment (e.g., a Fab, Fab' or F(ab')$_2$, FV or dAb). In addition, the antibodies can be single-domain antibodies such as camelid or human single VH or VL domains that bind to DLL4, such as a dAb fragment.

Embodiments of the invention described herein also provide cells for producing these antibodies. Examples of cells include hybridomas, or recombinantly created cells, such as Chinese hamster ovary (CHO) cells, variants of CHO cells (for example DG44) and NS0 cells that produce antibodies against DLL4. Additional information about variants of CHO cells can be found in Andersen and Reilly (2004) *Current Opinion in Biotechnology* 15, 456-462 which is incorporated herein in its entirety by reference. The antibody can be manufactured from a hybridoma that secretes the antibody, or from a recombinantly engineered cell that has been transformed or transfected with a gene or genes encoding the antibody.

In addition, one embodiment of the invention is a method of producing an antibody of the invention by culturing host cells under conditions wherein a nucleic acid molecule is expressed to produce the antibody followed by recovering the antibody. It should be realised that embodiments of the invention also include any nucleic acid molecule which encodes an antibody or fragment of an antibody of the invention including nucleic acid sequences optimised for increasing yields of antibodies or fragments thereof when transfected into host cells for antibody production.

A further embodiment herein includes a method of producing antibodies that specifically bind to and inhibit the biological activity of DLL4, by immunizing a mammal with cells expressing human DLL4, isolated cell membranes containing human DLL4, purified human DLL4, or a fragment thereof, and/or one or more orthologous sequences or fragments thereof.

In other embodiments the invention provides compositions, including a targeted binding agent or antibody of the invention or binding fragment thereof, and a pharmaceutically acceptable carrier or diluent.

Still further embodiments of the invention include methods of effectively treating an animal suffering from a proliferative, angiogenic disease by administering to the animal a therapeutically effective dose of a targeted binding agent that specifically binds to DLL4. In certain embodiments the method further comprises selecting an animal in need of treatment for a tumor, cancer, and/or a cell proliferative disorder, and administering to the animal a therapeutically effective dose of a targeted binding agent that specifically binds to DLL4.

Still further embodiments of the invention include methods of effectively treating an animal suffering from a neoplastic disease by administering to the animal a therapeutically effective dose of a targeted binding agent that specifically hinds to DLL4. In certain embodiments the method further comprises selecting an animal in need of treatment for a neoplastic disease, and administering to the animal a therapeutically effective dose of a targeted binding agent that specifically binds to DLL4.

Still further embodiments of the invention include methods of effectively ea an animal suffering from a malignant tumor by administering to the animal a therapeutically effective dose of a targeted binding agent that specifically binds to DLL4. In certain embodiments the method further comprises selecting an animal in need of treatment for a malignant tumor, and administering to the animal a therapeutically effective dose of a targeted binding agent that specifically binds to DLL4.

Still further embodiments of the invention include methods of effectively treating an animal suffering from a disease or condition associated with DLL4 expression by administering to the animal a therapeutically effective dose of a targeted binding agent that specifically binds to DLL4. In certain embodiments the method further comprises selecting an animal in need of treatment for a disease or condition associated with DLL4 expression, and administering to the animal a therapeutically effective dose of a targeted binding agent that specifically binds to DLL4.

A malignant tumor may be selected from the group consisting of: melanoma, small cell lung cancer, non-small cell lung cancer, glioma, hepatocellular (liver) carcinoma, thyroid tumor, gastric (stomach) cancer, prostate cancer, breast cancer, ovarian cancer, bladder cancer, lung cancer, glioblastoma, endometrial cancer, kidney cancer, colon cancer, pancreatic cancer, esophageal carcinoma, head and neck cancers, mesothelioma, sarcomas, biliary (cholangiocarcinoma), small bowel adenocarcinoma, pediatric malignancies and epidermoid carcinoma.

Treatable proliferative or angiogenic diseases include neoplastic diseases, such as, melanoma, small cell lung cancer, non-small cell lung cancer, glioma, hepatocellular (liver) carcinoma, thyroid tumor, gastric (stomach) cancer, gallbladder cancer, prostate cancer, breast cancer, ovarian cancer, bladder cancer, lung cancer, glioblastoma, endometrial cancer, kidney cancer, colon cancer, pancreatic cancer, ovarian, esophageal carcinoma, head and neck cancers, mesothelioma, sarcomas, biliary (cholangiocarcinoma), small bowel adenocarcinoma, pediatric malignancies, epidermoid carcinoma and leukaemia, including chronic myelogenous leukaemia.

In one embodiment the present invention is suitable for use in inhibiting DLL4, in patients with a tumor, which is dependent alone, or in part, on DLL4.

Still further embodiments of the invention include use of a targeted binding agent or antibody of the invention in the preparation of a medicament for the treatment of an animal suffering from a proliferative, or angiogenic related disease. In certain embodiments the use further comprises selecting an animal in need of treatment for a proliferative, or angiogenic-related disease.

Still further embodiments of the invention include use of a targeted binding agent or antibody of the invention in the preparation of a medicament for the treatment of an animal suffering from a neoplastic disease. In certain embodiments the use further comprises selecting an animal in need of treatment for a neoplastic disease.

Still further embodiments of the invention include use of a targeted binding agent or antibody of the invention in the preparation of a medicament for the treatment of an animal suffering from a non-neoplastic disease. In certain embodiments the use further comprises selecting an animal in need of treatment for a non-neoplastic disease.

Still further embodiments of the invention include use of a targeted binding agent or antibody of the invention in the preparation of a medicament for the treatment of an animal suffering from a malignant tumor. In certain embodiments the use further comprises selecting an animal in need of treatment for a malignant tumor.

Still further embodiments of the invention include use of a targeted binding agent or antibody of the invention in the preparation of a medicament for the treatment of an animal suffering from a disease or condition associated with DLL4 expression. In certain embodiments the use further comprises selecting an animal in need of treatment for a disease or condition associated with DLL4 expression.

Still further embodiments of the invention include a targeted binding agent or antibody of the invention for use as a medicament for the treatment of an animal suffering from a proliferative or angiogenic-related disease.

Still further embodiments of the invention include a targeted binding agent or antibody of the invention for use as a medicament for the treatment of an animal suffering from a neoplastic disease.

Still further embodiments of the invention include a targeted binding agent or antibody of the invention for use as a medicament for the treatment of an animal suffering from a malignant tumor.

Still further embodiments of the invention include a targeted binding agent or antibody of the invention for use as a medicament for the treatment of an animal suffering from a disease or condition associated with DLL4 expression.

Still further embodiments of the invention include a targeted binding agent or antibody of the invention for use as a medicament for the treatment of an animal suffering from a DLL4 induced disease.

In one embodiment treatment of a
a proliferative or angiogenic-related disease;
a neoplastic disease;
a malignant tumor; or
a disease or condition associated with DLL4 expression; or
comprises managing, ameliorating, preventing, any of the aforementioned diseases or conditions.

In one embodiment treatment of a neoplastic disease comprises inhibition of tumor growth, tumor growth delay, regression of tumor, shrinkage of tumor, increased time to regrowth of tumor on cessation of treatment, increased time to tumor recurrence, slowing of disease progression.

In some embodiments of the invention, the animal to be treated is a human.

In some embodiments of the invention, the targeted binding agent is a fully human monoclonal antibody.

In some embodiments of the invention, the targeted binding agent is selected from the group consisting of fully human monoclonal antibodies 4B4, 2H10, 21F7, 12A1, 17F3, 9G8, 20G8, 21H3, 1E4, 3A7, 4B3, 1D4 or 21H3RK.

Embodiments of the invention include a conjugate comprising the targeted binding agent as described herein, and a therapeutic agent. In some embodiments of the invention, the therapeutic agent is a toxin. In other embodiments, the therapeutic agent is a radioisotope. In still other embodiments, the therapeutic agent is a pharmaceutical composition.

In another aspect, a method of selectively killing a cancerous cell in a patient is provided. The method comprises administering a fully human antibody conjugate to a patient. The fully human antibody conjugate comprises an antibody that can bind to DLL4 and an agent. The agent is either a toxin, a radioisotope, or another substance that will kill a cancer cell. The antibody conjugate thereby selectively kills the cancer cell.

In one aspect, a conjugated fully human antibody that specifically binds to DLL4 is provided. Attached to the antibody is an agent, and the binding of the antibody to a cell results in the delivery of the agent to the cell. In one embodiment, the above conjugated fully human antibody binds to an extracellular domain of DLL4. In another embodiment, the antibody and conjugated toxin are internalised by a cell that expresses DLL4. In another embodiment, the agent is a cytotoxic agent. In another embodiment, the agent is, for example saporin, or auristatin, pseudomonas exotoxin, gelonin, ricin, calicheamicin or maytansine-based immunoconjugates, and the like. In still another embodiment, the agent is a radioisotope.

The targeted binding agent or antibody of the invention can be administered alone, or can be administered in combination with additional antibodies or chemotherapeutic drugs or radiation therapy. For example, a monoclonal, oligoclonal or polyclonal mixture of DLL4 antibodies that block cell adhesion, invasion, angiogenesis or proliferation can be administered in combination with a drug shown to inhibit tumor cell proliferation.

Another embodiment of the invention includes a method of diagnosing diseases or conditions in which an antibody as disclosed herein is utilised to detect the level of DLL4 in a patient or patient sample. In one embodiment, the patient sample is blood or blood serum or urine. In further embodiments, methods for the identification of risk factors, diagnosis of disease, and staging of disease is presented which involves the identification of the expression and/or overexpression of DLL4 using anti-DLL4 antibodies. In some embodiments, the methods comprise administering to a patient a fully human antibody conjugate that selectively binds to DLL4 on a cell. The antibody conjugate comprises an antibody that specifically binds to DLL4 and a label. The methods further comprise observing the presence of the label in the patient. A relatively high amount of the label will indicate a relatively high risk of the disease and a relatively low amount of the label will indicate a relatively low risk of the disease. In one embodiment, the label is a green fluorescent protein.

The invention further provides methods for assaying the level of DLL4 in a patient sample, comprising contacting an antibody as disclosed herein with a biological sample from a patient, and detecting the level of binding between said antibody and DLL4 in said sample. In more specific embodiments, the biological sample is blood, plasma or serum.

Another embodiment of the invention includes a method for diagnosing a condition associated with the expression of DLL4 in a cell by contacting the serum or a cell with an antibody as disclosed herein, and thereafter detecting the presence of DLL4. In one embodiment the condition can be a proliferative, angiogenic, cell adhesion or invasion-related disease including, but not limited to, a neoplastic disease.

In another embodiment, the invention includes an assay kit for detecting DLL4 in mammalian tissues, cells, or body fluids to screen for DLL4-related diseases. The kit includes an antibody as disclosed herein and a means for indicating the reaction of the antibody with DLL4, if present. In one embodiment the antibody is a monoclonal antibody. In one embodiment, the antibody that binds DLL4 is labelled. In another embodiment the antibody is an unlabelled primary antibody and the kit further includes a means for detecting the primary antibody. In one embodiment, the means for detecting includes a labelled second antibody that is an anti-immunoglobulin. The antibody may be labelled with a marker selected from the group consisting of a fluorochrome, an enzyme, a radionuclide and a radiopaque material.

In some embodiments, the targeted binding agents or antibodies as disclosed herein can be modified to enhance their capability of fixing complement and participating in complement-dependent cytotoxicity (CDC). In other embodiments, the targeted binding agents or antibodies can be modified to enhance their capability of activating effector cells and participating in antibody-dependent cytotoxicity (ADCC). In yet other embodiments, the targeted binding agents or antibodies as disclosed herein can be modified both to enhance their capability of activating effector cells and participating in antibody-dependent cytotoxicity (ADCC) and to enhance their capability of fixing complement and participating in complement-dependent cytotoxicity (CDC).

In some embodiments, the targeted binding agents or antibodies as disclosed herein can be modified to reduce their capability of fixing complement and participating in complement-dependent cytotoxicity (CDC). In other embodiments, the targeted binding agents or antibodies can be modified to reduce their capability of activating effector cells and participating in antibody-dependent cytotoxicity (ADCC). In yet other embodiments, the targeted binding agents or antibodies as disclosed herein can be modified both to reduce their capability of activating effector cells and participating in antibody-dependent cytotoxicity (ADCC) and to reduce their capability of fixing complement and participating in complement-dependent cytotoxicity (CDC).

In certain embodiments, the half-life of a targeted binding agent or antibody as disclosed herein and of compositions of the invention is at least about 4 to 7 days. In certain embodiments, the mean half-life of a targeted binding agent or antibody as disclosed herein and of compositions of the invention is at least about 2 to 5 days, 3 to 6 days, 4 to 7 days, 5 to 8 days, 6 to 9 days, 7 to 10 days, 8 to 11 days, 8 to 12, 9 to 13, 10 to 14, 11 to 15, 12 to 16, 13 to 17, 14 to 18, 15 to 19, or 16 to 20 days. In other embodiments, the mean half-life of a targeted binding agent or antibody as disclosed herein and of compositions of the invention is at least about to 21 days, 18 to 22 days, 19 to 23 days, 20 to 24 days, 21 to 25, days, 22 to 26 days, 23 to 27 days, 24 to 28 days, 25 to 29 days, or 26 to 30 days. In still further embodiments the half-life of a targeted binding agent or antibody as disclosed herein and of compositions of the invention can be up to about 50 days. In certain embodiments, the half-lives of antibodies and of compositions of the invention can be prolonged by methods known in the art. Such prolongation can in turn reduce the amount and/or frequency of dosing of the antibody compositions. Antibodies with improved in vivo half-lives and methods for preparing them are disclosed in U.S. Pat. No. 6,277,375; and international Publication Nos. WO 98/23289 and WO 97/3461.

In another embodiment, the invention provides an article of manufacture including a container. The container includes a composition containing a targeted binding agent or antibody as disclosed herein, and a package insert or label indicating that the composition can be used to treat cell adhesion, invasion, angiogenesis, and/or proliferation-related diseases, including, but not limited to, diseases characterised by the expression or overexpression of DLL4.

In other embodiments, the invention provides a kit comprising a composition containing, a targeted binding agent or antibody as disclosed herein, and instructions to administer the composition to a subject in need of treatment.

The present invention provides formulation of proteins comprising a variant Fc region. That is, a non-naturally occurring Fc region, for example an Fc region comprising one or more non naturally occurring amino acid residues. Also encompassed by the variant Fc regions of present invention are Fc regions which comprise amino acid deletions, additions and/or modifications.

The serum half-life of proteins comprising Fc regions may be increased by increasing the binding affinity of the Fc region for FcRn. In one embodiment, the Fc variant protein has enhanced serum half life relative to comparable molecule.

In another embodiment, the present invention provides an Fc variant, wherein the Fc region comprises at least one non naturally occurring amino acid at one or more positions selected from the group consisting of 239, 330 and 332, as numbered by the EU index as set forth in Kabat. In a specific embodiment, the present invention provides an Fc variant, wherein the Fc region comprises at least one non naturally occurring amino acid selected from the group consisting of 239D, 330L and 332E, as numbered by the EU index as set forth in Kabat. Optionally, the Fc region may further comprise additional non naturally occurring amino acids at one or more positions selected from the group consisting of 252, 254, and 256, as numbered by the EU index as set forth in Kabat. In a specific embodiment, the present invention provides an Fc variant, wherein the Fc region comprises at least one non naturally occurring amino acid selected from the group consisting of 239D, 330L and 332E, as numbered by the EU index as set forth in Kabat and at least one non naturally occurring amino acid at one or more positions selected from the group consisting of 252Y, 254T and 256E, as numbered by the EU index as set forth in Kabat.

In another embodiment, the present invention provides an Fc variant, wherein the Fc region comprises at least one non naturally occurring amino acid at one or more positions selected from the group consisting of 234, 235 and 331, as numbered by the EU index as set forth in Kabat. In a specific embodiment, the present invention provides an Fc variant, wherein the Fc region comprises at least one non naturally occurring amino acid selected from the group consisting of 234F, 235F, 235Y, and 331S, as numbered by the EU index as set forth in Kabat. In a further specific embodiment, an Fc variant of the invention comprises the 234F, 235F, and 331S non naturally occurring amino acid residues, as numbered by the EU index as set forth in Kabat. In another specific embodiment, an Fc variant of the invention comprises the 234F, 235Y, and 331S non naturally occurring amino acid residues, as numbered by the EU index as set forth in Kabat. Optionally, the Fc region may further comprise additional non naturally occurring amino acid at one or more positions selected from the group consisting of 252, 254, and 256, as numbered by the EU index as set forth in Kabat. In a specific embodiment, the present invention provides an Fc variant, wherein the Fc region comprises at least one non naturally occurring amino acid selected from the group consisting of 234F, 235F, 235Y, and 331S, as numbered by the EU index as set forth in Kabat; and at least one non naturally occurring amino acid at one or more positions are selected from the group consisting of 252Y, 254T and 256E, as numbered by the EU index as set forth in Kabat.

In another embodiment, the present invention provides an Fc variant protein formulation, wherein the Fc region comprises at least a non naturally occurring amino acid at one or more positions selected from the group consisting of 239, 330 and 332, as numbered by the EU index as set forth in Kabat. In a specific embodiment, the present invention provides an Fc variant protein formulation, wherein the Fc region comprises at least one non naturally occurring amino acid selected from the group consisting of 239D, 330L and 332E, as numbered by the EU index as set forth in Kabat. Optionally, the Fc region may further comprise additional non naturally occurring amino acid at one or more positions selected from the group consisting of 252, 254, and 256, as numbered by the EU index as set forth in Kabat. In a specific embodiment, the present invention provides an Fc variant protein formulation, wherein the Fc region comprises at least one non naturally occurring amino acid selected from the group consisting of 239D, 330L and 332E, as numbered by the EU index as set forth in Kabat and at least one non naturally occurring amino acid at one or more positions are selected from the group consisting of 252Y, 254T and 256E, as numbered by the EU index as set forth in Kabat.

In another embodiment, the present invention provides an Fc variant protein formulation, wherein the Fc region comprises at least one non naturally occurring amino acid at one or more positions selected from the group consisting of 234, 235 and 331, as numbered by the EU index as set forth in Kabat. In a specific embodiment, the present invention provides an Fc variant protein formulation, wherein the Fc region comprises at least one non naturally occurring amino acid selected from the group consisting of 234F, 235F, 235Y, and 331S, as numbered by the EU index as set forth in Kabat. Optionally, the Fc region may further comprise additional non naturally occurring amino acid at one or more positions selected from the group consisting of 252, 254, and 256, as numbered by the EU index as set forth in Kabat. In a specific embodiment, the present invention provides an Fc variant protein formulation, wherein the Fc region comprises at least one non naturally occurring amino acid selected from the group consisting of 234F, 235F, 235Y, and 331S, as numbered by the EU index as set forth in Kabat; and at least one non naturally occurring amino acid at one or more positions are selected from the group consisting of 252Y, 254T and 256E, as numbered by the EU index as set forth in Kabat.

Methods for generating non naturally occurring Fc regions are known in the art. For example, amino acid substitutions and/or deletions can be generated by mutagenesis methods, including, but not limited to, site-directed mutagenesis (Kunkel, Proc. Natl. Acad. Sci. USA 82:488-492 (1985)), PCR mutagenesis (Higuchi, in "PCR Protocols: A Guide to Methods and Applications", Academic Press, San Diego, pp. 177-183 (1990)), and cassette mutagenesis (Wells et al., Gene 34:315-323 (1985)). Preferably, site-directed mutagenesis is performed by the overlap-extension PCR method (Higuchi, in "PCR Technology: Principles and Applications for DNA Amplification", Stockton Press, New York, pp. 61-70 (1989)). The technique of overlap-extension PCR (Higuchi, ibid.) can also be used to introduce any desired mutation(s) into a target sequence (the starting DNA). For example, the first round of PCR in the overlap-extension method involves amplifying the target sequence with an outside primer (primer 1) and an internal mutagenesis primer (primer 3), and separately with a second outside primer (primer 4) and an internal primer (primer 2), yielding two PCR segments (segments A and B). The internal mutagenesis primer (primer 3) is designed to contain mismatches to the target sequence specifying the desired mutation(s). In the second round of PCR, the products of the first round of PCR (segments A and B) are amplified by PCR using the two outside primers (primers 1 and 4). The resulting full-length PCR segment (segment C) is digested with restriction enzymes and the resulting restriction fragment is cloned into an appropriate vector. As the first step of mutagenesis, the starting DNA (e.g., encoding an Fc fusion protein, an antibody or simply an Fc region), is operably cloned into a mutagenesis vector. The primers are designed to reflect the desired amino acid substitution. Other methods useful for the generation of variant Fc regions are known in the art (see, e.g., U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 6,821,505; 6,277,375; U.S. Patent Publication Nos. 2004/0002587 and PCT Publications WO 9429351; WO 99/58572; WO 00/42072; WO 02/060919; WO 04/029207; WO 04/099249; WO 04/063351).

In some embodiments of the invention, the glycosylation patterns of the antibodies provided herein are modified to enhance ADCC and CDC effector function. See Shields R L et al., (2002) JBC. 277:26733; Shinkawa T et al., (2003) JBC. 278:3466 and Okazaki A et al., (2004) J. Mol. Biol., 336:1239. In some embodiments, an Fc variant protein comprises one or more engineered glycoforms, i.e., a carbohydrate composition that is covalently attached to the molecule comprising an Fc region. Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, 1999, Nat. Biotechnol 17:176-480; Davies et al., 20017 Biotechnol Bioeng 74:288-294; Shields et al, 2002. J Biol Chem 277:26733-26740; Shinkawa et al., 2003, J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland). See, e.g., WO 00061739; EA01229125; US 20030115614; Okazaki et al., 2004, JMB, 336: 1239-49.

It is also known in the art that the glycosylation of the Fc region can be modified to increase or decrease effector function (see for examples, Umana et al, 1999, Nat. Biotechnol 17:176-180; Davies et al., 2001, Biotechnol Bioeng 74:288-294; Shields et al, 2002, J Biol Chem 277:26733-26740; Shinkawa et al., 2003, J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa. Inc. Princeton, N.J.); GlycoMAb™ glycosylation engineering technology (GLYCART biotechnology AG, Zurich, Switzerland). Accordingly, in one embodiment the Fc regions of the antibodies of the invention comprise altered glycosylation of amino acid residues. In another embodiment, the altered glycosylation of the amino acid residues results in lowered effector function. In another embodiment, the altered glycosylation of the amino acid residues results in increased effector function. In a specific embodiment, the Fc region has reduced fucosylation. In another embodiment, the Fc region is afucosylated (see for examples, U.S. Patent Application Publication No. 2005/0226867).

BRIEF DESCRIPTION OF THE DRAWINGS

FIG. 5A depicts binding data of 21H3RK to chimeric knock out variants where the DLL4 N-ter1, N-ter2 or DSL segments of the extracellular domain are substituted with the corresponding DLL1 domains. FIG. 5B depicts binding data of 21H3RK to chimeric knock out variants where the DLL4 EGF1, EGF12, EGF34 or EGF5678 segments of the extracellular domain are substituted with the corresponding DLL1 domains. FIG. 5C depicts binding data of 21H3RK to chimeric knock out variants where the DLL4 N-ter+DSL, DSL+EGF1, DSL+EGF12, or N-ter+DSL+EGF12 segments of the extracellular domain are substituted with the corresponding DLL1 domains. FIG. 5D depicts binding data of 21H3RK to HuDLL4, HDLL1 or untransfected cells.

FIG. 6A depicts binding data of 21H3RK to chimeric knock out variants where the DLL4 DSL+EGF1, A, B or C segments of the extracellular domain are substituted with the corresponding DLL1 domains. FIG. 6B depicts binding data of 21H3RK to chimeric knock in variants where the DLL1 DSL, EGF1, DSL+EGF1 regions are substituted with the corresponding DLL4 domains or to DLL4. FIG. 6C depicts binding data of 21H3RK to DLL1 or untransfected cells.

DETAILED DESCRIPTION OF THE PREFERRED EMBODIMENT

Figure 1:
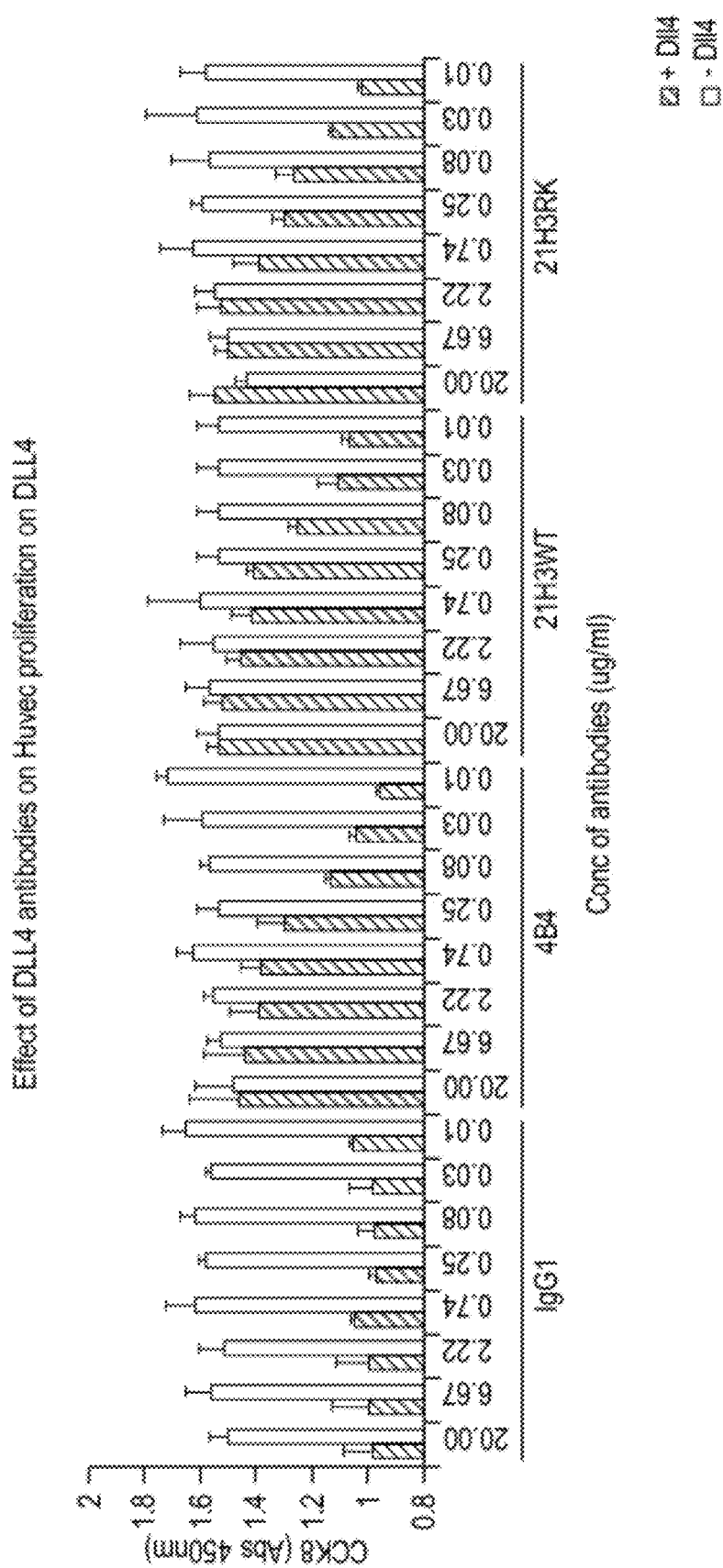
FIG. 1 depicts a bar graph showing the effects of IgG-1 DLL4 antibodies on DLL4-stimulated inhibition of HUVEC proliferation. Data is representative of n>2 independent experiments.

Embodiments of the invention relate to a novel set of DLL4 blocking molecules, such as, for example, antibodies, that inhibit notch receptor signaling. Such molecules can be used as single agents, or alternatively, in combination with other binding antibodies/agents. They can also be used in combination with any standard or novel anti-cancer agents.

Embodiments of the invention relate to targeted binding agents that bind to DLL4. In some embodiments, the targeted binding agents bind to DLL4 and inhibit the binding of DLL4 to a Notch receptor (such as Notch 1, Notch 2, Notch 3, and/or Notch 4). In some embodiments, this binding can neutralize, block, inhibit, abrogate, or interfere with one or more aspects of DLL4-associated effects. In one embodiment, the targeted binding agents are monoclonal antibodies, or binding fragments thereof. Such monoclonal antibodies may be referred to as anti-DLL4 antibodies herein.

Other embodiments of the invention include fully human anti-DLL4 antibodies, and antibody preparations that are therapeutically useful. In one embodiment, preparations of the anti-DLL4 antibody of the invention have desirable therapeutic properties, including strong binding affinity for DLL4, ability to block DLL4 receptor-ligand interactions, ability to block DLL4 mediated signaling, the ability to promote endothelial cell proliferation and formation of non-functional blood vessels, ability to modulate pericyte recruitment to vessels, ability to inhibit tumor growth, ability to increase tumor hypoxia/necrosis, ability to alter endothelial tip/stalk cell fate, and ability to modulate tumor cell survival or cancer stem cell survival and self renewal.

In addition, embodiments of the invention include methods of using the antibodies described herein for treating diseases. Anti-DLL4 antibodies of the invention are useful for preventing DLL4-mediated tumorigenesis and tumor invasion of healthy tissue. In addition DLL4 antibodies can be useful for treating diseases associated with angiogenesis such as ocular disease such as AMD, inflammatory disorders such as rheumatoid arthritis, and cardiovascular disease and sepsis as well as neoplastic diseases. Any disease that is characterized by any type of malignant tumor, including metastatic cancers, lymphatic tumors, and blood cancers, can also be treated by this inhibition mechanism, Exemplary cancers in humans include a bladder tumor, breast tumor, prostate tumor, basal cell carcinoma, biliary tract cancer, bladder cancer, bone cancer, brain and CNS cancer (e.g., glioma tumor), cervical cancer, choriocarcinoma, colon and rectum cancer, connective tissue cancer, cancer of the digestive system; endometrial cancer, esophageal cancer; eye cancer; cancer of the head and neck; gastric cancer; intra-epithelial neoplasm; kidney cancer; larynx cancer; leukemia; liver cancer; lung cancer (e.g. small cell and non-small cell); lymphoma including Hodgkin's and Non-Hodgkin's lymphoma; melanoma: myeloma, neuroblastoma, oral cavity cancer (e.g., lip, tongue, mouth, and pharynx); ovarian cancer; pancreatic cancer; retinoblastoma; rhabdomyosarcoma; rectal cancer, renal cancer, cancer of the respiratory system; sarcoma, skin cancer; stomach cancer, testicular cancer, thyroid cancer; uterine cancer, cancer of the urinary system, as well as other carcinomas and sarcomas. Malignant disorders commonly diagnosed in dogs, cats, and other pets include, but are not limited to, lymphosarcoma, osteosarcoma, mammary tumors, mastocytoma, brain tumor, melanoma, adenosquamous carcinoma, carcinoid lung tumor, bronchial gland tumor, bronchiolar adenocarcinoma, fibroma, myxochondroma, pulmonary sarcoma, neurosarcoma, osteoma, papilloma, retinoblastoma, Ewing's sarcoma, Wilms tumor, Burkitt's lymphoma, microglioma, neuroblastoma, osteoclastoma, oral neoplasia, fibrosarcoma, osteosarcoma and rhabdomyosarcoma, genital squamous cell carcinoma, transmissible venereal tumor, testicular tumor, seminoma, Sertoli cell tumor, hemangiopericytoma, histiocytoma, chloroma (e.g., granulocytic sarcoma), corneal papilloma, corneal squamous cell carcinoma, hemangiosarcoma, pleural mesothelioma, basal cell tumor, thymoma, stomach tumor, adrenal gland carcinoma, oral papillomatosis, hemangioendothelioma and cystadenoma, follicular lymphoma, intestinal lymphosarcoma, fibrosarcoma and pulmonary squamous cell carcinoma. In rodents, such as a ferret, exemplary cancers include insulinoma, lymphoma, sarcoma, neuroma, pancreatic islet cell tumor, gastric MALT lymphoma and gastric adenocarcinoma. Neoplasias affecting agricultural livestock include leukemia, hemangiopericytoma and bovine ocular neoplasia (in cattle); preputial fibrosarcoma, ulcerative squamous cell carcinoma, preputial carcinoma, connective tissue neoplasia and mastocytoma (in horses); hepatocellular carcinoma swine); lymphoma and pulmonary adenomatosis (in sheep); pulmonary sarcoma, lymphoma, Rous sarcoma, reticulo-endotheliosis, fibrosarcoma, nephroblastoma, lymphoma and lymphoid leukosis (in avian species); retinoblastoma, hepatic neoplasia, lymphosarcoma (lymphoblastic lymphoma), plasmacytoid leukemia and swimbladder sarcoma (in fish), caseous lumphadenitis (CLA): chronic, infectious, contagious disease of sheep and goats caused by the bacterium *Corynebacterium pseudotuberculosis*, and contagious lung tumor of sheep caused by jaagsiekte.

Other embodiments of the invention include diagnostic assays for specifically determining the quantity of DLL4 in a biological sample. The assay kit can include a targeted binding agent or antibody as disclosed herein along with the necessary labels for detecting such antibodies. These diagnostic assays are useful to screen for cell adhesion, invasion, angiogenesis or proliferation-related diseases including, but not limited to, neoplastic diseases.

Another aspect of the invention is an antagonist of the biological activity of DLL4 wherein the antagonist binds to DLL4. In one embodiment, the antagonist is a targeted binding agent, such as an antibody. The antagonist may be selected from an antibody described herein, for example, antibody 4B4, 2H10, 21F7, 12A1, 17F3, 9G8, 20G8, 21H3, 1E4, 3A7, 4B3, 1D4, or 21H3RK.

In one embodiment the antagonist of the biological activity of DLL4 may bind to DLL4 and thereby inhibit or suppress DLL4 binding to Notch, thereby inhibiting cell adhesion and/or invasion and/or angiogenesis and/or proliferation.

One embodiment is a targeted binding agent which binds to the same epitope or epitopes as fully human monoclonal antibody 4B4, 2H10, 21F7, 12A1, 17F3, 9G8, 20G8, 21H3, 1E4, 3A7, 4B3, 1D4, or 21H3RK.

One embodiment is an antibody which binds to the same epitope or epitopes as fully human monoclonal antibody 4B4, 2H10, 21F7, 12A1, 17F3, 9G8, 20G8, 21H3, 1E4, 3A7, 4B3, 1D4, or 21H3RK.

One embodiment is a hybridoma that produces the targeted binding agent as described hereinabove. In one embodiment is a hybridoma that produces the light chain and/or the heavy chain of the antibodies as described hereinabove. In one embodiment the hybridoma produces the light chain and/or the heavy chain of a fully human monoclonal antibody. In another embodiment the hybridoma produces the light chain and/or the heavy chain of fully human monoclonal antibody 4B4, 2H10, 21F7, 12A1, 17F3, 9G8, 20G8, 21H3, 1E4, 3A7, 4B3, 1D4, or 21H3RK. Alternatively the hybridoma may produce an antibody which binds to the same epitope or epitopes as fully human monoclonal antibody 4B4, 2H10, 21F7, 12A1, 17F3, 9G8, 20G8, 21H3, 1E4, 3A7, 4B3, 1D4, or 21H3RK.

Another embodiment is a nucleic acid molecule encoding the targeted binding agent as described hereinabove. In one embodiment is a nucleic acid molecule encoding the light chain or the heavy chain of an antibody as described hereinabove. In one embodiment the nucleic acid molecule encodes the light chain or the heavy chain of a fully human monoclonal antibody. Still another embodiment is a nucleic acid molecule encoding the light chain or the heavy chain of a fully human monoclonal antibody selected from antibodies 4B4, 2H10, 21F7, 12A1, 17F3, 9G8, 20G8, 21H3, 1E4, 3A7, 4B3, 1D4, or 21H3RK.

Another embodiment of the invention is a vector comprising a nucleic acid molecule or molecules as described hereinabove, wherein the vector encodes a targeted binding agent as defined hereinabove. In one embodiment of the invention is a vector comprising a nucleic acid molecule or molecules as described hereinabove, wherein the vector encodes a light chain and/or a heavy chain of an antibody as defined hereinabove.

Yet another embodiment of the invention is a host cell comprising a vector as described hereinabove. Alternatively the host cell may comprise more than one vector.

In addition, one embodiment of the invention is a method of producing a targeted binding agent of the invention by culturing host cells under conditions wherein a nucleic acid molecule is expressed to produce the targeted binding agent, followed by recovery of the targeted binding agent. In one embodiment of the invention is a method of producing an antibody of the invention by culturing host cells under conditions wherein a nucleic acid molecule is expressed to produce the antibody, followed by recovery of the antibody.

In one embodiment the invention includes a method of making a targeted binding agent by transfecting at least one host cell with at least one nucleic acid molecule encoding the targeted binding agent as described hereinabove, expressing the nucleic acid molecule in the host cell and isolating the targeted binding agent. In one embodiment the invention includes a method of making an antibody by transfecting at least one host cell with at least one nucleic acid molecule encoding the antibody as described hereinabove, expressing the nucleic acid molecule in the host cell and isolating the antibody.

According to another aspect, the invention includes a method of antagonizing the biological activity of DLL4 by administering an antagonist as described herein. The method may include selecting an animal in need of treatment for disease-related cell adhesion and/or invasion and/or angiogenesis and/or proliferation, and administering to the animal a therapeutically effective dose of an antagonist of the biological activity of DLL4.

Another aspect of the invention includes a method of antagonizing the biological activity of DLL4 by administering a targeted binding agent as described hereinabove, The method may include selecting an animal in need of treatment for disease-related cell adhesion and/or invasion and/or angiogenesis and/or proliferation, and administering to the animal a therapeutically effective dose of a targeted binding agent which antagonises the biological activity of DLL4.

Another aspect of the invention includes a method of antagonizing the biological activity of DLL4 by administering an antibody as described hereinabove. The method may include selecting an animal in need of treatment for disease-related cell adhesion and/or invasion and/or angiogenesis and/or proliferation, and administering to the animal a therapeutically effective dose of an antibody which antagonises the biological activity of DLL4.

According to another aspect there is provided a method of treating disease-related cell adhesion and/or invasion and/or angiogenesis and/or proliferation in an animal by administering a therapeutically effective amount of an antagonist of the biological activity of DLL4. The method may include selecting an animal in need of treatment for disease-related cell adhesion and/or invasion and/or angiogenesis and/or proliferation, and administering to the animal a therapeutically effective dose of an antagonist of the biological activity of DLL4.

According to another aspect there is provided a method of treating disease-related cell adhesion and/or invasion and/or angiogenesis and/or proliferation in an animal by administering a therapeutically effective amount of a targeted binding agent which antagonizes the biological activity of DLL4. The method may include selecting an animal in need of treatment for disease-related cell adhesion and/or invasion and/or angiogenesis and/or proliferation, and administering to the animal a therapeutically effective dose of a targeted binding agent which antagonises the biological activity DLL4. The targeted binding agent can be administered alone, or can be administered in combination with additional antibodies or chemotherapeutic drugs or radiation therapy.

According to another aspect there is provided a method of treating disease-related cell adhesion and/or invasion and/or angiogenesis and/or proliferation in an animal by administering a therapeutically effective amount of an antibody which antagonizes the biological activity of DLL4. The method may include selecting an animal in need of treatment for disease-related cell adhesion and/or invasion and/or angiogenesis and/or proliferation, and administering to the animal a therapeutically effective dose of an antibody which antagonises the biological activity of DLL4. The antibody can be administered alone, or can be administered in combination with additional antibodies or chemotherapeutic drugs or radiation therapy.

According to another aspect there is provided a method of treating cancer in an animal by administering a therapeutically effective amount of an antagonist of the biological activity of DLL4. The method may include selecting an animal in need of treatment for cancer, and administering to the animal a therapeutically effective dose of an antagonist which antagonises the biological activity of DLL4. The antagonist can be administered alone, or can be administered in combination with additional antibodies or chemotherapeutic drugs or radiation therapy.

According to another aspect there is provided a method of treating cancer in an animal by administering a therapeutically effective amount of a targeted binding agent which antagonizes the biological activity of DLL4. The method may include selecting an animal in need of treatment for cancer, and administering to the animal a therapeutically effective dose of a targeted binding agent which antagonises the biological activity of DLL4. The targeted binding agent can be administered alone, or can be administered in combination with additional antibodies or chemotherapeutic drugs or radiation therapy.

According to another aspect there is provided a method of treating cancer in an animal by administering a therapeutically effective amount of an antibody which antagonizes the biological activity of DLL4. The method may include selecting an animal in need of treatment for cancer, and administering to the animal a therapeutically effective dose of an antibody which antagonises the biological activity of DLL4. The antibody can be administered alone, or can be administered in combination with additional antibodies or chemotherapeutic drugs or radiation therapy.

According to another aspect there is provided a method of reducing or inhibiting tumor cell proliferation, adhesion, invasion and/or angiogenesis, in an animal by administering a therapeutically effective amount of an antibody which antagonizes the biological activity of DLL4. The method may include selecting an animal in need of a reduction or inhibition of proliferation, cell adhesion, invasion and/or angiogenesis, and administering to the animal a therapeutically effective dose of an antibody which antagonises the biological activity of DLL4. The antibody can be administered alone, or can be administered in combination with additional antibodies or chemotherapeutic drugs or radiation therapy.

According to another aspect there is provided a method of reducing tumor growth and/or metastasis, in an animal by administering a therapeutically effective amount of an antibody which antagonizes the biological activity of DLL4. The method may include selecting an animal in need of a reduction of tumor growth and/or metastasis, and administering to the animal a therapeutically effective dose of an antibody which antagonises the biological activity of DLL4. The antibody can be administered alone, or can be administered in combination with additional antibodies or chemotherapeutic drugs or radiation therapy.

According to another aspect of the invention there is provided the use of an antagonist of the biological activity of DLL4 for the manufacture of a medicament for the treatment of disease-related cell adhesion and/or invasion and/or angiogenesis and/or proliferation. In one embodiment the antagonist of the biological activity of DLL4 is a targeted binding agent of the invention. In one embodiment the antagonist of the biological activity of DLL4 is an antibody of the invention.

According to another aspect of the invention there is provided an antagonist of the biological activity of DLL4 for use as a medicament for the treatment of disease; related cell adhesion and/or invasion and/or angiogenesis and/or proliferation. In one embodiment the antagonist of the biological activity of DLL4 is a targeted binding agent of the invention. In one embodiment the antagonist of the biological activity of DLL4 is an antibody of the invention.

According to another aspect of the invention there is provided the use of a targeted binding agent or an antibody which antagonizes the biological activity of DLL4 for the manufacture of a medicament for the treatment of disease-related cell adhesion and/or invasion and/or angiogenesis and/or proliferation.

According to another aspect of the invention there is provided a targeted binding agent or an antibody which antagonizes the biological activity of DLL4 for use as a medicament for the treatment of disease-related cell adhesion and/or invasion and/or angiogenesis and/or proliferation.

According to another aspect of the invention there is provided the use of a targeted binding agent or an antibody which antagonizes the biological activity of DLL4 for the manufacture of a medicament for the treatment of disease-related cell adhesion and/or invasion and/or angiogenesis and/or proliferation.

According to another aspect of the invention there is provided an antibody which antagonizes the biological activity of DLL4 for use as a medicament for the treatment of disease-related cell adhesion and/or invasion and/or angiogenesis and/or proliferation.

According to another aspect of the invention there is provided the use of an antagonist of the biological activity of DLL4 for the manufacture of a medicament for the treatment of cancer in a mammal. In one embodiment the antagonist of the biological activity of DLL4 is a targeted binding agent of the invention. In one embodiment the antagonist of the biological activity of MIA is an antibody of the invention.

According to another aspect of the invention there is provided an antagonist of the biological activity of DLL4 for use as a medicament for the treatment of cancer in a mammal. In one embodiment the antagonist of the biological activity of DLL4 is a targeted binding agent of the invention. In one embodiment the antagonist of the biological activity of DLL4 is an antibody of the invention.

According to another aspect of the invention there is provided the use of a targeted binding agent which antagonizes the biological activity of DLL4 for the manufacture of a medicament for the treatment of cancer in a mammal.

According to another aspect of the invention there is provided a targeted binding agent which antagonizes the biological activity of DLL4 for use as a medicament for the treatment of cancer in a mammal.

According to another aspect of the invention there is provided the use of an antibody which antagonizes the biological activity of DLL4 for the manufacture of a medicament for the treatment of cancer in a mammal.

According to another aspect of the invention there is provided antibody which antagonizes the biological activity of DLL4 for use as a medicament for the treatment of cancer in a mammal.

According to another aspect there is provided the use of a targeted binding agent or an antibody which antagonizes the biological activity of DLL4 for the manufacture of a medicament for the reduction or inhibition proliferation, cell adhesion, invasion and/or angiogenesis in an animal.

According to another aspect there is provided a targeted binding agent or an antibody which antagonizes the biological activity of DLL4 for use as a medicament for the reduction or inhibition proliferation, cell adhesion, invasion and/or angiogenesis in an animal.

According to another aspect there is provided the use of a targeted binding agent or an antibody which antagonizes the biological activity of DLL4 for the manufacture of a medicament for reducing tumor growth and/or metastasis, in an animal.

According to another aspect there is provided a targeted binding agent or an antibody which antagonizes the biological activity of DLL4 for use as a medicament for reducing tumor growth and/or metastasis, in an animal.

In one embodiment the present invention is particularly suitable for use in antagonizing DLL4, in patients with a tumor, which is dependent alone, or in part, on According to another aspect of the invention there is provided a pharmaceutical composition comprising an antagonist of the biological activity of DLL4, and a pharmaceutically acceptable carrier. In one embodiment the antagonist comprises an antibody. According to another aspect of the invention there is provided a pharmaceutical composition comprising an antagonist of the biological activity of DLL4, and a pharmaceutically acceptable carrier. In one embodiment the antagonist comprises an antibody.

In some embodiments, following administration of the antibody that specifically binds to DLL4, a clearing agent is administered, to remove excess circulating antibody from the blood.

Anti-DLL4 antibodies are useful in the detection of DLL4 in patient samples and accordingly are useful as diagnostics for disease states as described herein. In addition, based on their ability to significantly inhibit DLL4-mediated signaling activity (as demonstrated in the Examples below), anti-DLL4 antibodies have therapeutic effects in treating symptoms and conditions resulting from DLL4 expression. In specific embodiments, the antibodies and methods herein relate to the treatment of symptoms resulting from DLL4 induced cell adhesion, invasion, angiogenesis, proliferation and/or intracellular signaling. Further embodiments involve using the antibodies and methods described herein to treat cell adhesion, invasion, angiogenesis and/or proliferation-related diseases including neoplastic diseases, such as, melanoma, small cell lung cancer, non-small cell lung cancer, glioma, hepatocellular (liver) carcinoma, thyroid tumor, gastric (stomach) cancer, prostate cancer, breast cancer, ovarian cancer, bladder cancer, lung cancer, glioblastoma, endometrial cancer, kidney cancer, colon cancer, and pancreatic cancer. The antibodies may also be useful in treating cell adhesion and/or invasion in arthritis, atherosclerosis and diseases involving angiogenesis.

In one specific embodiment, the anti-DLL4 antibodies or targeted binding agents can have therapeutic effects in treating solid tumors whose development relies on a small population of stem cells with the capacity to proliferate and efficiently give rise both to additional tumor stem cells, e.g., acute myeloid leukemia (AML) and breast tumors.

Another embodiment of the invention includes an assay kit for detecting DLL4 in mammalian tissues, cells, or body fluids to screen for cell adhesion-, invasion-, angiogenesis- or proliferation related diseases. The kit includes a targeted binding agent that binds to DLL4 and a means for indicating the reaction of the targeted binding agent with DLL4, if present. In one embodiment, the targeted binding agent that binds DLL4 is labeled. In another embodiment the targeted binding agent is an unlabeled and the kit further includes a means for detecting the targeted binding agent. Preferably the targeted binding agent is labeled with a marker selected from the group consisting of a fluorochrome, an enzyme, a radionuclide and a radio-opaque material.

Another embodiment of the invention includes an assay kit for detecting DLL4 in mammalian tissues, cells, or body fluids to screen for cell adhesion-, invasion-, angiogenesis or proliferation-related diseases. The kit includes an antibody that binds to DLL4 and a means for indicating the reaction of the antibody with DLL4, if present. The antibody may be a monoclonal antibody. In one embodiment, the antibody that binds DLL4 is labeled. In another embodiment the antibody is an unlabeled primary antibody and the kit further includes a means for detecting the primary antibody. In one embodiment, the means includes a labeled second antibody that is an anti-immunoglobulin. Preferably the antibody is labeled with a marker selected from the group consisting of a fluorochrome, an enzyme, a radionuclide and a radio-opaque material.

Further embodiments, features, and the like regarding the antibodies as disclosed herein are provided in additional detail below.

Sequence Listing

Embodiments of the invention include the specific antibodies listed below in Table 1. This table reports the identification number of each anti-DLL4 antibody, along with the SEQ ID number of the variable domain of the corresponding heavy chain and light chain genes and polypeptides, respectively. Each antibody has been given an identification number.

TABLE 1

| mAb ID No.: | Sequence | SEQ ID NO: |
|---|---|---|
| 4B4 | Nucleotide sequence encoding the variable region of the heavy chain | 1 |
| | Amino acid sequence encoding the variable region of the heavy chain | 2 |
| | Nucleotide sequence encoding the variable region of the light chain | 3 |
| | Amino acid sequence encoding the variable region of the light chain | 4 |
| 2H10 | Nucleotide sequence encoding the variable region of the heavy chain | 5 |
| | Amino acid sequence encoding the variable region of the heavy chain | 6 |
| | Nucleotide sequence encoding the variable region of the light chain | 7 |
| | Amino acid sequence encoding the variable region of the light chain | 8 |
| 21F7 | Nucleotide sequence encoding the variable region of the heavy chain | 9 |
| | Amino acid sequence encoding the variable region of the heavy chain | 10 |
| | Nucleotide sequence encoding the variable region of the light chain | 11 |
| | Amino acid sequence encoding the variable region of the light chain | 12 |
| 12A1 | Nucleotide sequence encoding the variable region of the heavy chain | 13 |
| | Amino acid sequence encoding the variable region of the heavy chain | 14 |
| | Nucleotide sequence encoding the variable region of the light chain | 15 |
| | Amino acid sequence encoding the variable region of the light chain | 16 |
| 17F3 | Nucleotide sequence encoding the variable region of the heavy chain | 17 |
| | Amino acid sequence encoding the variable region of the heavy chain | 18 |
| | Nucleotide sequence encoding the variable region of the light chain | 19 |
| | Amino acid sequence encoding the variable region of the light chain | 20 |
| 9G8 | Nucleotide sequence encoding the variable region of the heavy chain | 21 |
| | Amino acid sequence encoding the variable region of the heavy chain | 22 |
| | Nucleotide sequence encoding the variable region of the light chain | 23 |
| | Amino acid sequence encoding the variable region of the light chain | 24 |

TABLE 1-continued

| mAb ID No.: | Sequence | SEQ ID NO: |
|---|---|---|
| 20G8 | Nucleotide sequence encoding the variable region of the heavy chain | 25 |
| | Amino acid sequence encoding the variable region of the heavy chain | 26 |
| | Nucleotide sequence encoding the variable region of the light chain | 27 |
| | Amino acid sequence encoding the variable region of the light chain | 28 |
| 21H3 | Nucleotide sequence encoding the variable region of the heavy chain | 29 |
| | Amino acid sequence encoding the variable region of the heavy chain | 30 |
| | Nucleotide sequence encoding the variable region of the light chain | 31 |
| | Amino acid sequence encoding the variable region of the light chain | 32 |
| 1E4 | Nucleotide sequence encoding the variable region of the heavy chain | 33 |
| | Amino acid sequence encoding the variable region of the heavy chain | 34 |
| | Nucleotide sequence encoding the variable region of the light chain | 35 |
| | Amino acid sequence encoding the variable region of the light chain | 36 |
| 3A7 | Nucleotide sequence encoding the variable region of the heavy chain | 37 |
| | Amino acid sequence encoding the variable region of the heavy chain | 38 |
| | Nucleotide sequence encoding the variable region of the light chain | 39 |
| | Amino acid sequence encoding the variable region of the light chain | 40 |
| 4B3 | Nucleotide sequence encoding the variable region of the heavy chain | 41 |
| | Amino acid sequence encoding the variable region of the heavy chain | 42 |
| | Nucleotide sequence encoding the variable region of the light chain | 43 |
| | Amino acid sequence encoding the variable region of the light chain | 44 |
| 1D4 | Nucleotide sequence encoding the variable region of the heavy chain | 45 |
| | Amino acid sequence encoding the variable region of the heavy chain | 46 |
| | Nucleotide sequence encoding the variable region of the light chain | 47 |
| | Amino acid sequence encoding the variable region of the light chain | 48 |
| 21H3RK | Nucleotide sequence encoding the variable region of the heavy chain | 29 |
| | Amino acid sequence encoding the variable region of the heavy chain | 30 |
| | Nucleotide sequence encoding the variable region of the light chain | 49 |
| | Amino acid sequence encoding the variable region of the light chain | 50 |

Table 2 is a table comparing the antibody heavy chain regions to their cognate germ line heavy chain region and kappa light chain regions to their cognate germ line lightchain region.

TABLE 2

| Seq ID No | Chain | V | D | J | FR1 | CDR1 | FR2 | CDR2 | FR3 | CDR3 | FR4 |
|---|---|---|---|---|---|---|---|---|---|---|---|
| 2 | 4B4.1VH | | | | QVLLIQSGAEV KKPGASVQVSC KASGYTFT | NYGVI | WVRQAPGQ GLEYMG | WISAYNGNTN YAQKLQD | RVTMTSDTSTT TAYMELRSLRS DDTAVYYCAR | ELGSSFDY | WGQGTLVT VSS |
| 51 | Germline | VH1-18 | 7-27 | JH4 | QVLVQSGAEV KKPGASVKVSC KASGYTFT | SYGIS | WVRQAPGQ GLEWMG | WISAYNGNTN YAQKLQG | RVTMTTDTSTS TAYMELRSLRS DDTAVYYCAR | -LG-YFDY | WGQGTLVT VSS |
| 4 | 4B4.1VL | | | | SYELTQPPSVS VSPGQTARITC | SGDALPKKYAY | WYQQKSGQ APVLVIY | EDSKRPS | GIPERFSGSSS FSTDNSGDHS GTMATLTISGA V QVEDEADYYC | | FGGGTKLT VL |
| 52 | Germline | VL-3p | | JL2 | SYELTQPPSVS VSPGQTARITC | SGDALPKKYAY | WYQQKSGQ APVLVIY | EDSKRPS | GIPERFSGSSS YSTDSSGNHV GTMATLTISGA V QVEDEADYYC | | FGGGTKLT VL |
| 6 | 2H10VH | | | | QVQLVESGGGV VQPGRSLRLSC AASGFTFS | RHGMH | WVRQAPGK GLEWVA | VVWFDGSNIY YADSVKG | RFTISRDNSKN TLYLQMNSLRA EDTAMYYCAR | DSRIAAADY | WGQGTLVT VSS |
| 53 | Germline | VH3-33 | 6-13 | JH4 | QVQLVESGGGV VQPGRSLRLSC AASGFTFS | SYGMH | WVRQAPGK GLEWVA | VIWYDGSNKY YADSVKG | RFTISRDNSKN TLYLQMNSLRA EDTAVYYCAR | ---IAAADY | WGQGTLVT VSS |
| 8 | 2H10VL | | | | SYELTQPESVS VSPGQTVSITC | SGDKLGDKYVC | WYQQKPGQ SPVLVIY | QESKRPS | GIPERFSGSSS GNTATLTISGT QAMDEADYYC | QTWDSSL-VV | FGGGTKLT VL |
| 54 | Germline | VL 3r | | JL2 | SYELTQPPSVS VSPGQTASITC | SGDKLGDKYAC | WYQQKPGQ SPVLVIY | QDSKRPS | GIPERFSGSNS GNTATLTISGT QAMDEADYYC | QAWDSSTAVV | FGGGTKLT VL |
| 10 | 21F7VH | | | | QVQLVQSGAEV KKPGASVKVS CQASGYTFT | NYGIS | WVRQAPGQ GLEWMG | WINAYNGNTN YAQNLQG | RVTMTTDTSTN TAYMELRSLRS DDTAVYYCAR | VAAAAFFDY | WDQGTLVT VSS |
| 55 | Germline | VH1-18 | 6-25 | JH4 | QVQLVQSGAEV KKPGASVKVSC KASGYTFT | SYGIS | WVRQAPGQ GLEWMG | WISAYNGNTN YAQKLQG | RVTMTTDTSTS TAYMELRSLRS DDTAVYYCAR | --AAAYFDY | WGQGTLVT VSS |
| 12 | 21F7VL | | | | SYELTQPPSVS VSPGQTASITC | SGDKLGDKYVC | WYQQKPGQ SPVLVIY | QDSKRPS | GIPERFSGSNS GNTATLTISGT QAMDEADYYC | QAWDSST--V | FGGGTKLT VL |
| 56 | Germline | VL 3r | | JL2 | SYELTQPPSVS VSPGQTASITC | SGDKLGDKYAC | WYQQKPGQ SPVLVIY | QDSKRPS | GIPERFSGSNS GNTATLTISGT QAMDEADYYC | QAWDSSTAVV | FGGGTKLT VL |
| 14 | 12A1VH | | | | QVQLVQSGAEV KRPGASVKVSC KASGYTFT | SYGIT | WVRQAPGQ GLEYMG | WISTYNGNTD YAQKFQG | RVTMTADISTS TAYMELRSLRS DDTAVYYCAR | ERGSYFDY | WGQGTLVT VSS |
| 57 | Germline | VH1-18 | 1-20 | JH4 | QVQLVQSGAEV KKPGASVKVSC KASGYTFT | SYGIS | WVRQAPGQ GLEWMG | WISAYNGNTN YAQKLQG | RVTMTTDTSTS TAYMELRSLRS DDTAVYYCAR | ER--YFDY | WGQGTLVT VSS |
| 16 | 12A1VL | | | | SYELTQPPSVS VSPGQTARITC | SGDTLPKKYAY | WYQQKSGQ APVLVIY | EDIKRPS | GIPERFSGSSS FSTDSGGNHK GTMATLTISGA - QVEDEADYYC | | FGGGTKLT VL |
| 58 | Germline | VL-3p | | JL2 | SYELTQPPSVS VSPGQTARITC | SGDALPKKYAY | WYQQKSGQ APVLVIY | EDSKRPS | GIPERFSGSSS YSTDSSGNHV GTMATLTISGA V QVEDEADYYC | | FGGGTKLT VL |
| 18 | 17F3VH | | | | QVQLVQSGAEV KKPGASVKVSC KASGYTFT | NYGIS | WVRQAPGQ GLEWMG | WINAYNGNTN YAQNLQG | RVTMTTDTSTN TAYMELRSLRS DDTAVYYCAR | VAPAAFFDY | WDQGTLVT VSS |
| 59 | Germline | VH1-18 | 2-2 | JH4 | QVQLVQSGAEV KKPGASVKVSC KASGYTFT | SYGIS | WVRQAPGQ GLEWMG | WISAYNGNTN YAQKLQG | RVTMTTDTSTS TAYMELRSLRS DDTAVYYCAR | VVPAAYFDY | WGQGTLVT VSS |
| 20 | 17F3VL | | | | SYELTQPPSVS VSPGQTASITC | SGDKLGDKYVC | WYQQKPGQ SPVLVIY | QDNKRPS | GIPERFSGSNS GNTATLTISGT QAMDEADYYC | QAWDSST--V | FGGGTKLT VL |

TABLE 2-continued

| Seq ID No | Chain | V | D | J | FR1 | CDR1 | FR2 | CDR2 | FR3 | CDR3 | FR4 |
|---|---|---|---|---|---|---|---|---|---|---|---|
| 60 | Germline VL | 3r | | JL2 | SYELTQPPSVS VSPGQTASITC | SGDKLGDKYAC | WYQQKPGQ SPVLVIY | QDSKRPS | GIPERFSGSNS GNTATLTISGT QAMDEADYYC | QAWDSSTAVV VL | FGGGTKLT |
| 22 | 968VH | | | | QLQLQESGPGL VKPSETLSLSC TVSGGSIS | SSSSY | WGLIRQPP GKGLEVIG | SIYYSGSTYY SPSLKS | RVSISVDTSKN QFSLKLSSVTA ADTAVYFCAR | QGYGGHPDVF DI | WGQGTMVT VSS |
| 61 | Germline VH4-39 | 4-23 | | JH3 | QLQLQESGPGL VKPSETLILTC TVSGGSIS | SSSYY | WGWIRQPQ GKGLEWIG | SIYYSGSTYY NPSLKS | RVTISVDTSKN QFSLKLSSVTA ADTAVYYCAR | --YG--- AFDI | WGQGTMVT VSS |
| 24 | 9G8VL | | | | SSELTQPSVSV SPGQTARITC | SGDKLGDVYVC | WYQQKTGQ SPVLVIY | EDTKRPS | GIPERFSGSNS GNTATLTISGT QVMDEADYYC | QAWDSTTAVI VL | FGGGTKLT |
| 62 | Germline VL | 3r | | JL2 | SYELTQPSVSV SVPGQTASITC | SDGKLGKDYAC | WYQQKPGQ SPVLVIY | QDSRRPS | GIPERFSGSNS GNTATLTISGT QAMDEADYYC | QAWDSSTAVV VL | FGGGTKLT |
| 26 | 20G8VH | | | | QVQLVQSGAEV KKPGASVKVSC KASGYTFT | SYGIS | WVRQAPGQ GLEWMG | WISVYNGNTN YAQKLQG | RVTMTTDTSTS TAYMEVRSLPS DDTAVYYCAR | DRVPRIPTIR EAFDI | WGRGTMVT VCS |
| 663 | Germline VH1-18 | 2-15 | | JH3 | QVQLVQSGAEV KKPGASVKVSC KASGYTFT | SYGIS | WVRQAPGQ GLEWMG | WISAYNGNTN YAQLQG | RVTMTTDTSTS TAYMELRSLRS DDTAVYYCAR | DIVVVAAT- -AFDI | WGQGTMVT VSS |
| 28 | 20G8VL | | | | QSVLTQPPSAS GTPGQRVTISC | SGSSSNIGSYY VY | WYQQLPGT APKLLIY | RDNQRPS | GVPDRFSGSKS GTSASLAIRGL RSDDEADYYC | AAWDDSLSGH WV | FGGGTKLT VL |
| 64 | Germline VL1g | | | JL2 | QSVLTQPPSAS GTPGQRVTISC | SGSSSNIGSNY VY | WYQQLPGT APKLLIY | RNNQRPS | GVPDRFSGSKS GTSASLAISGL RSEDEADYYC | AAWDDSLSGV -V | FGGGTKLT VL |
| 30 | 21H3VH | | | | QVQLVQSGAEV KKPGASVKVSC KASGYTFT | NYGIT | WVRQAPGQ GPEWMG | WISAYNGNTN YAQKLQD | RVTVTTDTSTS TAYMELRSLRS DDTAVYYCAR | DRVPRIPVTT EAFDI | WGQGTMVT VSS |
| 65 | Germline VH1-18 | 2-15 | | JH3 | QVQLVQSGAEV KKPGASVKVSC KASGYTFT | SYGIS | WVRQAPGQ GLEWMG | WISAYNGNTN YAQKLQG | RVTMTTDTSTS TAYMELRSLRD DTAVYYCAR | DIVVVAAT- -AFDI | WGQGTMVT VSS |
| 32 | 21H3VL | | | | QSVLTQPPSAS GTPGQRVTISC | SGSSSNIGSYF VY | WYQQLPGT APKLLIY | RNNQRPS | GVPDFRSGSES GTSASLAISGL RSEDEADYYC | AAWDDSLSGH WV | FGGGTRLT VL |
| 66 | Germline VL1q | | | JL2 | QSVLTQPPSAS GTPGQPVTISC | SGSSSNIGSNY VY | WYQQLPGT APKLLIY | RNNQRPS | GVPDRFSGSKS GTSASLAISGL RSEDEADYYC | AAWDDSLSGV -V | FGGGTKLT VL |
| 34 | 1E4VH | | | | QVQLVESGGGV VQPGRSLRLSC AASGFTFS | SYGMH | WVRQAPGK GLEWVA | VTWYDGSNKY YADSVKG | RFTISRDNSKN TLYLQMNSLRA EDTAVYYCAR | ENCSSTSCYY TVTTDYYGMD V | WGQGTTVT VSS |
| 67 | Germline VH3-33 | 2-2 | | JH6 | QVQLVESGGGV VQPGRSLRSC AASGFTFS | SYGMH | WVRQAPGK GLEWVA | VIWYDGSNKY TADSVKG | RFTISRDNSKN TLYLQMNSLRA EDTAVYYCAR | --CSSTSCY- ----- YYGMDV | WGQGTTVT VSS |
| 36 | 1E4VL | | | | EIVLTQSPGTL SLSPGERATLS C | RASQRVSSSYL T | WYQQKPGQ APRLLIY | GASIRAT | GIPDRFSGSGS TGDFTLTITRL EPEDFAVYFC | QQCYTSPIT | FGQGTRLD IK |
| 68 | Germline VK | A27 | | JK5 | EVILTQSPGTL SLSPGERATLS C | RASQSVSSSTL A | WYQQKPGQ APRLLIY | GASSRAT | GIPDRFSGSGS GTDFTLTIRSL EPEDFAVYYC | QQYGSSPIT | FGQGTRLE IK |
| 38 | 3A7VH | | | | EVQVVESGGGL VQPGSLRLSCE ASGFTFS | NYWMI | WVRQAPGK GIEWVA | SIKEDGSERY YVDSVKG | RFTISRDNAKS SMLYLQNSLRA EDTAVYYCVR | DWELRGHYYY HGMDV | WGQGTTVT VSS |
| 69 | Germline VH3-07 | 1-26 | | JH6 | EVQLVESGGGL VQPGGSLRLSC AASGFTFS | SYWMS | WVRQAPGK GLEWVA | NIKQDGSEKY YVDSVKG | RFTISRDNAKN SLYLQMNSLRA EDTAVYYCAR | -WEL-- YYYYYGMDV | WGQGTTVT VSS |

TABLE 2-continued

| Seq ID No | Chain | V | D | J | FR1 | CDR1 | FR2 | CDR2 | FR3 | CDR3 | FR4 |
|---|---|---|---|---|---|---|---|---|---|---|---|
| 40 | 3A7VL | | | | DIQMTQSPSSL SASVGDRVTIT C | RASLDIRNDLG | WFLQKPGK APKRLIY | AASSLQS | GVPSRFSGSGS GTEFTLTINSL QPFEDATYYC | LQHRNYPFT | FGPGTKVD FK |
| 70 | Germline VK A30 | | | JK3 | DIQMTQSPSSL SASVGDRVTIT C | RASQGIRNDLG | WYQQKPGK APKRLIY | AASSLQS | GVPSRFSGSGS GTEFTLTISSL QPEDFATYYC | LQHNSYPFT | FGPGTKVD IK |
| 42 | 4B3VH | | | | QVQLVQSGAEV PKSGASVKVSC KASGTSFT | TYDIN | WVRQATGQ GLEWMG | WMNPNSGYTD YAQKFQG | RVTLTRMNSID TAYMELSSLRS EDTAVYYCAR | AYYYDSSAYY LFDY | WGQGTLVT VSS |
| 71 | Germline VH1-08 | 3-22 | | JH4 | QVQLVQSGAEV KKPGASVKVSC KASGYTFT | SYDIN | WVRQATGQ GLEWMG | WMNPNSGNTG YAWKFQG | RVTMTRNTSIS TAYMELSSLRS EDVTAYYCAR | YYYDSSGYYY EDY | WGQGTLVT VSS |
| 44 | 4B3VL | | | | DIQMTQSPSSL SASVGDRVTIT C | RASQGISNYLA | WFQQKPGK APSKSLIY | AASSLQS | GVPSKFSGSGS GTDFTLTISSL QPEDFATYFC | QQYISYPLT | FGGGTKVE IK |
| 72 | Germline VK L1 | | | JK4 | DIQMTQSPSSI SASVGDRVTIT C | RASQGISNYLA | WFQQKPGK APKSLIY | AASSLQS | GVPSRFSGSGS GTDFTLTISSL QPEDFATYYC | QQYNSYPLT | FGGGTKVE IK |
| 46 | 1DAVH | | | | QLQLQESPGPL VKPSRTLSTCT VSGGSIS | SSSYY | WGWIRQPP GKGLEWIG | SFYYSRSTYY NPSLKS | RVTISVDTSNK QFSLKLSSVTA ADTAVHYCAR | GSIAVPDAFD I | WGQGTMVT VSS |
| 73 | Germline VH4-39 | 6-19 | | JH3 | QLQLQESPGPL VKPSETLSLTC TVSGGSIS | SSSYY | WGWIRQPP GKGLEWIG | SIYYSGSTYY NPSLKS | RVTISVDTSKN QFSLKLSSVTA ADTAVYYCAR | ::IAV:: AFDI | WGQGTMVT VSS |
| 48 | 1D4VL | | | | SYELTQPPSVS VSPGQTASITC | SGDLGDKFAC | WYQQDKGH SPVLVVY | QDNKRPS | GIPERFSGSNS GNSATLTISGT QAMDEADYYC | QAWDSNTA-V | FGGGTKLT VL |
| 74 | Germline VL 3r | | | JL2 | SYELTQPPSVS VSPGQTASITC | SGDKLGDKYAC | WYQQKPGQ SPVLVIY | QDSKRPS | GIPERFSGSNS GNTATLTISGT QAMDEADYYC | QAWDSSTAVV | FGGGTKLT VL |

DEFINITIONS

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods web known in the art and as described in various general and more specific references that are cited and discussed throughout the present specification. See e.g., Sambrook et al. *Molecular Cloning: A Laboratory Manual* (3rd ed., Cold Spring Harbor Laboratory Press, Cold Spring Harbor, N.Y. (2001)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following, terms, unless otherwise indicated, shall be understood to have the following meanings:

An antagonist or inhibitor may be a polypeptide, nucleic acid, carbohydrate, lipid, small molecular weight compound, an oligonucleotide, an oligopeptide, RNA interference (RNAi), antisense, a recombinant protein, an antibody, or fragments thereof or conjugates or fusion proteins thereof. For a review of RNAi see Milhavet O, Gary D S, Mattson M P. (Pharmacol Rev. 2003 December; 55(4):629-48. Review) and antisense (see Opalinska J B, Gewirtz A M. (Sci STKE. 2003 Oct. 28, 2003 (206):pe47.)

A compound refers to any small molecular weight compound with a molecular weight of less than about 2000 Daltons.

The term "DLL4" refers to the molecule that is DLL4 protein, also known as Delta-like protein 4 precursor, Drosophila Delta homolog 4, hdelta2, MGC126344, or UNQ1895/PRO4341. The terms "neutralizing" or "inhibits" when referring to a targeted binding agent, such as an antibody, relates to the ability of an antibody to eliminate, reduce, or significantly reduce, the activity of a target antigen. Accordingly, a "neutralizing" anti-DLL4 antibody of the invention is capable of eliminating or significantly reducing the activity of DLL4. A neutralizing DLL4 antibody may, for example, act by blocking the binding of a native DLL4 to its receptor Notch, such as, for example, Notch 1 or Notch 4. By blocking this binding, DLL4 signal-mediated activity is significantly, or completely, eliminated. Ideally, a neutralizing antibody against DLL4 antagonism promotes EC proliferation. A neutralizing DLL4 antibody may, for example increase angiogenesis by promoting formation of non-functional vessels.

An "antagonist of the biological activity of DLL4" is capable of eliminating, reducing or significantly reducing the activity of DLL4. An "antagonist of the biological activity of DLL4" is capable of eliminating, reducing or significantly reducing DLL4 signaling. An "antagonist of the biological activity of DLL4" may eliminate or significantly reduce angiogenesis and/or proliferation.

"Reducing DLL4 signaling" encompasses a reduction of DLL4 signaling by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% in comparison with the level of signaling in the absence of a targeted binding agent, antibody or antagonist of the invention.

An "optimized" sequence is an antibody sequence (variable heavy or light chain of any of the antibodies described herein) that has been mutated such that the non-germline sequence is mutated back at one or more residues to the germline sequence, and can further include the removal of structural liabilities from the sequence such as glycosylation sites or unpaired cysteines.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules and the human kappa light chain immunoglobulin molecules, as well as antibody molecules formed by combinations comprising the heavy chain immunoglobulin molecules with light chain immunoglobulin molecules, such as the kappa or lambda light chain immunoglobulin molecules, and vice versa, as well as fragments and analogs thereof. Preferred polypeptides in accordance with the invention may also comprise solely the human heavy chain immunoglobulin molecules or fragments thereof.

The terms "native" or "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described that are in a relationship permitting them to function in their intended manner. For example, a control sequence "operably linked" to a coding sequence is connected in such a way that expression of the coding sequence is achieved under conditions compatible with the control sequences.

The term "polynucleotide" as referred to herein means a polymeric form of nucleotides of at least 10 bases in length, either ribonucleotides or deoxynucleotides or a modified form of either type of nucleotide, or RNA-DNA hetero-duplexes. The term includes single and double stranded forms of DNA.

The term "oligonucleotide" referred to herein includes naturally occurring, and modified nucleotides linked together by naturally occurring, and non-naturally occurring linkages. Oligonucleotides are a poly nucleotide subset generally comprising a length of 200 bases or fewer. Preferably, oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroaniiothioate, phosphoraniladate, phosphoroamidate, and the like. See e.g., LaPlanche et al., *Nucl. Acids Res.* 14:9081 (1986); Stec et al., *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "selectively hybridize" referred to herein means to delectably and specifically bind. Polynucleotides, oligonucleotides and fragments thereof selectively hybridise to nucleic acid strands under hybridisation and wash conditions that minimise appreciable amounts of detectable binding to nonspecific nucleic acids. High stringency conditions can be used to achieve selective hybridisation conditions as known in the art and discussed herein. Generally, the nucleic acid sequence homology between the polynucleotides, oligonucleotides, or antibody fragments and a nucleic acid sequence of interest will be at least 80%, and more typically with preferably increasing homologies of at least 85%, 90%, 95%, 99%, and 100%.

Stringent hybridization conditions include, but are not limited to, hybridization to filter-bound DNA in 6× sodium chloride/sodium citrate (SSC) (0.9 M NaCl/90 mM NaCitrate, pH 7.0) at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 60° C., or any other stringent hybridization conditions known to those skilled in the art (see, for example, Ausubel, F. M. et al., eds. 1989 Current Protocols in Molecular Biology, vol. 1, Green Publishing Associates. Inc. and John Wiley and Sons Inc., NY at pages 6.3.1 to 6.3.6 and 2.10.3). Two amino acid sequences are "homologous" if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least about 30 amino acids in length) are homologous, as this term is used herein, if they have an alignment score of more than 5 (in standard deviation units) using the program ALIGN with the mutation data matrix and a gap penalty of 6 or greater. See Dayhoff, M. O., in *Atlas of Protein Sequence and Structure*, pp. 101-110 (Volume 5, National Biomedical Research Foundation (1972)) and Supplement 2 to this volume, pp, 1-10. The two sequences or parts thereof are more preferably homologous if their amino acids are greater than or equal to 50% identical when optimally aligned using the ALIGN program. It should be appreciated that there can be differing regions of homology within two orthologous sequences. For example, the functional sites of mouse and human orthologues may have a higher degree of homology than non-functional regions.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence.

In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or amino acid residue occurs in both sequences to yield the number of matched positions, dividing the number of matched positions by the total number of positions in the comparison window (i.e. the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more preferably at least 99 percent sequence identity, as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See *Immunology—A Synthesis* ($2^{nd}$ Edition, E. S. Golub and D. R. Oren, Eds. Sinauer Associates, Sunderland, Mass. (1991)), which is incorporated herein by reference. Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carbo terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99% sequence identity to the antibodies or immunoglobulin molecules described herein. In particular, conservative amino acid replacements are contemplated. Conservative replacements are those that take place within a family of amino acids that have related side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding function or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253:164 (1991). Thus, the foregoing examples demonstrate that those of skill in the art can recognize sequence motifs and structural conformations that may be used to define structural and functional domains in accordance with the antibodies described herein.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

In general, cysteine residues in proteins are either engaged in cysteine-cysteine disulfide bonds or sterically protected from the disulfide bond formation when they are a part of folded protein region. Disulfide bond formation in proteins is a complex process, which is determined by the redox potential of the environment and specialized thiol-disulfide exchanging enzymes (Creighton, Methods Enzymol. 107, 305-329, 1.984; Houee-Levin, Methods Enzymol. 353, 35-44, 2002). When a cysteine residue does not have a pair in protein structure and is not sterically protected by folding, it can form a disulfide bond with a free cysteine from solution in a process known as disulfide shuffling. In another process known as disulfide scrambling, free cysteines may also interfere with naturally occurring disulfide bonds (such as those present in antibody structures) and lead to low binding, low biological activity and/or low stability.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various mutations of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W.H. Freeman and Company, New York (1984)); *Introduction to Protein Structure* (C. Branden and J. Tooze, eds., Garland Publishing, New York, N.Y. (1991)); and Thornton et al. *Nature* 354:105 (1991), which are each incorporated herein by reference.

Additionally, such methods may be used to make amino acid substitutions or deletions of one or more variable region cysteine residues participating in an intrachain disulfide bond to generate antibody molecules lacking one or more intrachain disulfide bonds.

The term "CDR region" or "CDR" is intended to indicate the hypervariable regions of the heavy and light chains of an antibody which confer antigen-binding specificity to the antibody. CDRs may be defined according to the Kabat system (Kabat, E. A. et al. (1991) Sequences of Proteins of Immunological Interest, 5th Edition. US Department of Health and Human Services, Public Service, NIH, Washington), and later editions. An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognises.

The third CDR of the heavy chain (HCDR3) has a greater size variability (greater diversity essentially due to the mechanisms of arrangement of the genes which give rise to it). It may be as short as 2 amino acids although the longest size known is 26. CDR length may also vary according to the length that can be accommodated by the particular underlying framework. Functionally, HCDR3 plays a role in part in the determination of the specificity of the antibody (Segal et al., PNAS, 71:4298-4302, 1974, Amit et al., Science, 233:747-753, 1986, Chothia et al., J. Mol. Biol., 196:901-917, 1987, Chothia et al., Nature, 342:877-883, 1989, Caton et al., J. Immunol., 144:1965-1968, 1990, Sharon et al., PNAS, 87:4814-4817, 1990, Sharon et al., J. Immunol., 144:4863-4869, 1990, Cabal et al., J. Immunol., 147:1709-1719, 1991).

The term a "set of CDRs" referred to herein comprises CDR1, CDR2 and CDR3. Thus, a set of HCDRs refers to HCDR1, HCDR2 and HCDR3, and a set of LCDRs refers to LCDR1, LCDR2 and LCDR3.

Variants of the VH and VL domains and CDRs of the present invention, including those for which amino acid sequences are set out herein, and which can be employed in targeting agents and antibodies for DLL4 can be obtained by means of methods of sequence alteration or mutation and screening for antigen targeting with desired characteristics. Examples of desired characteristics include but are not limited to: increased binding affinity for antigen relative to known antibodies which are specific for the antigen; increased neutralisation of an antigen activity relative to known antibodies which are specific for the antigen if the activity is known; specified competitive ability with a known antibody or ligand to the antigen at a specific molar ratio; ability to immunoprecipitate ligand-receptor complex; ability to bind to a specified epitope; linear epitope, e.g. peptide sequence identified using peptide-binding scan, e.g. using peptides screened in linear and/or constrained conformation; conformational epitope, formed by non-continuous residues; ability to modulate a new biological activity of DLL4, or downstream molecule; ability to bind and/or neutralise DLL4 and/or for any other desired property.

The techniques required to make substitutions within amino acid sequences of CDRs, antibody VH or VL domains and antigen binding sites are available in the art. Variants of antibody molecules disclosed herein may be produced and used in the present invention. Following the lead of computational chemistry in applying multivariate data analysis techniques to the structure/property-activity relationships (Wold, et al. Multivariate data analysis in chemistry. Chemometrics—Mathematics and Statistics in Chemistry (Ed.: B. Kowalski), D. Reidel Publishing Company, Dordrecht, Holland, 1984) quantitative activity-property relationships of antibodies can be derived using well-known mathematical techniques, such as statistical regression, pattern recognition and classification (Norman et al. Applied Regression Analysis.

Wiley-Interscience; 3rd edition (April 1998); Kandel, Abraham & Backer, Eric. Computer-Assisted Reasoning in Cluster Analysis. Prentice Hall PTR, (May 11, 1995); Krzanowski, Wojtek. Principles of Multivariate Analysis: A User's Perspective (Oxford Statistical Science Series, No 22 (Paper)). Oxford University Press; (December 2000); Witten, Ian H. & Frank, Eibe. Data Mining Practical Machine Learning Tools and Techniques with Java Implementations. Morgan Kaufmann; (Oct. 11, 1999); Denison David G. T. (Editor), Christopher C. Holmes, Bani K. Mallick. Adrian F. M. Smith. Bayesian Methods for Nonlinear Classification and Regression (Wiley Series in Probability and Statistics), John Wiley & Sons; (July 2002); Ghose, Arup & Viswanadhan, Vellarkad N. Combinatorial Library Design and Evaluation Principles, Software, Tools, and Applications in Drug Discovery). In some cases the properties of antibodies can be derived from empirical and theoretical models (for example, analysis of likely contact residues or calculated physicochemical property) of antibody sequence, functional and three-dimensional structures and these properties can be considered singly and in combination.

An antibody antigen-binding site composed of a VH domain and a VL domain is typically formed by six loops of polypeptide: three from the light chain variable domain (VL) and three from the heavy chain variable domain (VH). Analysis of antibodies of known atomic structure has elucidated relationships between the sequence and three-dimensional structure of antibody combining sites. These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions.

This study of sequence-structure relationship can be used for prediction of those residues in an antibody of known sequence, but of an unknown three-dimensional structure, which are important in maintaining the three-dimensional structure of its CDR loops and hence maintain binding specificity. These predictions can be backed up by comparison of the predictions to the output from lead optimisation experiments. In a structural approach, a model can be created of the antibody molecule using any freely available or commercial package, such as WAM. A protein visualisation and analysis software package, such as Insight II (Accelrys, Inc.) or Deep View may then be used to evaluate possible substitutions at each position in the CDR. This information may then be used to make substitutions likely to have a minimal or beneficial effect on activity or confer other desirable properties.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to DLL4, under suitable binding conditions, (2) ability to block appropriate VEGF/DLL4 binding, or (3) ability to inhibit DLL4 receptor tyrosine kinase activity. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics" (Fauchere, *J. Adv. Drug Res.* 15:29 (1986); Veber and Freidinger *TINS* p. 392 (1985); and Evans et al. *J. Med. Chem.* 30:1229 (1987), which are incorporated herein by reference). Such compounds are often developed with the aid of computerized molecular modeling. Peptide mimetics that are structurally similar to therapeutically useful peptides may used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, —$CH(OH)CH_2$—, and —$CH_2SO$—, by methods well known in the art, Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch. *Ann. Rev, Biochem.* 61:387 (1992), incorporated herein by reference); for example, by adding internal cysteine residues capable of forming intramolecular disulfide bridges which cyclize the peptide.

An antibody may be oligoclonal, a polyclonal antibody, a monoclonal antibody, a chimeric antibody, a CDR-grafted antibody, a multi-specific antibody, a bi-specific antibody, a catalytic antibody, a chimeric antibody, a humanized antibody, a fully human antibody, an anti-idiotypic antibody and antibodies that can be labeled in soluble or bound form as well as fragments, variants or derivatives thereof, either alone or in combination with other amino acid sequences provided by known techniques. An antibody may be from any species.

As used herein, the terms "antibody" and "antibodies" (immunoglobulins) encompass monoclonal antibodies (including full-length monoclonal antibodies), polyclonal antibodies, camelised antibodies and chimeric antibodies. As used herein, the term "antibody" or "antibodies" refers to a polypeptide or group of polypeptides that are comprised of at least one binding domain that is formed from the folding of polypeptide chains having three-dimensional binding spaces with internal surface shapes and charge distributions complementary to the features of an antigenic determinant of an antigen. chain. Native antibodies are usually heterotetrameric glycoproteins of about 150,000 daltons, composed of two identical light (L) chains and two identical heavy (H) chains. Each light chain is linked to a heavy chain by one covalent disulfide bond, while the member of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Light chains are classified as either lambda chains or kappa chains based on the amino acid sequence of the light chain constant region. The variable domain of a kappa light chain may also be denoted herein as VK. The term "variable region" may also be used to describe the variable domain of a heavy chain or light chain. Particular amino acid residues are believed to form an interface between the light and heavy chain variable domains. The variable regions of each light/heavy chain pair form an antibody binding site. Such antibodies may be derived from any mammal, including, but not limited to, humans, monkeys, pigs, horses, rabbits, dogs, cats, mice, etc.

The term "antibody" or "antibodies" includes binding fragments of the antibodies of the invention, exemplary fragments include single-chain Fvs (scFv), single-chain antibodies, single domain antibodies, domain antibodies, Fv fragments, Fab fragments, F(ab') fragments, F(ab')2 fragments, antibody fragments that exhibit the desired biological activity, disulfide-stabilised variable region (dsFv), dimeric variable region (Diabody), anti-idiotypic (anti-Id) antibodies (including, e.g., anti-Id antibodies to antibodies of the invention), intrabodies, linear antibodies, single-chain antibody molecules and multispecific antibodies formed from antibody fragments and epitope-binding fragments of any of the above. In particular, antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA, and IgY), class (e.g., IgG1, IgG2, IgG3, IgG4, IgA1 and IgA2) or subclass.

Digestion of antibodies with the enzyme, papain, results in two identical antigen-binding fragments, known also as "Fab" fragments, and a "Fc" fragment, having no antigen-binding activity but having the ability to crystallize Digestion of antibodies with the enzyme, pepsin, results in the a F(ab')$_2$ fragment in which the two arms of the antibody molecule remain linked and comprise two-antigen binding sites. The F(ab')$_2$ fragment has the ability to crosslink antigen.

"Fv" when used herein refers to the minimum fragment of an antibody that retains both antigen-recognition and antigen-binding sites. This region consists of a dimer of one heavy and one light chain variable domain in tight, non-covalent or covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

"Fab" when used herein refers to a fragment of an antibody that comprises the constant domain of the light chain and the CH1 domain of the heavy chain.

"dAb" When used herein refers to a fragment of an antibody that is the smallest functional binding unit of a human antibodies. A "dAb" is a single domain antibody and comprises either the variable domain of an antibody heavy chain (VH domain) or the variable domain of an antibody light chain (VL domain). Each dAb contains three of the six naturally occurring CDRs (Ward et al., Binding activities of a repertoire of single immunoglobulin variable domains secreted from *Escherichia coli*. Nature 341, 544-546 (1989); Holt, et al., Domain antibodies: protein for therapy, *Trends Biotechnol*. 21, 484-49 (2003)). With molecular weights ranging from 11 to 15 kDa, they are four times smaller than a fragment antigen binding (Fab)2 and half the size of a single chain Fv (scFv) molecule.

"Camelid" when used herein refers to antibody molecules are composed of heavy-chain dimers which are devoid of light chains, but nevertheless have an extensive antigen-binding repertoire (Hamers-Casterman C, Atarhouch T, Muyldermans S, Robinson G, Hamers C, Songa E B, Bendahman N, Hamers R (1993) Naturally occurring antibodies devoid of light chains. Nature 363:446-448).

The term "diabodies" refers to small antibody fragments with two antigen-binding sites, which fragments comprise a heavy chain variable domain (V$_H$) connected to a light chain variable domain (V$_L$) in the same polypeptide chain (V$_H$-V$_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et at., *Proc. Natl. Acad. Sci. USA*, 90:6444-6448 (1993).

It has been shown that fragments of a whole antibody can perform the function of binding antigens. Examples of binding fragments are (Ward, E. S. et al., (1989) Nature 341, 544-546) the Fab fragment consisting of VL, VH, CL and CH1 domains; (McCafferty et al (1990) Nature, 348, 552-554) the Ed fragment consisting of the VH and CH1 domains; (Holt et al (2003) Trends in Biotechnology 21, 484-490) the Fv fragment consisting of the VL and VH domains of a single antibody; (iv) the dAb fragment (Ward, E. S. et al., Nature 341, 544-546 (1989), McCafferty et al (1990) Nature, 348, 552-554, Holt et al (2003) Trends in Biotechnology 21, 484-4901, which consists of a VH or a VL domain; (v) isolated CDR regions; (vi) F(ab')2 fragments, a bivalent fragment comprising two linked Lab fragments (vii) single chain Fv molecules (scFv), wherein a VH domain and a VL domain are linked by a peptide linker which allows the two domains to associate to form an antigen binding site (Bird et al, (1988) Science, 242, 423-426, Huston et al, (1988) PNAS USA, 85, 5879-5883); (viii) bispecific single chain Fv dimers (PCT/US92/09965) and (ix) "diabodies", multivalent or multispecific fragments constructed by gene fusion (WO94/13804; Holliger, P. (1993) et al, Proc. Natl. Acad. Sci. USA 90 6444-6448). Fv, scFv or diabody molecules may be stabilised by the incorporation of disulphide bridges linking the VH and VL domains (Reiter, Y. et al, Nature Biotech, 14, 1239-1245, 1996). Minibodies comprising a scFv joined to a CH3 domain may also be made (Hu, S. et al. (1996) Cancer Res., 56, 3055-3061). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in segments called Complementarity Determining Regions (CDRs) both in the light chain and the heavy chain variable domains. The more highly conserved portions of the variable domains are called the framework regions (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see, Kabat et al., Sequences of Proteins of Immunological interest, 5th Ed. Public Health Service, National Institutes of Health, Bethesda, Md. (1991)). The constant domains are generally not involved directly in antigen binding, but may influence antigen binding affinity and may exhibit various effector functions, such as participation of the antibody in ADCC, CDC, and/or apoptosis.

The term "hypervariable region" when used herein refers to the amino acid residues of an antibody which are associated with its binding to antigen. The hypervariable regions encompass the amino acid residues of the "complementarity determining regions" or "CDRs" (e.g., residues 24-34 (L1), 50-56 (L2) and 89-97 (L3) of the light chain variable domain and residues 31-35 (H1), 50-65 (H2) and 95-102 (H3) of the heavy chain variable domain; Kabat et al., Sequences of Proteins of Immunological Interest, 5th Ed. Public Health Service, National Institutes of Health Bethesda, Md. (1991)) and/or those residues from a "hypervariable loop" (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, J. Mol. Biol., 196:901-917 (1987)). "Framework" or "FR" residues are those variable domain residues flanking the CDRs. FR residues are present in chimeric, humanized, human, domain antibodies, diahodies, vaccibodies, linear antibodies, and bispecific antibodies.

As used herein, targeted binding agent, targeted binding protein, specific binding protein and like terms refer to an antibody, or binding fragment thereof that preferentially binds to a target site. In one embodiment, the targeted binding agent is specific for only one target site. In other embodiments, the targeted binding agent is specific for more than one target site. In one embodiment, the targeted binding agent may be a monoclonal antibody and the target site may be an epitope.

"Binding fragments" of an antibody are produced by recombinant DNA techniques, or by enzymatic or chemical cleavage of intact antibodies. Binding fragments include Fab, Fab', F(ab')$_2$, Fv, dAb and single-chain antibodies. An antibody other than a "bispecific" or "bifunctional" antibody is understood to have each of its binding sites identical. An antibody substantially inhibits adhesion of a receptor to a counter-receptor when an excess of antibody reduces the quantity of receptor bound to counter-receptor by at least about 20%, 40%, 60% or 80%, and more usually greater than about 85% (as measured in an in vitro competitive binding assay).

The term "epitope" includes any protein determinant capable of specific binding to an immunoglobulin T-cell receptor. Epitopic determinants usually consist of chemically active surface groupings of molecules such as amino acids or sugar side chains and may, but not always, have specific three-dimensional structural characteristics, as well as specific charge characteristics. An antibody is said to specifically bind an antigen when the dissociation constant is ≤1 µM, preferably ≤100 nM and most preferably ≤10 nM.

The term "agent" is used herein to denote a chemical compound, a mixture of chemical compounds, a biological macromolecule, or an extract made from biological materials.

"Active" or "activity" in regard to an DLL4 polypeptide refers to a portion of an DLL4 polypeptide that has a biological or an immunological activity of a native DLL4 polypeptide. "Biological" when used herein refers to a biological function that results from the activity of the native DLL4 polypeptide. A preferred DLL4 biological activity includes, for example, DLL4 induced cell adhesion and invasion and/or angiogenesis and/or proliferation.

"Mammal" when used herein refers to any animal that is considered a mammal. Preferably, the mammal is human.

"Animal" when used herein encompasses animals considered a mammal. Preferably the animal is human.

The term "mAb" refers to monoclonal antibody.

"Liposome" when used herein refers to a small vesicle that may be useful for delivery of drugs that may include the DLL4 polypeptide of the invention or antibodies to such an DLL4 polypeptide to a mammal.

"Label" or "labeled" as used herein refers to the addition of a detectable moiety to a polypeptide, for example, a radiolabel, fluorescent label, enzymatic label chemiluminescent labeled or a biotinyl group. Radioisotopes or radionuclides may include $^3$H, $^{14}$C, $^{35}$S, $^{90}$Y, $^{99}$Tc, $^{111}$In, $^{125}$I, $^{131}$I, fluorescent labels may include rhodamine, lanthanide phosphors or FITC and enzymatic labels may include horseradish peroxidase, β-galactosidase, luciferase, alkaline phosphatase.

Additional labels include, by way of illustration and not limitation: enzymes, such as glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase; dyes; additional fluorescent labels or fluorescers include, such as fluorescein and its derivatives, fluorochrome, GFP (GFP for "Green Fluorescent Protein"), dansyl, umbelliferone, phycoerythrin, phycocyanin, allophycocyanin, o-phthaldehyde, and fluorescamine; fluorophores such as lanthanide cryptates and chelates e.g. Europium etc (Perkin Elmer and Cis Biointernational); chemoluminescent labels or chemiluminescers, such as isoluminol, luminal and the dioxetanes; sensitisers; coenzymes; enzyme substrates; particles, such as latex or carbon particles; metal sol; crystallite; liposomes; cells, etc., which may be further labelled with a dye, catalyst or other detectable group; molecules such as biotin, digoxygenin or 5-bromodeoxyuridine; toxin moieties, such as for example a toxin moiety selected from a group of Pseudomonas exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), (incorporated herein by reference).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "patient" includes human and veterinary subjects.

"Antibody-dependent cell-mediated cytotoxicity" and "ADCC" refer to a cell-mediated reaction in which non-specific cytotoxic cells that express Ig Fc receptors (FcRs) (e.g. Natural Killer (NK) cells, monocytes, neutrophils, and macrophages) recognise bound antibody on a target cell and subsequently cause lysis of the target cell. The primary cells for mediating ADCC, NK cells, express FcγRIII only, whereas monocytes express FcγRI, FcγRII and FcγRIII. FcRs expression on hematopoietic cells is summarised in Table 3 on page 464 of Ravetch and Kinet, *Annu. Rev. Immunol* 9:457-92 (1991). To assess ADCC activity of a molecule of interest, in vitro ADCC assay, such as that described in U.S. Pat. No. 5,500,362, or 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in an animal model such as that disclosed in Clynes et al. *PNAS (USA)* 95:652-656 (1988). "Complement dependent cytotoxicity" and "CDC:" refer to the mechanism by which antibodies carry out their cell-killing function. It is initiated by the binding of C1q, a constituent of the first component of complement, to the Fc domain of Igs, IgG or IgM, which are in complex with antigen (Hughs-Jones, N. C., and B. Gardner. 1979, Mol. Immunol. 16:697). C1q is a large, structurally complex glycoprotein of ~410 kDa present in human serum at a concentration of 70 µg/ml (Cooper, N. R. 1985. Adv. Immunol. 37:151). Together with two serine proteases, C1r and C1s, C1q forms the complex C1, the first component of complement. At least two of the N-terminal globular heads of C1q must be bound to the Fc of Igs for C1 activation, hence for initiation of the complement cascade (Cooper, N. R. 1985. Adv. Immunol. 37:151).

The term "antibody half-life" as used herein means a pharmacokinetic property of an antibody that is a measure of the mean survival time of antibody molecules following their administration. Antibody half-life can be expressed as the time required to eliminate 50 percent of a known quantity of immunoglobulin from the patient's body or a specific compartment thereof, for example, as measured in serum or plasma, i.e., circulating half-life, or in other tissues. Half-life may vary from one immunoglobulin or class of immunoglobulin to another. In general, an increase in antibody half-life results in an increase in mean residence time (MRT) in circulation for the antibody administered.

The term "isotype" refers to the classification of an antibody's heavy or light chain constant region. The constant domains of antibodies are not involved in binding to antigen, but exhibit various effector functions. Depending on the amino acid sequence of the heavy chain constant region, a given human antibody or immunoglobulin can be assigned to one of five major classes of immunoglobulins: IgA, IgD, IgE, IgG, and IgM. Several of these classes may be further divided into subclasses (isotypes), e.g., IgG1 (gamma 1), IgG2 (gamma 2), IgG3 (gamma 3), and IgG4 (gamma 4), and IgA1 and IgA2. The heavy chain constant regions that correspond to the different classes of immunoglobulins are called α, δ, ε, γ, and µ, respectively. The structures and three-dimensional configurations of different classes of immunoglobulins are well-known. Of the various human immunoglobulin classes, only human IgG1, IgG2, IgG3, IgG4, and IgM are known to activate complement. Human IgG1 and IgG3 are known to mediate in humans. Human light chain constant regions may be classified into two major classes, kappa and lambda.

If desired, the isotype of an antibody that specifically binds DLL4 can be switched, for example to take advantage of a biological property of a different isotype. For example, in some circumstances it can be desirable in connection with the generation of antibodies as therapeutic antibodies against DLL4 that the antibodies be capable of fixing complement and participating in complement-dependent cytotoxicity (CDC). There are a number of isotypes of antibodies that are capable of the same, including, without limitation, the following: murine IgM, murine IgG2a, murine IgG2b, murine IgG3, human IgM, human IgA, human IgG1, and human IgG3. In other embodiments it can be desirable in connection with the generation of antibodies as therapeutic antibodies against DLL4 that the antibodies be capable of binding Fc receptors on effector cells and participating in antibody-dependent cytotoxicity (ADCC). There are a number of isotypes of antibodies that are capable of the same, including, without limitation, the following: murine IgG2a, murine IgG2b, murine IgG3, human IgG1, and human IgG3. It will be appreciated that antibodies that are generated need not initially possess such an isotype hut, rather, the antibody as generated can possess any isotype and the antibody can be isotype switched thereafter using conventional techniques that are well known in the art. Such techniques include the use of direct recombinant techniques (see e.g., U.S. Pat. No. 4,816, 397), cell-cell fusion techniques (see e.g., U.S. Pat. Nos. 5,916,771 and 6,207,418), among others.

By way of example, the anti-DLL4 antibodies discussed herein are fully human antibodies. If an antibody possessed desired binding to DLL4, it could be readily isotype switched to generate a human IgM, human IgG1, or human IgG3 isotype, while still possessing the same variable region (which defines the antibody's specificity and some of its affinity). Such molecule would then be capable of fixing complement and participating in CDC and/or be capable of binding to Fc receptors on effector cells and participating in ADCC.

"Whole blood assays" use unfractionated blood as a source of natural effectors. Blood contains complement in the plasma, together with FcR-expressing cellular effectors, such as polymorphonuclear cells (PMNs) and mononuclear cells (MNCs). Thus, whole blood assays allow simultaneous evaluation of the synergy of both ADCC and CDC effector mechanisms in vitro.

A "therapeutically effective" amount as used herein is an amount that provides some improvement or benefit to the subject. Stated in another way, a "therapeutically effective" amount is an amount that provides some alleviation, mitigation, and/or decrease in at least one clinical symptom. Clinical symptoms associated with the disorders that can be treated by the methods of the invention are well-known to those skilled in the art. Further, those skilled in the art will appreciate that the therapeutic effects need not be complete or curative, as long as some benefit is provided to the subject.

The term "and/or" as used herein is to be taken as specific disclosure of each of the two specified features or components with or without the other. For example "A and/or B" is to be taken as specific disclosure of each of (i) A, (ii) B and (iii) A and B, just as if each is set out individually herein.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch, 7 (Paul, W., ed., 2nd ed. Raven Press, N.Y. (1989)) (incorporated by reference in its entirety for all purposes). The variable regions of each light/heavy chain pair form the antibody binding site.

Thus, an intact antibody has two binding sites, Except in bifunctional or bispecific antibodies, the two binding sites are the same.

The chains all exhibit the same general structure of relatively conserved framework regions (FR) joined by three hyper variable regions, also called CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences Proteins of Immunological Interest* (National Institutes of Health, Bethesda, Md. (1987 and 1991)), or Chothia & Lesk *J. Mol. Biol.* 196:901-917 (1987); Chothia et al. *Nature* 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann *Clin. Exp. Immunol,* 79: 315-321 (1990), Kostelny et al. *J. Immunol.* 1.48:1547-1553 (1992). Bispecific antibodies do not exist in the form of fragments having a single binding site (e.g., Fab, Fab', and Fv).

Typically, a VH domain is paired with a VL domain to provide an antibody antigen-binding site, although a VH or VL domain alone may be used to bind antigen. The VH domain (see Table 2) may be paired with the VL domain (see Table so that an antibody antigen-binding site is formed comprising both the VH and VL domains.

Human Antibodies and Humanization of Antibodies

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of functional human antibody loci into a rodent, other mammal or animal so that the rodent, other mammal or animal produces fully human antibodies.

One method for generating fully human antibodies is through the use of XenoMouse® strains of mice that have been engineered to contain up to but less than 1000 kb-sized germline configured fragments of the human heavy chain locus and kappa light chain locus. See Mendez et al. *Nature Genetics* 15:146-156 (1997) and Green and Jakobovits *J. Exp. Med.* 188:483-495 (1998). The XenoMouse® strains are available from Amgen, Inc. (Fremont, Calif., U.S.A).

Such mice, then, are capable of producing human immunoglobulin molecules and antibodies and are deficient in the production of murine immunoglobulin molecules and antibodies. Technologies utilised for achieving the same are disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al. *Nature Genetics* 15:146-156 (1997), the disclosure of which is hereby incorporated by reference.

The production of the XenoMouse® strains of mice is further discussed and delineated in U.S. patent application Ser. Nos. 07/466,008, filed Jan. 12, 1990, 07/610,515, filed Nov. 8, 1990, 07/919,297, filed Jul. 24, 1992, 07/922,649, filed Jul. 30, 1992, 08/031,801, filed Mar. 15, 1993, 08/112, 848, filed Aug. 27, 1993, 08/234,145, filed Apr. 28, 1994, 08/376,279, filed Jan. 20, 1995, 08/430, 938, filed Apr. 27, 1995, 08/464,584, filed Jun. 5, 1995, 08/464,582, filed Jun. 5, 1995, 08/463,191, filed Jun. 5, 1995, 08/462,837, filed Jun. 5, 1995, 08/486,853, filed Jun. 5, 1995, 08/486,857, filed Jun. 5, 1995, 08/486,859, filed Jun. 5, 1995, 08/462,513, filed Jun. 5, 1995, 08/724,752, filed Oct. 2, 1996, 08/759,620, filed Dec. 3, 1996, U.S. Publication 2003/0093820, filed Nov. 30, 2001 and U.S. Pat. Nos. 6,162,963, 6,150,584, 6,114,598, 6,075, 181, and 5,939,598 and Japanese Patent Nos. 3 068 180 132, 3 068 506 132, and 3 068 507 B2, See also European Patent No., EP 0 463 151 B1, grant published Jun. 12, 1996. International Patent Application No., WO 94/02602, published Feb. 3, 1994. International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc. have utilised a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and usually a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255.458 each to Lonberg and Kay, U.S. Pat. Nos. 5,591,669 and 6,023.010 to Krimpenfort and Berns, U.S. Pat. Nos. 5,612,205, 5,721,367, and 5,789, 215 to Berns et al., and U.S. Pat. No. 5,643,763 to Choi and Dunn, and GenPharm International U.S. patent application Ser. Nos. 07/574,748, filed Aug. 29, 1990, 07/575,962, filed Aug. 31, 1990, 07/810,279, filed Dec. 17, 1991, 07/853,408, filed Mar. 18, 1992, 07/904,068, filed Jun. 23, 1992, 07/990, 860, filed Dec. 16, 1992, 08/053,131, filed Apr. 26, 1993, 08/096,762, filed Jul. 22, 1993, 08/155,301, filed Nov. 18, 1993,08/161,739, filed Dec. 3, 1993, 08/165,699, filed Dec. 10, 1993, 08/209,741, filed Mar. 9, 1994, the disclosures of which are hereby incorporated by reference. See also European Patent No. 0 546 073 B1. International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al. 1993, Choi et al., 1993. Lonberg et al., (1994), Taylor et al., (1994), and Tuaillon et al. (1995), Fishwild et al., (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference. Additionally, KM™—mice, which are the result of cross-breeding of Kirin's Tc mice with Medarex's minilocus (Humab) mice have been generated. These mice possess the human IgH transchromosome of the Kirin mice and the kappa chain transgene of the Genpharm mice (Ishida et al., Cloning Stem Cells, (2002) 4:91-102).

Human antibodies can also be derived by in vitro methods. Suitable examples include but are not limited to phage display (MedImmune, Morphosys, Dyax, Biosite/Medarex, Xoma, Symphogen, Alexion (formerly Proliferon), Affimed) ribosome display (MedImmune), yeast display, and the like.

Preparation of Antibodies

Antibodies, as described herein, were prepared through the utilization of the XenoMouse® technology, as described below. Such mice are capable of producing human immunoglobulin molecules and antibodies and are deficient in the production of murine immunoglobulin molecules and antibodies. Technologies utilised for achieving the same are disclosed in the patents, applications, and references disclosed in the background section herein. In particular, however, a preferred embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al. Nature Genetics 15:146-156 (1997), the disclosure of which is hereby incorporated by reference.

Through the use of such technology, fully human monoclonal antibodies to a variety of antigens have been produced. Essentially, XenoMouse® lines of mice are immunized with an antigen of interest (e.g. DLL4), lymphatic cells (such as B-cells) are recovered from the hyper-immunized mice, and the recovered lymphocytes are fused with a myeloid-type cell line to prepare immortal hybridoma cell lines. These hybridoma cell lines are screened and selected to identify hybridoma cell lines that produced antibodies specific to the antigen of interest. Provided herein are methods for the production of multiple hybridoma cell lines that produce antibodies specific to DLL4. Further, provided herein are characterisation of the antibodies produced by such cell lines, including nucleotide and amino acid sequence analyses of the heavy and light chains of such antibodies.

Alternatively, instead of being fused to myeloma cells to generate hybridomas, B cells can be directly assayed. For example, CD19+ B cells can be isolated from hyperimmune XenoMouse® mice and allowed to proliferate and differentiate into antibody-secreting plasma cells. Antibodies from the cell supernatants are then screened by, for example, ELISA, FACS or FMAT, for reactivity against the immunogen. The supernatants might also be screened for immunoreactivity against fragments of DLL4 to further map the different antibodies for binding to domains of functional interest on DLL4. The antibodies may also be screened other related human DLL4s and against the rat, the mouse, and non-human primate, such as Cynomolgus monkey, orthologues of DLL4, the last to determine species cross-reactivity. B cells from wells containing antibodies of interest may be immortalised by various methods including fusion to make hybridomas either from individual or from pooled wells, or by infection with EBV or transfection by known immortalising genes and then plating in suitable medium. Alternatively, single plasma cells secreting antibodies with the desired specificities are then isolated using an DLL4-specific hemolytic plaque assay (see for example Babcook et al., Proc. Nod. Acad. Sci. USA 93:7843-48 (1996)). Cells targeted for lysis are preferably sheep red blood cells (SRBCs) coated with the DLL4 antigen.

In the presence of a B-cell culture containing plasma cells secreting the immunoglobulin of interest and complement, the formation of a plaque indicates specific DLL4-mediated lysis of the sheep red blood cells surrounding the plasma cell of interest. The single antigen-specific plasma cell in the center of the plaque can be isolated and the genetic information that encodes the specificity of the antibody is isolated from the single plasma cell. Using reverse-transcription followed by PCR (RT-PCR), the DNA encoding the heavy and light chain variable regions of the antibody can be cloned. Such cloned DNA can then be further inserted into a suitable expression vector, preferably a vector cassette such as a pcDNA, more preferably such a pcDNA vector containing the constant domains of immunoglobulin heavy and light chain. The generated vector can then be transfected into host cells, e.g., HEK293 cells, CHO cells, and cultured in conventional nutrient media modified as appropriate for inducing transcription, selecting transformants, or amplifying the genes encoding the desired sequences.

As will be appreciated, antibodies that specifically bind DLL4 can be expressed in cell lines other than hybridoma cell lines. Sequences encoding particular antibodies can be used to transform a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Cell lines of particular preference are selected through determining which cell lines have high expression levels and produce antibodies with constitutive DLL4 binding properties.

In the cell-cell fusion technique, a myeloma, CHO cell or other cell line is prepared that possesses a heavy chain with any desired isotype and another myeloma, CHO cell or other cell line is prepared that possesses the light chain. Such cells can, thereafter, be fused and a cell line expressing an intact antibody can be isolated.

Accordingly, as antibody candidates are generated that meet desired "structural" attributes as discussed above, they can generally be provided with at least certain of the desired "functional" attributes through isotype switching.

Therapeutic Administration and Formulations

Embodiments of the invention include sterile pharmaceutical formulations of anti-DLL4 antibodies that are useful as treatments for diseases. Such formulations would inhibit the binding of a native DLL4 to the Notch 1 or Notch 4 receptor, thereby effectively treating pathological conditions where, for example, serum or tissue NIA expression is abnormally elevated. Anti-DLL4 antibodies preferably possess adequate affinity to potently inhibit native DLL4 binding to the Notch 1 or Notch 4 receptor and preferably have an adequate duration of action to allow for infrequent dosing in humans. A prolonged duration of action will allow for less frequent and more convenient dosing schedules by alternate parenteral routes such as subcutaneous or intramuscular injection.

Sterile formulations can be created, for example, by filtration through sterile filtration membranes, prior to or following lyophilization and reconstitution of the antibody. The antibody ordinarily will be stored in lyophilized form or in solution. Therapeutic antibody compositions generally are placed into a container having a sterile access port, for example, an intravenous solution bag or vial having an adapter that allows retrieval of the formulation, such as a stopper pierceable by a hypodermic injection needle.

The route of antibody administration is in accord with known methods, e.g., injection or infusion by intravenous, intraperitoneal, intracerebral, intramuscular, intraocular, intraarterial, intrathecal, inhalation or intralesional routes, direct injection to a tumor site, or by sustained release systems as noted below. The antibody is preferably administered continuously by infusion or by bolus injection.

An effective amount of antibody to be employed therapeutically will depend, for example, upon the therapeutic objectives, the route of administration, and the condition of the patient. Accordingly, it is preferred that the therapist titer the dosage and modify the route of administration as required to obtain the optimal therapeutic effect. Typically, the clinician will administer antibody until a dosage is reached that achieves the desired effect. The progress of this therapy is easily monitored by conventional assays or by the assays described herein.

Antibodies, as described herein, can be prepared in a mixture with a pharmaceutically acceptable carrier. This therapeutic composition can be administered intravenously or through the nose or lung, preferably as a liquid or powder aerosol (lyophilized). The composition may also be administered parenterally or subcutaneously as desired. When administered systemically, the therapeutic composition should be sterile, pyrogen-free and in a parenterally acceptable solution having due regard for pH, isotonicity, and stability. These conditions are known to those skilled in the art. Briefly, dosage formulations of the compounds described herein are prepared for storage or administration by mixing the compound having the desired degree of purity with pharmaceutically acceptable carriers, excipients, or stabilizers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional pharmaceutical practice as described in *Remington: The Science and Practice of Pharmacy* (20th ed, Lippincott Williams & Wilkens Publishers (2003)). For example, dissolution or suspension of the active compound in a pharmaceutically acceptable carrier such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

Suitable examples of sustained-release preparations include semipermeable matrices of solid hydrophobic polymers containing the polypeptide, which matrices are in the form of shaped articles, films or microcapsules. Examples of sustained-release matrices include polyesters, hydrogels (e.g., poly(2-hydroxyethyl-methacrylate) as described by Langer et al., *J. Biomed Mater. Res.*, (1981) 15:167-277 and Langer, *Chem. Tech.*, (1982) 12:98-105, or poly(vinylalcohol)), polylactides (U.S. Pat. No. 3,773,919, EP 58,481), copolymers of L-glutamic acid and gamma ethyl-L-glutamate (Sidman et al., *Biopolymers*, (1983) 22:547-556), non-degradable ethylene-vinyl acetate (Langer et al., supra), degradable lactic acid-glycolic acid copolymers such as the LUPRON Depot™ (injectable microspheres composed of lactic acid-glycolic acid copolymer and leuprolide acetate), and poly-D-(−)-3-hydroxybutyric acid (EP 133.988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through disulfide interchange, stabilization may be achieved by modifying sulfhydryl residues, lyophilizing from acidic solutions, controlling moisture content, using appropriate additives, and developing specific polymer matrix compositions.

Sustained-released compositions also include preparations of crystals of the antibody suspended in suitable formulations capable of maintaining crystals in suspension. These preparations when injected subcutaneously or intraperitonealy can produce a sustained release effect. Other compositions also include liposomally entrapped antibodies. Liposomes containing such antibodies are prepared by methods known per se: U.S. Pat. No. DE 3,218,121; Epstein et al., *Proc. Natl. Acad. Sci. USA*, (1985) 82:3688-3692; Hwang et al., *Proc. Natl. Acad. Sci. USA*. (1980) 77:4030-4034; EP 52,322; EP 36,676; EP 88,046; EP 143,949; 142,641; Japanese patent application 83-118008; U.S. Pat. Nos. 4,485,045 and 4,544,545; and EP 102,324.

The dosage of the antibody formulation for a given patient will be determined by the attending physician taking into consideration various factors known to modify the action of drugs including severity and type of disease, body weight, sex, diet, time and route of administration, other medications and other relevant clinical factors. Therapeutically effective dosages may be determined by either in vitro or in vivo methods.

An effective amount of the antibodies, described herein, to be employed therapeutically will depend, for example, upon the therapeutic objectives, the rout of administration, and the condition of the patient. Accordingly, it is preferred for the therapist to titer the dosage and modify the route of administration as required to obtain the optimal therapeutic effect. A typical daily dosage might range from about 0.0001 mg/kg, 0.001 mg/kg, 0.01 mg/kg, 0.1 mg/kg, 1 mg/kg, 10 mg/kg to up to 100 mg/kg, 1000 mg/kg, 10000 mg/kg or more, of the patient's body weight depending on the factors mentioned above. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight depending on the factors mentioned above. Typically, the clinician will administer the therapeutic antibody until a dosage is reached that achieves the desired effect. The progress of this therapy is easily monitored by conventional assays or as described herein.

Doses of antibodies of the invention may be repeated and the administrations may be separated by at least 1 day, 2 days, 3 days, 5 days, 10 days, 15 days, 30 days, 45 days, 2 months, 75 days, 3 months, or at least 6 months.

It will be appreciated that administration of therapeutic entities in accordance with the compositions and methods herein will be administered with suitable carriers, excipients, and other agents that are incorporated into formulations to provide improved transfer, delivery, tolerance, and the like. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regal. Toxicol. Pharmacol.* 32(2): 210-8 (2000), Wang W. "Lyophilization and development of solid protein pharmaceuticals." *Int. J. Pharm.* 203(1-2):1-60 (2000), Charman W N "Lipids, lipophilic drugs, and oral drug delivery-some emerging concepts." *J. Pharm Sci.* 89(8):967-78 (2000), Powell et al. "Compendium of excipients for parenteral formulations" *PDA J Pharm Sci Technol.* 52:238-311 (1998) and the citations therein for additional information related to formulations, excipients and carriers well known to pharmaceutical chemists.

Design and Generation of Other Therapeutics

In accordance with the present invention and based on the activity of the antibodies that are produced and characterized herein with respect to DLL4, the design of other therapeutic modalities beyond antibody moieties is facilitated. Such modalities include, without limitation, advanced antibody therapeutics, such as bispecific antibodies, immunotoxins, and radiolabeled therapeutics, single domain antibodies, antibody fragments, such as a Fab, Fab', F(ab')$_2$, Fv or dAb, generation of peptide therapeutics, DLL4 binding domains in novel scaffolds, gene therapies, particularly intrabodies, antisense therapeutics, and small molecules.

An antigen binding site may be provided by means of arrangement of CDRs on non-antibody protein scaffolds, such as fibronectin or cytochrome B etc. (Haan & Maggos (2004) BioCentury, 12(5): A1-A6; Koide et al. (1998) Journal of Molecular Biology, 284: 1141-1151; Nygren et al. (1997) Current Opinion in Structural Biology, 7: 463-469) or by randomising or mutating amino acid residues of a loop within a protein scaffold to confer binding specificity for a desired target. Scaffolds for engineering novel binding sites in proteins have been reviewed in detail by Nygren et al. (Nygren et al. (1997) Current Opinion in Structural Biology, 7: 463-469).

Protein scaffolds for antibody mimics are disclosed in WO/0034784, which is herein incorporated by reference in its entirety, in which the inventors describe proteins (antibody mimics) that include a fibronectin type III domain having at least one randomised loop. A suitable scaffold into which to graft one or more CDRs, e.g. a set of HCDRs, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties, such as an ability to enter cells, penetrate deep into tissues or reach targets within other structures, or to bind within protein cavities of the target antigen. Use of antigen binding sites in non-antibody protein scaffolds is reviewed in Wess, 2004 (Wess, L. In: BioCentury, The Bernstein Report on BioBusiness, 12(42), A1-A7, 2004). Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from *S. aureus*, transferrin, albumin, tetranectin, fibronectin (e.g. 10th fibronectin type III domain), lipocalins as well as gamma-crystalline and other Affilin™ scaffolds (Scil Proteins). Examples of other approaches include synthetic "Microbodies" based on cyclotides—small proteins having intra-molecular disulphide bonds, Microproteins (Versabodies™, Amunix) and ankyrin repeat proteins (DARPins, Molecular Partners).

In addition to antibody sequences and/or an antigen-binding site, a targeted binding agent according to the present invention may comprise other amino acids, e.g. forming a peptide or polypeptide, such as a folded domain, or to impart to the molecule another functional characteristic in addition to ability to bind antigen. Targeted binding agents of the invention may carry a detectable label, or may be conjugated to a toxin or a targeting moiety or enzyme (e.g. via a peptidyl bond or linker). For example, a targeted binding agent may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

In connection with the generation of advanced antibody therapeutics, where complement fixation is a desirable attribute, it may be possible to sidestep the dependence on complement for cell killing through the use of bispecific antibodies, immunotoxins, or radiolabels, for example.

For example, bispecific antibodies can be generated that comprise (i) two antibodies one with a specificity to DLL4 and another to a second molecule that are conjugated together, (ii) a single antibody that has one chain specific to DLL4 and a second chain specific to a second molecule, or (iii) a single chain antibody that has specificity to DLL4 and the other molecule. Such bispecific antibodies can be generated using techniques that are well known; for example, in connection with (i) and (ii) see e.g., Fanger et al. *Immunol Methods* 4:72-81 (1994) and Wright and Harris, supra. and in connection with (iii) see e.g., Traunecker et al. *Int. J. Cancer (Suppl.)* 7:51-52 (1992). In each case, the second specificity can be made to the heavy chain activation receptors, including, without limitation, CD16 or CD64 (see e.g., Deo et al. *Immunol. Today* 18:127 (1997)) or CD89 (see e.g., Valerius et al. *Blood* 90:4485-4492 (1997)).

Antibodies can also be modified to act as immunotoxins, utilizing techniques that are well known in the art. See e.g., Vitetta *Immunol Today* 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in *Cancer Chemotherapy and Biotherapy* 655-686 (2d edition, Chafner and Longo, eds., Lippincott Raven (1996)). See also U.S. Pat. Nos. 4,681,581, 4,735,210, 5,101,827, 5,102,990 (RE 35,500), 5,648,471, and 5,697,902. Each immunotoxin or radiolabeled molecule would be likely to kill cells expressing the desired multimeric enzyme subunit oligomerisation domain.

When an antibody is linked to an agent (e.g., radioisotope, pharmaceutical composition, or a toxin), it is contemplated that the agent possess a pharmaceutical property selected from the group of antimitotic, alkylating, antimetabolite, anti-angiogenic, apoptotic, alkaloid, COX-2, and antibiotic agents and combinations thereof. The drug can be selected from the group of nitrogen mustards, ethylenimine derivatives, alkyl sulfonates, nitrosoureas, triazenes, folic acid analogs, anthracyclines, taxanes, COX-2 inhibitors, pyrimidine analogs, purine analogs, antimetabolites, antibiotics, enzymes, epipodophyllotoxins, platinum coordination complexes, vinca alkaloids, substituted ureas, methyl hydrazine derivatives, adrenocortical suppressants, antagonists, endostatin, taxols, camptothecins, oxaliplatin, doxorubicins and their analogs, and a combination thereof.

Examples of toxins further include gelonin, Pseudomonas exotoxin (PE), PE40, PE38, diphtheria toxin, ricin, abrin, alpha toxin, saporin, ribonuclease (RNase), DNase I, Staphylococcal enterotoxin-A, pokeweed antiviral protein, gelonin, Pseudomonas endotoxin, members of the enediyne family of molecules, such as calicheamicin and esperamicin, as well as derivatives, combinations and modifications thereof. Chemical toxins can also be taken from the group consisting of duocarmycin (see, e.g., U.S. Pat. No. 5,703,080 and U.S. Pat. No. 4,923,990), methotrexate, doxorubicin, melphalan, chlorambucil, ARA-C, vindesine, mitomycin C, cis-platinum, etoposide, bleomycin and 5-fluorouracil. Examples of chemotherapeutic agents also include Adriamycin, Doxorubicin, 5-Fluorouracil, Cytosine arabinoside (Ara-C), Cyclophosphamide, Thiotepa, Taxotere (docetaxel). Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Caminomycin, Aminopterin, Dactinomycin, Mitomycins, Esperamicins (see, U.S. Pat. No. 4,675,187), Melphalan, and other related nitrogen mustards. Suitable toxins and chemotherapeutic agents are described in Remington's Pharmaceutical Sciences, 19th Ed, (Mack Publishing Co, 1995), and in Goodman And Gilman's The Pharmacological Basis of Therapeutics, 7th Ed. (MacMillan Publishing Co. 1985). Other suitable toxins and/or chemotherapeutic agents are known to those of skill in the art.

Examples of radioisotopes include gamma-emitters, positron-emitters, and x-ray emitters that can be used for localisation and/or therapy, and beta-emitters and alpha-emitters that can be used for therapy. The radioisotopes described previously as useful for diagnostics, prognostics and staging are also useful for therapeutics.

Non-limiting examples of anti-cancer or anti-leukemia agents include anthracyclines such as doxorubicin (adriamycin), daunorubicin (daunomycin), idarubicin, detorubicin, caminomycin, epirubicin, esorubicin, and morpholino and substituted derivatives, combinations and modifications thereof. Exemplary pharmaceutical agents include cis-platinum, taxol, calicheamicin, vincristine, cytarabine (Ara-C), cyclophosphamide, prednisone, daunorubicin, idarubicin, fludarabine, chlorambucil, interferon alpha, hydroxyurea, temozolomide, thalidomide, and bleomycin, and derivatives, combinations and modifications thereof. Preferably, the anti-cancer or anti-leukemia is doxorubicin, morpholinodoxorubicin, or morpholinodaunorubicin.

The antibodies of the invention also encompass antibodies that have half-lives (e.g., serum half-lives) in a mammal, preferably a human, of greater than that of an unmodified antibody. Said antibody half life may be greater than about 15 days, greater than about 20 days, greater than about 25 days, greater than about 30 days, greater than about 35 days, greater than about 40 days, greater than about 45 days, greater than about 2 months, greater than about 3 months, greater than about 4 months, or greater than about 5 months. The increased half-lives of the antibodies of the present invention or fragments thereof in a mammal, preferably a human, result in a higher serum titer of said antibodies or antibody fragments in the mammal, and thus, reduce the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor (see, e.g., International Publication Nos. WO 97/34631 and WO 02/060919, which are incorporated herein by reference in their entireties). Antibodies or fragments thereof with increased in vivo half-lives can be generated by attaching to said antibodies or antibody fragments polymer molecules such as high molecular weight polyethyleneglycol (PEG), PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatisation that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

As will be appreciated by one of skill in the art, in the above embodiments, Chile affinity values can be important, other factors can be as important or more so, depending upon the particular function of the antibody. For example, for an immunotoxin (toxin associated with an antibody), the act of binding of the antibody to the target can be useful; however, in some embodiments, it is the internalisation of the toxin into the cell that is the desired end result. As such, antibodies with a high percent internalisation can be desirable in these situations. Thus, in one embodiment, antibodies with a high efficiency in internalisation are contemplated. A high efficiency of internalisation can be measured as a percent internalised antibody, and can be from a low value to 100%. For example, in varying embodiments, 0.1-5, 5-10, 10-20, 20-30, 30-40, 40-45, 45-50, 50-60, 60-70, 70-80, 80-90, 90-99, and 99-100% can be a high efficiency. As will be appreciated by one of skill in the art, the desirable efficiency can be different in different embodiments, depending upon, for example, the associated agent, the amount of antibody that can be administered to an area, the side effects of the antibody-agent complex, the type (e.g., cancer type) and severity of the problem to be treated.

In other embodiments, the antibodies disclosed herein provide an assay kit for the detection of DLL4 expression in mammalian tissues or cells in order to screen for a disease or disorder associated with changes in expression of DLL4. The kit comprises an antibody that binds DLL4 and means for indicating the reaction of the antibody with the antigen, if present.

Combinations

The targeted binding agent or antibody defined herein may be applied as a sole therapy or may involve, in addition to the compounds of the invention, conventional surgery or radiotherapy or chemotherapy. Such chemotherapy may include one or more of the following categories of anti tumor agents:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumor antibiotics (for example anthracyclines like adriamycin, Neomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661), and metalloproteinase inhibitors like marimastat, inhibitors of urokinase plasminogen activator receptor function or, inhibitors of cathepsins, inhibitors of serine proteases for example matriptase, hepsin, urokinase, inhibitors of heparanase);

(iv) cytotoxic agents such as fludarabine, 2-chlorodeoxyadenosine, chlorambucil or doxorubicin and combination thereof such as Fludarabine+cyclophosphamide, CVP: cyclophosphamide+vincristine+prednisone, ACVBP: doxorubicin+cyclophosphamide+vindesine+bleomycin+prednisone, CHOP: cyclophosphamide+doxorubicin+vincristine+prednisone, CHOP: cyclophosphamide+mitoxantrone+vincristine+prednisone, m-BACOD: methotrexate+bleomycin+doxorubicin+cyclophosphamide+vincristine+dexamethasone+leucovorin., MACOP-B: methotrexate+doxorubicin+cyclophosphamide+vincristine+prednisones fixed dose+bleomycin+leucovorin, or ProMACE CytaBOM: prednisone+doxoruhicin+cyclophosphamide+etoposide+cytarabine+bleomycin+vincristine+methotrexate+leucovorin.

(v) inhibitors of growth factor function, for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKI kinases, inhibitors of the hepatocyte growth factor family, c-kit inhibitors, abl kinase inhibitors. IGF receptor (insulin-like growth factor) kinase inhibitors, aurora kinase inhibitors (for example AZD1152, PH739358, VX-680, MLN8054, R763, MP235, MP529, VX-528 and AX39459), cyclin dependent kinase inhibitors such as CDK2 and/or CDK4 inhibitors, and inhibitors of survival signaling proteins such as Bcl-2, Bcl-XL for example ABT-737;

(vi) antiangiogenic agents such as those which inhibit the effects of vascular endothelial growth factor, [for example the anti-vascular endothelial cell growth factor antibody bevacizumab (Avastin™), Angiopoietin-2 inhibitors, and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)quinazoline (AZD2171: Example 240 within WO 00/47212), vatalanib (PTK787; WO 98/35985) and SU11248 (sunitinib; WO 01/60814; Sutent™), Sorafenib (Nexxavar™), compounds such as those disclosed in International Patent Applications WO97/22596, WO 97/30035, WO 97/32856, WO 98/13354, WO00/47212 and WO01/32651 and compounds that work by other mechanisms (for example linomide, inhibitors of integrin αvβ3 function and angiostatin)] or colony stimulating factor 1 (CSF1) or CSF1 receptor;

(vii) vascular damaging agents such as Combretastatin A4 and compounds disclosed in International Patent Applications WO 99/02166, WO 00/40529, WO 00/41669, WO 01/92224, WO 02/04434 and WO 02/08213;

(viii) antisense therapies, for example those which are directed to the targets listed above, such as G-3139 (Genasense), an anti bcl2 antisense;

(ix) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (x) immunotherapy approaches, including for example treatment with Alemtuzumab (campath-1H™), a monoclonal antibody directed at CD52, or treatment with antibodies directed at CD22, ex vivo and in vivo approaches to increase the immunogenicity of patient tumor cells, transfection with cytokines such as interleukin 2, interleukin 4 or granulocyte macrophage colony stimulating factor, approaches to decrease T cell anergy such as treatment with monoclonal antibodies inhibiting CTLA-4 function, approaches using transfected immune cells such as cytokine transfected dendritic cells, approaches using cytokine transfected tumor cell lines and approaches using anti idiotypic antibodies.

(xi) inhibitors of protein degradation such as proteasome inhibitor such as Velcade (bortezomib).

(xii) biotherapeutic therapeutic approaches for example those which use peptides or proteins (such as antibodies or soluble external receptor domain constructions) which either sequester receptor ligands, block ligand binding to receptor or decrease receptor signalling (e.g. due to enhanced receptor degradation or lowered expression levels).

In one embodiment the anti-tumor treatment defined herein may involve, in addition to the compounds of the invention, treatment with other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumor antibiotics (for example anthracyclines like adriamycin, Neomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin).

In one embodiment the anti-tumor treatment defined herein may it valve, in addition to the compounds of the invention, treatment with gemcitabine.

Such conjoint treatment may be achieved by way of the simultaneous, sequential or separate dosing of the individual components of the treatment. Such combination products employ the compounds of this invention, or pharmaceutically acceptable salts thereof, within the dosage range described hereinbefore and the other pharmaceutically active agent within its approved dosage range.

EXAMPLES

The following examples, including the experiments conducted and results achieved are provided for illustrative purposes only and are not to be construed as limiting upon the teachings herein.

Example 1

Immunization and Titering

Immunogens
The extracellular domain of human DLL4 (amino acids 1-524) and recombinant human DLL4 transiently expressed in Chinese Hamster Ovary (CHO) cells were used as antigens for immunizations. For the generation of the CHO transfectants, human full length DLL4 cDNA (Yoneya et al., 2001, J. Biochem., 129, 27-34) was inserted into pcDNA3.1 vector and lipofected into CHO cells (American Type Tissue Collection, catalog #CCL-61). Expression of human DLL4 at the cell surface at the level suitable for the purpose of immunization was confirmed by fluorescent activated cell sorting (FACS) analysis. The extracellular domain of human DLL4 was subcloned from full length DLL4 using the forward 5'-AAGCTGGCTAGCGCGAATGGCG-GCAGCGTCCCGGAG (SEQ ID NO: 92) and reverse 5'-CAGCCTCGAGCGGCCGCCCAGGG-GAAGCTGGGCGGCAAGC (SEQ ID NO: 93) primers. The PCR product was purified and ligated into the pSecTag expression vector from Invitrogen. The clone was subsequently transfected into 293T cells using 293fectin transfection reagent. After 7 days, the cell supernatants containing the target protein were harvested and run over a pre-equilibrated HisTrap column (GE Healthcare, catalog #17-5247) overnight. The column was washed with a binding buffer containing 20 mM sodium phosphate, 500 mM sodium chloride and 5 mM imidazole, pH 7.4 before the his-tagged protein was eluted in a buffer containing 20 mM sodium phosphate, 500 mM sodium chloride and 500 mM imidazole, pH 7.4. The protein sample was dialyzed in binding buffer for 1 h at 4° C. before being further dialyzed in PBS, pH 7.4 for 2 h prior to filter sterilization, quantification and purity assessment by SDS-PAGE followed by staining with Gelcode (Pierce, catalog #24950).

Immunization

Monoclonal antibodies against DLL4 were developed by sequentially immunizing XenoMouse® mice (XenoMouse strains: XMG2 (IgG2 kappa/lambda) and XMG4 (IgG4 kappa/lambda) Amgen, Inc. Vancouver, British Columbia, Canada) with either the extracellular domain of DLL4 or CHO cells overexpressing recombinant human DLL4 as described in Example 1. XenoMouse animals were immunized via intraperitoneal and base of tail routes for all injections by conventional means. Adjuvants included Titermax Gold™ (Sigma, catalog #T2684), aluminum phosphate gel adjuvant, HCL Biosector, (catalog #1452-250) and ImmuneEasy mouse adjuvant (qCpG, Qiagen catalog #303105). For the soluble immunogen, the first injection of 10 μg DLL4 extracellular domain was administered with Titermax Gold™ (Day 0) and alternate boosts were administered using either aluminum phosphate gel adjuvant and qCpG or Titremax Gold™ along with 5 μg of DLL4 extracellular domain. For the cell-based immunogen, the first injection was administered with aluminum phosphate gel adjuvant and 2E6 cells. During subsequent boosts 1E6 cells were administered using the same adjuvant. For both immunization campaigns, boosting occurred on days 2, 6, 10, 16, 23, 30, 37, 44, 50, 64, 71, 75, 89, 104 and 108.

Selections of Animals for Harvest by Titer

Titers of the antibodies against human DLL4 were tested by for binding to human and mouse DLL4 expressed in 293T cells using a Fluorometric microvolume assay technology (FMAT) cellular detection instrument (Applied Biosystems). This analysis showed that there were some mice that had titers, which appeared to be specific for DLL4. Therefore, at the end of the immunization programme, 17 mice were selected for harvest, and lymphocytes were isolated from the spleens and lymph nodes of the immunized mice as described in example 2 below.

Example 2

Recovery of Lymphocytes, B-Cell Isolations, Fusions and Generation of Hybridomas Immunized mice were sacrificed by cervical dislocation and the draining lymph nodes were harvested and pooled from each cohort. The lymphoid cells were dissociated by grinding in DMEM to release the cells from the tissues, and the cells were suspended in DMEM. B cells were enriched by positive selection using CD19 labelled Dynal beads. A fusion was performed by mixing washed enriched B cells from above and nonsecretory myeloma P3X63Ag8.653 cells purchased from ATCC (catalog #CRL 1580) (Kearney et al., J. Immunol. 123, 1979, 1548-1550) at a ratio of 1:1. The cell mixture was gently pelleted by centrifugation at 800×g. After complete removal of the supernatant, the cells were treated with 2-4 ml of Pronase solution (CalBiochem, catalog #53702; 0.5 mg/ml in PBS) for no more than 2 minutes. Then 3-5 ml of FBS was added to stop the enzyme activity and the suspension was adjusted to 40 ml total volume using electro cell fusion solution, ECFS (0.3 M sucrose, Sigma, catalog #S7903, 0.1 mM magnesium acetate, Sigma, catalog #M2545, 0.1 mM calcium acetate, Sigma, catalog #C4705). The supernatant was removed after centrifugation and the cells were resuspended in 40 ml ECFS. This wash step was repeated and the cells again were resuspended in ECFS to a concentration of 2E6 cells/ml, Electro-cell fusion was performed using a fusion generator, model ECM2001, Genetronic, Inc., San Diego, Calif. The fusion chamber size used was 2.0 ml, using the following instrument settings: alignment condition: voltage: 50 V, time: 50 seconds; membrane breaking at: voltage: 3000 V, time: 30µ seconds; post-fusion holding time: 3 seconds, After ECF, the cell suspensions were carefully removed from the fusion chamber under sterile conditions and transferred into a sterile tube containing the same volume of Hybridoma Culture Medium (DMEM Biosciences), 15% FBS (Hyclone), supplemented with 2 mM L-glutamine (Sigma, catalog #G2150), 10 U/ml penicillin/ 0.1 mg/ml streptomycin (Sigma, catalog #P7539), 1 vial/L OPI (oxaloacetate, pyruvate, bovine insulin; Sigma catalog #O5003) and 10 U/ml recombinant human IL-6 (Boehringer Mannheim, catalog #1131567). The cells were incubated for 15-30 minutes at 37° C., and then centrifuged at 400×g for 5 min. The cells were gently resuspended in a small volume of Hybridoma Selection Medium (Hybridoma Culture Medium supplemented with 0.5×HA (Sigma, catalog #A9666)), and the volume was adjusted appropriately with more Hybridoma Selection Medium, based on a final plating of 5E6 B cells total per 96-well plate and 200 µl per well. The cells were mixed gently and pipetted into 96-well plates and allowed to grow. Exhaustive supernatants were collected from the cells that potentially produce anti-DLL4 antibodies and subjected to subsequent screening assays as exemplified below.

Example 3

Binding to Cell Bound Human and Cynomolgus Monkey DLL4 and Human Jagged1

Supernatants collected from harvested cells were tested to assess the ability of the secreted antibodies to bind to 293T cells transiently overexpressing either full length human or cynomolgus monkey DLL4 or human Jagged1. A mock-transfected 293T cell line was used as a negative control. Cells diluted in PBS containing 2% FBS were seeded at a density of 3000 expressing and 15000 mock transfected cells per well in 384 well plates (Corning Costar, catalog #3712). Immediately after plating, 15 or 20 µl/well of hybridoma supernatants and 10 µl/well of secondary antibody (Goat anti-human IgG Fc Cy5, final concentration 750 ng/ml) were added and plates incubated for 3 h at room temperature prior to reading the fluoresence on the FMAT 8200 instrument (Applied Biosystems). The binding of human Notch1/Fc chimera (R&D systems, catalog #3647-TK), diluted 1:2 from 0.86 µg/ml was used as a positive control for DLL4 and human Notch3/Fc chimera diluted from 10 µg/ml was used a positive control for binding to Jagged1, Results for 12 hybridoma supernatants showing binding of hybridoma supernatants to human/cynomolgus monkey DLL4 and human Jagged are shown in Table 3.

TABLE 3

| Antibody ID | Human DLL4 binding | | | Cynomolgus monkey DLL4 binding | | | Human Jagged1 binding | | |
| --- | --- | --- | --- | --- | --- | --- | --- | --- | --- |
| | Count | FL1 | FL1 × count | Count | FL1 | FL1 × count | Count | FL1 | FL1 × count |
| 1D4 | 196 | 10600 | 2.08E6 | 103 | 11700 | 1.21E6 | 23 | 3250 | 74800 |
| 1E4 | 206 | 10400 | 2.14E6 | 107 | 13200 | 1.41E6 | 2 | 8020 | 16000 |
| 4B4 | 194 | 9930 | 1.93E6 | 117 | 12300 | 1044E6 | 2 | 2590 | 5180 |
| 2H10 | 191 | 10800 | 2.06E6 | 103 | 13100 | 1.35E6 | 5 | 5030 | 25200 |
| 3A7 | 166 | 9470 | 1.57E6 | 121 | 9960 | 1.20E6 | 1 | 1940 | 1940 |
| 4B3 | 206 | 11000 | 2.27E6 | 97 | 12600 | 1.22E6 | 2 | 4720 | 9450 |
| 9G8 | 198 | 9810 | 1.94E6 | 120 | 11700 | 1.41E6 | 0 | 0 | 0 |
| 12A1 | 179 | 9520 | 1.76E6 | 106 | 12900 | 1.37E6 | 25 | 988 | 24700 |
| 17F3 | 219 | 11300 | 2.47E6 | 120 | 10700 | 1.29E6 | 30 | 1440 | 43100 |
| 21F7 | 200 | 10400 | 2.08E6 | 103 | 12500 | 1.28E6 | 1 | 2070 | 2070 |
| 20G8 | 182 | 10500 | 1.90E6 | 128 | 11200 | 1.44E6 | 3 | 1500 | 4490 |
| 21H3 | 181 | 10500 | 1.91E6 | 120 | 11700 | 1.40E6 | 0 | 0 | 0 |

Example 4

Inhibition Of Notch1-DLL4 Receptor-Ligand Binding

In order to determine the relative potency of the antibody containing supernatants, their ability to inhibit the binding of human Notch1/Fc to human DLL 4 transiently overexpressed in 293T cells was evaluated. Transfected and untransfected 239T cells were reconstituted in PBS containing 2% FCS and 5000 transfected and 17500 non-transfected cells were plated in 20 µl into wells of a 384-well tissue culture plate (Corning Costar, catalog #3712). Subsequently, 20 µl of hybridoma supernatant was added and plates were incubated at 4° C. for 1 h at which time 20 µl of Alexa-647 labeled human Notch1/ Fc was added at a final concentration of 6.7 ng/ml. After a further 3 h incubation at 4° C., the amount of bound Notch1/ Fc was determined by reading the fluorescence in each well using an FMAT 8200 instrument (Applied Biosystems). The results for 12 hybridoma supernatants are shown in Table 4. Results are expressed as % inhibitions with the minimum inhibition in the assay being determined by the effects of non-DLL4 binding supernatants prepared in a similar way as described in example 2, and the maximum inhibition being defined as the signal obtained in the presence of a saturating concentration of unlabeled Notch1/Fc. N.T.=not tested

TABLE 4

| Antibody ID | % inhibition n = 1 | % inhibition n = 2 | % inhibition n = 3 | Mean % inhibition |
|---|---|---|---|---|
| 1D4 | 105 | 71 | 146 | 107 |
| 1E4 | 98 | 99 | 113 | 110 |
| 4B4 | 105 | 109 | 148 | 121 |
| 2H10 | 107 | 150 | 124 | 127 |
| 3A7 | 105 | 120 | 142 | 122 |
| 4B3 | 106 | 145 | 147 | 133 |
| 9G8 | 112 | 98 | 143 | 118 |
| 12A1 | 103 | 147 | 144 | 131 |
| 17F3 | N.T. | 108 | 131 | 120 |
| 21F7 | N.T. | 93 | 140 | 117 |
| 20G8 | N.T. | 88 | 143 | 116 |
| 21H3 | N.T. | 131 | 140 | 136 |

Example 5

Structural Analysis of Anti-DLL4 Antibodies

The variable heavy chains and the variable light chains of the antibodies were sequenced to determine their DNA sequences. The complete sequence information for the anti-DLL4 antibodies is provided in the sequence listing with nucleotide and amino acid sequences for each gamma and kappa chain combination. The variable heavy sequences were analyzed to determine the VH family, the D-region sequence and the region sequence. The sequences were then translated to determine the primary amino acid sequence and compared to the germline VH, D and J-region sequences to assess somatic hypermutations.

Table 2 is a table comparing the antibody heavy chain regions to their cognate germ line heavy chain region and kappa light chain regions to their cognate germ line lightchain region. The variable (V) regions of immunoglobulin chains are encoded by multiple germ line DNA segments, which are joined into functional variable regions ($V_H D J_H$ or $V_K J_K$) during B-cell ontogeny. The molecular and genetic diversity of the antibody response to DLL4 was studied in detail.

It should also be appreciated that where a particular antibody differs from its respective germline sequence at the amino acid level, the antibody sequence can be mutated back to the germline sequence. Such corrective mutations can occur at one, two, three or more positions, or a combination of any of the mutated positions, using standard molecular biological techniques. By way of non-limiting example, Table 8 shows that the light chain sequence of 2H10 (SEQ ID NO.: 6) differs from the corresponding germline sequence (see Table 2) through a V to an A at position 18 (mutation 1), a V to an A at position 32 (mutation 2), an E to a D at position 50 (mutation 3), an S to an N at position 65 (mutation 4), a T to an A at position 89 (mutation 5) and an L to a at position 94 (mutation 6). Thus, the amino acid or nucleotide sequence encoding the light chain of 2H10 can be modified at any or all of these sites. Tables 2-9 below illustrate the positions of such variations from the germline for 2H10, 9G8, 21H3 and 4B4. Each row represents a unique combination of germline and non-germline residues at the position indicated by bold type.

In another embodiment, the invention includes replacing any structural liabilities in the sequence that might affect the heterogeneity of the antibodies of the invention. Such liabilities include glycosylation sites, un-paired cysteines, surface exposed methinones, etc. To reduce the risk of such heterogeneity it is proposed that changes are made to remove one or more of such structural liabilities.

In one example, unpaired cysteines can be replaced alone or in conjunction with other structural changes. An example of an unpaired cysteine occurs in the light chain CDR1 of antibody 2H10 or 9G8 at position 33. This unpaired cysteine can be mutated to an appropriate amino acid that has comparable side chain property such as a serine. In another example, an unpaired cysteine occurs in the heavy chain FR4 of antibody 20G8 at position 203. This unpaired cysteine can likewise be mutated to an appropriate amino acid that has comparable side chain properties such as a serine.

TABLE 5

Exemplary Mutations of 21H3 Heavy Chain (SEQ ID NO: 30) to Germline at the Indicated Residue Number

| 31 | 35 | 45 | 66 | 70 | 100 |
|---|---|---|---|---|---|
| N | T | P | G | V | R |
| S | T | P | G | V | R |
| N | S | P | G | V | R |
| S | S | P | G | V | R |
| N | T | L | G | V | R |
| S | T | L | G | V | R |
| N | S | L | G | V | R |
| S | S | L | G | V | R |
| N | T | P | D | V | R |
| S | T | P | D | V | R |
| N | S | P | D | V | R |
| S | S | P | D | V | R |
| N | T | L | D | V | R |
| S | T | L | D | V | R |
| N | S | L | D | V | R |
| S | S | L | D | V | R |
| N | T | P | G | M | R |
| S | T | P | G | M | R |
| N | S | P | G | M | R |
| S | S | P | G | M | R |
| N | T | L | G | M | R |
| S | T | L | G | M | R |
| N | S | L | G | M | R |
| S | S | L | G | M | R |
| N | T | P | D | M | R |
| S | T | P | D | M | R |
| N | S | P | D | M | R |
| S | S | P | D | M | R |
| N | T | L | D | M | R |
| S | T | L | D | M | R |
| N | S | L | D | M | R |
| S | S | L | D | M | R |
| N | T | P | G | V | I |
| S | T | P | G | V | I |
| N | S | P | G | V | I |
| S | S | P | G | V | I |
| N | T | L | G | V | I |
| S | T | L | G | V | I |
| N | S | L | G | V | I |
| S | S | L | G | V | I |
| N | T | P | D | V | I |
| S | T | P | D | V | I |
| N | S | P | D | V | I |
| S | S | P | D | V | I |
| N | T | L | D | V | I |
| S | T | L | D | V | I |
| N | S | L | D | V | I |
| S | S | L | D | V | I |
| N | T | P | G | M | I |
| S | T | P | G | M | I |
| N | S | P | G | M | I |
| S | S | P | G | M | I |
| N | T | L | G | M | I |
| S | T | L | G | M | I |
| N | S | L | G | M | I |

TABLE 5-continued

| Exemplary Mutations of 21H3 Heavy Chain (SEQ ID NO: 30) to Germline at the Indicated Residue Number | | | | | |
|---|---|---|---|---|---|
| 31 | 35 | 45 | 66 | 70 | 100 |
| S | S | L | G | M | I |
| N | T | P | D | M | I |
| S | T | P | D | M | I |
| N | S | P | D | M | I |
| S | S | P | D | M | I |
| N | T | L | D | M | I |
| S | T | L | D | M | I |
| N | S | L | D | M | I |
| S | S | L | D | M | I |

In some embodiments of the invention, the targeted binding agent or antibody comprises a sequence comprising SEQ ID NO.: 30. In certain embodiments, SEQ ID NO.: 30 comprises any one of the combinations of germline and non-germline residues indicated by each row of Table 5. In some embodiments, SEQ ID NO: 30 comprises any one, any two, any three, any four, any five, any six, or all six of the germline residues as indicated in Table 5. In certain embodiments, SEQ ID NO.: 30 comprises any one of the unique combinations of germline and non-germline residues indicated by each row of Table 5. In other embodiments, the targeted binding agent or antibody is derived from a germline sequence with VH1-18, D2-15 and JH3 domains, wherein one or more residues has been mutated to yield the corresponding germline residue at that position. Specific examples of 21H3 variable heavy domain which has been mutated to particular germline sequences include 21H3VHOP (optimized where the non-germline sequence has been mutated to an L at position 45 and an M at position 70) as shown in Table 13.

TABLE 6

| Exemplary Mutations of 21H3 Light Chain (SEQ ID NO: 32) to Germline at the Indicated Residue Number | | | | |
|---|---|---|---|---|
| 32 | 33 | 67 | 99 | 107 |
| Y | F | E | H | R |
| N | F | E | H | R |
| Y | Y | E | H | R |
| N | Y | E | H | R |
| Y | F | K | H | R |
| N | F | K | H | R |
| Y | Y | K | H | R |
| N | Y | K | H | R |
| Y | F | E | V | R |
| N | F | E | V | R |
| Y | Y | E | V | R |
| N | Y | E | V | R |
| Y | F | K | V | R |
| N | F | K | V | R |
| Y | Y | K | V | R |
| N | Y | K | V | R |
| Y | F | E | H | K |
| N | F | E | H | K |
| Y | Y | E | H | K |
| N | Y | E | H | K |
| Y | F | K | H | K |
| N | F | K | H | K |
| Y | Y | K | H | K |
| N | Y | K | H | K |
| Y | F | E | V | K |
| N | F | E | V | K |
| Y | Y | E | V | K |
| N | Y | E | V | K |
| Y | F | K | V | K |
| N | F | K | V | K |
| Y | Y | K | V | K |
| N | Y | K | V | K |

In some embodiments of the invention, the targeted binding agent or antibody comprises a sequence comprising SEQ ID NO.: 32. In certain embodiments, SEQ ID NO.: 32 comprises any one of the combinations of germline and non-germline residues indicated by each row of Table 6. In some embodiments, SEQ ID NO: 32 comprises any one, any two, any three, any four, any five, or all five of the germline residues as indicated in Table 6. In other embodiments, the targeted binding agent or antibody is derived from a germline sequence with VL, 1 g, JL2 domains, wherein one or more residues has been mutated to yield the corresponding germline residue at that position. Specific examples of 21H3 variable light domain which has been mutated to particular germline sequences include 21H3 VLOP1 (optimized where the non-germline sequence has been mutated to a K at position 107) and 21H3 VLOP2 (optimized where the non-germline sequence has been mutated to a K at positions 67 and 107). See Table 13.

TABLE 7

| Exemplary Mutations of 4B4 Heavy Chain (SEQ ID NO: 2) to Germline at the Indicated Residue Number | | | | | | | | | | |
|---|---|---|---|---|---|---|---|---|---|---|
| 3 | 5 | 19 | 31 | 34 | 35 | 47 | 66 | 72 | 77 | 103 |
| L | I | Q | N | V | I | Y | D | S | T | S |
| Q | I | Q | N | V | I | Y | D | S | T | S |
| L | V | Q | N | V | I | Y | D | S | T | S |
| Q | V | Q | N | V | I | Y | D | S | T | S |
| L | I | K | N | V | I | Y | D | S | T | S |
| Q | I | K | N | V | I | Y | D | S | T | S |
| L | V | K | N | V | I | Y | D | S | T | S |
| Q | V | K | N | V | I | Y | D | S | T | S |
| L | I | Q | S | V | I | Y | D | S | T | S |
| Q | I | Q | S | V | I | Y | D | S | T | S |
| L | V | Q | S | V | I | Y | D | S | T | S |
| Q | V | Q | S | V | I | Y | D | S | T | S |
| L | I | K | S | V | I | Y | D | S | T | S |
| Q | I | K | S | V | I | Y | D | S | T | S |
| L | V | K | S | V | I | Y | D | S | T | S |
| Q | V | K | S | V | I | Y | D | S | T | S |
| L | I | Q | N | I | I | Y | D | S | T | S |
| Q | I | Q | N | I | I | Y | D | S | T | S |
| L | V | Q | N | I | I | Y | D | S | T | S |
| Q | V | Q | N | I | I | Y | D | S | T | S |
| L | I | K | N | I | I | Y | D | S | T | S |
| Q | I | K | N | I | I | Y | D | S | T | S |
| L | V | K | N | I | I | Y | D | S | T | S |
| Q | V | K | N | I | I | Y | D | S | T | S |
| L | I | Q | S | I | I | Y | D | S | T | S |
| Q | I | Q | S | I | I | Y | D | S | T | S |
| L | V | Q | S | I | I | Y | D | S | T | S |
| Q | V | Q | S | I | I | Y | D | S | T | S |
| L | I | K | S | I | I | Y | D | S | T | S |
| Q | I | K | S | I | I | Y | D | S | T | S |
| L | V | K | S | I | I | Y | D | S | T | S |
| Q | V | K | S | I | I | Y | D | S | T | S |
| L | I | Q | N | V | S | Y | D | S | T | S |
| Q | I | Q | N | V | S | Y | D | S | T | S |
| L | V | Q | N | V | S | Y | D | S | T | S |
| Q | V | Q | N | V | S | Y | D | S | T | S |
| L | I | K | N | V | S | Y | D | S | T | S |
| Q | I | K | N | V | S | Y | D | S | T | S |
| L | V | K | N | V | S | Y | D | S | T | S |
| Q | V | K | N | V | S | Y | D | S | T | S |
| L | I | Q | S | V | S | Y | D | S | T | S |
| Q | I | Q | S | V | S | Y | D | S | T | S |
| L | V | Q | S | V | S | Y | D | S | T | S |
| Q | V | Q | S | V | S | Y | D | S | T | S |
| L | I | K | S | V | S | Y | D | S | T | S |
| Q | I | K | S | V | S | Y | D | S | T | S |
| L | V | K | S | V | S | Y | D | S | T | S |
| Q | V | K | S | V | S | Y | D | S | T | S |
| L | I | Q | N | I | S | Y | D | S | T | S |
| Q | I | Q | N | I | S | Y | D | S | T | S |
| L | V | Q | N | I | S | Y | D | S | T | S |

TABLE 7-continued

Exemplary Mutations of 4B4 Heavy Chain (SEQ ID NO: 2) to Germline at the Indicated Residue Number

| 3 | 5 | 19 | 31 | 34 | 35 | 47 | 66 | 72 | 77 | 103 |
|---|---|----|----|----|----|----|----|----|----|-----|
| Q | V | Q | N | I | S | Y | D | S | T | S |
| L | I | K | N | I | S | Y | D | S | T | S |
| Q | I | K | N | I | S | Y | D | S | T | S |
| L | V | K | N | I | S | Y | D | S | T | S |
| Q | V | K | N | I | S | Y | D | S | T | S |
| L | I | Q | S | I | S | Y | D | S | T | S |
| Q | I | Q | S | I | S | Y | D | S | T | S |
| L | V | Q | S | I | S | Y | D | S | T | S |
| Q | V | Q | S | I | S | Y | D | S | T | S |
| L | I | K | S | I | S | Y | D | S | T | S |
| Q | I | K | S | I | S | Y | D | S | T | S |
| L | V | K | S | I | S | Y | D | S | T | S |
| Q | V | K | S | I | S | Y | D | S | T | S |
| L | I | Q | N | V | I | W | D | S | T | S |
| Q | I | Q | N | V | I | W | D | S | T | S |
| L | V | Q | N | V | I | W | D | S | T | S |
| Q | V | Q | N | V | I | W | D | S | T | S |
| L | I | K | N | V | I | W | D | S | T | S |
| Q | I | K | N | V | I | W | D | S | T | S |
| L | V | K | N | V | I | W | D | S | T | S |
| Q | V | K | N | V | I | W | D | S | T | S |
| L | I | Q | S | V | I | W | D | S | T | S |
| Q | I | Q | S | V | I | W | D | S | T | S |
| L | V | Q | S | V | I | W | D | S | T | S |
| Q | V | Q | S | V | I | W | D | S | T | S |
| L | I | K | S | V | I | W | D | S | T | S |
| Q | I | K | S | V | I | W | D | S | T | S |
| L | V | K | S | V | I | W | D | S | T | S |
| Q | V | K | S | V | I | W | D | S | T | S |
| L | I | Q | N | I | I | W | D | S | T | S |
| Q | I | Q | N | I | I | W | D | S | T | S |
| L | V | Q | N | I | I | W | D | S | T | S |
| Q | V | Q | N | I | I | W | D | S | T | S |
| L | I | K | N | I | I | W | D | S | T | S |
| Q | I | K | N | I | I | W | D | S | T | S |
| L | V | K | N | I | I | W | D | S | T | S |
| Q | V | K | N | I | I | W | D | S | T | S |
| L | I | Q | S | I | I | W | D | S | T | S |
| Q | I | Q | S | I | I | W | D | S | T | S |
| L | V | Q | S | I | I | W | D | S | T | S |
| Q | V | Q | S | I | I | W | D | S | T | S |
| L | I | K | S | I | I | W | D | S | T | S |
| Q | I | K | S | I | I | W | D | S | T | S |
| L | V | K | S | I | I | W | D | S | T | S |
| Q | V | K | S | I | I | W | D | S | T | S |
| L | I | Q | N | V | S | W | D | S | T | S |
| Q | I | Q | N | V | S | W | D | S | T | S |
| L | V | Q | N | V | S | W | D | S | T | S |
| Q | V | Q | N | V | S | W | D | S | T | S |
| L | I | K | N | V | S | W | D | S | T | S |
| Q | I | K | N | V | S | W | D | S | T | S |
| L | V | K | N | V | S | W | D | S | T | S |
| Q | V | K | N | V | S | W | D | S | T | S |
| L | I | Q | S | V | S | W | D | S | T | S |
| Q | I | Q | S | V | S | W | D | S | T | S |
| L | V | Q | S | V | S | W | D | S | T | S |
| Q | V | Q | S | V | S | W | D | S | T | S |
| L | I | K | S | V | S | W | D | S | T | S |
| Q | I | K | S | V | S | W | D | S | T | S |
| L | V | K | S | V | S | W | D | S | T | S |
| Q | V | K | S | V | S | W | D | S | T | S |
| L | I | Q | N | I | S | W | D | S | T | S |
| Q | I | Q | N | I | S | W | D | S | T | S |
| L | V | Q | N | I | S | W | D | S | T | S |
| Q | V | Q | N | I | S | W | D | S | T | S |
| L | I | K | N | I | S | W | D | S | T | S |
| Q | I | K | N | I | S | W | D | S | T | S |
| L | V | K | N | I | S | W | D | S | T | S |
| Q | V | K | N | I | S | W | D | S | T | S |
| L | I | Q | S | I | S | W | D | S | T | S |
| Q | I | Q | S | I | S | W | D | S | T | S |
| L | V | Q | S | I | S | W | D | S | T | S |
| Q | V | Q | S | I | S | W | D | S | T | S |
| L | I | K | S | I | S | W | D | S | T | S |
| Q | I | K | S | I | S | W | D | S | T | S |
| L | V | K | S | I | S | W | D | S | T | S |
| Q | V | K | S | I | S | W | D | S | T | S |
| L | I | Q | N | V | I | Y | G | S | T | S |
| Q | I | Q | N | V | I | Y | G | S | T | S |
| L | V | Q | N | V | I | Y | G | S | T | S |
| Q | V | Q | N | V | I | Y | G | S | T | S |
| L | I | K | N | V | I | Y | G | S | T | S |
| Q | I | K | N | V | I | Y | G | S | T | S |
| L | V | K | N | V | I | Y | G | S | T | S |
|

TABLE 7-continued

| Exemplary Mutations of 4B4 Heavy Chain (SEQ ID NO: 2) to Germline at the Indicated Residue Number | | | | | | | | | | |
|---|---|---|---|---|---|---|---|---|---|---|
| 3 | 5 | 19 | 31 | 34 | 35 | 47 | 66 | 72 | 77 | 103 |
| Q | I | Q | S | V | I | W | G | S | T | S |
| L | V | Q | S | V | I | W | G | S | T | S |
| Q | V | Q | S | V | I | W | G | S | T | S |
| L | I | K | S | V | I | W | G | S | T | S |
| Q | I | K | S | V | I | W | G | S | T | S |
| L | V | K | S | V | I | W | G | S | T | S |
| Q | V | K | S | V | I | W | G | S | T | S |
| L | I | Q | N | I | I | W | G | S | T | S |
| Q | I | Q | N | I | I | W | G | S | T | S |
| L | V | Q | N | I | I | W | G | S | T | S |
| Q | V | Q | N | I | I | W | G | S | T | S |
| L | I | K | N | I | I | W | G | S | T | S |
| Q | I | K | N | I | I | W | G | S | T | S |
| L | V | K | N | I | I | W | G | S | T | S |
| Q | V | K | N | I | I | W | G | S | T | S |
| L | I | Q | S | I | I | W | G | S | T | S |
| Q | I | Q | S | I | I | W | G | S | T | S |
| L | V | Q | S | I | I | W | G | S | T | S |
| Q | V | Q | S | I | I | W | G | S | T | S |
| L | I | K | S | I | I | W | G | S | T | S |
| Q | I | K | S | I | I | W | G | S | T | S |
| L | V | K | S | I | I | W | G | S | T | S |
| Q | V | K | S | I | I | W | G | S | T | S |
| L | I | Q | N | V | S | W | G | S | T | S |
| Q | I | Q | N | V | S | W | G | S | T | S |
| L | V | Q | N | V | S | W | G | S | T | S |
| Q | V | Q | N | V | S | W | G | S | T | S |
| L | I | K | N | V | S | W | G | S | T | S |
| Q | I | K | N | V | S | W | G | S | T | S |
| L | V | K | N | V | S | W | G | S | T | S |
| Q | V | K | N | V | S | W | G | S | T | S |
| L | I | Q | S | V | S | W | G | S | T | S |
| Q | I | Q | S | V | S | W | G | S | T | S |
| L | V | Q | S | V | S | W | G | S | T | S |
| Q | V | Q | S | V | S | W | G | S | T | S |
| L | I | K | S | V | S | W | G | S | T | S |
| Q | I | K | S | V | S | W | G | S | T | S |
| L | V | K | S | V | S | W | G | S | T | S |
| Q | V | K | S | V | S | W | G | S | T | S |
| L | I | Q | N | I | S | W | G | S | T | S |
| Q | I | Q | N | I | S | W | G | S | T | S |
| L | V | Q | N | I | S | W | G | S | T | S |
| Q | V | Q | N | I | S | W | G | S | T | S |
| L | I | K | N | I | S | W | G | S | T | S |
| Q | I | K | N | I | S | W | G | S | T | S |
| L | V | K | N | I | S | W | G | S | T | S |
| Q | V | K | N | I | S | W | G | S | T | S |
| L | I | Q | S | I | S | W | G | S | T | S |
| Q | I | Q | S | I | S | W | G | S | T | S |
| L | V | Q | S | I | S | W | G | S | T | S |
| Q | V | Q | S | I | S | W | G | S | T | S |
| L | I | K | S | I | S | W | G | S | T | S |
| Q | I | K | S | I | S | W | G | S | T | S |
| L | V | K | S | I | S | W | G | S | T | S |
| Q | V | K | S | I | S | W | G | S | T | S |
| L | I | Q | N | V | I | Y | D | T | T | S |
| Q | I | Q | N | V | I | Y | D | T | T | S |
| L | V | Q | N | V | I | Y | D | T | T | S |
| Q | V | Q | N | V | I | Y | D | T | T | S |
| L | I | K | N | V | I | Y | D | T | T | S |
| Q | I | K | N | V | I | Y | D | T | T | S |
| L | V | K | N | V | I | Y | D | T | T | S |
| Q | V | K | N | V | I | Y | D | T | T | S |
| L | I | Q | S | V | I | Y | D | T | T | S |
| Q | I | Q | S | V | I | Y | D | T | T | S |
| L | V | Q | S | V | I | Y | D | T | T | S |
| Q | V | Q | S | V | I | Y | D | T | T | S |
| L | I | K | S | V | I | Y | D | T | T | S |
| Q | I | K | S | V | I | Y | D | T | T | S |
| L | V | K | S | V | I | Y | D | T | T | S |
| Q | V | K | S | V | I | Y | D | T | T | S |
| L | I | Q | N | I | I | Y | D | T | T | S |
| Q | I | Q | N | I | I | Y | D | T | T | S |
| L | V | Q | N | I | I | Y | D | T | T | S |
| Q | V | Q | N | I | I | Y | D | T | T | S |

TABLE 7-continued

| Exemplary Mutations of 4B4 Heavy Chain (SEQ ID NO: 2) to Germline at the Indicated Residue Number | | | | | | | | | | |
|---|---|---|---|---|---|---|---|---|---|---|
| 3 | 5 | 19 | 31 | 34 | 35 | 47 | 66 | 72 | 77 | 103 |
| L | I | K | N | I | I | Y | D | T | T | S |
| Q | I | K | N | I | I | Y | D | T | T | S |
| L | V | K | N | I | I | Y | D | T | T | S |
| Q | V | K | N | I | I | Y | D | T | T | S |
| L | I | Q | S | I | I | Y | D | T | T | S |
| Q | I | Q | S | I | I | Y | D | T | T | S |
| L | V | Q | S | I | I | Y | D | T | T | S |
| Q | V | Q | S | I | I | Y | D | T | T | S |
| L | I | K | S | I | I | Y | D | T | T | S |
| Q | I | K | S | I | I | Y | D | T | T | S |
| L | V | K | S | I | I | Y | D | T | T | S |
| Q | V | K | S | I | I | Y | D | T | T | S |
| L | I | Q | N | V | S | Y | D | T | T | S |
| Q | I | Q | N | V | S | Y | D | T | T | S |
| L | V | Q | N | V | S | Y | D | T | T | S |
| Q | V | Q | N | V | S | Y | D | T | T | S |
| L | I | K | N | V | S | Y | D | T | T | S |
| Q | I | K | N | V | S | Y | D | T | T | S |
| L | V | K | N | V | S | Y | D | T | T | S |
| Q | V | K | N | V | S | Y | D | T | T | S |
| L | I | Q | S | V | S | Y | D | T | T | S |
| Q | I | Q | S | V | S | Y | D | T | T | S |
| L | V | Q | S | V | S | Y | D | T | T | S |
| Q | V | Q | S | V | S | Y | D | T | T | S |
| L | I | K | S | V | S | Y | D | T | T | S |
| Q | I | K | S | V | S | Y | D | T | T | S |
| L | V | K | S | V | S | Y | D | T | T | S |
| Q | V | K | S | V | S | Y | D | T | T | S |
| L | I | Q | N | I | S | Y | D | T | T | S |
| Q | I | Q | N | I | S | Y | D | T | T | S |
| L | V | Q | N | I | S | Y | D | T | T | S |
| Q | V | Q | N | I | S | Y | D | T | T | S |
| L | I | K | N | I | S | Y | D | T | T | S |
| Q | I | K | N | I | S | Y | D | T | T | S |
| L | V | K | N | I | S | Y | D | T | T | S |
| Q | V | K | N | I | S | Y | D | T | T | S |
| L | I | Q | S | I | S | Y | D | T | T | S |
| Q | I | Q | S | I | S | Y | D | T | T | S |
| L | V | Q | S | I | S | Y | D | T | T | S |
| Q | V | Q | S | I | S | Y | D | T | T | S |
| L | I | K | S | I | S | Y | D | T | T | S |
| Q | I | K | S | I | S | Y | D | T | T | S |
| L | V | K | S | I | S | Y | D | T | T | S |
| Q | V | K | S | I | S | Y | D | T | T | S |
| L | I | Q | N | V | I | W | D | T | T | S |
| Q | I | Q | N | V | I | W | D | T | T | S |
| L | V | Q | N | V | I | W | D | T | T | S |
| Q | V | Q | N | V | I | W | D | T | T | S |
| L | I | K | N | V | I | W | D | T | T | S |
| Q | I | K | N | V | I | W | D | T | T | S |
| L | V | K | N | V | I | W | D | T | T | S |
| Q | V | K | N | V | I | W | D | T | T | S |
| L | I | Q | S | V | I | W | D | T | T | S |
| Q | I | Q | S | V | I | W | D | T | T | S |
| L | V | Q | S | V | I | W | D | T | T | S |
| Q | V | Q | S | V | I | W | D | T | T | S |
| L | I | K | S | V | I | W | D | T | T | S |
| Q | I | K | S | V | I | W | D | T | T | S |
| L | V | K | S | V | I | W | D | T | T | S |
| Q | V | K | S | V | I | W | D | T | T | S |
| L | I | Q | N | I | I | W | D | T | T | S |
| Q | I | Q | N | I | I | W | D | T | T | S |
| L | V | Q | N | I | I | W | D | T | T | S |
| Q | V | Q | N | I | I | W | D | T | T | S |
| L | I | K | N | I | I | W | D | T | T | S |
| Q | I | K | N | I | I | W | D | T | T | S |
| L | V | K | N | I | I | W | D | T | T | S |
| Q | V | K | N | I | I | W | D | T | T | S |
| L | I | Q | S | I | I | W | D | T | T | S |
| Q | I | Q | S | I | I | W | D | T | T | S |
| L | V | Q | S | I | I | W | D | T | T | S |
| Q | V | Q | S | I | I | W | D | T | T | S |
| L | I | K | S | I | I | W | D | T | T | S |
| Q | I | K | S | I | I | W | D | T | T | S |
| L | V | K | S | I | I | W | D | T | T | S |

TABLE 7-continued

Exemplary Mutations of 4B4 Heavy Chain (SEQ ID NO: 2) to Germline at the Indicated Residue Number

| 3 | 5 | 19 | 31 | 34 | 35 | 47 | 66 | 72 | 77 | 103 |
|---|---|----|----|----|----|----|----|----|----|-----|
| Q | V | K | S | I | I | W | D | T | T | S |
| L | I | Q | N | V | S | W | D | T | T | S |
| Q | I | Q | N | V | S | W | D | T | T | S |
| L | V | Q | N | V | S | W | D | T | T | S |
| Q | V | Q | N | V | S | W | D | T | T | S |
| L | I | K | N | V | S | W | D | T | T | S |
| Q | I | K | N | V | S | W | D | T | T | S |
| L | V | K | N | V | S | W | D | T | T | S |
| Q | V | K | N | V | S | W | D | T | T | S |
| L | I | Q | S | V | S | W | D | T | T | S |
| Q | I | Q | S | V | S | W | D | T | T | S |
| L | V | Q | S | V | S | W | D | T | T | S |
| Q | V | Q | S | V | S | W | D | T | T | S |
| L | I | K | S | V | S | W | D | T | T | S |
| Q | I | K | S | V | S | W | D | T | T | S |
| L | V | K | S | V | S | W | D | T | T | S |
| Q | V | K | S | V | S | W | D | T | T | S |
| L | I | Q | N | I | S | W | D | T | T | S |
| Q | I | Q | N | I | S | W | D | T | T | S |
| L | V | Q | N | I | S | W | D | T | T | S |
| Q | V | Q | N | I | S | W | D | T | T | S |
| L | I | K | N | I | S | W | D | T | T | S |
| Q | I | K | N | I | S | W | D | T | T | S |
| L | V | K | N | I | S | W | D | T | T | S |
| Q | V | K | N | I | S | W | D | T | T | S |
| L | I | Q | S | I | S | W | D | T | T | S |
| Q | I | Q | S | I | S | W | D | T | T | S |
| L | V | Q | S | I | S | W | D | T | T | S |
| Q | V | Q | S | I | S | W | D | T | T | S |
| L | I | K | S | I | S | W | D | T | T | S |
| Q | I | K | S | I | S | W | D | T | T | S |
| L | V | K | S | I | S | W | D | T | T | S |
| Q | V | K | S | I | S | W | D | T | T | S |
| L | I | Q | N | V | I | Y | G | T | T | S |
| Q | I | Q | N | V | I | Y | G | T | T | S |
| L | V | Q | N | V | I | Y | G | T | T | S |
| Q | V | Q | N | V | I | Y | G | T | T | S |
| L | I | K | N | V | I | Y | G | T | T | S |
| Q | I | K | N | V | I | Y | G | T | T | S |
| L | V | K | N | V | I | Y | G | T | T | S |
| Q | V | K | N | V | I | Y | G | T | T | S |
| L | I | Q | S | V | I | Y | G | T | T | S |
| Q | I | Q | S | V | I | Y | G | T | T | S |
| L | V | Q | S | V | I | Y | G | T | T | S |
| Q | V | Q | S | V | I | Y | G | T | T | S |
| L | I | K | S | V | I | Y | G | T | T | S |
| Q | I | K | S | V | I | Y | G | T | T | S |
| L | V | K | S | V | I | Y | G | T | T | S |
| Q | V | K | S | V | I | Y | G | T | T | S |
| L | I | Q | N | I | I | Y | G | T | T | S |
| Q | I | Q | N | I | I | Y | G | T | T | S |
| L | V | Q | N | I | I | Y | G | T | T | S |
| Q | V | Q | N | I | I | Y | G | T | T | S |
| L | I | K | N | I | I | Y | G | T | T | S |
| Q | I | K | N | I | I | Y | G | T | T | S |
| L | V | K | N | I | I | Y | G | T | T | S |
| Q | V | K | N | I | I | Y | G | T | T | S |
| L | I | Q | S | I | I | Y | G | T | T | S |
| Q | I | Q | S | I | I | Y | G | T | T | S |
| L | V | Q | S | I | I | Y | G | T | T | S |
| Q | V | Q | S | I | I | Y | G | T | T | S |
| L | I | K | S | I | I | Y | G | T | T | S |
| Q | I | K | S | I | I | Y | G | T | T | S |
| L | V | K | S | I | I | Y | G | T | T | S |
| Q | V | K | S | I | I | Y | G | T | T | S |
| L | I | Q | N | V | S | Y | G | T | T | S |
| Q | I | Q | N | V | S | Y | G | T | T | S |
| L | V | Q | N | V | S | Y | G | T | T | S |
| Q | V | Q | N | V | S | Y | G | T | T | S |
| L | I | K | N | V | S | Y | G | T | T | S |
| Q | I | K | N | V | S | Y | G | T | T | S |
| L | V | K | N | V | S | Y | G | T | T | S |
| Q | V | K | N | V | S | Y | G | T | T | S |
| L | I | Q | S | V | S | Y | G | T | T | S |
| Q | I | Q | S | V | S | Y | G | T | T | S |
| L | V | Q | S | V | S | Y | G | T | T | S |
| Q | V | Q | S | V | S | Y | G | T | T | S |
| L | I | K | S | V | S | Y | G | T | T | S |
| Q | I | K | S | V | S | Y | G | T | T | S |
| L | V | K | S | V | S | Y | G | T | T | S |
| Q | V | K | S | V | S | Y | G | T | T | S |
| L | I | Q | N | I | S | Y | G | T | T | S |
| Q | I | Q | N | I | S | Y | G | T | T | S |
| L | V | Q | N | I | S | Y | G | T | T | S |
| Q | V | Q | N | I | S | Y | G | T | T | S |
| L | I | K | N | I | S | Y | G | T | T | S |
| Q | I | K | N | I | S | Y | G | T | T | S |
| L | V | K | N | I | S | Y | G | T | T | S |
| Q | V | K | N | I | S | Y | G | T | T | S |
| L | I | Q | S | I | S | Y | G | T | T | S |
| Q | I | Q | S | I | S | Y | G | T | T | S |
| L | V | Q | S | I | S | Y | G | T | T | S |
| Q | V | Q | S | I | S | Y | G | T | T | S |
| L | I | K | S | I | S | Y | G | T | T | S |
| Q | I | K | S | I | S | Y | G | T | T | S |
| L | V | K | S | V | I | W | G | T | T | S |
| Q | I | Q | N | V | I | W | G | T | T | S |
| L | V | Q | N | V | I | W | G | T | T | S |
| Q | V | Q | N | V | I | W | G | T | T | S |
| L | I | K | N | V | I | W | G | T | T | S |
| Q | I | K | N | V | I | W | G | T | T | S |
| L | V | K | N | V | I | W | G | T | T | S |
| Q | V | K | N | V | I | W | G | T | T | S |
| L | I | Q | S | V | I | W | G | T | T | S |
| Q | I | Q | S | V | I | W | G | T | T | S |
| L | V | Q | S | V | I | W | G | T | T | S |
| Q | V | Q | S | V | I | W | G | T | T | S |
| L | I | K | S | V | I | W | G | T | T | S |
| Q | I | K | S | V | I | W | G | T | T | S |
| L | V | K | S | V | I | W | G | T | T | S |
| Q | V | K | S | V | I | W | G | T | T | S |
| L | I | Q | N | I | I | W | G | T | T | S |
| Q | I | Q | N | I | I | W | G | T | T | S |
| L | V | Q | N | I | I | W | G | T | T | S |
| Q | V | Q | N | I | I | W | G | T | T | S |
| L | I | K | N | I | I | W | G | T | T | S |
| Q | I | K | N | I | I | W | G | T | T | S |
| L | V | K | N | I | I | W | G | T | T | S |
| Q | V | K | N | I | I | W | G | T | T | S |
| L | I | Q | S | I | I | W | G | T | T | S |
| Q | I | Q | S | I | I | W | G | T | T | S |
| L | V | Q | S | I | I | W | G | T | T | S |
| Q | V | Q | S | I | I | W | G | T | T | S |
| L | I | K | S | I | I | W | G | T | T | S |
| Q | I | K | S | I | I | W | G | T | T | S |
| L | V | K | S | I | I | W | G | T | T | S |
| Q | V | K | S | I | I | W | G | T | T | S |
| L | I | Q | N | V | S | W | G | T | T | S |
| Q | I | Q | N | V | S | W | G | T | T | S |
| L | V | Q | N | V | S | W | G | T | T | S |
| Q | V | Q | N | V | S | W | G | T | T | S |
| L | I | K | N | V | S | W | G | T | T | S |
| Q | I | K | N | V | S | W | G | T | T | S |
| L | V | K | N | V | S | W | G | T | T | S |
| Q | V | K | N | V | S | W | G | T | T | S |
| L | I | Q | S | V | S | W | G | T | T | S |
| Q | I | Q | S | V | S | W | G | T | T | S |
| L | V | Q | S | V | S | W | G | T | T | S |
| Q | V | Q | S | V | S | W | G | T | T | S |
| L | I | K | S | V | S | W | G | T | T | S |
| Q | I | K | S | V | S | W | G | T | T | S |
| L | V | K | S | V | S | W | G | T | T | S |
| Q | V | K | S | V | S | W | G | T | T | S |
| L | I | Q | N | I | S | W | G | T | T | S |
| Q | I | Q | N | I | S | W | G | T | T | S |
| L | V | Q | N | I | S | W | G | T | T | S |
| Q | V | Q | N | I | S | W | G | T | T | S |
| L | I | K | N | I | S | W | G | T | T | S |

TABLE 7-continued

Exemplary Mutations of 4B4 Heavy Chain (SEQ ID NO: 2) to Germline at the Indicated Residue Number

| 3 | 5 | 19 | 31 | 34 | 35 | 47 | 66 | 72 | 77 | 103 |
|---|---|---|---|---|---|---|---|---|---|---|
| Q | I | K | N | I | S | W | G | T | T | S |
| L | V | K | N | I | S | W | G | T | T | S |
| Q | V | K | N | I | S | W | G | T | T | S |
| L | I | Q | S | I | S | W | G | T | T | S |
| Q | I | Q | S | I | S | W | G | T | T | S |
| L | V | Q | S | I | S | W | G | T | T | S |
| Q | V | Q | S | I | S | W | G | T | T | S |
| L | I | K | S | I | S | W | G | T | T | S |
| Q | I | K | S | I | S | W | G | T | T | S |
| L | V | K | S | I | S | W | G | T | T | S |
| Q | V | K | S | I | S | W | G | T | T | S |
| L | I | Q | N | V | I | Y | D | S | S | S |
| Q | I | Q | N | V | I | Y | D | S | S | S |
| L | V | Q | N | V | I | Y | D | S | S | S |
| Q | V | Q | N | V | I | Y | D | S | S | S |
| L | I | K | N | V | I | Y | D | S | S | S |
| Q | I | K | N | V | I | Y | D | S | S | S |
| L | V | K | N | V | I | Y | D | S | S | S |
| Q | V | K | N | V | I | Y | D | S | S | S |
| L | I | Q | S | V | I | Y | D | S | S | S |
| Q | I | Q | S | V | I | Y | D | S | S | S |
| L | V | Q | S | V | I | Y | D | S | S | S |
| Q | V | Q | S | V | I | Y | D | S | S | S |
| L | I | K | S | V | I | Y | D | S | S | S |
| Q | I | K | S | V | I | Y | D | S | S | S |
| L | V | K | S | V | I | Y | D | S | S | S |
| Q | V | K | S | V | I | Y | D | S | S | S |
| L | I | Q | N | I | I | Y | D | S | S | S |
| Q | I | Q | N | I | I | Y | D | S | S | S |
| L | V | Q | N | I | I | Y | D | S | S | S |
| Q | V | Q | N | I | I | Y | D | S | S | S |
| L | I | K | N | I | I | Y | D | S | S | S |
| Q | I | K | N | I | I | Y | D | S | S | S |
| L | V | K | N | I | I | Y | D | S | S | S |
| Q | V | K | N | I | I | Y | D | S | S | S |
| L | I | Q | S | I | I | Y | D | S | S | S |
| Q | I | Q | S | I | I | Y | D | S | S | S |
| L | V | Q | S | I | I | Y | D | S | S | S |
| Q | V | Q | S | I | I | Y | D | S | S | S |
| L | I | K | S | I | I | Y | D | S | S | S |
| Q | I | K | S | I | I | Y | D | S | S | S |
| L | V | K | S | I | I | Y | D | S | S | S |
| Q | V | K | S | I | I | Y | D | S | S | S |
| L | I | Q | N | V | S | Y | D | S | S | S |
| Q | I | Q | N | V | S | Y | D | S | S | S |
| L | V | Q | N | V | S | Y | D | S | S | S |
| Q | V | Q | N | V | S | Y | D | S | S | S |
| L | I | K | N | V | S | Y | D | S | S | S |
| Q | I | K | N | V | S | Y | D | S | S | S |
| L | V | K | N | V | S | Y | D | S | S | S |
| Q | V | K | N | V | S | Y | D | S | S | S |
| L | I | Q | S | V | S | Y | D | S | S | S |
| Q | I | Q | S | V | S | Y | D | S | S | S |
| L | V | Q | S | V | S | Y | D | S | S | S |
| Q | V | Q | S | V | S | Y | D | S | S | S |
| L | I | K | S | V | S | Y | D | S | S | S |
| Q | I | K | S | V | S | Y | D | S | S | S |
| L | V | K | S | V | S | Y | D | S | S | S |
| Q | V | K | S | V | S | Y | D | S | S | S |
| L | I | Q | N | I | S | Y | D | S | S | S |
| Q | I | Q | N | I | S | Y | D | S | S | S |
| L | V | Q | N | I | S | Y | D | S | S | S |
| Q | V | Q | N | I | S | Y | D | S | S | S |
| L | I | K | N | I | S | Y | D | S | S | S |
| Q | I | K | N | I | S | Y | D | S | S | S |
| L | V | K | N | I | S | Y | D | S | S | S |
| Q | V | K | N | I | S | Y | D | S | S | S |
| L | I | Q | S | I | S | Y | D | S | S | S |
| Q | I | Q | S | I | S | Y | D | S | S | S |
| L | V | Q | S | I | S | Y | D | S | S | S |
| Q | V | Q | S | I | S | Y | D | S | S | S |
| L | I | K | S | I | S | Y | D | S | S | S |
| Q | I | K | S | I | S | Y | D | S | S | S |
| L | V | K | S | I | S | Y | D | S | S | S |
| Q | V | K | S | I | S | Y | D | S | S | S |
| L | I | Q | N | V | I | W | D | S | S | S |
| Q | I | Q | N | V | I | W | D | S | S | S |
| L | V | Q | N | V | I | W | D | S |

TABLE 7-continued

Exemplary Mutations of 4B4 Heavy Chain (SEQ ID NO: 2) to Germline at the Indicated Residue Number

| 3 | 5 | 19 | 31 | 34 | 35 | 47 | 66 | 72 | 77 | 103 |
|---|---|---|---|---|---|---|---|---|---|---|
| Q | V | Q | S | V | I | Y | G | S | S | S |
| L | I | K | S | V | I | Y | G | S | S | S |
| Q | I | K | S | V | I | Y | G | S | S | S |
| L | V | K | S | V | I | Y | G | S | S | S |
| Q | V | K | S | V | I | Y | G | S | S | S |
| L | I | Q | N | I | I | Y | G | S | S | S |
| Q | I | Q | N | I | I | Y | G | S | S | S |
| L | V | Q | N | I | I | Y | G | S | S | S |
| Q | V | Q | N | I | I | Y | G | S | S | S |
| L | I | K | N | I | I | Y | G | S | S | S |
| Q | I | K | N | I | I | Y | G | S | S | S |
| L | V | K | N | I | I | Y | G | S | S | S |
| Q | V | K | N | I | I | Y | G | S | S | S |
| L | I | Q | S | I | I | Y | G | S | S | S |
| Q | I | Q | S | I | I | Y | G | S | S | S |
| L | V | Q | S | I | I | Y | G | S | S | S |
| Q | V | Q | S | I | I | Y | G | S | S | S |
| L | I | K | S | I | I | Y | G | S | S | S |
| Q | I | K | S | I | I | Y | G | S | S | S |
| L | V | K | S | I | I | Y | G | S | S | S |
| Q | V | K | S | I | I | Y | G | S | S | S |
| L | I | Q | N | V | S | Y | G | S | S | S |
| Q | I | Q | N | V | S | Y | G | S | S | S |
| L | V | Q | N | V | S | Y | G | S | S | S |
| Q | V | Q | N | V | S | Y | G | S | S | S |
| L | I | K | N | V | S | Y | G | S | S | S |
| Q | I | K | N | V | S | Y | G | S | S | S |
| L | V | K | N | V | S | Y | G | S | S | S |
| Q | V | K | N | V | S | Y | G | S | S | S |
| L | I | Q | S | V | S | Y | G | S | S | S |
| Q | I | Q | S | V | S | Y | G | S | S | S |
| L | V | Q | S | V | S | Y | G | S | S | S |
| Q | V | Q | S | V | S | Y | G | S | S | S |
| L | I | K | S | V | S | Y | G | S | S | S |
| Q | I | K | S | V | S | Y | G | S | S | S |
| L | V | K | S | V | S | Y | G | S | S | S |
| Q | V | K | S | V | S | Y | G | S | S | S |
| L | I | Q | N | I | S | Y | G | S | S | S |
| Q | I | Q | N | I | S | Y | G | S | S | S |
| L | V | Q | N | I | S | Y | G | S | S | S |
| Q | V | Q | N | I | S | Y | G | S | S | S |
| L | I | K | N | I | S | Y | G | S | S | S |
| Q | I | K | N | I | S | Y | G | S | S | S |
| L | V | K | N | I | S | Y | G | S | S | S |
| Q | V | K | N | I | S | Y | G | S | S | S |
| L | I | Q | S | I | S | Y | G | S | S | S |
| Q | I | Q | S | I | S | Y | G | S | S | S |
| L | V | Q | S | I | S | Y | G | S | S | S |
| Q | V | Q | S | I | S | Y | G | S | S | S |
| L | I | K | S | I | S | Y | G | S | S | S |
| Q | I | K | S | I | S | Y | G | S | S | S |
| L | V | K | S | I | S | Y | G | S | S | S |
| Q | V | K | S | I | S | Y | G | S | S | S |
| L | I | Q | N | V | I | W | G | S | S | S |
| Q | I | Q | N | V | I | W | G | S | S | S |
| L | V | Q | N | V | I | W | G | S | S | S |
| Q | V | Q | N | V | I | W | G | S | S | S |
| L | I | K | N | V | I | W | G | S | S | S |
| Q | I | K | N | V | I | W | G | S | S | S |
| L | V | K | N | V | I | W | G | S | S | S |
| Q | V | K | N | V | I | W | G | S | S | S |
| L | I | Q | S | V | I | W | G | S | S | S |
| Q | I | Q | S | V | I | W | G | S | S | S |
| L | V | Q | S | V | I | W | G | S | S | S |
| Q | V | Q | S | V | I | W | G | S | S | S |
| L | I | K | S | V | I | W | G | S | S | S |
| Q | I | K | S | V | I | W | G | S | S | S |
| L | V | K | S | V | I | W | G | S | S | S |
| Q | V | K | S | V | I | W | G | S | S | S |
| L | I | Q | N | I | I | W | G | S | S | S |
| Q | I | Q | N | I | I | W | G | S | S | S |
| L | V | Q | N | I | I | W | G | S | S | S |
| Q | V | Q | N | I | I | W | G | S | S | S |
| L | I | K | N | I | I | W | G | S | S | S |
| Q | I | K | N | I | I | W | G | S | S | S |
| L | V | K | N | I | I | W | G | S | S | S |
| Q | V | K | N | I | I | W | G | S | S | S |
| L | I | Q | S | I | I | W | G | S | S | S |
| Q | I | Q | S | I | I | W | G | S | S | S |
| L | V | Q | S | I | I | W | G | S | S | S |
| Q | V | Q | S | I | I | W | G | S | S | S |
| L | I | K | S | I | I | W | G | S | S | S |
| Q | I | K | S | I | I | W | G | S | S | S |
| L | V | K | S | I | I | W | G | S | S | S |
| Q | V | K | S | I | I | W | G | S | S | S |
| L | I | Q | N | V | S | W | G | S | S | S |
| Q | I | Q | N | V | S | W | G | S | S | S |
| L | V | Q | N | V | S | W | G | S | S | S |
| Q | V | Q | N | V | S | W | G | S | S | S |
| L | I | K | N | V | S | W | G | S | S | S |
| Q | I | K | N | V | S | W | G | S | S | S |
| L | V | K | N | V | S | W | G | S | S | S |
| Q | V | K | N | V | S | W | G | S | S | S |
| L | I | Q | S | V | S | W | G | S | S | S |
| Q | I | Q | S | V | S | W | G | S | S | S |
| L | V | Q | S | V | S | W | G | S | S | S |
| Q | V | Q | S | V | S | W | G | S | S | S |
| L | I | K | S | V | S | W | G | S | S | S |
| Q | I | K | S | V | S | W | G | S | S | S |
| L | V | K | S | V | S | W | G | S | S | S |
| Q | V | K | S | V | S | W | G | S | S | S |
| L | I | Q | N | I | S | W | G | S | S | S |
| Q | I | Q | N | I | S | W | G | S | S | S |
| L | V | Q | N | I | S | W | G | S | S | S |
| Q | V | Q | N | I | S | W | G | S | S | S |
| L | I | K | N | I | S | W | G | S | S | S |
| Q | I | K | N | I | S | W | G | S | S | S |
| L | V | K | N | I | S | W | G | S | S | S |
| Q | V | K | N | I | S | W | G | S | S | S |
| L | I | Q | S | I | S | W | G | S | S | S |
| Q | I | Q | S | I | S | W | G | S | S | S |
| L | V | Q | S | I | S | W | G | S | S | S |
| Q | V | Q | S | I | S | W | G | S | S | S |
| L | I | K | S | I | S | W | G | S | S | S |
| Q | I | K | S | I | S | W | G | S | S | S |
| L | V | K | S | I | S | W | G | S | S | S |
| Q | V | K | S | I | S | W | G | S | S | S |
| L | I | Q | N | V | I | Y | D | T | S | S |
| Q | I | Q | N | V | I | Y | D | T | S | S |
| L | V | Q | N | V | I | Y | D | T | S | S |
| Q | V | Q | N | V | I | Y | D | T | S | S |
| L | I | K | N | V | I | Y | D | T | S | S |
| Q | I | K | N | V | I | Y | D | T | S | S |
| L | V | K | N | V | I | Y | D | T | S | S |
| Q | V | K | N | V | I | Y | D | T | S | S |
| L | I | Q | S | V | I | Y | D | T | S | S |
| Q | I | Q | S | V | I | Y | D | T | S | S |
| L | V | Q | S | V | I | Y | D | T | S | S |
| Q | V | Q | S | V | I | Y | D | T | S | S |
| L | I | K | S | V | I | Y | D | T | S | S |
| Q | I | K | S | V | I | Y | D | T | S | S |
| L | V | K | S | V | I | Y | D | T | S | S |
| Q | V | K | S | V | I | Y | D | T | S | S |
| L | I | Q | N | I | I | Y | D | T | S | S |
| Q | I | Q | N | I | I | Y | D | T | S | S |
| L | V | Q | N | I | I | Y | D | T | S | S |
| Q | V | Q | N | I | I | Y | D | T | S | S |
| L | I | K | N | I | I | Y | D | T | S | S |
| Q | I | K | N | I | I | Y | D | T | S | S |
| L | V | K | N | I | I | Y | D | T | S | S |
| Q | V | K | N | I | I | Y | D | T | S | S |
| L | I | Q | S | I | I | Y | D | T | S | S |
| Q | I | Q | S | I | I | Y | D | T | S | S |
| L | V | Q | S | I | I | Y | D | T | S | S |
| Q | V | Q | S | I | I | Y | D | T | S | S |
| L | I | K | S | I | I | Y | D | T | S | S |
| Q | I | K | S | I | I | Y | D | T | S | S |
| L | V | K | S | I | I | Y | D | T | S | S |
| Q | V | K | S | I | I | Y | D | T | S | S |
| L | I | Q | N | V | S | Y | D | T | S | S |

TABLE 7-continued

Exemplary Mutations of 4B4 Heavy Chain (SEQ ID NO: 2) to Germline at the Indicated Residue Number

| 3 | 5 | 19 | 31 | 34 | 35 | 47 | 66 | 72 | 77 | 103 |
|---|---|---|---|---|---|---|---|---|---|---|
| Q | I | Q | N | V | S | Y | D | T | S | S |
| L | V | Q | N | V | S | Y | D | T | S | S |
| Q | V | Q | N | V | S | Y | D | T | S | S |
| L | I | K | N | V | S | Y | D | T | S | S |
| Q | I | K | N | V | S | Y | D | T | S | S |
| L | V | K | N | V | S | Y | D | T | S | S |
| Q | V | K | N | V | S | Y | D | T | S | S |
| L | I | Q | S | V | S | Y | D | T | S | S |
| Q | I | Q | S | V | S | Y | D | T | S | S |
| L | V | Q | S | V | S | Y | D | T | S | S |
| Q | V | Q | S | V | S | Y | D | T | S | S |
| L | I | K | S | V | S | Y | D | T | S | S |
| Q | I | K | S | V | S | Y | D | T | S | S |
| L | V | K | S | V | S | Y | D | T | S | S |
| Q | V | K | S | V | S | Y | D | T | S | S |
| L | I | Q | N | I | S | Y | D | T | S | S |
| Q | I | Q | N | I | S | Y | D | T | S | S |
| L | V | Q | N | I | S | Y | D | T | S | S |
| Q | V | Q | N | I | S | Y | D | T | S | S |
| L | I | K | N | I | S | Y | D | T | S | S |
| Q | I | K | N | I | S | Y | D | T | S | S |
| L | V | K | N | I | S | Y | D | T | S | S |
| Q | V | K | N | I | S | Y | D | T | S | S |
| L | I | Q | S | I | S | Y | D | T | S | S |
| Q | I | Q | S | I | S | Y | D | T | S | S |
| L | V | Q | S | I | S | Y | D | T | S | S |
| Q | V | Q | S | I | S | Y | D | T | S | S |
| L | I | K | S | I | S | Y | D | T | S | S |
| Q | I | K | S | I | S | Y | D | T | S | S |
| L | V | K | S | I | S | Y | D | T | S | S |
| Q | V | K | S | I | S | Y | D | T | S | S |
| L | I | Q | N | V | I | W | D | T | S | S |
| Q | I | Q | N | V | I | W | D | T | S | S |
| L | V | Q | N | V | I | W | D | T | S | S |
| Q | V | Q | N | V | I | W | D | T | S | S |
| L | I | K | N | V | I | W | D | T | S | S |
| Q | I | K | N | V | I | W | D | T | S | S |
| L | V | K | N | V | I | W | D | T | S | S |
| Q | V | K | N | V | I | W | D | T | S | S |
| L | I | Q | S | V | I | W | D | T | S | S |
| Q | I | Q | S | V | I | W | D | T | S | S |
| L | V | Q | S | V | I | W | D | T | S | S |
| Q | V | Q | S | V | I | W | D | T | S | S |
| L | I | K | S | V | I | W | D | T | S | S |
| Q | I | K | S | V | I | W | D | T | S | S |
| L | V | K | S | V | I | W | D | T | S | S |
| Q | V | K | S | V | I | W | D | T | S | S |
| L | I | Q | N | I | I | W | D | T | S | S |
| Q | I | Q | N | I | I | W | D | T | S | S |
| L | V | Q | N | I | I | W | D | T | S | S |
| Q | V | Q | N | I | I | W | D | T | S | S |
| L | I | K | N | I | I | W | D | T | S | S |
| Q | I | K | N | I | I | W | D | T | S | S |
| L | V | K | N | I | I | W | D | T | S | S |
| Q | V | K | N | I | I | W | D | T | S | S |
| L | I | Q | S | I | I | W | D | T | S | S |
| Q | I | Q | S | I | I | W | D | T | S | S |
| L | V | Q | S | I | I | W | D | T | S | S |
| Q | V | Q | S | I | I | W | D | T | S | S |
| L | I | K | S | I | I | W | D | T | S | S |
| Q | I | K | S | I | I | W | D | T | S | S |
| L | V | K | S | I | I | W | D | T | S | S |
| Q | V | K | S | I | I | W | D | T | S | S |
| L | I | Q | N | V | S | W | D | T | S | S |
| Q | I | Q | N | V | S | W | D | T | S | S |
| L | V | Q | N | V | S | W | D | T | S | S |
| Q | V | Q | N | V | S | W | D | T | S | S |
| L | I | K | N | V | S | W | D | T | S | S |
| Q | I | K | N | V | S | W | D | T | S | S |
| L | V | K | N | V | S | W | D | T | S | S |
| Q | V | K | N | V | S | W | D | T | S | S |
| L | I | Q | S | V | S | W | D | T | S | S |
| Q | I | Q | S | V | S | W | D | T | S | S |
| L | V | Q | S | V | S | W | D | T | S | S |
| Q | V | Q | S | V | S | W | D | T | S | S |
| L | I | K | S | V | S | W | D | T | S | S |
| Q | I | K | S | V | S | W | D | T | S | S |
| L | V | K | S | V | S | W | D | T | S | S |
| Q | V | K | S | V | S | W | D | T | S | S |
| L | I | Q | N | I | S | W | D | T | S | S |
| Q | I | Q | N | I | S | W | D | T | S | S |
| L | V | Q | N | I | S | W | D | T | S | S |
| Q | V | Q | N | I | S | W | D | T | S | S |
| L | I | K | N | I | S | W | D | T | S | S |
| Q | I | K | N | I | S | W | D | T | S | S |
| L | V | K | N | I | S | W | D | T | S | S |
| Q | V | K | N | I | S | W | D | T | S | S |
| L | I | Q | S | I | S | W | D | T | S | S |
| Q | I | Q | S | I | S | W | D | T | S | S |
| L | V | Q | S | I | S | W | D | T | S | S |
| Q | V | Q | S | I | S | W | D | T | S | S |
| L | I | K | S | I | S | W | D | T | S | S |
| Q | I | K | S | I | S | W | D | T | S | S |
| L | V | K | S | I | S | W | D | T | S | S |
| Q | V | K | S | I | S | W | D | T | S | S |
| L | I | Q | N | V | I | Y | G | T | S | S |
| Q | I | Q | N | V | I | Y | G | T | S | S |
| L | V | Q | N | V | I | Y | G | T | S | S |
| Q | V | Q | N | V | I | Y | G | T | S | S |
| L | I | K | N | V | I | Y | G | T | S | S |
| Q | I | K | N | V | I | Y | G | T | S | S |
| L | V | K | N | V | I | Y | G | T | S | S |
| Q | V | K | N | V | I | Y | G | T | S | S |
| L | I | Q | S | V | I | Y | G | T | S | S |
| Q | I | Q | S | V | I | Y | G | T | S | S |
| L | V | Q | S | V | I | Y | G | T | S | S |
| Q | V | Q | S | V | I | Y | G | T | S | S |
| L | I | K | S | V | I | Y | G | T | S | S |
| Q | I | K | S | V | I | Y | G | T | S | S |
| L | V | K | S | V | I | Y | G | T | S | S |
| Q | V | K | S | V | I | Y | G | T | S | S |
| L | I | Q | N | I | I | Y | G | T | S | S |
| Q | I | Q | N | I | I | Y | G | T | S | S |
| L | V | Q | N | I | I | Y | G | T | S | S |
| Q | V | Q | N | I | I | Y | G | T | S | S |
| L | I | K | N | I | I | Y | G | T | S | S |
| Q | I | K | N | I | I | Y | G | T | S | S |
| L | V | K | N | I | I | Y | G | T | S | S |
| Q | V | K | N | I | I | Y | G | T | S | S |
| L | I | Q | S | I | I | Y | G | T | S | S |
| Q | I | Q | S | I | I | Y | G | T | S | S |
| L | V | Q | S | I | I | Y | G | T | S | S |
| Q | V | Q | S | I | I | Y | G | T | S | S |
| L | I | K | S | I | I | Y | G | T | S | S |
| Q | I | K | S | I | I | Y | G | T | S | S |
| L | V | K | S | I | I | Y | G | T | S | S |
| Q | V | K | S | I | I | Y | G | T | S | S |
| L | I | Q | N | V | S | Y | G | T | S | S |
| Q | I | Q | N | V | S | Y | G | T | S | S |
| L | V | Q | N | V | S | Y | G | T | S | S |
| Q | V | Q | N | V | S | Y | G | T | S | S |
| L | I | K | N | V | S | Y | G | T | S | S |
| Q | I | K | N | V | S | Y | G | T | S | S |
| L | V | K | N | V | S | Y | G | T | S | S |
| Q | V | K | N | V | S | Y | G | T | S | S |
| L | I | Q | S | V | S | Y | G | T | S | S |
| Q | I | Q | S | V | S | Y | G | T | S | S |
| L | V | Q | S | V | S | Y | G | T | S | S |
| Q | V | Q | S | V | S | Y | G | T | S | S |
| L | I | K | S | V | S | Y | G | T | S | S |
| Q | I | K | S | V | S | Y | G | T | S | S |
| L | V | K | S | V | S | Y | G | T | S | S |
| Q | V | K | S | V | S | Y | G | T | S | S |
| L | I | Q | N | I | S | Y | G | T | S | S |
| Q | I | Q | N | I | S | Y | G | T | S | S |
| L | V | Q | N | I | S | Y | G | T | S | S |
| Q | V | Q | N | I | S | Y | G | T | S | S |
| L | I | K | N | I | S | Y | G | T | S | S |
| Q | I | K | N | I | S | Y | G | T | S | S |
| L | V | K | N | I | S | Y | G | T | S | S |

TABLE 7-continued

Exemplary Mutations of 4B4 Heavy Chain (SEQ ID NO: 2) to Germline at the Indicated Residue Number

| 3 | 5 | 19 | 31 | 34 | 35 | 47 | 66 | 72 | 77 | 103 |
|---|---|---|---|---|---|---|---|---|---|---|
| Q | V | K | N | I | S | Y | G | T | S | S |
| L | I | Q | S | I | S | Y | G | T | S | S |
| Q | I | Q | S | I | S | Y | G | T | S | S |
| L | V | Q | S | I | S | Y | G | T | S | S |
| Q | V | Q | S | I | S | Y | G | T | S | S |
| L | I | K | S | I | S | Y | G | T | S | S |
| Q | I | K | S | I | S | Y | G | T | S | S |
| L | V | K | S | I | S | Y | G | T | S | S |
| Q | V | K | S | I | S | Y | G | T | S | S |
| L | I | Q | N | V | I | W | G | T | S | S |
| Q | I | Q | N | V | I | W | G | T | S | S |
| L | V | Q | N | V | I | W | G | T | S | S |
| Q | V | Q | N | V | I | W | G | T | S | S |
| L | I | K | N | V | I | W | G | T | S | S |
| Q | I | K | N | V | I | W | G | T | S | S |
| L | V | K | N | V | I | W | G | T | S | S |
| Q | V | K | N | V | I | W | G | T | S | S |
| L | I | Q | S | V | I | W | G | T | S | S |
| Q | I | Q | S | V | I | W | G | T | S | S |
| L | V | Q | S | V | I | W | G | T | S | S |
| Q | V | Q | S | V | I | W | G | T | S | S |
| L | I | K | S | V | I | W | G | T | S | S |
| Q | I | K | S | V | I | W | G | T | S | S |
| L | V | K | S | V | I | W | G | T | S | S |
| Q | V | K | S | V | I | W | G | T | S | S |
| L | I | Q | N | I | I | W | G | T | S | S |
| Q | I | Q | N | I | I | W | G | T | S | S |
| L | V | Q | N | I | I | W | G | T | S | S |
| Q | V | Q | N | I | I | W | G | T | S | S |
| L | I | K | N | I | I | W | G | T | S | S |
| Q | I | K | N | I | I | W | G | T | S | S |
| L | V | K | N | I | I | W | G | T | S | S |
| Q | V | K | N | I | I | W | G | T | S | S |
| L | I | Q | S | I | I | W | G | T | S | S |
| Q | I | Q | S | I | I | W | G | T | S | S |
| L | V | Q | S | I | I | W | G | T | S | S |
| Q | V | Q | S | I | I | W | G | T | S | S |
| L | I | K | S | I | I | W | G | T | S | S |
| Q | I | K | S | I | I | W | G | T | S | S |
| L | V | K | S | I | I | W | G | T | S | S |
| Q | V | K | S | I | I | W | G | T | S | S |
| L | I | Q | N | V | S | W | G | T | S | S |
| Q | I | Q | N | V | S | W | G | T | S | S |
| L | V | Q | N | V | S | W | G | T | S | S |
| Q | V | Q | N | V | S | W | G | T | S | S |
| L | I | K | N | V | S | W | G | T | S | S |
| Q | I | K | N | V | S | W | G | T | S | S |
| L | V | K | N | V | S | W | G | T | S | S |
| Q | V | K | N | V | S | W | G | T | S | S |
| L | I | Q | S | V | S | W | G | T | S | S |
| Q | I | Q | S | V | S | W | G | T | S | S |
| L | V | Q | S | V | S | W | G | T | S | S |
| Q | V | Q | S | V | S | W | G | T | S | S |
| L | I | K | S | V | S | W | G | T | S | S |
| Q | I | K | S | V | S | W | G | T | S | S |
| L | V | K | S | V | S | W | G | T | S | S |
| Q | V | K | S | V | S | W | G | T | S | S |
| L | I | Q | N | I | S | W | G | T | S | S |
| Q | I | Q | N | I | S | W | G | T | S | S |
| L | V | Q | N | I | S | W | G | T | S | S |
| Q | V | Q | N | I | S | W | G | T | S | S |
| L | I | K | N | I | S | W | G | T | S | S |
| Q | I | K | N | I | S | W | G | T | S | S |
| L | V | K | N | I | S | W | G | T | S | S |
| Q | V | K | N | I | S | W | G | T | S | S |
| L | I | Q | S | I | S | W | G | T | S | S |
| Q | I | Q | S | I | S | W | G | T | S | S |
| L | V | Q | S | I | S | W | G | T | S | S |
| Q | V | Q | S | I | S | W | G | T | S | S |
| L | I | K | S | I | S | W | G | T | S | S |
| Q | I | K | S | I | S | W | G | T | S | S |
| L | V | K | S | I | S | W | G | T | S | S |
| Q | V | K | S | I | S | W | G | T | S | S |
| L | I | Q | N | V | I | Y | D | S | T | Y |
| Q | I | Q | N | V | I | Y | D | S | T | Y |
| L | V | Q | N | V | I | Y | D | S | T | Y |
| Q | V | Q | N | V | I | Y | D | S | T | Y |
| L | I | K | N | V | I | Y | D | S | T | Y |
| Q | I | K | N | V | I | Y | D | S | T | Y |
| L | V | K | N | V | I | Y | D | S | T | Y |
| Q | V | K | N | V | I | Y | D | S | T | Y |
| L | I | Q | S | V | I | Y | D | S | T | Y |
| Q | I | Q | S | V | I | Y | D | S | T | Y |
| L | V | Q | S | V | I | Y | D | S | T | Y |
| Q | V | Q | S | V | I | Y | D | S | T | Y |
| L | I | K | S | V | I | Y | D | S | T | Y |
| Q | I | K | S | V | I | Y | D | S | T | Y |
| L | V | K | S | V | I | Y | D | S | T | Y |
| Q | V | K | S | V | I | Y | D | S | T | Y |
| L | I | Q | N | I | I | Y | D | S | T | Y |
| Q | I | Q | N | I | I | Y | D | S | T | Y |
| L | V | Q | N | I | I | Y | D | S | T | Y |
| Q | V | Q | N | I | I | Y | D | S | T | Y |
| L | I | K | N | I | I | Y | D | S | T | Y |
| Q | I | K | N | I | I | Y | D | S | T | Y |
| L | V | K | N | I | I | Y | D | S | T | Y |
| Q | V | K | N | I | I | Y | D | S | T | Y |
| L | I | Q | S | I | I | Y | D | S | T | Y |
| Q | I | Q | S | I | I | Y | D | S | T | Y |
| L | V | Q | S | I | I | Y | D | S | T | Y |
| Q | V | Q | S | I | I | Y | D | S | T | Y |
| L | I | K | S | I | I | Y | D | S | T | Y |
| Q | I | K | S | I | I | Y | D | S | T | Y |
| L | V | K | S | I | I | Y | D | S | T | Y |
| Q | V | K | S | I | I | Y | D | S | T | Y |
| L | I | Q | N | V | S | Y | D | S | T | Y |
| Q | I | Q | N | V | S | Y | D | S | T | Y |
| L | V | Q | N | V | S | Y | D | S | T | Y |
| Q | V | Q | N | V | S | Y | D | S | T | Y |
| L | I | K | N | V | S | Y | D | S | T | Y |
| Q | I | K | N | V | S | Y | D | S | T | Y |
| L | V | K | N | V | S | Y | D | S | T | Y |
| Q | V | K | N | V | S | Y | D | S | T | Y |
| L | I | Q | S | V | S | Y | D | S | T | Y |
| Q | I | Q | S | V | S | Y | D | S | T | Y |
| L | V | Q | S | V | S | Y | D | S | T | Y |
| Q | V | Q | S | V | S | Y | D | S | T | Y |
| L | I | K | S | V | S | Y | D | S | T | Y |
| Q | I | K | S | V | S | Y | D | S | T | Y |
| L | V | K | S | V | S | Y | D | S | T | Y |
| Q | V | K | S | V | S | Y | D | S | T | Y |
| L | I | Q | N | I | S | Y | D | S | T | Y |
| Q | I | Q | N | I | S | Y | D | S | T | Y |
| L | V | Q | N | I | S | Y | D | S | T | Y |
| Q | V | Q | N | I | S | Y | D | S | T | Y |
| L | I | K | N | I | S | Y | D | S | T | Y |
| Q | I | K | N | I | S | Y | D | S | T | Y |
| L | V | K | N | I | S | Y | D | S | T | Y |
| Q | V | K | N | I | S | Y | D | S | T | Y |
| L | I | Q | S | I | S | Y | D | S | T | Y |
| Q | I | Q | S | I | S | Y | D | S | T | Y |
| L | V | Q | S | I | S | Y | D | S | T | Y |
| Q | V | Q | S | I | S | Y | D | S | T | Y |
| L | I | K | S | I | S | Y | D | S | T | Y |
| Q | I | K | S | I | S | Y | D | S | T | Y |
| L | V | K | S | I | S | Y | D | S | T | Y |
| Q | V | K | S | I | S | Y | D | S | T | Y |
| L | I | Q | N | V | I | W | D | S | T | Y |
| Q | I | Q | N | V | I | W | D | S | T | Y |
| L | V | Q | N | V | I | W | D | S | T | Y |
| Q | V | Q | N | V | I | W | D | S | T | Y |
| L | I | K | N | V | I | W | D | S | T | Y |
| Q | I | K | N | V | I | W | D | S | T | Y |
| L | V | K | N | V | I | W | D | S | T | Y |
| Q | V | K | N | V | I | W | D | S | T | Y |
| L | I | Q | S | V | I | W | D | S | T | Y |
| Q | I | Q | S | V | I | W | D | S | T | Y |
| L | V | Q | S | V | I | W | D | S | T | Y |
| Q | V | Q | S | V | I | W | D | S | T | Y |
| L | I | K | S | V | I | W | D | S | T | Y |

TABLE 7-continued

Exemplary Mutations of 4B4 Heavy Chain (SEQ ID NO: 2) to Germline at the Indicated Residue Number

| 3 | 5 | 19 | 31 | 34 | 35 | 47 | 66 | 72 | 77 | 103 |
|---|---|----|----|----|----|----|----|----|----|-----|
| Q | I | K | S | V | I | W | D | S | T | Y |
| L | V | K | S | V | I | W | D | S | T | Y |
| Q | V | K | S | V | I | W | D | S | T | Y |
| L | I | Q | N | I | I | W | D | S | T | Y |
| Q | I | Q | N | I | I | W | D | S | T | Y |
| L | V | Q | N | I | I | W | D | S | T | Y |
| Q | V | Q | N | I | I | W | D | S | T | Y |
| L | I | K | N | I | I | W | D | S | T | Y |
| Q | I | K | N | I | I | W | D | S | T | Y |
| L | V | K | N | I | I | W | D | S | T | Y |
| Q | V | K | N | I | I | W | D | S | T | Y |
| L | I | Q | S | I | I | W | D | S | T | Y |
| Q | I | Q | S | I | I | W | D | S | T | Y |
| L | V | Q | S | I | I | W | D | S | T | Y |
| Q | V | Q | S | I | I | W | D | S | T | Y |
| L | I | K | S | I | I | W | D | S | T | Y |
| Q | I | K | S | I | I | W | D | S | T | Y |
| L | V | K | S | I | I | W | D | S | T | Y |
| Q | V | K | S | I | I | W | D | S | T | Y |
| L | I | Q | N | V | S | W | D | S | T | Y |
| Q | I | Q | N | V | S | W | D | S | T | Y |
| L | V | Q | N | V | S | W | D | S | T | Y |
| Q | V | Q | N | V | S | W | D | S | T | Y |
| L | I | K | N | V | S | W | D | S | T | Y |
| Q | I | K | N | V | S | W | D | S | T | Y |
| L | V | K | N | V | S | W | D | S | T | Y |
| Q | V | K | N | V | S | W | D | S | T | Y |
| L | I | Q | S | V | S | W | D | S | T | Y |
| Q | I | Q | S | V | S | W | D | S | T | Y |
| L | V | Q | S | V | S | W | D | S | T | Y |
| Q | V | Q | S | V | S | W | D | S | T | Y |
| L | I | K | S | V | S | W | D | S | T | Y |
| Q | I | K | S | V | S | W | D | S | T | Y |
| L | V | K | S | V | S | W | D | S | T | Y |
| Q | V | K | S | V | S | W | D | S | T | Y |
| L | I | Q | N | I | S | W | D | S | T | Y |
| Q | I | Q | N | I | S | W | D | S | T | Y |
| L | V | Q | N | I | S | W | D | S | T | Y |
| Q | V | Q | N | I | S | W | D | S | T | Y |
| L | I | K | N | I | S | W | D | S | T | Y |
| Q | I | K | N | I | S | W | D | S | T | Y |
| L | V | K | N | I | S | W | D | S | T | Y |
| Q | V | K | N | I | S | W | D | S | T | Y |
| L | I | Q | S | I | S | W | D | S | T | Y |
| Q | I | Q | S | I | S | W | D | S | T | Y |
| L | V | Q | S | I | S | W | D | S | T | Y |
| Q | V | Q | S | I | S | W | D | S | T | Y |
| L | I | K | S | I | S | W | D | S | T | Y |
| Q | I | K | S | I | S | W | D | S | T | Y |
| L | V | K | S | I | S | W | D | S | T | Y |
| Q | V | K | S | I | S | W | D | S | T | Y |
| L | I | Q | N | V | I | Y | G | S | T | Y |
| Q | I | Q | N | V | I | Y | G | S | T | Y |
| L | V | Q | N | V | I | Y | G | S | T | Y |
| Q | V | Q | N | V | I | Y | G | S | T | Y |
| L | I | K | N | V | I | Y | G | S | T | Y |
| Q | I | K | N | V | I | Y | G | S | T | Y |
| L | V | K | N | V | I | Y | G | S | T | Y |
| Q | V | K | N | V | I | Y | G | S | T | Y |
| L | I | Q | S | V | I | Y | G | S | T | Y |
| Q | I | Q | S | V | I | Y | G | S | T | Y |
| L | V | Q | S | V | I | Y | G | S | T | Y |
| Q | V | Q | S | V | I | Y | G | S | T | Y |
| L | I | K | S | V | I | Y | G | S | T | Y |
| Q | I | K | S | V | I | Y | G | S | T | Y |
| L | V | K | S | V | I | Y | G | S | T | Y |
| Q | V | K | S | V | I | Y | G | S | T | Y |
| L | I | Q | N | I | I | Y | G | S | T | Y |
| Q | I | Q | N | I | I | Y | G | S | T | Y |
| L | V | Q | N | I | I | Y | G | S | T | Y |
| Q | V | Q | N | I | I | Y | G | S | T | Y |
| L | I | K | N | I | I | Y | G | S | T | Y |
| Q | I | K | N | I | I | Y | G | S | T | Y |
| L | V | K | N | I | I | Y | G | S | T | Y |
| Q | V | K | N | I | I | Y | G | S | T | Y |

TABLE 7-continued

Exemplary Mutations of 4B4 Heavy Chain (SEQ ID NO: 2) to Germline at the Indicated Residue Number

| 3 | 5 | 19 | 31 | 34 | 35 | 47 | 66 | 72 | 77 | 103 |
|---|---|----|----|----|----|----|----|----|----|-----|
| L | I | Q | S | I | I | Y | G | S | T | Y |
| Q | I | Q | S | I | I | Y | G | S | T | Y |
| L | V | Q | S | I | I | Y | G | S | T | Y |
| Q | V | Q | S | I | I | Y | G | S | T | Y |
| L | I | K | S | I | I | Y | G | S | T | Y |
| Q | I | K | S | I | I | Y | G | S | T | Y |
| L | V | K | S | I | I | Y | G | S | T | Y |
| Q | V | K | S | I | I | Y | G | S | T | Y |
| L | I | Q | N | V | S | Y | G | S | T | Y |
| Q | I | Q | N | V | S | Y | G | S | T | Y |
| L | V | Q | N | V | S | Y | G | S | T | Y |
| Q | V | Q | N | V | S | Y | G | S | T | Y |
| L | I | K | N | V | S | Y | G | S | T | Y |
| Q | I | K | N | V | S | Y | G | S | T | Y |
| L | V | K | N | V | S | Y | G | S | T | Y |
| Q | V | K | N | V | S | Y | G | S | T | Y |
| L | I | Q | S | V | S | Y | G | S | T | Y |
| Q | I | Q | S | V | S | Y | G | S | T | Y |
| L | V | Q | S | V | S | Y | G | S | T | Y |
| Q | V | Q | S | V | S | Y | G | S | T | Y |
| L | I | K | S | V | S | Y | G | S | T | Y |
| Q | I | K | S | V | S | Y | G | S | T | Y |
| L | V | K | S | V | S | Y | G | S | T | Y |
| Q | V | K | S | V | S | Y | G | S | T | Y |
| L | I | Q | N | I | S | Y | G | S | T | Y |
| Q | I | Q | N | I | S | Y | G | S | T | Y |
| L | V | Q | N | I | S | Y | G | S | T | Y |
| Q | V | Q | N | I | S | Y | G | S | T | Y |
| L | I | K | N | I | S | Y | G | S | T | Y |
| Q | I | K | N | I | S | Y | G | S | T | Y |
| L | V | K | N | I | S | Y | G | S | T | Y |
| Q | V | K | N | I | S | Y | G | S | T | Y |
| L | I | Q | S | I | S | Y | G | S | T | Y |
| Q | I | Q | S | I | S | Y | G | S | T | Y |
| L | V | Q | S | I | S | Y | G | S | T | Y |
| Q | V | Q | S | I | S | Y | G | S | T | Y |
| L | I | K | S | I | S | Y | G | S | T | Y |
| Q | I | K | S | I | S | Y | G | S | T | Y |
| L | V | K | S | I | S | Y | G | S | T | Y |
| Q | V | K | S | I | S | Y | G | S | T | Y |
| L | I | Q | N | V | I | W | G | S | T | Y |
| Q | I | Q | N | V | I | W | G | S | T | Y |
| L | V | Q | N | V | I | W | G | S | T | Y |
| Q | V | Q | N | V | I | W | G | S | T | Y |
| L | I | K | N | V | I | W | G | S | T | Y |
| Q | I | K | N | V | I | W | G | S | T | Y |
| L | V | K | N | V | I | W | G | S | T | Y |
| Q | V | K | N | V | I | W | G | S | T | Y |
| L | I | Q | S | V | I | W | G | S | T | Y |
| Q | I | Q | S | V | I | W | G | S | T | Y |
| L | V | Q | S | V | I | W | G | S | T | Y |
| Q | V | Q | S | V | I | W | G | S | T | Y |
| L | I | K | S | V | I | W | G | S | T | Y |
| Q | I | K | S | V | I | W | G | S | T | Y |
| L | V | K | S | V | I | W | G | S | T | Y |
| Q | V | K | S | V | I | W | G | S | T | Y |
| L | I | Q | N | I | I | W | G | S | T | Y |
| Q | I | Q | N | I | I | W | G | S | T | Y |
| L | V | Q | N | I | I | W | G | S | T | Y |
| Q | V | Q | N | I | I | W | G | S | T | Y |
| L | I | K | N | I | I | W | G | S | T | Y |
| Q | I | K | N | I | I | W | G | S | T | Y |
| L | V | K | N | I | I | W | G | S | T | Y |
| Q | V | K | N | I | I | W | G | S | T | Y |
| L | I | Q | S | I | I | W | G | S | T | Y |
| Q | I | Q | S | I | I | W | G | S | T | Y |
| L | V | Q | S | I | I | W | G | S | T | Y |
| Q | V | Q | S | I | I | W | G | S | T | Y |
| L | I | K | S | I | I | W | G | S | T | Y |
| Q | I | K | S | I | I | W | G | S | T | Y |
| L | V | K | S | I | I | W | G | S | T | Y |
| Q | V | K | S | I | I | W | G | S | T | Y |
| L | I | Q | N | V | S | W | G | S | T | Y |
| Q | I | Q | N | V | S | W | G | S | T | Y |
| L | V | Q | N | V | S | W | G | S | T | Y |

TABLE 7-continued

Exemplary Mutations of 4B4 Heavy Chain (SEQ ID NO: 2) to Germline at the Indicated Residue Number

| 3 | 5 | 19 | 31 | 34 | 35 | 47 | 66 | 72 | 77 | 103 |
|---|---|----|----|----|----|----|----|----|----|-----|
| Q | V | Q | N | V | S | W | G | S | T | Y |
| L | I | K | N | V | S | W | G | S | T | Y |
| Q | I | K | N | V | S | W | G | S | T | Y |
| L | V | K | N | V | S | W | G | S | T | Y |
| Q | V | K | N | V | S | W | G | S | T | Y |
| L | I | Q | S | V | S | W | G | S | T | Y |
| Q | I | Q | S | V | S | W | G | S | T | Y |
| L | V | Q | S | V | S | W | G | S | T | Y |
| Q | V | Q | S | V | S | W | G | S | T | Y |
| L | I | K | S | V | S | W | G | S | T | Y |
| Q | I | K | S | V | S | W | G | S | T | Y |
| L | V | K | S | V | S | W | G | S | T | Y |
| Q | V | K | S | V | S | W | G | S | T | Y |
| L | I | Q | N | I | S | W | G | S | T | Y |
| Q | I | Q | N | I | S | W | G | S | T | Y |
| L | V | Q | N | I | S | W | G | S | T | Y |
| Q | V | Q | N | I | S | W | G | S | T | Y |
| L | I | K | N | I | S | W | G | S | T | Y |
| Q | I | K | N | I | S | W | G | S | T | Y |
| L | V | K | N | I | S | W | G | S | T | Y |
| Q | V | K | N | I | S | W | G | S | T | Y |
| L | I | Q | S | I | S | W | G | S | T | Y |
| Q | I | Q | S | I | S | W | G | S | T | Y |
| L | V | Q | S | I | S | W | G | S | T | Y |
| Q | V | Q | S | I | S | W | G | S | T | Y |
| L | I | K | S | I | S | W | G | S | T | Y |
| Q | I | K | S | I | S | W | G | S | T | Y |
| L | V | K | S | I | S | W | G | S | T | Y |
| Q | V | K | S | I | S | W | G | S | T | Y |
| L | I | Q | N | V | I | Y | D | T | T | Y |
| Q | I | Q | N | V | I | Y | D | T | T | Y |
| L | V | Q | N | V | I | Y | D | T | T | Y |
| Q | V | Q | N | V | I | Y | D | T | T | Y |
| L | I | K | N | V | I | Y | D | T | T | Y |
| Q | I | K | N | V | I | Y | D | T | T | Y |
| L | V | K | N | V | I | Y | D | T | T | Y |
| Q | V | K | N | V | I | Y | D | T | T | Y |
| L | I | Q | S | V | I | Y | D | T | T | Y |
| Q | I | Q | S | V | I | Y | D | T | T | Y |
| L | V | Q | S | V | I | Y | D | T | T | Y |
| Q | V | Q | S | V | I | Y | D | T | T | Y |
| L | I | K | S | V | I | Y | D | T | T | Y |
| Q | I | K | S | V | I | Y | D | T | T | Y |
| L | V | K | S | V | I | Y | D | T | T | Y |
| Q | V | K | S | V | I | Y | D | T | T | Y |
| L | I | Q | N | I | I | Y | D | T | T | Y |
| Q | I | Q | N | I | I | Y | D | T | T | Y |
| L | V | Q | N | I | I | Y | D | T | T | Y |
| Q | V | Q | N | I | I | Y | D | T | T | Y |
| L | I | K | N | I | I | Y | D | T | T | Y |
| Q | I | K | N | I | I | Y | D | T | T | Y |
| L | V | K | N | I | I | Y | D | T | T | Y |
| Q | V | K | N | I | I | Y | D | T | T | Y |
| L | I | Q | S | I | I | Y | D | T | T | Y |
| Q | I | Q | S | I | I | Y | D | T | T | Y |
| L | V | Q | S | I | I | Y | D | T | T | Y |
| Q | V | Q | S | I | I | Y | D | T | T | Y |
| L | I | K | S | I | I | Y | D | T | T | Y |
| Q | I | K | S | I | I | Y | D | T | T | Y |
| L | V | K | S | I | I | Y | D | T | T | Y |
| Q | V | K | S | I | I | Y | D | T | T | Y |
| L | I | Q | N | V | S | Y | D | T | T | Y |
| Q | I | Q | N | V | S | Y | D | T | T | Y |
| L | V | Q | N | V | S | Y | D | T | T | Y |
| Q | V | Q | N | V | S | Y | D | T | T | Y |
| L | I | K | N | V | S | Y | D | T | T | Y |
| Q | I | K | N | V | S | Y | D | T | T | Y |
| L | V | K | N | V | S | Y | D | T | T | Y |
| Q | V | K | N | V | S | Y | D | T | T | Y |
| L | I | Q | S | V | S | Y | D | T | T | Y |
| Q | I | Q | S | V | S | Y | D | T | T | Y |
| L | V | Q | S | V | S | Y | D | T | T | Y |
| Q | V | Q | S | V | S | Y | D | T | T | Y |
| L | I | K | S | V | S | Y | D | T | T | Y |
| Q | I | K | S | V | S | Y | D | T | T | Y |
| L | V | K | S | V | S | Y | D | T | T | Y |
| Q | V | K | S | V | S | Y | D | T | T | Y |
| L | I | Q | N | I | S | Y | D | T | T | Y |
| Q | I | Q | N | I | S | Y | D | T | T | Y |
| L | V | Q | N | I | S | Y | D | T | T | Y |
| Q | V | Q | N | I | S | Y | D | T | T | Y |
| L | I | K | N | I | S | Y | D | T | T | Y |
| Q | I | K | N | I | S | Y | D | T | T | Y |
| L | V | K | N | I | S | Y | D | T | T | Y |
| Q | V | K | N | I | S | Y | D | T | T | Y |
| L | I | Q | S | I | S | Y | D | T | T | Y |
| Q | I | Q | S | I | S | Y | D | T | T | Y |
| L | V | Q | S | I | S | Y | D | T | T | Y |
| Q | V | Q | S | I | S | Y | D | T | T | Y |
| L | I | K | S | I | S | Y | D | T | T | Y |
| Q | I | K | S | I | S | Y | D | T | T | Y |
| L | V | K | S | I | S | Y | D | T | T | Y |
| Q | V | K | S | I | S | Y | D | T | T | Y |
| L | I | Q | N | V | I | W | D | T | T | Y |
| Q | I | Q | N | V | I | W | D | T | T | Y |
| L | V | Q | N | V | I | W | D | T | T | Y |
| Q | V | Q | N | V | I | W | D | T | T | Y |
| L | I | K | N | V | I | W | D | T | T | Y |
| Q | I | K | N | V | I | W | D | T | T | Y |
| L | V | K | N | V | I | W | D | T | T | Y |
| Q | V | K | N | V | I | W | D | T | T | Y |
| L | I | Q | S | V | I | W | D | T | T | Y |
| Q | I | Q | S | V | I | W | D | T | T | Y |
| L | V | Q | S | V | I | W | D | T | T | Y |
| Q | V | Q | S | V | I | W | D | T | T | Y |
| L | I | K | S | V | I | W | D | T | T | Y |
| Q | I | K | S | V | I | W | D | T | T | Y |
| L | V | K | S | V | I | W | D | T | T | Y |
| Q | V | K | S | V | I | W | D | T | T | Y |
| L | I | Q | N | I | I | W | D | T | T | Y |
| Q | I | Q | N | I | I | W | D | T | T | Y |
| L | V | Q | N | I | I | W | D | T | T | Y |
| Q | V | Q | N | I | I | W | D | T | T | Y |
| L | I | K | N | I | I | W | D | T | T | Y |
| Q | I | K | N | I | I | W | D | T | T | Y |
| L | V | K | N | I | I | W | D | T | T | Y |
| Q | V | K | N | I | I | W | D | T | T | Y |
| L | I | Q | S | I | I | W | D | T | T | Y |
| Q | I | Q | S | I | I | W | D | T | T | Y |
| L | V | Q | S | I | I | W | D | T | T | Y |
| Q | V | Q | S | I | I | W | D | T | T | Y |
| L | I | K | S | I | I | W | D | T | T | Y |
| Q | I | K | S | I | I | W | D | T | T | Y |
| L | V | K | S | I | I | W | D | T | T | Y |
| Q | V | K | S | I | I | W | D | T | T | Y |
| L | I | Q | N | V | S | W | D | T | T | Y |
| Q | I | Q | N | V | S | W | D | T | T | Y |
| L | V | Q | N | V | S | W | D | T | T | Y |
| Q | V | Q | N | V | S | W | D | T | T | Y |
| L | I | K | N | V | S | W | D | T | T | Y |
| Q | I | K | N | V | S | W | D | T | T | Y |
| L | V | K | N | V | S | W | D | T | T | Y |
| Q | V | K | N | V | S | W | D | T | T | Y |
| L | I | Q | S | V | S | W | D | T | T | Y |
| Q | I | Q | S | V | S | W | D | T | T | Y |
| L | V | Q | S | V | S | W | D | T | T | Y |
| Q | V | Q | S | V | S | W | D | T | T | Y |
| L | I | K | S | V | S | W | D | T | T | Y |
| Q | I | K | S | V | S | W | D | T | T | Y |
| L | V | K | S | V | S | W | D | T | T | Y |
| Q | V | K | S | V | S | W | D | T | T | Y |
| L | I | Q | N | I | S | W | D | T | T | Y |
| Q | I | Q | N | I | S | W | D | T | T | Y |
| L | V | Q | N | I | S | W | D | T | T | Y |
| Q | V | Q | N | I | S | W | D | T | T | Y |
| L | I | K | N | I | S | W | D | T | T | Y |
| Q | I | K | N | I | S | W | D | T | T | Y |
| L | V | K | N | I | S | W | D | T | T | Y |
| Q | V | K | N | I | S | W | D | T | T | Y |
| L | I | Q | S | I | S | W | D | T | T | Y |

TABLE 7-continued

Exemplary Mutations of 4B4 Heavy Chain (SEQ ID NO: 2) to Germline at the Indicated Residue Number

| 3 | 5 | 19 | 31 | 34 | 35 | 47 | 66 | 72 | 77 | 103 |
|---|---|----|----|----|----|----|----|----|----|-----|
| Q | I | Q | S | I | S | W | D | T | T | Y |
| L | V | Q | S | I | S | W | D | T | T | Y |
| Q | V | Q | S | I | S | W | D | T | T | Y |
| L | I | K | S | I | S | W | D | T | T | Y |
| Q | I | K | S | I | S | W | D | T | T | Y |
| L | V | K | S | I | S | W | D | T | T | Y |
| Q | V | K | S | I | S | W | D | T | T | Y |
| L | I | Q | N | V | I | Y | G | T | T | Y |
| Q | I | Q | N | V | I | Y | G | T | T | Y |
| L | V | Q | N | V | I | Y | G | T | T | Y |
| Q | V | Q | N | V | I | Y | G | T | T | Y |
| L | I | K | N | V | I | Y | G | T | T | Y |
| Q | I | K | N | V | I | Y | G | T | T | Y |
| L | V | K | N | V | I | Y | G | T | T | Y |
| Q | V | K | N | V | I | Y | G | T | T | Y |
| L | I | Q | S | V | I | Y | G | T | T | Y |
| Q | I | Q | S | V | I | Y | G | T | T | Y |
| L | V | Q | S | V | I | Y | G | T | T | Y |
| Q | V | Q | S | V | I | Y | G | T | T | Y |
| L | I | K | S | V | I | Y | G | T | T | Y |
| Q | I | K | S | V | I | Y | G | T | T | Y |
| L | V | K | S | V | I | Y | G | T | T | Y |
| Q | V | K | S | V | I | Y | G | T | T | Y |
| L | I | Q | N | I | I | Y | G | T | T | Y |
| Q | I | Q | N | I | I | Y | G | T | T | Y |
| L | V | Q | N | I | I | Y | G | T | T | Y |
| Q | V | Q | N | I | I | Y | G | T | T | Y |
| L | I | K | N | I | I | Y | G | T | T | Y |
| Q | I | K | N | I | I | Y | G | T | T | Y |
| L | V | K | N | I | I | Y | G | T | T | Y |
| Q | V | K | N | I | I | Y | G | T | T | Y |
| L | I | Q | S | I | I | Y | G | T | T | Y |
| Q | I | Q | S | I | I | Y | G | T | T | Y |
| L | V | Q | S | I | I | Y | G | T | T | Y |
| Q | V | Q | S | I | I | Y | G | T | T | Y |
| L | I | K | S | I | I | Y | G | T | T | Y |
| Q | I | K | S | I | I | Y | G | T | T | Y |
| L | V | K | S | I | I | Y | G | T | T | Y |
| Q | V | K | S | I | I | Y | G | T | T | Y |
| L | I | Q | N | V | S | Y | G | T | T | Y |
| Q | I | Q | N | V | S | Y | G | T | T | Y |
| L | V | Q | N | V | S | Y | G | T | T | Y |
| Q | V | Q | N | V | S | Y | G | T | T | Y |
| L | I | K | N | V | S | Y | G | T | T | Y |
| Q | I | K | N | V | S | Y | G | T | T | Y |
| L | V | K | N | V | S | Y | G | T | T | Y |
| Q | V | K | N | V | S | Y | G | T | T | Y |
| L | I | Q | S | V | S | Y | G | T | T | Y |
| Q | I | Q | S | V | S | Y | G | T | T | Y |
| L | V | Q | S | V | S | Y | G | T | T | Y |
| Q | V | Q | S | V | S | Y | G | T | T | Y |
| L | I | K | S | V | S | Y | G | T | T | Y |
| Q | I | K | S | V | S | Y | G | T | T | Y |
| L | V | K | S | V | S | Y | G | T | T | Y |
| Q | V | K | S | V | S | Y | G | T | T | Y |
| L | I | Q | N | I | S | Y | G | T | T | Y |
| Q | I | Q | N | I | S | Y | G | T | T | Y |
| L | V | Q | N | I | S | Y | G | T | T | Y |
| Q | V | Q | N | I | S | Y | G | T | T | Y |
| L | I | K | N | I | S | Y | G | T | T | Y |
| Q | I | K | N | I | S | Y | G | T | T | Y |
| L | V | K | N | I | S | Y | G | T | T | Y |
| Q | V | K | N | I | S | Y | G | T | T | Y |
| L | I | Q | S | I | S | Y | G | T | T | Y |
| Q | I | Q | S | I | S | Y | G | T | T | Y |
| L | V | Q | S | I | S | Y | G | T | T | Y |
| Q | V | Q | S | I | S | Y | G | T | T | Y |
| L | I | K | S | I | S | Y | G | T | T | Y |
| Q | I | K | S | I | S | Y | G | T | T | Y |
| L | V | K | S | I | S | Y | G | T | T | Y |
| Q | V | K | S | I | S | Y | G | T | T | Y |
| L | I | Q | N | V | I | W | G | T | T | Y |
| Q | I | Q | N | V | I | W | G | T | T | Y |
| L | V | Q | N | V | I | W | G | T | T | Y |
| Q | V | Q | N | V | I | W | G | T | T | Y |
| L | I | K | N | V | I | W | G | T | T | Y |
| Q | I | K | N | V | I | W | G | T | T | Y |
| L | V | K | N | V | I | W | G | T | T | Y |
| Q | V | K | N | V | I | W | G | T | T | Y |
| L | I | Q | S | V | I | W | G | T | T | Y |
| Q | I | Q | S | V | I | W | G | T | T | Y |
| L | V | Q | S | V | I | W | G | T | T | Y |
| Q | V | Q | S | V | I | W | G | T | T | Y |
| L | I | K | S | V | I | W | G | T | T | Y |
| Q | I | K | S | V | I | W | G | T | T | Y |
| L | V | K | S | V | I | W | G | T | T | Y |
| Q | V | K | S | V | I | W | G | T | T | Y |
| L | I | Q | N | I | I | W | G | T | T | Y |
| Q | I | Q | N | I | I | W | G | T | T | Y |
| L | V | Q | N | I | I | W | G | T | T | Y |
| Q | V | Q | N | I | I | W | G | T | T | Y |
| L | I | K | N | I | I | W | G | T | T | Y |
| Q | I | K | N | I | I | W | G | T | T | Y |
| L | V | K | N | I | I | W | G | T | T | Y |
| Q | V | K | N | I | I | W | G | T | T | Y |
| L | I | Q | S | I | I | W | G | T | T | Y |
| Q | I | Q | S | I | I | W | G | T | T | Y |
| L | V | Q | S | I | I | W | G | T | T | Y |
| Q | V | Q | S | I | I | W | G | T | T | Y |
| L | I | K | S | I | I | W | G | T | T | Y |
| Q | I | K | S | I | I | W | G | T | T | Y |
| L | V | K | S | I | I | W | G | T | T | Y |
| Q | V | K | S | I | I | W | G | T | T | Y |
| L | I | Q | N | V | S | W | G | T | T | Y |
| Q | I | Q | N | V | S | W | G | T | T | Y |
| L | V | Q | N | V | S | W | G | T | T | Y |
| Q | V | Q | N | V | S | W | G | T | T | Y |
| L | I | K | N | V | S | W | G | T | T | Y |
| Q | I | K | N | V | S | W | G | T | T | Y |
| L | V | K | N | V | S | W | G | T | T | Y |
| Q | V | K | N | V | S | W | G | T | T | Y |
| L | I | Q | S | V | S | W | G | T | T | Y |
| Q | I | Q | S | V | S | W | G | T | T | Y |
| L | V | Q | S | V | S | W | G | T | T | Y |
| Q | V | Q | S | V | S | W | G | T | T | Y |
| L | I | K | S | V | S | W | G | T | T | Y |
| Q | I | K | S | V | S | W | G | T | T | Y |
| L | V | K | S | V | S | W | G | T | T | Y |
| Q | V | K | S | V | S | W | G | T | T | Y |
| L | I | Q | N | I | S | W | G | T | T | Y |
| Q | I | Q | N | I | S | W | G | T | T | Y |
| L | V | Q | N | I | S | W | G | T | T | Y |
| Q | V | Q | N | I | S | W | G | T | T | Y |
| L | I | K | N | I | S | W | G | T | T | Y |
| Q | I | K | N | I | S | W | G | T | T | Y |
| L | V | K | N | I | S | W | G | T | T | Y |
| Q | V | K | N | I | S | W | G | T | T | Y |
| L | I | Q | S | I | S | W | G | T | T | Y |
| Q | I | Q | S | I | S | W | G | T | T | Y |
| L | V | Q | S | I | S | W | G | T | T | Y |
| Q | V | Q | S | I | S | W | G | T | T | Y |
| L | I | K | S | I | S | W | G | T | T | Y |
| Q | I | K | S | I | S | W | G | T | T | Y |
| L | V | K | S | I | S | W | G | T | T | Y |
| Q | V | K | S | I | S | W | G | T | T | Y |
| L | I | Q | N | V | I | Y | D | S | S | Y |
| Q | I | Q | N | V | I | Y | D | S | S | Y |
| L | V | Q | N | V | I | Y | D | S | S | Y |
| Q | V | Q | N | V | I | Y | D | S | S | Y |
| L | I | K | N | V | I | Y | D | S | S | Y |
| Q | I | K | N | V | I | Y | D | S | S | Y |
| L | V | K | N | V | I | Y | D | S | S | Y |
| Q | V | K | N | V | I | Y | D | S | S | Y |
| L | I | Q | S | V | I | Y | D | S | S | Y |
| Q | I | Q | S | V | I | Y | D | S | S | Y |
| L | V | Q | S | V | I | Y | D | S | S | Y |
| Q | V | Q | S | V | I | Y | D | S | S | Y |
| L | I | K | S | V | I | Y | D | S | S | Y |
| Q | I | K | S | V | I | Y | D | S | S | Y |
| L | V | K | S | V | I | Y | D | S | S | Y |

TABLE 7-continued

Exemplary Mutations of 4B4 Heavy Chain (SEQ ID NO: 2) to Germline at the Indicated Residue Number

| 3 | 5 | 19 | 31 | 34 | 35 | 47 | 66 | 72 | 77 | 103 |
|---|---|---|---|---|---|---|---|---|---|---|
| Q | V | K | S | V | I | Y | D | S | S | Y |
| L | I | Q | N | I | I | Y | D | S | S | Y |
| Q | I | Q | N | I | I | Y | D | S | S | Y |
| L | V | Q | N | I | I | Y | D | S | S | Y |
| Q | V | Q | N | I | I | Y | D | S | S | Y |
| L | I | K | N | I | I | Y | D | S | S | Y |
| Q | I | K | N | I | I | Y | D | S | S | Y |
| L | V | K | N | I | I | Y | D | S | S | Y |
| Q | V | K | N | I | I | Y | D | S | S | Y |
| L | I | Q | S | I | I | Y | D | S | S | Y |
| Q | I | Q | S | I | I | Y | D | S | S | Y |
| L | V | Q | S | I | I | Y | D | S | S | Y |
| Q | V | Q | S | I | I | Y | D | S | S | Y |
| L | I | K | S | I | I | Y | D | S | S | Y |
| Q | I | K | S | I | I | Y | D | S | S | Y |
| L | V | K | S | I | I | Y | D | S | S | Y |
| Q | V | K | S | I | I | Y | D | S | S | Y |
| L | I | Q | N | V | S | Y | D | S | S | Y |
| Q | I | Q | N | V | S | Y | D | S | S | Y |
| L | V | Q | N | V | S | Y | D | S | S | Y |
| Q | V | Q | N | V | S | Y | D | S | S | Y |
| L | I | K | N | V | S | Y | D | S | S | Y |
| Q | I | K | N | V | S | Y | D | S | S | Y |
| L | V | K | N | V | S | Y | D | S | S | Y |
| Q | V | K | N | V | S | Y | D | S | S | Y |
| L | I | Q | S | V | S | Y | D | S | S | Y |
| Q | I | Q | S | V | S | Y | D | S | S | Y |
| L | V | Q | S | V | S | Y | D | S | S | Y |
| Q | V | Q | S | V | S | Y | D | S | S | Y |
| L | I | K | S | V | S | Y | D | S | S | Y |
| Q | I | K | S | V | S | Y | D | S | S | Y |
| L | V | K | S | V | S | Y | D | S | S | Y |
| Q | V | K | S | V | S | Y | D | S | S | Y |
| L | I | Q | N | I | S | Y | D | S | S | Y |
| Q | I | Q | N | I | S | Y | D | S | S | Y |
| L | V | Q | N | I | S | Y | D | S | S | Y |
| Q | V | Q | N | I | S | Y | D | S | S | Y |
| L | I | K | N | I | S | Y | D | S | S | Y |
| Q | I | K | N | I | S | Y | D | S | S | Y |
| L | V | K | N | I | S | Y | D | S | S | Y |
| Q | V | K | N | I | S | Y | D | S | S | Y |
| L | I | Q | S | I | S | Y | D | S | S | Y |
| Q | I | Q | S | I | S | Y | D | S | S | Y |
| L | V | Q | S | I | S | Y | D | S | S | Y |
| Q | V | Q | S | I | S | Y | D | S | S | Y |
| L | I | K | S | I | S | Y | D | S | S | Y |
| Q | I | K | S | I | S | Y | D | S | S | Y |
| L | V | K | S | I | S | Y | D | S | S | Y |
| Q | V | K | S | I | S | Y | D | S | S | Y |
| L | I | Q | N | V | I | W | D | S | S | Y |
| Q | I | Q | N | V | I | W | D | S | S | Y |
| L | V | Q | N | V | I | W | D | S | S | Y |
| Q | V | Q | N | V | I | W | D | S | S | Y |
| L | I | K | N | V | I | W | D | S | S | Y |
| Q | I | K | N | V | I | W | D | S | S | Y |
| L | V | K | N | V | I | W | D | S | S | Y |
| Q | V | K | N | V | I | W | D | S | S | Y |
| L | I | Q | S | V | I | W | D | S | S | Y |
| Q | I | Q | S | V | I | W | D | S | S | Y |
| L | V | Q | S | V | I | W | D | S | S | Y |
| Q | V | Q | S | V | I | W | D | S | S | Y |
| L | I | K | S | V | I | W | D | S | S | Y |
| Q | I | K | S | V | I | W | D | S | S | Y |
| L | V | K | S | V | I | W | D | S | S | Y |
| Q | V | K | S | V | I | W | D | S | S | Y |
| L | I | Q | N | I | I | W | D | S | S | Y |
| Q | I | Q | N | I | I | W | D | S | S | Y |
| L | V | Q | N | I | I | W | D | S | S | Y |
| Q | V | Q | N | I | I | W | D | S | S | Y |
| L | I | K | N | I | I | W | D | S | S | Y |
| Q | I | K | N | I | I | W | D | S | S | Y |
| L | V | K | N | I | I | W | D | S | S | Y |
| Q | V | K | N | I | I | W | D | S | S | Y |
| L | I | Q | S | I | I | W | D | S | S | Y |
| Q | I | Q | S | I | I | W | D | S | S | Y |
| L | V | Q | S | I | I | W | D | S | S | Y |
| Q | V | Q | S | I | I | W | D | S | S | Y |
| L | I | K | S | I | I | W | D | S | S | Y |
| Q | I | K | S | I | I | W | D | S | S | Y |
| L | V | K | S | I | I | W | D | S | S | Y |
| Q | V | K | S | I | I | W | D | S | S | Y |
| L | I | Q | N | V | S | W | D | S | S | Y |
| Q | I | Q | N | V | S | W | D | S | S | Y |
| L | V | Q | N | V | S | W | D | S | S | Y |
| Q | V | Q | N | V | S | W | D | S | S | Y |
| L | I | K | N | V | S | W | D | S | S | Y |
| Q | I | K | N | V | S | W | D | S | S | Y |
| L | V | K | N | V | S | W | D | S | S | Y |
| Q | V | K | N | V | S | W | D | S | S | Y |
| L | I | Q | S | V | S | W | D | S | S | Y |
| Q | I | Q | S | V | S | W | D | S | S | Y |
| L | V | Q | S | V | S | W | D | S | S | Y |
| Q | V | Q | S | V | S | W | D | S | S | Y |
| L | I | K | S | V | S | W | D | S | S | Y |
| Q | I | K | S | V | S | W | D | S | S | Y |
| L | V | K | S | V | S | W | D | S | S | Y |
| Q | V | K | S | V | S | W | D | S | S | Y |
| L | I | Q | N | I | S | W | D | S | S | Y |
| Q | I | Q | N | I | S | W | D | S | S | Y |
| L | V | Q | N | I | S | W | D | S | S | Y |
| Q | V | Q | N | I | S | W | D | S | S | Y |
| L | I | K | N | I | S | W | D | S | S | Y |
| Q | I | K | N | I | S | W | D | S | S | Y |
| L | V | K | N | I | S | W | D | S | S | Y |
| Q | V | K | N | I | S | W | D | S | S | Y |
| L | I | Q | S | I | S | W | D | S | S | Y |
| Q | I | Q | S | I | S | W | D | S | S | Y |
| L | V | Q | S | I | S | W | D | S | S | Y |
| Q | V | Q | S | I | S | W | D | S | S | Y |
| L | I | K | S | I | S | W | D | S | S | Y |
| Q | I | K | S | I | S | W | D | S | S | Y |
| L | V | K | S | I | S | W | D | S | S | Y |
| Q | V | K | S | I | S | W | D | S | S | Y |
| L | I | Q | N | V | I | Y | G | S | S | Y |
| Q | I | Q | N | V | I | Y | G | S | S | Y |
| L | V | Q | N | V | I | Y | G | S | S | Y |
| Q | V | Q | N | V | I | Y | G | S | S | Y |
| L | I | K | N | V | I | Y | G | S | S | Y |
| Q | I | K | N | V | I | Y | G | S | S | Y |
| L | V | K | N | V | I | Y | G | S | S | Y |
| Q | V | K | N | V | I | Y | G | S | S | Y |
| L | I | Q | S | V | I | Y | G | S | S | Y |
| Q | I | Q | S | V | I | Y | G | S | S | Y |
| L | V | Q | S | V | I | Y | G | S | S | Y |
| Q | V | Q | S | V | I | Y | G | S | S | Y |
| L | I | K | S | V | I | Y | G | S | S | Y |
| Q | I | K | S | V | I | Y | G | S | S | Y |
| L | V | K | S | V | I | Y | G | S | S | Y |
| Q | V | K | S | V | I | Y | G | S | S | Y |
| L | I | Q | N | I | I | Y | G | S | S | Y |
| Q | I | Q | N | I | I | Y | G | S | S | Y |
| L | V | Q | N | I | I | Y | G | S | S | Y |
| Q | V | Q | N | I | I | Y | G | S | S | Y |
| L | I | K | N | I | I | Y | G | S | S | Y |
| Q | I | K | N | I | I | Y | G | S | S | Y |
| L | V | K | N | I | I | Y | G | S | S | Y |
| Q | V | K | N | I | I | Y | G | S | S | Y |
| L | I | Q | S | I | I | Y | G | S | S | Y |
| Q | I | Q | S | I | I | Y | G | S | S | Y |
| L | V | Q | S | I | I | Y | G | S | S | Y |
| Q | V | Q | S | I | I | Y | G | S | S | Y |
| L | I | K | S | I | I | Y | G | S | S | Y |
| Q | I | K | S | I | I | Y | G | S | S | Y |
| L | V | K | S | I | I | Y | G | S | S | Y |
| Q | V | K | S | I | I | Y | G | S | S | Y |
| L | I | Q | N | V | S | Y | G | S | S | Y |
| Q | I | Q | N | V | S | Y | G | S | S | Y |
| L | V | Q | N | V | S | Y | G | S | S | Y |
| Q | V | Q | N | V | S | Y | G | S | S | Y |
| L | I | K | N | V | S | Y | G | S | S | Y |

TABLE 7-continued

Exemplary Mutations of 4B4 Heavy Chain (SEQ ID NO: 2) to Germline at the Indicated Residue Number

| 3 | 5 | 19 | 31 | 34 | 35 | 47 | 66 | 72 | 77 | 103 |
|---|---|---|---|---|---|---|---|---|---|---|
| Q | I | K | N | V | S | Y | G | S | S | Y |
| L | V | K | N | V | S | Y | G | S | S | Y |
| Q | V | K | N | V | S | Y | G | S | S | Y |
| L | I | Q | S | V | S | Y | G | S | S | Y |
| Q | I | Q | S | V | S | Y | G | S | S | Y |
| L | V | Q | S | V | S | Y | G | S | S | Y |
| Q | V | Q | S | V | S | Y | G | S | S | Y |
| L | I | K | S | V | S | Y | G | S | S | Y |
| Q | I | K | S | V | S | Y | G | S | S | Y |
| L | V | K | S | V | S | Y | G | S | S | Y |
| Q | V | K | S | V | S | Y | G | S | S | Y |
| L | I | Q | N | I | S | Y | G | S | S | Y |
| Q | I | Q | N | I | S | Y | G | S | S | Y |
| L | V | Q | N | I | S | Y | G | S | S | Y |
| Q | V | Q | N | I | S | Y | G | S | S | Y |
| L | I | K | N | I | S | Y | G | S | S | Y |
| Q | I | K | N | I | S | Y | G | S | S | Y |
| L | V | K | N | I | S | Y | G | S | S | Y |
| Q | V | K | N | I | S | Y | G | S | S | Y |
| L | I | Q | S | I | S | Y | G | S | S | Y |
| Q | I | Q | S | I | S | Y | G | S | S | Y |
| L | V | Q | S | I | S | Y | G | S | S | Y |
| Q | V | Q | S | I | S | Y | G | S | S | Y |
| L | I | K | S | I | S | Y | G | S | S | Y |
| Q | I | K | S | I | S | Y | G | S | S | Y |
| L | V | K | S | I | S | Y | G | S | S | Y |
| Q | V | K | S | I | S | Y | G | S | S | Y |
| L | I | Q | N | V | I | W | G | S | S | Y |
| Q | I | Q | N | V | I | W | G | S | S | Y |
| L | V | Q | N | V | I | W | G | S | S | Y |
| Q | V | Q | N | V | I | W | G | S | S | Y |
| L | I | K | N | V | I | W | G | S | S | Y |
| Q | I | K | N | V | I | W | G | S | S | Y |
| L | V | K | N | V | I | W | G | S | S | Y |
| Q | V | K | N | V | I | W | G | S | S | Y |
| L | I | Q | S | V | I | W | G | S | S | Y |
| Q | I | Q | S | V | I | W | G | S | S | Y |
| L | V | Q | S | V | I | W | G | S | S | Y |
| Q | V | Q | S | V | I | W | G | S | S | Y |
| L | I | K | S | V | I | W | G | S | S | Y |
| Q | I | K | S | V | I | W | G | S | S | Y |
| L | V | K | S | V | I | W | G | S | S | Y |
| Q | V | K | S | V | I | W | G | S | S | Y |
| L | I | Q | N | I | I | W | G | S | S | Y |
| Q | I | Q | N | I | I | W | G | S | S | Y |
| L | V | Q | N | I | I | W | G | S | S | Y |
| Q | V | Q | N | I | I | W | G | S | S | Y |
| L | I | K | N | I | I | W | G | S | S | Y |
| Q | I | K | N | I | I | W | G | S | S | Y |
| L | V | K | N | I | I | W | G | S | S | Y |
| Q | V | K | N | I | I | W | G | S | S | Y |
| L | I | Q | S | I | I | W | G | S | S | Y |
| Q | I | Q | S | I | I | W | G | S | S | Y |
| L | V | Q | S | I | I | W | G | S | S | Y |
| Q | V | Q | S | I | I | W | G | S | S | Y |
| L | I | K | S | I | I | W | G | S | S | Y |
| Q | I | K | S | I | I | W | G | S | S | Y |
| L | V | K | S | I | I | W | G | S | S | Y |
| Q | V | K | S | I | I | W | G | S | S | Y |
| L | I | Q | N | V | S | W | G | S | S | Y |
| Q | I | Q | N | V | S | W | G | S | S | Y |
| L | V | Q | N | V | S | W | G | S | S | Y |
| Q | V | Q | N | V | S | W | G | S | S | Y |
| L | I | K | N | V | S | W | G | S | S | Y |
| Q | I | K | N | V | S | W | G | S | S | Y |
| L | V | K | N | V | S | W | G | S | S | Y |
| Q | V | K | N | V | S | W | G | S | S | Y |
| L | I | Q | S | V | S | W | G | S | S | Y |
| Q | I | Q | S | V | S | W | G | S | S | Y |
| L | V | Q | S | V | S | W | G | S | S | Y |
| Q | V | Q | S | V | S | W | G | S | S | Y |
| L | I | K | S | V | S | W | G | S | S | Y |
| Q | I | K | S | V | S | W | G | S | S | Y |
| L | V | K | S | V | S | W | G | S | S | Y |
| Q | V | K | S | V | S | W | G | S | S | Y |
| L | I | Q | N | I | S | W | G | S | S | Y |
| Q | I | Q | N | I | S | W | G | S | S | Y |
| L | V | Q | N | I | S | W | G | S | S | Y |
| Q | V | Q | N | I | S | W | G | S | S | Y |
| L | I | K | N | I | S | W | G | S | S | Y |
| Q | I | K | N | I | S | W | G | S | S | Y |
| L | V | K | N | I | S | W | G | S | S | Y |
| Q | V | K | N | I | S | W | G | S | S | Y |
| L | I | Q | S | I | S | W | G | S | S | Y |
| Q | I | Q | S | I | S | W | G | S | S | Y |
| L | V | Q | S | I | S | W | G | S | S | Y |
| Q | V | Q | S | I | S | W | G | S | S | Y |
| L | I | K | S | I | S | W | G | S | S | Y |
| Q | I | K | S | I | S | W | G | S | S | Y |
| L | V | K | S | I | S | W | G | S | S | Y |
| Q | V | K | S | I | S | W | G | S | S | Y |
| L | I | Q | N | V | I | Y | D | T | S | Y |
| Q | I | Q | N | V | I | Y | D | T | S | Y |
| L | V | Q | N | V | I | Y | D | T | S | Y |
| Q | V | Q | N | V | I | Y | D | T | S | Y |
| L | I | K | N | V | I | Y | D | T | S | Y |
| Q | I | K | N | V | I | Y | D | T | S | Y |
| L | V | K | N | V | I | Y | D | T | S | Y |
| Q | V | K | N | V | I | Y | D | T | S | Y |
| L | I | Q | S | V | I | Y | D | T | S | Y |
| Q | I | Q | S | V | I | Y | D | T | S | Y |
| L | V | Q | S | V | I | Y | D | T | S | Y |
| Q | V | Q | S | V | I | Y | D | T | S | Y |
| L | I | K | S | V | I | Y | D | T | S | Y |
| Q | I | K | S | V | I | Y | D | T | S | Y |
| L | V | K | S | V | I | Y | D | T | S | Y |
| Q | V | K | S | V | I | Y | D | T | S | Y |
| L | I | Q | N | I | I | Y | D | T | S | Y |
| Q | I | Q | N | I | I | Y | D | T | S | Y |
| L | V | Q | N | I | I | Y | D | T | S | Y |
| Q | V | Q | N | I | I | Y | D | T | S | Y |
| L | I | K | N | I | I | Y | D | T | S | Y |
| Q | I | K | N | I | I | Y | D | T | S | Y |
| L | V | K | N | I | I | Y | D | T | S | Y |
| Q | V | K | N | I | I | Y | D | T | S | Y |
| L | I | Q | S | I | I | Y | D | T | S | Y |
| Q | I | Q | S | I | I | Y | D | T | S | Y |
| L | V | Q | S | I | I | Y | D | T | S | Y |
| Q | V | Q | S | I | I | Y | D | T | S | Y |
| L | I | K | S | I | I | Y | D | T | S | Y |
| Q | I | K | S | I | I | Y | D | T | S | Y |
| L | V | K | S | I | I | Y | D | T | S | Y |
| Q | V | K | S | I | I | Y | D | T | S | Y |
| L | I | Q | N | V | S | Y | D | T | S | Y |
| Q | I | Q | N | V | S | Y | D | T | S | Y |
| L | V | Q | N | V | S | Y | D | T | S | Y |
| Q | V | Q | N | V | S | Y | D | T | S | Y |
| L | I | K | N | V | S | Y | D | T | S | Y |
| Q | I | K | N | V | S | Y | D | T | S | Y |
| L | V | K | N | V | S | Y | D | T | S | Y |
| Q | V | K | N | V | S | Y | D | T | S | Y |
| L | I | Q | S | V | S | Y | D | T | S | Y |
| Q | I | Q | S | V | S | Y | D | T | S | Y |
| L | V | Q | S | V | S | Y | D | T | S | Y |
| Q | V | Q | S | V | S | Y | D | T | S | Y |
| L | I | K | S | V | S | Y | D | T | S | Y |
| Q | I | K | S | V | S | Y | D | T | S | Y |
| L | V | K | S | V | S | Y | D | T | S | Y |
| Q | V | K | S | V | S | Y | D | T | S | Y |
| L | I | Q | N | I | S | Y | D | T | S | Y |
| Q | I | Q | N | I | S | Y | D | T | S | Y |
| L | V | Q | N | I | S | Y | D | T | S | Y |
| Q | V | Q | N | I | S | Y | D | T | S | Y |
| L | I | K | N | I | S | Y | D | T | S | Y |
| Q | I | K | N | I | S | Y | D | T | S | Y |
| L | V | K | N | I | S | Y | D | T | S | Y |
| Q | V | K | N | I | S | Y | D | T | S | Y |
| L | I | Q | S | I | S | Y | D | T | S | Y |
| Q | I | Q | S | I | S | Y | D | T | S | Y |
| L | V | Q | S | I | S | Y | D | T | S | Y |

TABLE 7-continued

Exemplary Mutations of 4B4 Heavy Chain (SEQ ID NO: 2) to Germline at the Indicated Residue Number

| 3 | 5 | 19 | 31 | 34 | 35 | 47 | 66 | 72 | 77 | 103 |
|---|---|----|----|----|----|----|----|----|----|-----|
| Q | V | Q | S | I | S | Y | D | T | S | Y |
| L | I | K | S | I | S | Y | D | T | S | Y |
| Q | I | K | S | I | S | Y | D | T | S | Y |
| L | V | K | S | I | S | Y | D | T | S | Y |
| Q | V | K | S | I | S | Y | D | T | S | Y |
| L | I | Q | N | V | I | W | D | T | S | Y |
| Q | I | Q | N | V | I | W | D | T | S | Y |
| L | V | Q | N | V | I | W | D | T | S | Y |
| Q | V | Q | N | V | I | W | D | T | S | Y |
| L | I | K | N | V | I | W | D | T | S | Y |
| Q | I | K | N | V | I | W | D | T | S | Y |
| L | V | K | N | V | I | W | D | T | S | Y |
| Q | V | K | N | V | I | W | D | T | S | Y |
| L | I | Q | S | V | I | W | D | T | S | Y |
| Q | I | Q | S | V | I | W | D | T | S | Y |
| L | V | Q | S | V | I | W | D | T | S | Y |
| Q | V | Q | S | V | I | W | D | T | S | Y |
| L | I | K | S | V | I | W | D | T | S | Y |
| Q | I | K | S | V | I | W | D | T | S | Y |
| L | V | K | S | V | I | W | D | T | S | Y |
| Q | V | K | S | V | I | W | D | T | S | Y |
| L | I | Q | N | I | I | W | D | T | S | Y |
| Q | I | Q | N | I | I | W | D | T | S | Y |
| L | V | Q | N | I | I | W | D | T | S | Y |
| Q | V | Q | N | I | I | W | D | T | S | Y |
| L | I | K | N | I | I | W | D | T | S | Y |
| Q | I | K | N | I | I | W | D | T | S | Y |
| L | V | K | N | I | I | W | D | T | S | Y |
| Q | V | K | N | I | I | W | D | T | S | Y |
| L | I | Q | S | I | I | W | D | T | S | Y |
| Q | I | Q | S | I | I | W | D | T | S | Y |
| L | V | Q | S | I | I | W | D | T | S | Y |
| Q | V | Q | S | I | I | W | D | T | S | Y |
| L | I | K | S | I | I | W | D | T | S | Y |
| Q | I | K | S | I | I | W | D | T | S | Y |
| L | V | K | S | I | I | W | D | T | S | Y |
| Q | V | K | S | I | I | W | D | T | S | Y |
| L | I | Q | N | V | S | W | D | T | S | Y |
| Q | I | Q | N | V | S | W | D | T | S | Y |
| L | V | Q | N | V | S | W | D | T | S | Y |
| Q | V | Q | N | V | S | W | D | T | S | Y |
| L | I | K | N | V | S | W | D | T | S | Y |
| Q | I | K | N | V | S | W | D | T | S | Y |
| L | V | K | N | V | S | W | D | T | S | Y |
| Q | V | K | N | V | S | W | D | T | S | Y |
| L | I | Q | S | V | S | W | D | T | S | Y |
| Q | I | Q | S | V | S | W | D | T | S | Y |
| L | V | Q | S | V | S | W | D | T | S | Y |
| Q | V | Q | S | V | S | W | D | T | S | Y |
| L | I | K | S | V | S | W | D | T | S | Y |
| Q | I | K | S | V | S | W | D | T | S | Y |
| L | V | K | S | V | S | W | D | T | S | Y |
| Q | V | K | S | V | S | W | D | T | S | Y |
| L | I | Q | N | I | S | W | D | T | S | Y |
| Q | I | Q | N | I | S | W | D | T | S | Y |
| L | V | Q | N | I | S | W | D | T | S | Y |
| Q | V | Q | N | I | S | W | D | T | S | Y |
| L | I | K | N | I | S | W | D | T | S | Y |
| Q | I | K | N | I | S | W | D | T | S | Y |
| L | V | K | N | I | S | W | D | T | S | Y |
| Q | V | K | N | I | S | W | D | T | S | Y |
| L | I | Q | S | I | S | W | D | T | S | Y |
| Q | I | Q | S | I | S | W | D | T | S | Y |
| L | V | Q | S | I | S | W | D | T | S | Y |
| Q | V | Q | S | I | S | W | D | T | S | Y |
| L | I | K | S | I | S | W | D | T | S | Y |
| Q | I | K | S | I | S | W | D | T | S | Y |
| L | V | K | S | I | S | W | D | T | S | Y |
| Q | V | K | S | I | S | W | D | T | S | Y |
| L | I | Q | N | V | I | Y | G | T | S | Y |
| Q | I | Q | N | V | I | Y | G | T | S | Y |
| L | V | Q | N | V | I | Y | G | T | S | Y |
| Q | V | Q | N | V | I | Y | G | T | S | Y |
| L | I | K | N | V | I | Y | G | T | S | Y |
| Q | I | K | N | V | I | Y | G | T | S | Y |
| L | V | K | N | V | I | Y | G | T | S | Y |
| Q | V | K | N | V | I | Y | G | T | S | Y |
| L | I | Q | S | V | I | Y | G | T | S | Y |
| Q | I | Q | S | V | I | Y | G | T | S | Y |
| L | V | Q | S | V | I | Y | G | T | S | Y |
| Q | V | Q | S | V | I | Y | G | T | S | Y |
| L | I | K | S | V | I | Y | G | T | S | Y |
| Q | I | K | S | V | I | Y | G | T | S | Y |
| L | V | K | S | V | I | Y | G | T | S | Y |
| Q | V | K | S | V | I | Y | G | T | S | Y |
| L | I | Q | N | I | I | Y | G | T | S | Y |
| Q | I | Q | N | I | I | Y | G | T | S | Y |
| L | V | Q | N | I | I | Y | G | T | S | Y |
| Q | V | Q | N | I | I | Y | G | T | S | Y |
| L | I | K | N | I | I | Y | G | T | S | Y |
| Q | I | K | N | I | I | Y | G | T | S | Y |
| L | V | K | N | I | I | Y | G | T | S | Y |
| Q | V | K | N | I | I | Y | G | T | S | Y |
| L | I | Q | S | I | I | Y | G | T | S | Y |
| Q | I | Q | S | I | I | Y | G | T | S | Y |
| L | V | Q | S | I | I | Y | G | T | S | Y |
| Q | V | Q | S | I | I | Y | G | T | S | Y |
| L | I | K | S | I | I | Y | G | T | S | Y |
| Q | I | K | S | I | I | Y | G | T | S | Y |
| L | V | K | S | I | I | Y | G | T | S | Y |
| Q | V | K | S | I | I | Y | G | T | S | Y |
| L | I | Q | N | V | S | Y | G | T | S | Y |
| Q | I | Q | N | V | S | Y | G | T | S | Y |
| L | V | Q | N | V | S | Y | G | T | S | Y |
| Q | V | Q | N | V | S | Y | G | T | S | Y |
| L | I | K | N | V | S | Y | G | T | S | Y |
| Q | I | K | N | V | S | Y | G | T | S | Y |
| L | V | K | N | V | S | Y | G | T | S | Y |
| Q | V | K | N | V | S | Y | G | T | S | Y |
| L | I | Q | S | V | S | Y | G | T | S | Y |
| Q | I | Q | S | V | S | Y | G | T | S | Y |
| L | V | Q | S | V | S | Y | G | T | S | Y |
| Q | V | Q | S | V | S | Y | G | T | S | Y |
| L | I | K | S | V | S | Y | G | T | S | Y |
| Q | I | K | S | V | S | Y | G | T | S | Y |
| L | V | K | S | V | S | Y | G | T | S | Y |
| Q | V | K | S | V | S | Y | G | T | S | Y |
| L | I | Q | N | I | S | Y | G | T | S | Y |
| Q | I | Q | N | I | S | Y | G | T | S | Y |
| L | V | Q | N | I | S | Y | G | T | S | Y |
| Q | V | Q | N | I | S | Y | G | T | S | Y |
| L | I | K | N | I | S | Y | G | T | S | Y |
| Q | I | K | N | I | S | Y | G | T | S | Y |
| L | V | K | N | I | S | Y | G | T | S | Y |
| Q | V | K | N | I | S | Y | G | T | S | Y |
| L | I | Q | S | I | S | Y | G | T | S | Y |
| Q | I | Q | S | I | S | Y | G | T | S | Y |
| L | V | Q | S | I | S | Y | G | T | S | Y |
| Q | V | Q | S | I | S | Y | G | T | S | Y |
| L | I | K | S | I | S | Y | G | T | S | Y |
| Q | I | K | S | I | S | Y | G | T | S | Y |
| L | V | K | S | I | S | Y | G | T | S | Y |
| Q | V | K | S | I | S | Y | G | T | S | Y |
| L | I | Q | N | V | I | W | G | T | S | Y |
| Q | I | Q | N | V | I | W | G | T | S | Y |
| L | V | Q | N | V | I | W | G | T | S | Y |
| Q | V | Q | N | V | I | W | G | T | S | Y |
| L | I | K | N | V | I | W

TABLE 7-continued

Exemplary Mutations of 4B4 Heavy Chain (SEQ ID NO: 2) to Germline at the Indicated Residue Number

| 3 | 5 | 19 | 31 | 34 | 35 | 47 | 66 | 72 | 77 | 103 |
|---|---|----|----|----|----|----|----|----|----|-----|
| Q | I | Q | N | I | I | W | G | T | S | Y |
| L | V | Q | N | I | I | W | G | T | S | Y |
| Q | V | Q | N | I | I | W | G | T | S | Y |
| L | I | K | N | I | I | W | G | T | S | Y |
| Q | I | K | N | I | I | W | G | T | S | Y |
| L | V | K | N | I | I | W | G | T | S | Y |
| Q | V | K | N | I | I | W | G | T | S | Y |
| L | I | Q | S | I | I | W | G | T | S | Y |
| Q | I | Q | S | I | I | W | G | T | S | Y |
| L | V | Q | S | I | I | W | G | T | S | Y |
| Q | V | Q | S | I | I | W | G | T | S | Y |
| L | I | K | S | I | I | W | G | T | S | Y |
| Q | I | K | S | I | I | W | G | T | S | Y |
| L | V | K | S | I | I | W | G | T | S | Y |
| Q | V | K | S | I | I | W | G | T | S | Y |
| L | I | Q | N | V | S | W | G | T | S | Y |
| Q | I | Q | N | V | S | W | G | T | S | Y |
| L | V | Q | N | V | S | W | G | T | S | Y |
| Q | V | Q | N | V | S | W | G | T | S | Y |
| L | I | K | N | V | S | W | G | T | S | Y |
| Q | I | K | N | V | S | W | G | T | S | Y |
| L | V | K | N | V | S | W | G | T | S | Y |
| Q | V | K | N | V | S | W | G | T | S | Y |
| L | I | Q | S | V | S | W | G | T | S | Y |
| Q | I | Q | S | V | S | W | G | T | S | Y |
| L | V | Q | S | V | S | W | G | T | S | Y |
| Q | V | Q | S | V | S | W | G | T | S | Y |
| L | I | K | S | V | S | W | G | T | S | Y |
| Q | I | K | S | V | S | W | G | T | S | Y |
| L | V | K | S | V | S | W | G | T | S | Y |
| Q | V | K | S | V | S | W | G | T | S | Y |
| L | I | Q | N | I | S | W | G | T | S | Y |
| Q | I | Q | N | I | S | W | G | T | S | Y |
| L | V | Q | N | I | S | W | G | T | S | Y |
| Q | V | Q | N | I | S | W | G | T | S | Y |
| L | I | K | N | I | S | W | G | T | S | Y |
| Q | I | K | N | I | S | W | G | T | S | Y |
| L | V | K | N | I | S | W | G | T | S | Y |
| Q | V | K | N | I | S | W | G | T | S | Y |
| L | I | Q | S | I | S | W | G | T | S | Y |
| Q | I | Q | S | I | S | W | G | T | S | Y |
| L | V | Q | S | I | S | W | G | T | S | Y |
| Q | V | Q | S | I | S | W | G | T | S | Y |
| L | I | K | S | I | S | W | G | T | S | Y |
| Q | I | K | S | I | S | W | G | T | S | Y |
| L | V | K | S | I | S | W | G | T | S | Y |
| Q | V | K | S | I | S | W | G | T | S | Y |

In some embodiments of the invention, the targeted binding agent or antibody comprises a sequence comprising SEQ ID NO.: 2. In certain embodiments, SEQ ID NO.: 2 comprises any one of the combinations of germline and non-germline residues indicated by each row of Table 7. In some embodiments, SEQ ID NO: 2 comprises any one, any two, any three, any four, any five, any six, any seven, any eight, any nine, any ten, any eleven, or all eleven of the germline residues as indicated in Table 7. In certain embodiments, SEQ ID NO.: 2 comprises any one of the unique combinations of germline and non-germline residues indicated by each row of Table 7. In other embodiments, the targeted binding agent or antibody is derived from a germline sequence with VH1-18, D7-27 and JH4 domains, wherein one or more residues has been mutated to yield the corresponding germline residue at that position.

TABLE 8

Exemplary Mutations of 4B4 light Chain (SEQ ID NO: 4) to Germline at the Indicated Residue Number

| 51 | 88 | 92 | 95 | 97 |
|----|----|----|----|----|
| I | F | N | D | S |
| S | F | N | D | S |
| I | Y | N | D | S |
| S | Y | N | D | S |
| I | F | S | D | S |
| S | F | S | D | S |
| I | Y | S | D | S |
| S | Y | S | D | S |
| I | F | N | N | S |
| S | F | N | N | S |
| I | Y | N | N | S |
| S | Y | N | N | S |
| I | F | S | N | S |
| S | F | S | N | S |
| I | Y | S | N | S |
| S | Y | S | N | S |
| I | F | N | D | V |
| S | F | N | D | V |
| I | Y | N | D | V |
| S | Y | N | D | V |
| I | F | S | D | V |
| S | F | S | D | V |
| I | Y | S | D | V |
| S | Y | S | D | V |
| I | F | N | N | V |
| S | F | N | N | V |
| I | Y | N | N | V |
| S | Y | N | N | V |
| I | F | S | N | V |
| S | F | S | N | V |
| I | Y | S | N | V |
| S | Y | S | N | V |

In some embodiments of the invention, the targeted binding agent or antibody comprises a sequence comprising SEQ ID NO.: 4. In certain embodiments, SEQ ID NO.: 4 comprises any one of the combinations of germline and non-germline residues indicated by each row of Table 8. In some embodiments, SEQ ID NO: 4 comprises any one, any two, any three, any four, any five, or all five of the germline residues as indicated in Table 8. In certain embodiments, SEQ ID NO.: 4 comprises any one of the unique combinations of germline and non-germline residues indicated by each row of Table 8. In other embodiments, the targeted binding agent or antibody is derived from a germline sequence with VL, 3p and JL2 domains, wherein one or more residues has been mutated to yield the corresponding germline residue at that position.

TABLE 9

Exemplary Mutations of 2H10 Heavy Chain (SEQ ID NO: 6) to Germline at the Indicated Residue Number

| 31 | 32 | 51 | 53 | 58 | 93 |
|----|----|----|----|----|----|
| R | H | V | F | I | M |
| S | H | V | F | I | M |
| R | Y | V | F | I | M |
| S | Y | V | F | I | M |
| R | H | I | F | I | M |
| S | H | I | F | I | M |
| R | Y | I | F | I | M |
| S | Y | I | F | I | M |
| R | H | V | Y | I | M |
| S | H | V | Y | I | M |
| R | Y | V | Y | I | M |
| S | Y | V | Y | I | M |
| R | H | I | Y | I | M |
| S | H | I | Y | I | M |
| R | Y | I | Y | I | M |

TABLE 9-continued

Exemplary Mutations of 2H10 Heavy Chain (SEQ ID NO: 6) to Germline at the Indicated Residue Number

| 31 | 32 | 51 | 53 | 58 | 93 |
|---|---|---|---|---|---|
| S | Y | I | Y | I | M |
| R | H | V | F | K | M |
| S | H | V | F | K | M |
| R | Y | V | F | K | M |
| S | Y | V | F | K | M |
| R | H | I | F | K | M |
| S | H | I | F | K | M |
| R | Y | I | F | K | M |
| S | Y | I | F | K | M |
| R | H | V | Y | K | M |
| S | H | V | Y | K | M |
| R | Y | V | Y | K | M |
| S | Y | V | Y | K | M |
| R | H | I | Y | K | M |
| S | H | I | Y | K | M |
| R | Y | I | Y | K | M |
| S | Y | I | Y | K | M |
| R | H | V | F | I | V |
| S | H | V | F | I | V |
| R | Y | V | F | I | V |
| S | Y | V | F | I | V |
| R | H | I | F | I | V |
| S | H | I | F | I | V |
| R | Y | I | F | I | V |
| S | Y | I | F | I | V |
| R | H | V | Y | I | V |
| S | H | V | Y | I | V |
| R | Y | V | Y | I | V |
| S | Y | V | Y | I | V |
| R | H | I | Y | I | V |
| S | H | I | Y | I | V |
| R | Y | I | Y | I | V |
| S | Y | I | Y | I | V |
| R | H | V | F | K | V |
| S | H | V | F | K | V |
| R | Y | V | F | K | V |
| S | Y | V | F | K | V |
| R | H | I | F | K | V |
| S | H | I | F | K | V |
| R | Y | I | F | K | V |
| S | Y | I | F | K | V |
| R | H | V | Y | K | V |
| S | H | V | Y | K | V |
| R | Y | V | Y | K | V |
| S | Y | V | Y | K | V |
| R | H | I | Y | K | V |
| S | H | I | Y | K | V |
| R | Y | I | Y | K | V |
| S | Y | I | Y | K | V |

A further embodiment In some embodiments of the invention, the targeted binding agent or antibody comprises a sequence comprising SEQ ID NO.: 6. In certain embodiments, SEQ ID NO.: 6 comprises any one of the combinations of germline and non-germline residues indicated by each row of Table 9. In some embodiments, SEQ NO: 6 comprises any one, any two, any three, any four, any five, any six or all six of the germline residues as indicated in Table 9. In certain embodiments, SEQ ID NO.: 6 comprises any one of the unique combinations of germline and non-germline residues indicated by each row of Table 9. In other embodiments, the targeted binding agent or antibody is derived from a germline sequence with Vh3-33, D6-13 and JH4 domains, wherein one or more residues has been mutated to yield the corresponding germline residue at that position. An example of a sequence, which has been mutated is 2H10 VHOP where the M at position 93 has been mutated to a V. See Table 13.

TABLE 10

Exemplary Mutations of 2H10 light Chain (SEQ ID NO: 8) to Germline the Indicated Residue Number

| 18 | 32 | 50 | 65 | 89 | 94 |
|---|---|---|---|---|---|
| V | V | E | S | T | L |
| A | V | E | S | T | L |
| V | A | E | S | T | L |
| A | A | E | S | T | L |
| V | V | D | S | T | L |
| A | V | D | S | T | L |
| V | A | D | S | T | L |
| A | A | D | S | T | L |
| V | V | E | N | T | L |
| A | V | E | N | T | L |
| V | A | E | N | T | L |
| A | A | E | N | T | L |
| V | V | D | N | T | L |
| A | V | D | N | T | L |
| V | A | D | N | T | L |
| A | A | D | N | T | L |
| V | V | E | S | A | L |
| A | V | E | S | A | L |
| V | A | E | S | A | L |
| A | A | E | S | A | L |
| V | V | D | S | A | L |
| A | V | D | S | A | L |
| V | A | D | S | A | L |
| A | A | D | S | A | L |
| V | V | E | N | A | L |
| A | V | E | N | A | L |
| V | A | E | N | A | L |
| A | A | E | N | A | L |
| V | V | D | N | A | L |
| A | V | D | N | A | L |
| V | A | D | N | A | L |
| A | A | D | N | A | L |
| V | V | E | S | T | T |
| A | V | E | S | T | T |
| V | A | E | S | T | T |
| A | A | E | S | T | T |
| V | V | D | S | T | T |
| A | V | D | S | T | T |
| V | A | D | S | T | T |
| A | A | D | S | T | T |
| V | V | E | N | T | T |
| A | V | E | N | T | T |
| V | A | E | N | T | T |
| A | A | E | N | T | T |
| V | V | D | N | T | T |
| A | V | D | N | T | T |
| V | A | D | N | T | T |
| A | A | D | N | T | T |
| V | V | E | S | A | T |
| A | V | E | S | A | T |
| V | A | E | S | A | T |
| A | A | E | S | A | T |
| V | V | D | S | A | T |
| A | V | D | S | A | T |
| V | A | D | S | A | T |
| A | A | D | S | A | T |
| V | V | E | N | A | T |
| A | V | E | N | A | T |
| V | A | E | N | A | T |
| A | A | E | N | A | T |
| V | V | D | N | A | T |
| A | V | D | N | A | T |
| V | A | D | N | A | T |
| A | A | D | N | A | T |

A further embodiment In some embodiments of the invention, the targeted binding agent or antibody comprises a sequence comprising SEQ ID NO.: 8. In certain embodiments, SEQ ID NO.: 8 comprises any one of the combinations of germline and non-germline residues indicated by each row of Table 10. In some embodiments, SEQ ID NO: 8 comprises any one, any two, any three, any four, any five, any six or all six of the germline residues as indicated in Table 10. In certain embodiments, SEQ ID NO.: 8 comprises any one of the unique combinations of germline and non-germline residues indicated by each row of Table 10. In other embodiments, the targeted binding agent or antibody is derived from a germline sequence with VL, 3r and JL2 domains, wherein one or more residues has been mutated to yield the corresponding germline residue at that position. In certain embodiments, SEQ ID NO.: 8 can comprise further modifications that include removing structural liabilities. For example, in addition to germlining, the C33 can be mutated to an S—see for example 21H10 VLOP1 in Table 13. Thus, SEQ ID NO.: 8 can comprise any one of the unique combinations of germline and non-germline residues indicated by each row of Table 10 and further include the mutation of C33 to a S. Examples of a sequence where the light chain has been mutated to remove the structural liability at C33 and further mutated back to the germline sequence is 2H10 VLOP2 as shown in Table 13 where C33 has been mutated to an S and V at position 18 has been mutated to an A, and S at position 65 has been mutated to a N.

TABLE 11

Exemplary Mutations of 9G8 Heavy Chain (SEQ ID NO: 22) to Germline at the Indicated Residue Number

| 21 | 34 | 38 | 62 | 70 | 96 | 108 |
|---|---|---|---|---|---|---|
| S | S | L | S | S | F | V |
| T | S | L | S | S | F | V |
| S | Y | L | S | S | F | V |
| T | Y | L | S | S | F | V |
| S | S | W | S | S | F | V |
| T | S | W | S | S | F | V |
| S | Y | W | S | S | F | V |
| T | Y | W | S | S | F | V |
| S | S | L | N | S | F | V |
| T | S | L | N | S | F | V |
| S | Y | L | N | S | F | V |
| T | Y | L | N | S | F | V |
| S | S | W | N | S | F | V |
| T | S | W | N | S | F | V |
| S | Y | W | N | S | F | V |
| T | Y | W | N | S | F | V |
| S | S | L | S | T | F | V |
| T | S | L | S | T | F | V |
| S | Y | L | S | T | F | V |
| T | Y | L | S | T | F | V |
| S | S | W | S | T | F | V |
| T | S | W | S | T | F | V |
| S | Y | W | S | T | F | V |
| T | Y | W | S | T | F | V |
| S | S | L | N | T | F | V |
| T | S | L | N | T | F | V |
| S | Y | L | N | T | F | V |
| T | Y | L | N | T | F | V |
| S | S | W | N | T | F | V |
| T | S | W | N | T | F | V |
| S | Y | W | N | T | F | V |
| T | Y | W | N | T | F | V |
| S | S | L | S | S | Y | V |
| T | S | L | S | S | Y | V |
| S | Y | L | S | S | Y | V |
| T | Y | L | S | S | Y | V |
| S | S | W | S | S | Y | V |
| T | S | W | S | S | Y | V |
| S | Y | W | S | S | Y | V |
| T | Y | W | S | S | Y | V |
| S | S | L | N | S | Y | V |
| T | S | L | N | S | Y | V |
| S | Y | L | N | S | Y | V |
| T | Y | L | N | S | Y | V |
| S | S | W | N | S | Y | V |
| T | S | W | N | S | Y | V |
| S | Y | W | N | S | Y | V |
| T | Y | W | N | S | Y | V |
| S | S | L | S | T | Y | V |
| T | S | L | S | T | Y | V |
| S | Y | L | S | T | Y | V |
| T | Y | L | S | T | Y | V |
| S | S | W | S | T | Y | V |
| T | S | W | S | T | Y | V |
| S | Y | W | S | T | Y | V |
| T | Y | W | S | T | Y | V |
| S | S | L | N | T | Y | V |
| T | S | L | N | T | Y | V |
| S | Y | L | N | T | Y | V |
| T | Y | L | N | T | Y | V |
| S | S | W | N | T | Y | V |
| T | S | W | N | T | Y | V |
| S | Y | W | N | T | Y | V |
| T | Y | W | N | T | Y | V |
| S | S | L | S | S | F | A |
| T | S | L | S | S | F | A |
| S | Y | L | S | S | F | A |
| T | Y | L | S | S | F | A |
| S | S | W | S | S | F | A |
| T | S | W | S | S | F | A |
| S | Y | W | S | S | F | A |
| T | Y | W | S | S | F | A |
| S | S | L | N | S | F | A |
| T | S | L | N | S | F | A |
| S | Y | L | N | S | F | A |
| T | Y | L | N | S | F | A |
| S | S | W | N | S | F | A |
| T | S | W | N | S | F | A |
| S | Y | W | N | S | F | A |
| T | Y | W | N | S | F | A |
| S | S | L | S | T | F | A |
| T | S | L | S | T | F | A |
| S | Y | L | S | T | F | A |
| T | Y | L | S | T | F | A |
| S | S | W | S | T | F | A |
| T | S | W | S | T | F | A |
| S | Y | W | S | T | F | A |
| T | Y | W | S | T | F | A |
| S | S | L | N | T | F | A |
| T | S | L | N | T | F | A |
| S | Y | L | N | T | F | A |
| T | Y | L | N | T | F | A |
| S | S | W | N | T | F | A |
| T | S | W | N | T | F | A |
| S | Y | W | N | T | F | A |
| T | Y | W | N | T | F | A |
| S | S | L | S | S | Y | A |
| T | S | L | S | S | Y | A |
| S | Y | L | S | S | Y | A |
| T | Y | L | S | S | Y | A |
| S | S | W | S | S | Y | A |
| T | S | W | S | S | Y | A |
| S | Y | W | S | S | Y | A |
| T | Y | W | S | S | Y | A |
| S | S | L | N | S | Y | A |
| T | S | L | N | S | Y | A |
| S | Y | L | N | S | Y | A |
| T | Y | L | N | S | Y | A |
| S | S | W | N | S | Y | A |
| T | S | W | N | S | Y | A |
| S | Y | W | N | S | Y | A |
| T | Y | W | N | S | Y | A |
| S | S | L | S | T | Y | A |
| T | S | L | S | T | Y | A |
| S | Y | L | S | T | Y | A |
| T | Y | L | S | T | Y | A |
| S | S | W | S | T | Y | A |
| T | S | W | S | T | Y | A |
| S | Y | W | S | T | Y | A |
| T | Y | W | S | T | Y | A |
| S | S | L | N | T | Y | A |
| T | S | L | N | T | Y | A |
| S | Y | L | N | T | Y | A |
| T | Y | L | N | T | Y | A |

TABLE 11-continued

Exemplary Mutations of 9G8 Heavy Chain (SEQ ID NO: 22) to Germline at the Indicated Residue Number

| 21 | 34 | 38 | 62 | 70 | 96 | 108 |
|---|---|---|---|---|---|---|
| S | S | W | N | T | Y | A |
| T | S | W | N | T | Y | A |
| S | Y | W | N | T | Y | A |
| T | Y | W | N | T | Y | A |

In some embodiments of the invention, the targeted binding agent or antibody comprises a sequence comprising SEQ ID NO.: 22. In certain embodiments, SEQ ID NO.: 22 comprises any one of the combinations of germline and non-germline residues indicated by each row of Table 11. In some embodiments, SEQ NO: 22 comprises any one, any two, any three, any four, any five, any six, any seven, or all seven of the germline residues as indicated in Table 11. In certain embodiments, SEQ ID NO.: 22 comprises any one of the unique combinations of germline and non-germline residues indicated by each row of Table 11. In other embodiments, the targeted binding agent or antibody is derived from a germline sequence with VH4-39, D4-23 and JH3 domains, wherein one or more residues has been mutated to yield the corresponding germline residue at that position. An example of a sequence where the heavy chain has been mutated back to the germline sequence is 9G8 VHOP1 shown in Table 13 where L at position 38 has been mutated to a W. Another example of a sequence where the heavy chain has been mutated back to the germline sequence is 9G8 VHOP2 shown in Table 13 where S at position 21 has been mutated to a L at position 38 has been mutated to a W, S at position 70 has been mutated to a T, and F at position 96 has been mutated to a Y.

TABLE 12

Exemplary Mutations of 9G8 Light Chain (SEQ ID NO: 24) to Germline at the Indicated Residue Number

| 2 | 7 | 19 | 30 | 32 | 39 | 49 | 51 | 79 | 94 | 97 |
|---|---|---|---|---|---|---|---|---|---|---|
| S | S | R | V | V | T | E | T | V | T | I |
| Y | S | R | V | V | T | E | T | V | T | I |
| S | P | R | V | V | T | E | T | V | T | I |
| Y | P | R | V | V | T | E | T | V | T | I |
| S | S | S | V | V | T | E | T | V | T | I |
| Y | S | S | V | V | T | E | T | V | T | I |
| S | P | S | V | V | T | E | T | V | T | I |
| Y | P | S | V | V | T | E | T | V | T | I |
| S | S | R | K | V | T | E | T | V | T | I |
| Y | S | R | K | V | T | E | T | V | T | I |
| S | P | R | K | V | T | E | T | V | T | I |
| Y | P | R | K | V | T | E | T | V | T | I |
| S | S | S | K | V | T | E | T | V | T | I |
| Y | S | S | K | V | T | E | T | V | T | I |
| S | P | S | K | V | T | E | T | V | T | I |
| Y | P | S | K | V | T | E | T | V | T | I |
| S | S | R | V | A | T | E | T | V | T | I |
| Y | S | R | V | A | T | E | T | V | T | I |
| S | P | R | V | A | T | E | T | V | T | I |
| Y | P | R | V | A | T | E | T | V | T | I |
| S | S | S | V | A | T | E | T | V | T | I |
| Y | S | S | V | A | T | E | T | V | T | I |
| S | P | S | V | A | T | E | T | V | T | I |
| Y | P | S | V | A | T | E | T | V | T | I |
| S | S | R | K | A | T | E | T | V | T | I |
| Y | S | R | K | A | T | E | T | V | T | I |
| S | P | R | K | A | T | E | T | V | T | I |
| Y | P | R | K | A | T | E | T | V | T | I |
| S | S | S | K | A | T | E | T | V | T | I |
| Y | S | S | K | A | T | E | T | V | T | I |
| S | P | S | K | A | T | E | T | V | T | I |
| Y | P | S | K | A | T | E | T | V | T | I |

TABLE 12-continued

Exemplary Mutations of 9G8 Light Chain (SEQ ID NO: 24) to Germline at the Indicated Residue Number

| 2 | 7 | 19 | 30 | 32 | 39 | 49 | 51 | 79 | 94 | 97 |
|---|---|---|---|---|---|---|---|---|---|---|
| S | S | R | V | V | P | E | T | V | T | I |
| Y | S | R | V | V | P | E | T | V | T | I |
| S | P | R | V | V | P | E | T | V | T | I |
| Y | P | R | V | V | P | E | T | V | T | I |
| S | S | S | V | V | P | E | T | V | T | I |
| Y | S | S | V | V | P | E | T | V | T | I |
| S | P | S | V | V | P | E | T | V | T | I |
| Y | P | S | V | V | P | E | T | V | T | I |
| S | S | R | K | V | P | E | T | V | T | I |
| Y | S | R | K | V | P | E | T | V | T | I |
| S | P | R | K | V | P | E | T | V | T | I |
| Y | P | R | K | V | P | E | T | V | T | I |
| S | S | S | K | V | P | E | T | V | T | I |
| Y | S | S | K | V | P | E | T | V | T | I |
| S | P | S | K | V | P | E | T | V | T | I |
| Y | P | S | K | V | P | E | T | V | T | I |
| S | S | R | V | A | P | E | T | V | T | I |
| Y | S | R | V | A | P | E | T | V | T | I |
| S | P | R | V | A | P | E | T | V | T | I |
| Y | P | R | V | A | P | E | T | V | T | I |
| S | S | S | V | A | P | E | T | V | T | I |
| Y | S | S | V | A | P | E | T | V | T | I |
| S | P | S | V | A | P | E | T | V | T | I |
| Y | P | S | V | A | P | E | T | V | T | I |
| S | S | R | K | A | P | E | T | V | T | I |
| Y | S | R | K | A | P | E | T | V | T | I |
| S | P | R | K | A | P | E | T | V | T | I |
| Y | P | R | K | A | P | E | T | V | T | I |
| S | S | S | K | A | P | E | T | V | T | I |
| Y | S | S | K | A | P | E | T | V | T | I |
| S | P | S | K | A | P | E | T | V | T | I |
| Y | P | S | K | A | P | E | T | V | T | I |
| S | S | R | V | V | T | Q | T | V | T | I |
| Y | S | R | V | V | T | Q | T | V | T | I |
| S | P | R | V | V | T | Q | T | V | T | I |
| Y | P | R | V | V | T | Q | T | V | T | I |
| S | S | S | V | V | T | Q | T | V | T | I |
| Y | S | S | V | V | T | Q | T | V | T | I |
| S | P | S | V | V | T | Q | T | V | T | I |
| Y | P | S | V | V | T | Q | T | V | T | I |
| S | S | R | K | V | T | Q | T | V | T | I |
| Y | S | R | K | V | T | Q | T | V | T | I |
| S | P | R | K | V | T | Q | T | V | T | I |
| Y | P | R | K | V | T | Q | T | V | T | I |
| S | S | S | K | V | T | Q | T | V | T | I |
| Y | S | S | K | V | T | Q | T | V | T | I |
| S | P | S | K | V | T | Q | T | V | T | I |
| Y | P | S | K | V | T | Q | T | V | T | I |
| S | S | R | V | A | T | Q | T | V | T | I |
| Y | S | R | V | A | T | Q | T | V | T | I |
| S | P | R | V | A | T | Q | T | V | T | I |
| Y | P | R | V | A | T | Q | T | V | T | I |
| S | S | S | V | A | T | Q | T | V | T | I |
| Y | S | S | V | A | T | Q | T | V | T | I |
| S | P | S | V | A | T | Q | T | V | T | I |
| Y | P | S | V | A | T | Q | T | V | T | I |
| S | S | R | K | A | T | Q | T | V | T | I |
| Y | S | R | K | A | T | Q | T | V | T | I |
| S | P | R | K | A | T | Q | T | V | T | I |
| Y | P | R | K | A | T | Q | T | V | T | I |
| S | S | S | K | A | T | Q | T | V | T | I |
| Y | S | S | K | A | T | Q | T | V | T | I |
| S | P | S | K | A | T | Q | T | V | T | I |
| Y | P | S | K | A | T | Q | T | V | T | I |
| S | S | R | V | V | P | Q | T | V | T | I |
| Y | S | R | V | V | P | Q | T | V | T | I |
| S | P | R | V | V | P | Q | T | V | T | I |
| Y | P | R | V | V | P | Q | T | V | T | I |
| S | S | S | V | V | P | Q | T | V | T | I |
| Y | S | S | V | V | P | Q | T | V | T | I |
| S | P | S | V | V | P | Q | T | V | T | I |
| Y | P | S | V | V | P | Q | T | V | T | I |
| S | S | R | K | V | P | Q | T | V | T | I |
| Y | S | R | K | V | P | Q | T | V | T | I |
| S | P | R | K | V | P | Q | T | V | T | I |

TABLE 12-continued

Exemplary Mutations of 9G8 Light Chain (SEQ ID NO: 24) to Germline at the Indicated Residue Number

| 2 | 7 | 19 | 30 | 32 | 39 | 49 | 51 | 79 | 94 | 97 |
|---|---|----|----|----|----|----|----|----|----|----|
| Y | P | R | K | V | P | Q | T | V | T | I |
| S | S | S | K | V | P | Q | T | V | T | I |
| Y | S | S | K | V | P | Q | T | V | T | I |
| S | P | S | K | V | P | Q | T | V | T | I |
| Y | P | S | K | V | P | Q | T | V | T | I |
| S | S | R | V | A | P | Q | T | V | T | I |
| Y | S | R | V | A | P | Q | T | V | T | I |
| S | P | R | V | A | P | Q | T | V | T | I |
| Y | P | R | V | A | P | Q | T | V | T | I |
| S | S | S | V | A | P | Q | T | V | T | I |
| Y | S | S | V | A | P | Q | T | V | T | I |
| S | P | S | V | A | P | Q | T | V | T | I |
| Y | P | S | V | A | P | Q | T | V | T | I |
| S | S | R | K | A | P | Q | T | V | T | I |
| Y | S | R | K | A | P | Q | T | V | T | I |
| S | P | R | K | A | P | Q | T | V | T | I |
| Y | P | R | K | A | P | Q | T | V | T | I |
| S | S | S | K | A | P | Q | T | V | T | I |
| Y | S | S | K | A | P | Q | T | V | T | I |
| S | P | S | K | A | P | Q | T | V | T | I |
| Y | P | S | K | A | P | Q | T | V | T | I |
| S | S | R | V | V | T | E | S | V | T | I |
| Y | S | R | V | V | T | E | S | V | T | I |
| S | P | R | V | V | T | E | S | V | T | I |
| Y | P | R | V | V | T | E | S | V | T | I |
| S | S | S | V | V | T | E | S | V | T | I |
| Y | S | S | V | V | T | E | S | V | T | I |
| S | P | S | V | V | T | E | S | V | T | I |
| Y | P | S | V | V | T | E | S | V | T | I |
| S | S | R | K | V | T | E | S | V | T | I |
| Y | S | R | K | V | T | E | S | V | T | I |
| S | P | R | K | V | T | E | S | V | T | I |
| Y | P | R | K | V | T | E | S | V | T | I |
| S | S | S | K | V | T | E | S | V | T | I |
| Y | S | S | K | V | T | E | S | V | T | I |
| S | P | S | K | V | T | E | S | V | T | I |
| Y | P | S | K | V | T | E | S | V | T | I |
| S | S | R | V | A | T | E | S | V | T | I |
| Y | S | R | V | A | T | E | S | V | T | I |
| S | P | R | V | A | T | E | S | V | T | I |
| Y | P | R | V | A | T | E | S | V | T | I |
| S | S | S | V | A | T | E | S | V | T | I |
| Y | S | S | V | A | T | E | S | V | T | I |
| S | P | S | V | A | T | E | S | V | T | I |
| Y | P | S | V | A | T | E | S | V | T | I |
| S | S | R | K | A | T | E | S | V | T | I |
| Y | S | R | K | A | T | E | S | V | T | I |
| S | P | R | K | A | T | E | S | V | T | I |
| Y | P | R | K | A | T | E | S | V | T | I |
| S | S | S | K | A | T | E | S | V | T | I |
| Y | S | S | K | A | T | E | S |

TABLE 12-continued

| Exemplary Mutations of 9G8 Light Chain (SEQ ID NO: 24) to Germline at the Indicated Residue Number | | | | | | | | | | |
|---|---|---|---|---|---|---|---|---|---|---|
| 2 | 7 | 19 | 30 | 32 | 39 | 49 | 51 | 79 | 94 | 97 |
| Y | S | R | V | V | T | E | T | A | T | I |
| S | P | R | V | V | T | E | T | A | T | I |
| Y | P | R | V | V | T | E | T | A | T | I |
| S | S | S | V | V | T | E | T | A | T | I |
| Y | S | S | V | V | T | E | T | A | T | I |
| S | P | S | V | V | T | E | T | A | T | I |
| Y | P | S | V | V | T | E | T | A | T | I |
| S | S | R | K | V | T | E | T | A | T | I |
| Y | S | R | K | V | T | E | T | A | T | I |
| S | P | R | K | V | T | E | T | A | T | I |
| Y | P | R | K | V | T | E | T | A | T | I |
| S | S | S | K | V | T | E | T | A | T | I |
| Y | S | S | K | V | T | E | T | A | T | I |
| S | P | S | K | V | T | E | T | A | T | I |
| Y | P | S | K | V | T | E | T | A | T | I |
| S | S | R | V | A | T | E | T | A | T | I |
| Y | S | R | V | A | T | E | T | A | T | I |
| S | P | R | V | A | T | E | T | A | T | I |
| Y | P | R | V | A | T | E | T | A | T | I |
| S | S | S | V | A | T | E | T | A | T | I |
| Y | S | S | V | A | T | E | T | A | T | I |
| S | P | S | V | A | T | E | T | A | T | I |
| Y | P | S | V | A | T | E | T | A | T | I |
| S | S | R | K | A | T | E | T | A | T | I |
| Y | S | R | K | A | T | E | T | A | T | I |
| S | P | R | K | A | T | E | T | A | T | I |
| Y | P | R | K | A | T | E | T | A | T | I |
| S | S | S | K | A | T | E | T | A | T | I |
| Y | S | S | K | A | T | E | T | A | T | I |
| S | P | S | K | A | T | E | T | A | T | I |
| Y | P | S | K | A | T | E | T | A | T | I |
| S | S | R | V | V | P | E | T | A | T | I |
| Y | S | R | V | V | P | E | T | A | T | I |
| S | P | R | V | V | P | E | T | A | T | I |
| Y | P | R | V | V | P | E | T | A | T | I |
| S | S | S | V | V | P | E | T | A | T | I |
| Y | S | S | V | V | P | E | T | A | T | I |
| S | P | S | V | V | P | E | T | A | T | I |
| Y | P | S | V | V | P | E | T | A | T | I |
| S | S | R | K | V | P | E | T | A | T | I |
| Y | S | R | K | V | P | E | T | A | T | I |
| S | P | R | K | V | P | E | T | A | T | I |
| Y | P | R | K | V | P | E | T | A | T | I |
| S | S | S | K | V | P | E | T | A | T | I |
| Y | S | S | K | V | P | E | T | A | T | I |
| S | P | S | K | V | P | E | T | A | T | I |
| Y | P | S | K | V | P | E | T | A | T | I |
| S | S | R | V | A | P | E | T | A | T | I |
| Y | S | R | V | A | P | E | T | A | T | I |
| S | P | R | V | A | P | E | T | A | T | I |
| Y | P | R | V | A | P | E | T | A | T | I |
| S | S | S | V | A | P | E | T | A | T | I |
| Y | S | S | V | A | P | E | T | A | T | I |
| S | P | S | V | A | P | E | T | A | T | I |
| Y | P | S | V | A | P | E | T | A | T | I |
| S | S | R | K | A | P | E | T | A | T | I |
| Y | S | R | K | A | P | E | T | A | T | I |
| S | P | R | K | A | P | E | T | A | T | I |
| Y | P | R | K | A | P | E | T | A | T | I |
| S | S | S | K | A | P | E | T | A | T | I |
| Y | S | S | K | A | P | E | T | A | T | I |
| S | P | S | K | A | P | E | T | A | T | I |
| Y | P | S | K | A | P | E | T | A | T | I |
| S | S | R | V | V | T | Q | T | A | T | I |
| Y | S | R | V | V | T | Q | T | A | T | I |
| S | P | R | V | V | T | Q | T | A | T | I |
| Y | P | R | V | V | T | Q | T | A | T | I |
| S | S | S | V | V | T | Q | T | A | T | I |
| Y | S | S | V | V | T | Q | T | A | T | I |
| S | P | S | V | V | T | Q | T | A | T | I |
| Y | P | S | V | V | T | Q | T | A | T | I |
| S | S | R | K | V | T | Q | T | A | T | I |
| Y | S | R | K | V | T | Q | T | A | T | I |
| S | P | R | K | V | T | Q | T | A | T | I |
| Y | P | R | K | V | T | Q | T | A | T | I |
| S | S | S | K | V | T | Q | T | A | T | I |
| Y | S | S | K | V | T | Q | T | A | T | I |
| S | P | S | K | V | T | Q | T | A | T | I |
| Y | P | S | K | V | T | Q | T | A | T | I |
| S | S | R | V | A | T | Q | T | A | T | I |
| Y | S | R | V | A | T | Q | T | A | T | I |
| S | P | R | V | A | T | Q | T | A | T | I |
| Y | P | R | V | A | T | Q | T | A | T | I |
| S | S | S | V | A | T | Q | T | A | T | I |
| Y | S | S | V | A | T | Q | T | A | T | I |
| S | P | S | V | A | T | Q | T | A | T | I |
| Y | P | S | V | A | T | Q | T | A | T | I |
| S | S | R | K | A | T | Q | T | A | T | I |
| Y | S | R | K | A | T | Q | T | A | T | I |
| S | P | R | K | A | T | Q | T | A | T | I |
| Y | P | R | K | A | T | Q | T | A | T | I |
| S | S | S | K | A | T | Q | T | A | T | I |
| Y | S | S | K | A | T | Q | T | A | T | I |
| S | P | S | K | A | T | Q | T | A | T | I |
| Y | P | S | K | A | T | Q | T | A | T | I |
| S | S | R | V | V | P | Q | T | A | T | I |
| Y | S | R | V | V | P | Q | T | A | T | I |
| S | P | R | V | V | P | Q | T | A | T | I |
| Y | P | R | V | V | P | Q | T | A | T | I |
| S | S | S | V | V | P | Q | T | A | T | I |
| Y | S | S | V | V | P | Q | T | A | T | I |
| S | P | S | V | V | P | Q | T | A | T | I |
| Y | P | S | V | V | P | Q | T | A | T | I |
| S | S | R | K | V | P | Q | T | A | T | I |
| Y | S | R | K | V | P | Q | T | A | T | I |
| S | P | R | K | V | P | Q | T | A | T | I |
| Y | P | R | K | V | P | Q | T | A | T | I |
| S | S | S | K | V | P | Q | T | A | T | I |
| Y | S | S | K | V | P | Q | T | A | T | I |
| S | P | S | K | V | P | Q | T | A | T | I |
| Y | P | S | K | V | P | Q | T | A | T | I |
| S | S | R | V | A | P | Q | T | A | T | I |
| Y | S | R | V | A | P | Q | T | A | T | I |
| S | P | R | V | A | P | Q | T | A | T | I |
| Y | P | R | V | A | P | Q | T | A | T | I |
| S | S | S | V | A | P | Q | T | A | T | I |
| Y | S | S | V | A | P | Q | T | A | T | I |
| S | P | S | V | A | P | Q | T | A | T | I |
| Y | P | S | V | A | P | Q | T | A | T | I |
| S | S | R | K | A | P | Q | T | A | T | I |
| Y | S | R | K | A | P | Q | T | A | T | I |
| S | P | R | K | A | P | Q | T | A | T | I |
| Y | P | R | K | A | P | Q | T | A | T | I |
| S | S | S | K | A | P | Q | T | A | T | I |
| Y | S | S | K | A | P | Q | T | A | T | I |
| S | P | S | K | A | P | Q | T | A | T | I |
| Y | P | S | K | A | P | Q | T | A | T | I |
| S | S | R | V | V | T | E | S | A | T | I |
| Y | S | R | V | V | T | E | S | A | T | I |
| S | P | R | V | V | T | E | S | A | T | I |
| Y | P | R | V | V | T | E | S | A | T | I |
| S | S | S | V | V | T | E | S | A | T | I |
| Y | S | S | V | V | T | E | S | A | T | I |
| S | P | S | V | V | T | E | S | A | T | I |
| Y | P | S | V | V | T | E | S | A | T | I |
| S | S | R | K | V | T | E | S | A | T | I |
| Y | S | R | K | V | T | E | S | A | T | I |
| S | P | R | K | V | T | E | S | A | T | I |
| Y | P | R | K | V | T | E | S | A | T | I |
| S | S | S | K | V | T | E | S | A | T | I |
| Y | S | S | K | V | T | E | S | A | T | I |
| S | P | S | K | V | T | E | S | A | T | I |
| Y | P | S | K | V | T | E | S | A | T | I |
| S | S | R | V | A | T | E | S | A | T | I |
| Y | S | R | V | A | T | E | S | A | T | I |
| S | P | R | V | A | T | E | S | A | T | I |
| Y | P | R | V | A | T | E | S | A | T | I |
| S | S | S | V | A | T | E | S | A | T | I |
| Y | S | S | V | A | T | E | S | A | T | I |
| S | P | S | V | A | T | E | S | A | T | I |

TABLE 12-continued

Exemplary Mutations of 9G8 Light Chain (SEQ ID NO: 24) to Germline at the Indicated Residue Number

| 2 | 7 | 19 | 30 | 32 | 39 | 49 | 51 | 79 | 94 | 97 |
|---|---|---|---|---|---|---|---|---|---|---|
| Y | P | S | V | A | T | E | S | A | T | I |
| S | S | R | K | A | T | E | S | A | T | I |
| Y | S | R | K | A | T | E | S | A | T | I |
| S | P | R | K | A | T | E | S | A | T | I |
| Y | P | R | K | A | T | E | S | A | T | I |
| S | S | S | K | A | T | E | S | A | T | I |
| Y | S | S | K | A | T | E | S | A | T | I |
| S | P | S | K | A | T | E | S | A | T | I |
| Y | P | S | K | A | T | E | S | A | T | I |
| S | S | R | V | V | P | E | S | A | T | I |
| Y | S | R | V | V | P | E | S | A | T | I |
| S | P | R | V | V | P | E | S | A | T | I |
| Y | P | R | V | V | P | E | S | A | T | I |
| S | S | S | V | V | P | E | S | A | T | I |
| Y | S | S | V | V | P | E | S | A | T | I |
| S | P | S | V | V | P | E | S | A | T | I |
| Y | P | S | V | V | P | E | S | A | T | I |
| S | S | R | K | V | P | E | S | A | T | I |
| Y | S | R | K | V | P | E | S | A | T | I |
| S | P | R | K | V | P | E | S | A | T | I |
| Y | P | R | K | V | P | E | S | A | T | I |
| S | S | S | K | V | P | E | S | A | T | I |
| Y | S | S | K | V | P | E | S | A | T | I |
| S | P | S | K | V | P | E | S | A | T | I |
| Y | P | S | K | V | P | E | S | A | T | I |
| S | S | R | V | A | P | E | S | A | T | I |
| Y | S | R | V | A | P | E | S | A | T | I |
| S | P | R | V | A | P | E | S | A | T | I |
| Y | P | R | V | A | P | E | S | A | T | I |
| S | S | S | V | A | P | E | S | A | T | I |
| Y | S | S | V | A | P | E | S | A | T | I |
| S | P | S | V | A | P | E | S | A | T | I |
| Y | P | S | V | A | P | E | S | A | T | I |
| S | S | R | K | A | P | E | S | A | T | I |
| Y | S | R | K | A | P | E | S | A | T | I |
| S | P | R | K | A | P | E | S | A | T | I |
| Y | P | R | K | A | P | E | S | A | T | I |
| S | S | S | K | A | P | E | S | A | T | I |
| Y | S | S | K | A | P | E | S | A | T | I |
| S | P | S | K | A | P | E | S | A | T | I |
| Y | P | S | K | A | P | E | S | A | T | I |
| S | S | R | V | V | T | Q | S | A | T | I |
| Y | S | R | V | V | T | Q | S | A | T | I |
| S | P | R | V | V | T | Q | S | A | T | I |
| Y | P | R | V | V | T | Q | S | A | T | I |
| S | S | S | V | V | T | Q | S | A | T | I |
| Y | S | S | V | V | T | Q | S | A | T | I |
| S | P | S | V | V | T | Q | S | A | T | I |
| Y | P | S | V | V | T | Q | S | A | T | I |
| S | S | R | K | V | T | Q | S | A | T | I |
| Y | S | R | K | V | T | Q | S | A | T | I |
| S | P | R | K | V | T | Q | S | A | T | I |
| Y | P | R | K | V | T | Q | S | A | T | I |
| S | S | S | K | V | T | Q | S | A | T | I |
| Y | S | S | K | V | T | Q | S | A | T | I |
| S | P | S | K | V | T | Q | S | A | T | I |
| Y | P | S | K | V | T | Q | S | A | T | I |
| S | S | R | V | A | T | Q | S | A | T | I |
| Y | S | R | V | A | T | Q | S | A | T | I |
| S | P | R | V | A | T | Q | S | A | T | I |
| Y | P | R | V | A | T | Q | S | A | T | I |
| S | S | S | V | A | T | Q | S | A | T | I |
| Y | S | S | V | A | T | Q | S | A | T | I |
| S | P | S | V | A | T | Q | S | A | T | I |
| Y | P | S | V | A | T | Q | S | A | T | I |
| S | S | R | K | A | T | Q | S | A | T | I |
| Y | S | R | K | A | T | Q | S | A | T | I |
| S | P | R | K | A | T | Q | S | A | T | I |
| Y | P | R | K | A | T | Q | S | A | T | I |
| S | S | S | K | A | T | Q | S | A | T | I |
| Y | S | S | K | A | T | Q | S | A | T | I |
| S | P | S | K | A | T | Q | S | A | T | I |
| Y | P | S | K | A | T | Q | S | A | T | I |
| S | S | R | V | V | P | Q | S | A | T | I |
| Y | S | R | V | V | P | Q | S | A | T | I |
| S | P | R | V | V | P | Q | S | A | T | I |
| Y | P | R | V | V | P | Q | S | A | T | I |
| S | S | S | V | V | P | Q | S | A | T | I |
| Y | P | S | V | V | P | Q | S | A | T | I |
| S | P | S | V | V | P | Q | S | A | T | I |
| Y | P | S | V | V | P | Q | S | A | T | I |
| S | S | R | K | V | P | Q | S | A | T | I |
| Y | S | R | K | V | P | Q | S | A | T | I |
| S | P | R | K | V | P | Q | S | A | T | I |
| Y | P | R | K | V | P | Q | S | A | T | I |
| S | S | S | K | V | P | Q | S | A | T | I |
| Y | S | S | K | V | P | Q | S | A | T | I |
| S | P | S | K | V | P | Q | S | A | T | I |
| Y | P | S | K | V | P | Q | S | A | T | I |
| S | S | R | V | A | P | Q | S | A | T | I |
| Y | S | R | V | A | P | Q | S | A | T | I |
| S | P | R | V | A | P | Q | S | A | T | I |
| Y | P | R | V | A | P | Q | S | A | T | I |
| S | S | S | V | A | P | Q | S | A | T | I |
| Y | S | S | V | A | P | Q | S | A | T | I |
| S | P | S | V | A | P | Q | S | A | T | I |
| Y | P | S | V | A | P | Q | S | A | T | I |
| S | S | R | K | A | P | Q | S | A | T | I |
| Y | S | R | K | A | P | Q | S | A | T | I |
| S | P | R | K | A | P | Q | S | A | T | I |
| Y | P | R | K | A | P | Q | S | A | T | I |
| S | S | S | K | A | P | Q | S | A | T | I |
| Y | S | S | K | A | P | Q | S | A | T | I |
| S | P | S | K | A | P | Q | S | A | T | I |
| Y | P | S | K | A | P | Q | S | A | T | I |
| S | S | R | V | V | T | E | T | V | S | I |
| Y | S | R | V | V | T | E | T | V | S | I |
| S | P | R | V | V | T | E | T | V | S | I |
| Y | P | R | V | V | T | E | T | V | S | I |
| S | S | S | V | V | T | E | T | V | S | I |
| Y | S | S | V | V | T | E | T | V | S | I |
| S | P | S | V | V | T | E | T | V | S | I |
| Y | P | S | V | V | T | E | T | V | S | I |
| S | S | R | K | V | T | E | T | V | S | I |
| Y | S | R | K | V | T | E | T | V | S | I |
| S | P | R | K | V | T | E | T | V | S | I |
| Y | P | R | K | V | T | E | T | V | S | I |
| S | S | S | K | V | T | E | T | V | S | I |
| Y | S | S | K | V | T | E | T | V | S | I |
| S | P | S | K | V | T | E | T | V | S | I |
| Y | P | S | K | V | T | E | T | V | S | I |
| S | S | R | V | A | T | E | T | V | S | I |
| Y | S | R | V | A | T | E | T | V | S | I |
| S | P | R | V | A | T | E | T | V | S | I |
| Y | P | R | V | A | T | E | T | V | S | I |
| S | S | S | V | A | T | E | T | V | S | I |
| Y | S | S | V | A | T | E | T | V | S | I |
| S | P | S | V | A | T | E | T | V | S | I |
| Y | P | S | V | A | T | E | T | V | S | I |
| S | S | R | K | A | T | E | T | V | S | I |
| Y | S | R | K | A | T | E | T | V | S | I |
| S | P | R | K | A | T | E | T | V | S | I |
| Y | P | R | K | A | T | E | T | V | S | I |
| S | S | S | K | A | T | E | T | V | S | I |
| Y | S | S | K | A | T | E | T | V | S | I |
| S | P | S | K | A | T | E | T | V | S | I |
| Y | P | S | K | A | T | E | T | V | S | I |
| S | S | R | V | V | P | E | T | V | S | I |
| Y | S | R | V | V | P | E | T | V | S | I |
| S | P | R | V | V | P | E | T | V | S | I |
| Y | P | R | V | V | P | E | T | V | S | I |
| S | S | S | V | V | P | E | T | V | S | I |
| Y | S | S | V | V | P | E | T | V | S | I |
| S | P | S | V | V | P | E | T | V | S | I |
| Y | P | S | V | V | P | E | T | V | S | I |
| S | S | R | K | V | P | E | T | V | S | I |
| Y | S | R | K | V | P | E | T | V | S | I |
| S | P | R | K | V | P | E | T | V | S | I |
| Y | P | R | K | V | P | E | T | V | S | I |
| S | S | S | K | V | P | E | T | V | S | I |
| Y | S | S | K | V | P | E | T | V | S | I |

TABLE 12-continued

Exemplary Mutations of 9G8 Light Chain (SEQ ID NO: 24) to Germline at the Indicated Residue Number

| 2 | 7 | 19 | 30 | 32 | 39 | 49 | 51 | 79 | 94 | 97 |
|---|---|----|----|----|----|----|----|----|----|----|
| Y | S | S | K | V | P | E | T | V | S | I |
| S | P | S | K | V | P | E | T | V | S | I |
| Y | P | S | K | V | P | E | T | V | S | I |
| S | S | R | V | A | P | E | T | V | S | I |
| Y | S | R | V | A | P | E | T | V | S | I |
| S | P | R | V | A | P | E | T | V | S | I |
| Y | P | R | V | A | P | E | T | V | S | I |
| S | S | S | V | A | P | E | T | V | S | I |
| Y | S | S | V | A | P | E | T | V | S | I |
| S | P | S | V | A | P | E | T | V | S | I |
| Y | P | S | V | A | P | E | T | V | S | I |
| S | S | R | K | A | P | E | T | V | S | I |
| Y | S | R | K | A | P | E | T | V | S | I |
| S | P | R | K | A | P | E | T | V | S | I |
| Y | P | R | K | A | P | E | T | V | S | I |
| S | S | S | K | A | P | E | T | V | S | I |
| Y | S | S | K | A | P | E | T | V | S | I |
| S | P | S | K | A | P | E | T | V | S | I |
| Y | P | S | K | A | P | E | T | V | S | I |
| S | S | R | V | V | T | Q | T | V | S | I |
| Y | S | R | V | V | T | Q | T | V | S | I |
| S | P | R | V | V | T | Q | T | V | S | I |
| Y | P | R | V | V | T | Q | T | V | S | I |
| S | S | S | V | V | T | Q | T | V | S | I |
| Y | S | S | V | V | T | Q | T | V | S | I |
| S | P | S | V | V | T | Q | T | V | S | I |
| Y | P | S | V | V | T | Q | T | V | S | I |
| S | S | R | K | V | T | Q | T | V | S | I |
| Y | S | R | K | V | T | Q | T | V | S | I |
| S | P | R | K | V | T | Q | T | V | S | I |
| Y | P | R | K | V | T | Q | T | V | S | I |
| S | S | S | K | V | T | Q | T | V | S | I |
| Y | S | S | K | V | T | Q | T | V | S | I |
| S | P | S | K | V | T | Q | T | V | S | I |
| Y | P | S | K | V | T | Q | T | V | S | I |
| S | S | R | V | A | T | Q | T | V | S | I |
| Y | S | R | V | A | T | Q | T | V | S | I |
| S | P | R | V | A | T | Q | T | V | S | I |
| Y | P | R | V | A | T | Q | T | V | S | I |
| S | S | S | V | A | T | Q | T | V | S | I |
| Y | S | S | V | A | T | Q | T | V | S | I |
| S | P | S | V | A | T | Q | T | V | S | I |
| Y | P | S | V | A | T | Q | T | V | S | I |
| S | S | R | K | A | T | Q | T | V | S | I |
| Y | S | R | K | A | T | Q | T | V | S | I |
| S | P | R | K | A | T | Q | T | V | S | I |
| Y | P | R | K | A | T | Q | T | V | S | I |
| S | S | S | K | A | T | Q | T | V | S | I |
| Y | S | S | K | A | T | Q | T | V | S | I |
| S | P | S | K | A | T | Q | T | V | S | I |
| Y | P | S | K | A | T | Q | T | V | S | I |
| S | S | R | V | V | P | Q | T | V | S | I |
| Y | S | R | V | V | P | Q | T | V | S | I |
| S | P | R | V | V | P | Q | T | V | S | I |
| Y | P | R | V | V | P | Q | T | V | S | I |
| S | S | S | V | V | P | Q | T | V | S | I |
| Y | S | S | V | V | P | Q | T | V | S | I |
| S | P | S | V | V | P | Q | T | V | S | I |
| Y | P | S | V | V | P | Q | T | V | S | I |
| S | S | R | K | V | P | Q | T | V | S | I |
| Y | S | R | K | V | P | Q | T | V | S | I |
| S | P | R | K | V | P | Q | T | V | S | I |
| Y | P | R | K | V | P | Q | T | V | S | I |
| S | S | S | K | V | P | Q | T | V | S | I |
| Y | S | S | K | V | P | Q | T | V | S | I |
|

TABLE 12-continued

Exemplary Mutations of 9G8 Light Chain (SEQ ID NO: 24) to Germline at the Indicated Residue Number

| 2 | 7 | 19 | 30 | 32 | 39 | 49 | 51 | 79 | 94 | 97 |
|---|---|---|---|---|---|---|---|---|---|---|
| Y | P | R | V | V | T | Q | S | V | S | I |
| S | S | S | V | V | T | Q | S | V | S | I |
| Y | S | S | V | V | T | Q | S | V | S | I |
| S | P | S | V | V | T | Q | S | V | S | I |
| Y | P | S | V | V | T | Q | S | V | S | I |
| S | S | R | K | V | T | Q | S | V | S | I |
| Y | S | R | K | V | T | Q | S | V | S | I |
| S | P | R | K | V | T | Q | S | V | S | I |
| Y | P | R | K | V | T | Q | S | V | S | I |
| S | S | S | K | V | T | Q | S | V | S | I |
| Y | S | S | K | V | T | Q | S | V | S | I |
| S | P | S | K | V | T | Q | S | V | S | I |
| Y | P | S | K | V | T | Q | S | V | S | I |
| S | S | R | V | A | T | Q | S | V | S | I |
| Y | S | R | V | A | T | Q | S | V | S | I |
| S | P | R | V | A | T | Q | S | V | S | I |
| Y | P | R | V | A | T | Q | S | V | S | I |
| S | S | S | V | A | T | Q | S | V | S | I |
| Y | S | S | V | A | T | Q | S | V | S | I |
| S | P | S | V | A | T | Q | S | V | S | I |
| Y | P | S | V | A | T | Q | S | V | S | I |
| S | S | R | K | A | T | Q | S | V | S | I |
| Y | S | R | K | A | T | Q | S | V | S | I |
| S | P | R | K | A | T | Q | S | V | S | I |
| Y | P | R | K | A | T | Q | S | V | S | I |
| S | S | S | K | A | T | Q | S | V | S | I |
| Y | S | S | K | A | T | Q | S | V | S | I |
| S | P | S | K | A | T | Q | S | V | S | I |
| Y | P | S | K | A | T | Q | S | V | S | I |
| S | S | R | V | V | P | Q | S | V | S | I |
| Y | S | R | V | V | P | Q | S | V | S | I |
| S | P | R | V | V | P | Q | S | V | S | I |
| Y | P | R | V | V | P | Q | S | V | S | I |
| S | S | S | V | V | P | Q | S | V | S | I |
| Y | S | S | V | V | P | Q | S | V | S | I |
| S | P | S | V | V | P | Q | S | V | S | I |
| Y | P | S | V | V | P | Q | S | V | S | I |
| S | S | R | K | V | P | Q | S | V | S | I |
| Y | S | R | K | V | P | Q | S | V | S | I |
| S | P | R | K | V | P | Q | S | V | S | I |
| Y | P | R | K | V | P | Q | S | V | S | I |
| S | S | S | K | V | P | Q | S | V | S | I |
| Y | S | S | K | V | P | Q | S | V | S | I |
| S | P | S | K | V | P | Q | S | V | S | I |
| Y | P | S | K | V | P | Q | S | V | S | I |
| S | S | R | V | A | P | Q | S | V | S | I |
| Y | S | R | V | A | P | Q | S | V | S | I |
| S | P | R | V | A | P | Q | S | V | S | I |
| Y | P | R | V | A | P | Q | S | V | S | I |
| S | S | S | V | A | P | Q | S | V | S | I |
| Y | S | S | V | A | P | Q | S | V | S | I |
| S | P | S | V | A | P | Q | S | V | S | I |
| Y | P | S | V | A | P | Q | S | V | S | I |
| S | S | R | K | A | P | Q | S | V | S | I |
| Y | S | R | K | A | P | Q | S | V | S | I |
| S | P | R | K | A | P | Q | S | V | S | I |
| Y | P | R | K | A | P | Q | S | V | S | I |
| S | S | S | K | A | P | Q | S | V | S | I |
| Y | S | S | K | A | P | Q | S | V | S | I |
| S | P | S | K | A | P | Q | S | V | S | I |
| Y | P | S | K | A | P | Q | S | V | S | I |
| S | S | R | V | V | T | E | T | A | S | I |
| Y | S | R | V | V | T | E | T | A | S | I |
| S | P | R | V | V | T | E | T | A | S | I |
| Y | P | R | V | V | T | E | T | A | S | I |
| S | S | S | V | V | T | E | T | A | S | I |
| Y | S | S | V | V | T | E | T | A | S | I |
| S | P | S | V | V | T | E | T | A | S | I |
| Y | P | S | V | V | T | E | T | A | S | I |
| S | S | R | K | V | T | E | T | A | S | I |
| Y | S | R | K | V | T | E | T | A | S | I |
| S | P | R | K | V | T | E | T | A | S | I |
| Y | P | R | K | V | T | E | T | A | S | I |
| S | S | S | K | V | T | E | T | A | S | I |
| Y | S | S | K | V | T | E | T | A | S | I |
| S | P | S | K | V | T | E | T | A | S | I |
| Y | P | S | K | V | T | E | T | A | S | I |
| S | S | R | V | A | T | E | T | A | S | I |
| Y | S | R | V | A | T | E | T | A | S | I |
| S | P | R | V | A | T | E | T | A | S | I |
| Y | P | R | V | A | T | E | T | A | S | I |
| S | S | S | V | A | T | E | T | A | S | I |
| Y | S | S | V | A | T | E | T | A | S | I |
| S | P | S | V | A | T | E | T | A | S | I |
| Y | P | S | V | A | T | E | T | A | S | I |
| S | S | R | K | A | T | E | T | A | S | I |
| Y | S | R | K | A | T | E | T | A | S | I |
| S | P | R | K | A | T | E | T | A | S | I |
| Y | P | R | K | A | T | E | T | A | S | I |
| S | S | S | K | A | T | E | T | A | S | I |
| Y | S | S | K | A | T | E | T | A | S | I |
| S | P | S | K | A | T | E | T | A | S | I |
| Y | P | S | K | A | T | E | T | A | S | I |
| S | S | R | V | V | P | E | T | A | S | I |
| Y | S | R | V | V | P | E | T | A | S | I |
| S | P | R | V | V | P | E | T | A | S | I |
| Y | P | R | V | V | P | E | T | A | S | I |
| S | S | S | V | V | P | E | T | A | S | I |
| Y | S | S | V | V | P | E | T | A | S | I |
| S | P | S | V | V | P | E | T | A | S | I |
| Y | P | S | V | V | P | E | T | A | S | I |
| S | S | R | K | V | P | E | T | A | S | I |
| Y | S | R | K | V | P | E | T | A | S | I |
| S | P | R | K | V | P | E | T | A | S | I |
| Y | P | R | K | V | P | E | T | A | S | I |
| S | S | S | K | V | P | E | T | A | S | I |
| Y | S | S | K | V | P | E | T | A | S | I |
| S | P | S | K | V | P | E | T | A | S | I |
| Y | P | S | K | V | P | E | T | A | S | I |
| S | S | R | V | A | P | E | T | A | S | I |
| Y | S | R | V | A | P | E | T | A | S | I |
| S | P | R | V | A | P | E | T | A | S | I |
| Y | P | R | V | A | P | E | T | A | S | I |
| S | S | S | V | A | P | E | T | A | S | I |
| Y | S | S | V | A | P | E | T | A | S | I |
| S | P | S | V | A | P | E | T | A | S | I |
| Y | P | S | V | A | P | E | T | A | S | I |
| S | S | R | K | A | P | E | T | A | S | I |
| Y | S | R | K | A | P | E | T | A | S | I |
| S | P | R | K | A | P | E | T | A | S | I |
| Y | P | R | K | A | P | E | T | A | S | I |
| S | S | S | K | A | P | E | T | A | S | I |
| Y | S | S | K | A | P | E | T | A | S | I |
| S | P | S | K | A | P | E | T | A | S | I |
| Y | P | S | K | A | P | E | T | A | S | I |
| S | S | R | V | V | T | Q | T | A | S | I |
| Y | S | R | V | V | T | Q | T | A | S | I |
| S | P | R | V | V | T | Q | T | A | S | I |
| Y | P | R | V | V | T | Q | T | A | S | I |
| S | S | S | V | V | T | Q | T | A | S | I |
| Y | S | S | V | V | T | Q | T | A | S | I |
| S | P | S | V | V | T | Q | T | A | S | I |
| Y | P | S | V | V | T | Q | T | A | S | I |
| S | S | R | K | V | T | Q | T | A | S | I |
| Y | S | R | K | V | T | Q | T | A | S | I |
| S | P | R | K | V | T | Q | T | A | S | I |
| Y | P | R | K | V | T | Q | T | A | S | I |
| S | S | S | K | V | T | Q | T | A | S | I |
| Y | S | S | K | V | T | Q | T | A | S | I |
| S | P | S | K | V | T | Q | T | A | S | I |
| Y | P | S | K | V | T | Q | T | A | S | I |
| S | S | R | V | A | T | Q | T | A | S | I |
| Y | S | R | V | A | T | Q | T | A | S | I |
| S | P | R | V | A | T | Q | T | A | S | I |
| Y | P | R | V | A | T | Q | T | A | S | I |
| S | S | S | V | A | T | Q | T | A | S | I |
| Y | S | S | V | A | T | Q | T | A | S | I |
| S | P | S | V | A | T | Q | T | A | S | I |
| Y | P | S | V | A | T | Q | T | A | S | I |
| S | S | R | K | A | T | Q | T | A | S | I |

TABLE 12-continued

Exemplary Mutations of 9G8 Light Chain (SEQ ID NO: 24) to Germline at the Indicated Residue Number

| 2 | 7 | 19 | 30 | 32 | 39 | 49 | 51 | 79 | 94 | 97 |
|---|---|----|----|----|----|----|----|----|----|----|
| Y | S | R | K | A | T | Q | T | A | S | I |
| S | P | R | K | A | T | Q | T | A | S | I |
| Y | P | R | K | A | T | Q | T | A | S | I |
| S | S | S | K | A | T | Q | T | A | S | I |
| Y | S | S | K | A | T | Q | T | A | S | I |
| S | P | S | K | A | T | Q | T | A | S | I |
| Y | P | S | K | A | T | Q | T | A | S | I |
| S | S | R | V | V | P | Q | T | A | S | I |
| Y | S | R | V | V | P | Q | T | A | S | I |
| S | P | R | V | V | P | Q | T | A | S | I |
| Y | P | R | V | V | P | Q | T | A | S | I |
| S | S | S | V | V | P | Q | T | A | S | I |
| Y | S | S | V | V | P | Q | T | A | S | I |
| S | P | S | V | V | P | Q | T | A | S | I |
| Y | P | S | V | V | P | Q | T | A | S | I |
| S | S | R | K | V | P | Q | T | A | S | I |
| Y | S | R | K | V | P | Q | T | A | S | I |
| S | P | R | K | V | P | Q | T | A | S | I |
| Y | P | R | K | V | P | Q | T | A | S | I |
| S | S | S | K | V | P | Q | T | A | S | I |
| Y | S | S | K | V | P | Q | T | A | S | I |
| S | P | S | K | V | P | Q | T | A | S | I |
| Y | P | S | K | V | P | Q | T | A | S | I |
| S | S | R | V | A | P | Q | T | A | S | I |
| Y | S | R | V | A | P | Q | T | A | S | I |
| S | P | R | V | A | P | Q | T | A | S | I |
| Y | P | R | V | A | P | Q | T | A | S | I |
| S | S | S | V | A | P | Q | T | A | S | I |
| Y | S | S | V | A | P | Q | T | A | S | I |
| S | P | S | V | A | P | Q | T | A | S | I |
| Y | P | S | V | A | P | Q | T | A | S | I |
| S | S | R | K | A | P | Q | T | A | S | I |
| Y | S | R | K | A | P | Q | T | A | S | I |
| S | P | R | K | A | P | Q | T | A | S | I |
| Y | P | R | K | A | P | Q | T | A | S | I |
| S | S | S | K | A | P | Q | T | A | S | I |
| Y | S | S | K | A | P | Q | T | A | S | I |
| S | P | S | K | A | P | Q | T | A | S | I |
| Y | P | S | K | A | P | Q | T | A | S | I |
| S | S | R | V | V | T | E | S | A | S | I |
| Y | S | R | V | V | T | E | S | A | S | I |
| S | P | R | V | V | T | E | S | A | S | I |
| Y | P | R | V | V | T | E | S | A | S | I |
| S | S | S | V | V | T | E | S | A | S | I |
| Y | S | S | V | V | T | E | S | A | S | I |
| S | P | S | V | V | T | E | S | A | S | I |
| Y | P | S | V | V | T | E | S | A | S | I |
| S | S | R | K | V | T | E | S | A | S | I |
| Y | S | R | K | V | T | E | S | A | S | I |
| S | P | R | K | V | T | E | S | A | S | I |
| Y | P | R | K | V | T | E | S | A | S | I |
| S | S | S | K | V | T | E | S | A | S | I |
| Y | S | S | K | V | T | E | S | A | S | I |
| S | P | S | K | V | T | E | S | A | S | I |
| Y | P | S | K | V | T | E | S | A | S | I |
| S | S | R | V | A | T | E | S | A | S | I |
| Y | S | R | V | A | T | E | S | A | S | I |
| S | P | R | V | A | T | E | S | A | S | I |
| Y | P | R | V | A | T | E | S | A | S | I |
| S | S | S | V | A | T | E | S | A | S | I |
| Y | S | S | V | A | T | E | S | A | S | I |
| S | P | S | V | A | T | E | S | A | S | I |
| Y | P | S | V | A | T | E | S | A | S | I |
| S | S | R | K | A | T | E | S | A | S | I |
| Y | S | R | K | A | T | E | S | A | S | I |
| S | P | R | K | A | T | E | S | A | S | I |
| Y | P | R | K | A | T | E | S | A | S | I |
| S | S | S | K | A | T | E | S | A | S | I |
| Y | S | S | K | A | T | E | S | A | S | I |
| S | P | S | K | A | T | E | S | A | S | I |
| Y | P | S | K | A | T | E | S | A | S | I |
| S | S | R | V | V | P | E | S | A | S | I |
| Y | S | R | V | V | P | E | S | A | S | I |
| S | P | R | V | V | P | E | S | A | S | I |
| Y | P | R | V | V | P | E | S | A | S | I |
| S | S | S | V | V | P | E | S | A | S | I |
| Y | S | S | V | V | P | E | S | A | S | I |
| S | P | S | V | V | P | E | S | A | S | I |
| Y | P | S | V | V | P | E | S | A | S | I |
| S | S | R | K | V | P | E | S | A | S | I |
| Y | S | R | K | V | P | E | S | A | S | I |
| S | P | R | K | V | P | E | S | A | S | I |
| Y | P | R | K | V | P | E | S | A | S | I |
| S | S | S | K | V | P | E | S | A | S | I |
| Y | S | S | K | V | P | E | S | A | S | I |
| S | P | S | K | V | P | E | S | A | S | I |
| Y | P | S | K | V | P | E | S | A | S | I |
| S | S | R | V | A | P | E | S | A | S | I |
| Y | S | R | V | A | P | E | S | A | S | I |
| S | P | R | V | A | P | E | S | A | S | I |
| Y | P | R | V | A | P | E | S | A | S | I |
| S | S | S | K | A | T | Q | S | A | S | I |
| Y | S | S | K | A | T | Q | S | A | S | I |
| S | P | S | K | A | T | Q | S | A | S | I |
| Y | P | S | K | A | T | Q | S | A | S | I |
| S | S | R | V | A | T | Q | S | A | S | I |
| Y | S | R | V | A | T | Q | S | A | S | I |
| S | P | R | V | A | T | Q | S | A | S | I |
| Y | P | R | V | A | T | Q | S | A | S | I |
| S | S | S | V | A | T | Q | S | A | S | I |
| Y | S | S | V | A | T | Q | S | A | S | I |
| S | P | S | V | A | T | Q | S | A | S | I |
| Y | P | S | V | A | T | Q | S | A | S | I |
| S | S | R | K | A | T | Q | S | A | S | I |
| Y | S | R | K | A | T | Q | S | A | S | I |
| S | P | R | K | A | T | Q | S | A | S | I |
| Y | P | R | K | A | T | Q | S | A | S | I |
| S | S | S | K | A | T | Q | S | A | S | I |
| Y | S | S | K | A | T | Q | S | A | S | I |
| S | P | S | K | A | T | Q | S | A | S | I |
| Y | P | S | K | A | T | Q | S | A | S | I |
| S | S | R | V | V | P | Q | S | A | S | I |
| Y | S | R | V | V | P | Q | S | A | S | I |
| S | P | R | V | V | P | Q | S | A | S | I |
| Y | P | R | V | V | P | Q | S | A | S | I |
| S | S | S | V | V | P | Q | S | A | S | I |
| Y | S | S | V | V | P | Q | S | A | S | I |
| S | P | S | V | V | P | Q | S | A | S | I |
| Y | P | S | V | V | P | Q | S | A | S | I |
| S | S | R | K | V | P | Q | S | A | S | I |
| Y | S | R | K | V | P | Q | S | A | S | I |
| S | P | R | K | V | P | Q | S | A | S | I |
| Y | P | R | K | V | P | Q | S | A | S | I |
| S | S | S | K | V | P | Q | S | A | S | I |
| Y | S | S | K | V | P | Q | S | A | S | I |
| S | P | S | K | V | P | Q | S | A | S | I |
| Y | P | S | K | V | P | Q | S | A | S | I |

TABLE 12-continued

Exemplary Mutations of 9G8 Light Chain (SEQ ID NO: 24) to Germline at the Indicated Residue Number

| 2 | 7 | 19 | 30 | 32 | 39 | 49 | 51 | 79 | 94 | 97 |
|---|---|----|----|----|----|----|----|----|----|----|
| Y | P | S | K | V | P | Q | S | A | S | I |
| S | S | R | V | A | P | Q | S | A | S | I |
| Y | S | R | V | A | P | Q | S | A | S | I |
| S | P | R | V | A | P | Q | S | A | S | I |
| Y | P | R | V | A | P | Q | S | A | S | I |
| S | S | S | V | A | P | Q | S | A | S | I |
| Y | S | S | V | A | P | Q | S | A | S | I |
| S | P | S | V | A | P | Q | S | A | S | I |
| Y | P | S | V | A | P | Q | S | A | S | I |
| S | S | R | K | A | P | Q | S | A | S | I |
| Y | S | R | K | A | P | Q | S | A | S | I |
| S | P | R | K | A | P | Q | S | A | S | I |
| Y | P | R | K | A | P | Q | S | A | S | I |
| S | S | S | K | A | P | Q | S | A | S | I |
| Y | S | S | K | A | P | Q | S | A | S | I |
| S | P | S | K | A | P | Q | S | A | S | I |
| Y | P | S | K | A | P | Q | S | A | S | I |
| S | S | R | V | V | T | E | T | V | T | V |
| Y | S | R | V | V | T | E | T | V | T | V |
| S | P | R | V | V | T | E | T | V | T | V |
| Y | P | R | V | V | T | E | T | V | T | V |
| S | S | S | V | V | T | E | T | V | T | V |
| Y | S | S | V | V | T | E | T | V | T | V |
| S | P | S | V | V | T | E | T | V | T | V |
| Y | P | S | V | V | T | E | T | V | T | V |
| S | S | R | K | V | T | E | T | V | T | V |
| Y | S | R | K | V | T | E | T | V | T | V |
| S | P | R | K | V | T | E | T | V | T | V |
| Y | P | R | K | V | T | E | T | V | T | V |
| S | S | S | K | V | T | E | T | V | T | V |
| Y | S | S | K | V | T | E | T | V | T | V |
| S | P | S | K | V | T | E | T | V | T | V |
| Y | P | S | K | V | T | E | T | V | T | V |
| S | S | R | V | A | T | E | T | V | T | V |
| Y | S | R | V | A | T | E | T | V | T | V |
| S | P | R | V | A | T | E | T | V | T | V |
| Y | P | R | V | A | T | E | T | V | T | V |
| S | S | S | V | A | T | E | T | V | T | V |
| Y | S | S | V | A | T | E | T | V | T | V |
| S | P | S | V | A | T | E | T | V | T | V |
| Y | P | S | V | A | T | E | T | V | T | V |
| S | S | R | K | A | T | E | T | V | T | V |
| Y | S | R | K | A | T | E | T | V | T | V |
| S | P | R | K | A | T | E | T | V | T | V |
| Y | P | R | K | A | T | E | T | V | T | V |
| S | S | S | K | A | T | E | T | V | T | V |
| Y | S | S | K | A | T | E | T | V | T | V |
| S | P | S | K | A | T | E | T | V | T | V |
| Y | P | S | K | A | T | E | T | V | T | V |
| S | S | R | V | V | P | E | T | V | T | V |
| Y | S | R | V | V | P | E | T | V | T | V |
| S | P | R | V | V | P | E | T | V | T | V |
| Y | P | R | V | V | P | E | T | V | T | V |
| S | S | S | V | V | P | E | T | V | T | V |
| Y | S | S | V | V | P | E | T | V | T | V |
| S | P | S | V | V | P | E | T | V | T | V |
| Y | P | S | V | V | P | E | T | V | T | V |
| S | S | R | K | V | P | E | T | V | T | V |
| Y | S | R | K | V | P | E | T | V | T | V |
| S | P | R | K | V | P | E | T | V | T | V |
| Y | P | R | K | V | P | E | T | V | T | V |
| S | S | S | K | V | P | E | T | V | T | V |
| Y | S | S | K | V | P | E | T | V | T | V |
| S | P | S | K | V | P | E | T | V | T | V |
| Y | P | S | K | V | P | E | T | V | T | V |
| S | S | R | V | A | P | E | T | V | T | V |
| Y | S | R | V | A | P | E | T | V | T | V |
| S | P | R | V | A | P | E | T | V | T | V |
| Y | P | R | V | A | P | E | T | V | T | V |
| S | S | S | V | A | P | E | T | V | T | V |
| Y | S | S | V | A | P | E | T | V | T | V |
| S | P | S | V | A | P | E | T | V | T | V |
| Y | P | S | V | A | P | E | T | V | T | V |
| S | S | R | K | A | P | E | T | V | T | V |
| Y | S | R | K | A | P | E | T | V | T | V |
| S | P | R | K | A | P | E | T | V | T | V |
| Y | P | R | K | A | P | E | T | V | T | V |
| S | S | S | K | A | P | E | T | V | T | V |
| Y | S | S | K | A | P | E | T | V | T | V |
| S | P | S | K | A | P | E | T | V | T | V |
| Y | P | S | K | A | P | E | T | V | T | V |
| S | S | R | V | V | T | Q | T | V | T | V |
| Y | S | R | V | V | T | Q | T | V | T | V |
| S | P | R | V | V | T | Q | T | V | T | V |
| Y | P | R | V | V | T | Q | T | V | T | V |
| S | S | S | V | V | T | Q | T | V | T | V |
| Y | S | S | V | V | T | Q | T | V | T | V |
| S | P | S | V | V | T | Q | T | V | T | V |
| Y | P | S | V | V | T | Q | T | V | T | V |
| S | S | R | K | V | T | Q | T | V | T | V |
| Y | S | R | K | V | T | Q | T | V | T | V |
| S | P | R | K | V | T | Q | T | V | T | V |
| Y | P | R | K | V | T | Q | T | V | T | V |
| S | S | S | K | V | T | Q | T | V | T | V |
| Y | S | S | K | V | T | Q | T | V | T | V |
| S | P | S | K | V | T | Q | T | V | T | V |
| Y | P | S | K | V | T | Q | T | V | T | V |
| S | S | R | V | A | T | Q | T | V | T | V |
| Y | S | R | V | A | T | Q | T | V | T | V |
| S | P | R | V | A | T | Q | T | V | T | V |
| Y | P | R | V | A | T | Q | T | V | T | V |
| S | S | S | V | A | T | Q | T | V | T | V |
| Y | S | S | V | A | T | Q | T | V | T | V |
| S | P | S | V | A | T | Q | T | V | T | V |
| Y | P | S | V | A | T | Q | T | V | T | V |
| S | S | R | K | A | T | Q | T | V | T | V |
| Y | S | R | K | A | T | Q | T | V | T | V |
| S | P | R | K | A | T | Q | T | V | T | V |
| Y | P | R | K | A | T | Q | T | V | T | V |
| S | S | S | K | A | T | Q | T | V | T | V |
| Y | S | S | K | A | T | Q | T | V | T | V |
| S | P | S | K | A | T | Q | T | V | T | V |
| Y | P | S | K | A | T | Q | T | V | T | V |
| S | S | R | V | V | P | Q | T | V | T | V |
| Y | S | R | V | V | P | Q | T | V | T | V |
| S | P | R | V | V | P | Q | T | V | T | V |
| Y | P | R | V | V | P | Q | T | V | T | V |
| S | S | S | V | V | P | Q | T | V | T | V |
| Y | S | S | V | V | P | Q | T | V | T | V |
| S | P | S | V | V | P | Q | T | V | T | V |
| Y | P | S | V | V | P | Q | T | V | T | V |
| S | S | R | K | V | P | Q | T | V | T | V |
| Y | S | R | K | V | P | Q | T | V | T | V |
| S | P | R | K | V | P | Q | T | V | T | V |
| Y | P | R | K | V | P | Q | T | V | T | V |
| S | S | S | K | V | P | Q | T | V | T | V |
| Y | S | S | K | V | P | Q | T | V | T | V |
| S | P | S | K | V | P | Q | T | V | T | V |
| Y | P | S | K | V | P | Q | T | V | T | V |
| S | S | R | V | A | P | Q | T | V | T | V |
| Y | S | R | V | A | P | Q | T | V | T | V |
| S | P | R | V | A | P | Q | T | V | T | V |
| Y | P | R | V | A | P | Q | T | V | T | V |
| S | S | S | V | A | P | Q | T | V | T | V |
| Y | S | S | V | A | P | Q | T | V | T | V |
| S | P | S | V | A | P | Q | T | V | T | V |
| Y | P | S | V | A | P | Q | T | V | T | V |
| S | S | R | K | A | P | Q | T | V | T | V |
| Y | S | R | K | A | P | Q | T | V | T | V |
| S | P | R | K | A | P | Q | T | V | T | V |
| Y | P | R | K | A | P | Q | T | V | T | V |
| S | S | S | K | A | P | Q | T | V | T | V |
| Y | S | S | K | A | P | Q | T | V | T | V |
| S | P | S | K | A | P | Q | T | V | T | V |
| Y | P | S | K | A | P | Q | T | V | T | V |
| S | S | R | V | V | T | E | S | V | T | V |
| Y | S | R | V | V | T | E | S | V | T | V |
| S | P | R | V | V | T | E | S | V | T | V |
| Y | P | R | V | V | T | E | S | V | T | V |
| S | S | S | V | V | T | E | S | V | T | V |

TABLE 12-continued

Exemplary Mutations of 9G8 Light Chain (SEQ ID NO: 24) to Germline at the Indicated Residue Number

| 2 | 7 | 19 | 30 | 32 | 39 | 49 | 51 | 79 | 94 | 97 |
|---|---|----|----|----|----|----|----|----|----|----|
| Y | S | S | V | V | T | E | S | V | T | V |
| S | P | S | V | V | T | E | S | V | T | V |
| Y | P | S | V | V | T | E | S | V | T | V |
| S | S | R | K | V | T | E | S | V | T | V |
| Y | S | R | K | V | T | E | S | V | T | V |
| S | P | R | K | V | T | E | S | V | T | V |
| Y | P | R | K | V | T | E | S | V | T | V |
| S | S | S | K | V | T | E | S | V | T | V |
| Y | S | S | K | V | T | E | S | V | T | V |
| S | P | S | K | V | T | E | S | V | T | V |
| Y | P | S | K | V | T | E | S | V | T | V |
| S | S | R | V | A | T | E | S | V | T | V |
| Y | S | R | V | A | T | E | S | V | T | V |
| S | P | R | V | A | T | E | S | V | T | V |
| Y | P | R | V | A | T | E | S | V | T | V |
| S | S | S | V | A | T | E | S | V | T | V |
| Y | S | S | V | A | T | E | S | V | T | V |
| S | P | S | V | A | T | E | S | V | T | V |
| Y | P | S | V | A | T | E | S | V | T | V |
| S | S | R | K | A | T | E | S | V | T | V |
| Y | S | R | K | A | T | E | S | V | T | V |
| S | P | R | K | A | T | E | S | V | T | V |
| Y | P | R | K | A | T | E | S | V | T | V |
| S | S | S | K | A | T | E | S | V | T | V |
| Y | S | S | K | A | T | E | S | V | T | V |
| S | P | S | K | A | T | E | S | V | T | V |
| Y | P | S | K | A | T | E | S | V | T | V |
| S | S | R | V | V | P | E | S | V | T | V |
| Y | S | R | V | V | P | E | S | V | T | V |
| S | P | R | V | V | P | E | S | V | T | V |
| Y | P | R | V | V | P | E | S | V | T | V |
| S | S | S | V | V | P | E | S | V | T | V |
| Y | S | S | V | V | P | E | S | V | T | V |
| S | P | S | V | V | P | E | S | V | T | V |
| Y | P | S | V | V | P | E | S | V | T | V |
| S | S | R | K | V | P | E | S | V | T | V |
| Y | S | R | K | V | P | E | S | V | T | V |
| S | P | R | K | V | P | E | S | V | T | V |
| Y | P | R | K | V | P | E | S | V | T | V |
| S | S | S | K | V | P | E | S | V | T | V |
| Y | S | S | K | V | P | E | S | V | T | V |
| S | P | S | K | V | P | E | S | V | T | V |
| Y | P | S | K | V | P | E | S | V | T | V |
| S | S | R | V | A | P | E | S | V | T | V |
| Y | S | R | V | A | P | E | S | V | T | V |
| S | P | R | V | A | P | E | S | V | T | V |
| Y | P | R | V | A | P | E | S | V | T | V |
| S | S | S | V | A | P | E | S | V | T | V |
| Y | S | S | V | A | P | E | S | V | T | V |
| S | P | S | V | A | P | E | S | V | T | V |
| Y | P | S | V | A | P | E | S | V | T | V |
| S | S | R | K | A | P | E | S | V | T | V |
| Y | S | R | K | A | P | E | S | V | T | V |
| S | P | R | K | A | P | E | S | V | T | V |
| Y | P | R | K | A | P | E | S | V | T | V |
| S | S | S | K | A | P | E | S | V | T | V |
| Y | S | S | K | A | P | E | S | V | T | V |
| S | P | S | K | A | P | E | S | V | T | V |
| Y | P | S | K | A | P | E | S | V | T | V |
| S | S | R | V | V | T | Q | S | V | T | V |
| Y | S | R | V | V | T | Q | S | V | T | V |
| S | P | R | V | V | T | Q | S | V | T | V |
| Y | P | R | V | V | T | Q | S | V | T | V |
| S | S | S | V | V | T | Q | S | V | T | V |
| Y | S | S | V | V | T | Q | S | V | T | V |
| S | P | S | V | V | T | Q | S | V | T | V |
| Y | P | S | V | V | T | Q | S | V | T | V |
| S | S | R | K | V | T | Q | S | V | T | V |
| Y | S | R | K | V | T | Q | S | V | T | V |
| S | P | R | K | V | T | Q | S | V | T | V |
| Y | P | R | K | V | T | Q | S | V | T | V |
| S | S | S | K | V | T | Q | S | V | T | V |
| Y | S | S | K | V | T | Q | S | V | T | V |
| S | P | S | K | V | T | Q | S | V | T | V |
| Y | P | S | K | V | T | Q | S | V | T | V |
| S | S | R | V | A | T | Q | S | V | T | V |
| Y | S | R | V | A | T | Q | S | V | T | V |
| S | P | R | V | A | T | Q | S | V | T | V |
| Y | P | R | V | A | T | Q | S | V | T | V |
| S | S | S | V | A | T | Q | S | V | T | V |
| Y | S | S | V | A | T | Q | S | V | T | V |
| S | P | S | V | A | T | Q | S | V | T | V |
| Y | P | S | V | A | T | Q | S | V | T | V |
| S | S | R | K | A | T | Q | S | V | T | V |
| Y | S | R | K | A | T | Q | S | V | T | V |
| S | P | R | K | A | T | Q | S | V | T | V |
| Y | P | R | K | A | T | Q | S | V | T | V |
| S | S | S | K | A | T | Q | S | V | T | V |
| Y | S | S | K | A | T | Q | S | V | T | V |
| S | P | S | K | A | T | Q | S | V | T | V |
| Y | P | S | K | A | T | Q | S | V | T | V |
| S | S | R | V | V | P | Q | S | V | T | V |
| Y | S | R | V | V | P | Q | S | V | T | V |
| S | P | R | V | V | P | Q | S | V | T | V |
| Y | P | R | V | V | P | Q | S | V | T | V |
| S | S | S | V | V | P | Q | S | V | T | V |
| Y | S | S | V | V | P | Q | S | V | T | V |
| S | P | S | V | V | P | Q | S | V | T | V |
| Y | P | S | V | V | P | Q | S | V | T | V |
| S | S | R | K | V | P | Q | S | V | T | V |
| Y | S | R | K | V | P | Q | S | V | T | V |
| S | P | R | K | V | P | Q | S | V | T | V |
| Y | P | R | K | V | P | Q | S | V | T | V |
| S | S | S | K | V | P | Q | S | V | T | V |
| Y | S | S | K | V | P | Q | S | V | T | V |
| S | P | S | K | V | P | Q | S | V | T | V |
| Y | P | S | K | V | P | Q | S | V | T | V |
| S | S | R | V | A | P | Q | S | V | T | V |
| Y | S | R | V | A | P | Q | S | V | T | V |
| S | P | R | V | A | P | Q | S | V | T | V |
| Y | P | R | V | A | P | Q | S | V | T | V |
| S | S | S | V | A | P | Q | S | V | T | V |
| Y | S | S | V | A | P | Q | S | V | T | V |
| S | P | S | V | A | P | Q | S | V | T | V |
| Y | P | S | V | A | P | Q | S | V | T | V |
| S | S | R | K | A | P | Q | S | V | T | V |
| Y | S | R | K | A | P | Q | S | V | T | V |
| S | P | R | K | A | P | Q | S | V | T | V |
| Y | P | R | K | A | P | Q | S | V | T | V |
| S | S | S | K | A | P | Q | S | V | T | V |
| Y | S | S | K | A | P | Q | S | V | T | V |
| S | P | S | K | A | P | Q | S | V | T | V |
| Y | P | S | K | A | P | Q | S | V | T | V |
| S | S | R | V | V | T | E | T | A | T | V |
| Y | S | R | V | V | T | E | T | A | T | V |
| S | P | R | V | V | T | E | T | A | T | V |
| Y | P | R | V | V | T | E | T | A | T | V |
| S | S | S | V | V | T | E | T | A | T | V |
| Y | S | S | V | V | T | E | T | A | T | V |
| S | P | S | V | V | T | E | T | A | T | V |
| Y | P | S | V | V | T | E | T | A | T | V |
| S | S | R | K | V | T | E | T | A | T | V |
| Y | S | R | K | V | T | E | T | A | T | V |
| S | P | R | K | V | T | E | T | A | T | V |
| Y | P | R | K | V | T | E | T | A | T | V |
| S | S | S | K | V | T | E | T | A | T | V |
| Y | S | S | K | V | T | E | T | A | T | V |
| S | P | S | K | V | T | E | T | A | T | V |
| Y | P | S | K | V | T | E | T | A | T | V |
| S | S | R | V | A | T | E | T | A | T | V |
| Y | S | R | V | A | T | E | T | A | T | V |
| S | P | R | V | A | T | E | T | A | T | V |
| Y | P | R | V | A | T | E | T | A | T | V |
| S | S | S | V | A | T | E | T | A | T | V |
| Y | S | S | V | A | T | E | T | A | T | V |
| S | P | S | V | A | T | E | T | A | T | V |
| Y | P | S | V | A | T | E | T | A | T | V |
| S | S | R | K | A | T | E | T | A | T | V |
| Y | S | R | K | A | T | E | T | A | T | V |
| S | P | R | K | A | T | E | T | A | T | V |

TABLE 12-continued

Exemplary Mutations of 9G8 Light Chain (SEQ ID NO: 24) to Germline at the Indicated Residue Number

| 2 | 7 | 19 | 30 | 32 | 39 | 49 | 51 | 79 | 94 | 97 |
|---|---|----|----|----|----|----|----|----|----|----|
| Y | P | R | K | A | T | E | T | A | T | V |
| S | S | S | K | A | T | E | T | A | T | V |
| Y | S | S | K | A | T | E | T | A | T | V |
| S | P | S | K | A | T | E | T | A | T | V |
| Y | P | S | K | A | T | E | T | A | T | V |
| S | S | R | V | V | P | E | T | A | T | V |
| Y | S | R | V | V | P | E | T | A | T | V |
| S | P | R | V | V | P | E | T | A | T | V |
| Y | P | R | V | V | P | E | T | A | T | V |
| S | S | S | V | V | P | E | T | A | T | V |
| Y | S | S | V | V | P | E | T | A | T | V |
| S | P | S | V | V | P | E | T | A | T | V |
| Y | P | S | V | V | P | E | T | A | T | V |
| S | S | R | K | V | P | E | T | A | T | V |
| Y | S | R | K | V | P | E | T | A | T | V |
| S | P | R | K | V | P | E | T | A | T | V |
| Y | P | R | K | V | P | E | T | A | T | V |
| S | S | S | K | V | P | E | T | A | T | V |
| Y | S | S | K | V | P | E | T | A | T | V |
| S | P | S | K | V | P | E | T | A | T | V |
| Y | P | S | K | V | P | E | T | A | T | V |
| S | S | R | V | A | P | E | T | A | T | V |
| Y | S | R | V | A | P | E | T | A | T | V |
| S | P | R | V | A | P | E | T | A | T | V |
| Y | P | R | V | A | P | E | T | A | T | V |
| S | S | S | V | A | P | E | T | A | T | V |
| Y | S | S | V | A | P | E | T | A | T | V |
| S | P | S | V | A | P | E | T | A | T | V |
| Y | P | S | V | A | P | E | T | A | T | V |
| S | S | R | K | A | P | E | T | A | T | V |
| Y | S | R | K | A | P | E | T | A | T | V |
| S | P | R | K | A | P | E | T | A | T | V |
| Y | P | R | K | A | P | E | T | A | T | V |
| S | S | S | K | A | P | E | T | A | T | V |
| Y | S | S | K | A | P | E | T | A | T | V |
| S | P | S | K | A | P | E | T | A | T | V |
| Y | P | S | K | A | P | E | T | A | T | V |
| S | S | R | V | V | T | Q | T | A | T | V |
| Y | S | R | V | V | T | Q | T | A | T | V |
| S | P | R | V | V | T | Q | T | A | T | V |
| Y | P | R | V | V | T | Q | T | A | T | V |
| S | S | S | V | V | T | Q | T | A | T | V |
| Y | S | S | V | V | T | Q | T | A | T | V |
| S | P | S | V | V | T | Q | T | A | T | V |
| Y | P | S | V | V | T | Q | T | A | T | V |
| S | S | R | K | V | T | Q | T | A | T | V |
| Y | S | R | K | V | T | Q | T | A | T | V |
| S | P | R | K | V | T | Q | T | A | T | V |
| Y | P | R | K | V | T | Q | T | A | T | V |
| S | S | S | K | V | T | Q | T | A | T | V |
| Y | S | S | K | V | T | Q | T | A | T | V |
| S | P | S | K | V | T | Q | T | A | T | V |
| Y | P | S | K | V | T | Q | T | A | T | V |
| S | S | R | V | A | T | Q | T | A | T | V |
| Y | S | R | V | A | T | Q | T | A | T | V |
| S | P | R | V | A | T | Q | T | A | T | V |
| Y | P | R | V | A | T | Q | T | A | T | V |
| S | S | S | V | A | T | Q | T | A | T | V |
| Y | S | S | V | A | T | Q | T | A | T | V |
| S | P | S | V | A | T | Q | T | A | T | V |
| Y | P | S | V | A | T | Q | T | A | T | V |
| S | S | R | K | A | T | Q | T | A | T | V |
| Y | S | R | K | A | T | Q | T | A | T | V |
| S | P | R | K | A | T | Q | T | A | T | V |
| Y | P | R | K | A | T | Q | T | A | T | V |
| S | S | S | K | A | T | Q | T | A | T | V |
| Y | S | S | K | A | T | Q | T | A | T | V |
| S | P | S | K | A | T | Q | T | A | T | V |
| Y | P | S | K | A | T | Q | T | A | T | V |
| S | S | R | V | V | P | Q | T | A | T | V |
| Y | S | R | V | V | P | Q | T | A | T | V |
| S | P | R | V | V | P | Q | T | A | T | V |
| Y | P | R | V | V | P | Q | T | A | T | V |
| S | S | S | V | V | P | Q | T | A | T | V |
| Y | S | S | V | V | P | Q | T | A | T | V |
| S | P | S | V | V | P | Q | T | A | T | V |
| Y | P | S | V | V | P | Q | T | A | T | V |
| S | S | R | K | V | P | Q | T | A | T | V |
| S | P | R | K | V | P | Q | T | A | T | V |
| Y | P | R | K | V | P | Q | T | A | T | V |
| S | S | S | K | V | P | Q | T | A | T | V |
| Y | S | S | K | V | P | Q | T | A | T | V |
| S | P | S | K | V | P | Q | T | A | T | V |
| Y | P | S | K | V | P | Q | T | A | T | V |
| S | S | R | V | A | P | Q | T | A | T | V |
| Y | S | R | V | A | P | Q | T | A | T | V |
| S | P | R | V | A | P | Q | T | A | T | V |
| Y | P | R | V | A | P | Q | T | A | T | V |
| S | S | S | V | A | P | Q | T | A | T | V |
| Y | S | S | V | A | P | Q | T | A | T | V |
| S | P | S | V | A | P | Q | T | A | T | V |
| Y | P | S | V | A | P | Q | T | A | T | V |
| S | S | R | K | A | P | Q | T | A | T | V |
| Y | S | R | K | A | P | Q | T | A | T | V |
| S | P | R | K | A | P | Q | T | A | T | V |
| Y | P | R | K | A | P | Q | T | A | T | V |
| S | S | S | K | A | P | Q | T | A | T | V |
| Y | S | S | K | A | P | Q | T | A | T | V |
| S | P | S | K | A | P | Q | T | A | T | V |
| Y | P | S | K | A | P | Q | T | A | T | V |
| S | S | R | V | V | T | E | S | A | T | V |
| Y | S | R | V | V | T | E | S | A | T | V |
| S | P | R | V | V | T | E | S | A | T | V |
| Y | P | R | V | V | T | E | S | A | T | V |
| S | S | S | V | V | T | E | S | A | T | V |
| Y | S | S | V | V | T | E | S | A | T | V |
| S | P | S | V | V | T | E | S | A | T | V |
| Y | P | S | V | V | T | E | S | A | T | V |
| S | S | R | K | V | T | E | S | A | T | V |
| Y | S | R | K | V | T | E | S | A | T | V |
| S | P | R | K | V | T | E | S | A | T | V |
| Y | P | R | K | V | T | E | S | A | T | V |
| S | S | S | K | V | T | E | S | A | T | V |
| Y | S | S | K | V | T | E | S | A | T | V |
| S | P | S | K | V | T | E | S | A | T | V |
| Y | P | S | K | V | T | E | S | A | T | V |
| S | S | R | V | A | T | E | S | A | T | V |
| Y | S | R | V | A | T | E | S | A | T | V |
| S | P | R | V | A | T | E | S | A | T | V |
| Y | P | R | V | A | T | E | S | A | T | V |
| S | S | S | V | A | T | E | S | A | T | V |
| Y | S | S | V | A | T | E | S | A | T | V |
| S | P | S | V | A | T | E | S | A | T | V |
| Y | P | S | V | A | T | E | S | A | T | V |
| S | S | R | K | A | T | E | S | A | T | V |
| Y | S | R | K | A | T | E | S | A | T | V |
| S | P | R | K | A | T | E | S | A | T | V |
| Y | P | R | K | A | T | E | S | A | T | V |
| S | S | S | K | A | T | E | S | A | T | V |
| Y | S | S | K | A | T | E | S | A | T | V |
| S | P | S | K | A | T | E | S | A | T | V |
| Y | P | S | K | A | T | E | S | A | T | V |
| S | S | R | V | V | P | E | S | A | T | V |
| Y | S | R | V | V | P | E | S | A | T | V |
| S | P | R | V | V | P | E | S | A | T | V |
| Y | P | R | V | V | P | E | S | A | T | V |
| S | S | S | V | V | P | E | S | A | T | V |
| Y | S | S | V | V | P | E | S | A | T | V |
| S | P | S | V | V | P | E | S | A | T | V |
| Y | P | S | V | V | P | E | S | A | T | V |
| S | S | R | K | V | P | E | S | A | T | V |
| Y | S | R | K | V | P | E | S | A | T | V |
| S | P | R | K | V | P | E | S | A | T | V |
| Y | P | R | K | V | P | E | S | A | T | V |
| S | S | S | K | V | P | E | S | A | T | V |
| Y | S | S | K | V | P | E | S | A | T | V |
| S | P | S | K | V | P | E | S | A | T | V |
| Y | P | S | K | V | P | E | S | A | T | V |
| S | S | R | V | A | P | E | S | A | T | V |

TABLE 12-continued

Exemplary Mutations of 9G8 Light Chain (SEQ ID NO: 24) to Germline at the Indicated Residue Number

| 2 | 7 | 19 | 30 | 32 | 39 | 49 | 51 | 79 | 94 | 97 |
|---|---|----|----|----|----|----|----|----|----|----|
| Y | S | R | V | A | P | E | S | A | T | V |
| S | P | R | V | A | P | E | S | A | T | V |
| Y | P | R | V | A | P | E | S | A | T | V |
| S | S | S | V | A | P | E | S | A | T | V |
| Y | S | S | V | A | P | E | S | A | T | V |
| S | P | S | V | A | P | E | S | A | T | V |
| Y | P | S | V | A | P | E | S | A | T | V |
| S | S | R | K | A | P | E | S | A | T | V |
| Y | S | R | K | A | P | E | S | A | T | V |
| S | P | R | K | A | P | E | S | A | T | V |
| Y | P | R | K | A | P | E | S | A | T | V |
| S | S | S | K | A | P | E | S | A | T | V |
| Y | S | S | K | A | P | E | S | A | T | V |
| S | P | S | K | A | P | E | S | A | T | V |
| Y | P | S | K | A | P | E | S | A | T | V |
| S | S | R | V | V | T | Q | S | A | T | V |
| Y | S | R | V | V | T | Q | S | A | T | V |
| S | P | R | V | V | T | Q | S | A | T | V |
| Y | P | R | V | V | T | Q | S | A | T | V |
| S | S | S | V | V | T | Q | S | A | T | V |
| Y | S | S | V | V | T | Q | S | A | T | V |
| S | P | S | V | V | T | Q | S | A | T | V |
| Y | P | S | V | V | T | Q | S | A | T | V |
| S | S | R | K | V | T | Q | S | A | T | V |
| Y | S | R | K | V | T | Q | S | A | T | V |
| S | P | R | K | V | T | Q | S | A | T | V |
| Y | P | R | K | V | T | Q | S | A | T | V |
| S | S | S | K | V | T | Q | S | A | T | V |
| Y | S | S | K | V | T | Q | S | A | T | V |
| S | P | S | K | V | T | Q | S | A | T | V |
| Y | P | S | K | V | T | Q | S | A | T | V |
| S | S | R | V | A | T | Q | S | A | T | V |
| Y | S | R | V | A | T | Q | S | A | T | V |
| S | P | R | V | A | T | Q | S | A | T | V |
| Y | P | R | V | A | T | Q | S | A | T | V |
| S | S | S | V | A | T | Q | S | A | T | V |
| Y | S | S | V | A | T | Q | S | A | T | V |
| S | P | S | V | A | T | Q | S | A | T | V |
| Y | P | S | V | A | T | Q | S | A | T | V |
| S | S | R | K | A | T | Q | S | A | T | V |
| Y | S | R | K | A | T | Q | S | A | T | V |
| S | P | R | K | A | T | Q | S | A | T | V |
| Y | P | R | K | A | T | Q | S | A | T | V |
| S | S | S | K | A | T | Q | S | A | T | V |
| Y | S | S | K | A | T | Q | S | A | T | V |
| S | P | S | K | A | T | Q | S | A | T | V |
| Y | P | S | K | A | T | Q | S | A | T | V |
| S | S | R | V | V | P | Q | S | A | T | V |
| Y | S | R | V | V | P | Q | S | A | T | V |
| S | P | R | V | V | P | Q | S | A | T | V |
| Y | P | R | V | V | P | Q | S | A | T | V |
| S | S | S | V | V | P | Q | S | A | T | V |
| Y | S | S | V | V | P | Q | S | A | T | V |
| S | P | S | V | V | P | Q | S | A | T | V |
| Y | P | S | V | V | P | Q | S | A | T | V |
| S | S | R | K | V | P | Q | S | A | T | V |
| Y | S | R | K | V | P | Q | S | A | T | V |
| S | P | R | K | V | P | Q | S | A | T | V |
| Y | P | R | K | V | P | Q | S | A | T | V |
| S | S | S | K | V | P | Q | S | A | T | V |
| Y | S | S | K | V | P | Q | S | A | T | V |
| S | P | S | K | V | P | Q | S | A | T | V |
| Y | P | S | K | V | P | Q | S | A | T | V |
| S | S | R | V | A | P | Q | S | A | T | V |
| Y | S | R | V | A | P | Q | S | A | T | V |
| S | P | R | V | A | P | Q | S | A | T | V |
| Y | P | R | V | A | P | Q | S | A | T | V |
| S | S | S | V | A | P | Q | S | A | T | V |
| Y | S | S | V | A | P | Q | S | A | T | V |
| S | P | S | V | A | P | Q | S | A | T | V |
| Y | P | S | V | A | P | Q | S | A | T | V |
| S | S | R | K | A | P | Q | S | A | T | V |
| Y | S | R | K | A | P | Q | S | A | T | V |
| S | P | R | K | A | P | Q | S | A | T | V |
| Y | P | R | K | A | P | Q | S | A | T | V |
| S | S | S | K | A | P | Q | S | A | T | V |
| Y | S | S | K | A | P | Q | S | A | T | V |
| S | P | S | K | A | P | Q | S | A | T | V |
| Y | P | S | K | A | P | Q | S | A | T | V |
| S | S | R | V | V | T | E | T | V | S | V |
| Y | S | R | V | V | T | E | T | V | S | V |
| S | P | R | V | V | T | E | T | V | S | V |
| Y | P | R | V | V | T | E | T | V | S | V |
| S | S | S | V | V | T | E | T | V | S | V |
| Y | S | S | V | V | T | E | T | V | S | V |
| S | P | S | V | V | T | E | T | V | S | V |
| Y | P | S | V | V | T | E | T | V | S | V |
| S | S | R | K | V | T | E | T | V | S | V |
| Y | S | R | K | V | T | E | T | V | S | V |
| S | P | R | K | V | T | E | T | V | S | V |
| Y | P | R | K | V | T | E | T | V | S | V |
| S | S | S | K | V | T | E | T | V | S | V |
| Y | S | S | K | V | T | E | T | V | S | V |
| S | P | S | K | V | T | E | T | V | S | V |
| Y | P | S | K | V | T | E | T | V | S | V |
| S | S | R | V | A | T | E | T | V | S | V |
| Y | S | R | V | A | T | E | T | V | S | V |
| S | P | R | V | A | T | E | T | V | S | V |
| Y | P | R | V | A | T | E | T | V | S | V |
| S | S | S | V | A | T | E | T | V | S | V |
| Y | S | S | V | A | T | E | T | V | S | V |
| S | P | S | V | A | T | E | T | V | S | V |
| Y | P | S | V | A | T | E | T | V | S | V |
| S | S | R | K | A | T | E | T | V | S | V |
| Y | S | R | K | A | T | E | T | V | S | V |
| S | P | R | K | A | T | E | T | V | S | V |
| Y | P | R | K | A | T | E | T | V | S | V |
| S | S | S | K | A | T | E | T | V | S | V |
| Y | S | S | K | A | T | E | T | V | S | V |
| S | P | S | K | A | T | E | T | V | S | V |
| Y | P | S | K | A | T | E | T | V | S | V |
| S | S | R | V | V | P | E | T | V | S | V |
| Y | S | R | V | V | P | E | T | V | S | V |
| S | P | R | V | V | P | E | T | V | S | V |
| Y | P | R | V | V | P | E | T | V | S | V |
| S | S | S | V | V | P | E | T | V | S | V |
| Y | S | S | V | V | P | E | T | V | S | V |
| S | P | S | V | V | P | E | T | V | S | V |
| Y | P | S | V | V | P | E | T | V | S | V |
| S | S | R | K | V | P | E | T | V | S | V |
| Y | S | R | K | V | P | E | T | V | S | V |
| S | P | R | K | V | P | E | T | V | S | V |
| Y | P | R | K | V | P | E | T | V | S | V |
| S | S | S | K | V | P | E | T | V | S | V |
| Y | S | S | K | V | P | E | T | V | S | V |
| S | P | S | K | V | P | E | T | V | S | V |
| Y | P | S | K | V | P | E | T | V | S | V |
| S | S | R | V | A | P | E | T | V | S | V |
| Y | S | R | V | A | P | E | T | V | S | V |
| S | P | R | V | A | P | E | T | V | S | V |
| Y | P | R | V | A | P | E | T | V | S | V |
| S | S | S | V | A | P | E | T | V | S | V |
| Y | S | S | V | A | P | E | T | V | S | V |
| S | P | S | V | A | P | E | T | V | S | V |
| Y | P | S | V | A | P | E | T | V | S | V |
| S | S | R | K | A | P | E | T | V | S | V |
| Y | S | R | K | A | P | E | T | V | S | V |
| S | P | R | K | A | P | E | T | V | S | V |
| Y | P | R | K | A | P | E | T | V | S | V |
| S | S | S | K | A | P | E | T | V | S | V |
| Y | S | S | K | A | P | E | T | V | S | V |
| S | P | S | K | A | P | E | T | V | S | V |
| Y | P | S | K | A | P | E | T | V | S | V |
| S | S | R | V | V | T | Q | T | V | S | V |
| Y | S | R | V | V | T | Q | T | V | S | V |
| S | P | R | V | V | T | Q | T | V | S | V |
| Y | P | R | V | V | T | Q | T | V | S | V |
| S | S | S | V | V | T | Q | T | V | S | V |
| Y | S | S | V | V | T | Q | T | V | S | V |
| S | P | S | V | V | T | Q | T | V | S | V |

TABLE 12-continued

Exemplary Mutations of 9G8 Light Chain (SEQ ID NO: 24) to Germline at the Indicated Residue Number

| 2 | 7 | 19 | 30 | 32 | 39 | 49 | 51 | 79 | 94 | 97 |
|---|---|----|----|----|----|----|----|----|----|----|
| Y | P | S | V | V | T | Q | T | V | S | V |
| S | S | R | K | V | T | Q | T | V | S | V |
| Y | S | R | K | V | T | Q | T | V | S | V |
| S | P | R | K | V | T | Q | T | V | S | V |
| Y | P | R | K | V | T | Q | T | V | S | V |
| S | S | S | K | V | T | Q | T | V | S | V |
| Y | S | S | K | V | T | Q | T | V | S | V |
| S | P | S | K | V | T | Q | T | V | S | V |
| Y | P | S | K | V | T | Q | T | V | S | V |
| S | S | R | V | A | T | Q | T | V | S | V |
| Y | S | R | V | A | T | Q | T | V | S | V |
| S | P | R | V | A | T | Q | T | V | S | V |
| Y | P | R | V | A | T | Q | T | V | S | V |
| S | S | S | V | A | T | Q | T | V | S | V |
| Y | S | S | V | A | T | Q | T | V | S | V |
| S | P | S | V | A | T | Q | T | V | S | V |
| Y | P | S | V | A | T | Q | T | V | S | V |
| S | S | R | K | A | T | Q | T | V | S | V |
| Y | S | R | K | A | T | Q | T | V | S | V |
| S | P | R | K | A | T | Q | T | V | S | V |
| Y | P | R | K | A | T | Q | T | V | S | V |
| S | S | S | K | A | T | Q | T | V | S | V |
| Y | S | S | K | A | T | Q | T | V | S | V |
| S | P | S | K | A | T | Q | T | V | S | V |
| Y | P | S | K | A | T | Q | T | V | S | V |
| S | S | R | V | V | P | Q | T | V | S | V |
| Y | S | R | V | V | P | Q | T | V | S | V |
| S | P | R | V | V | P | Q | T | V | S | V |
| Y | P | R | V | V | P | Q | T | V | S | V |
| S | S | S | V | V | P | Q | T | V | S | V |
| Y | S | S | V | V | P | Q | T | V | S | V |
| S | P | S | V | V | P | Q | T | V | S | V |
| Y | P | S | V | V | P | Q | T | V | S | V |
| S | S | R | K | V | P | Q | T | V | S | V |
| Y | S | R | K | V | P | Q | T | V | S | V |
| S | P | R | K | V | P | Q | T | V | S | V |
| Y | P | R | K | V | P | Q | T | V | S | V |
| S | S | S | K | V | P | Q | T | V | S | V |
| Y | S | S | K | V | P | Q | T | V | S | V |
| S | P | S | K | V | P | Q | T | V | S | V |
| Y | P | S | K | V | P | Q | T | V | S | V |
| S | S | R | V | A | P | Q | T | V | S | V |
| Y | S | R | V | A | P | Q | T | V | S | V |
| S | P | R | V | A | P | Q | T | V | S | V |
| Y | P | R | V | A | P | Q | T | V | S | V |
| S | S | S | V | A | P | Q | T | V | S | V |
| Y | S | S | V | A | P | Q | T | V | S | V |
| S | P | S | V | A | P | Q | T | V | S | V |
| Y | P | S | V | A | P | Q | T | V | S | V |
| S | S | R | K | A | P | Q | T | V | S | V |
| Y | S | R | K | A | P | Q | T | V | S | V |
| S | P | R | K | A | P | Q | T | V | S | V |
| Y | P | R | K | A | P | Q | T | V | S | V |
| S | S | S | K | A | P | Q | T | V | S | V |
| Y | S | S | K | A | P | Q | T | V | S | V |
| S | P | S | K | A | P | Q | T | V | S | V |
| Y | P | S | K | A | P | Q | T | V | S | V |
| S | S | R | V | V | T | E | S | V | S | V |
| Y | S | R | V | V | T | E | S | V | S | V |
| S | P | R | V | V | T | E | S | V | S | V |
| Y | P | R | V | V | T | E | S | V | S | V |
| S | S | S | V | V | T | E | S | V | S | V |
| Y | S | S | V | V | T | E | S | V | S | V |
| S | P | S | V | V | T | E | S | V | S | V |
| Y | P | S | V | V | T | E | S | V | S | V |
| S | S | R | K | V | T | E | S | V | S | V |
| Y | S | R | K | V | T | E | S | V | S | V |
| S | P | R | K | V | T | E | S | V | S | V |
| Y | P | R | K | V | T | E | S | V | S | V |
| S | S | S | K | V | T | E | S | V | S | V |
| Y | S | S | K | V | T | E | S | V | S | V |
| S | P | S | K | V | T | E | S | V | S | V |
| Y | P | S | K | V | T | E | S | V | S | V |
| S | S | R | V | A | T | E | S | V | S | V |
| Y | S | R | V | A | T | E | S | V | S | V |
| S | P | R | V | A | T | E | S | V | S | V |
| Y | P | R | V | A | T | E | S | V | S | V |
| S | S | S | V | A | T | E | S | V | S | V |
| Y | S | S | V | A | T | E | S | V | S | V |
| S | P | S | V | A | T | E | S | V | S | V |
| Y | P | S | V | A | T | E | S | V | S | V |
| S | S | R | K | A | T | E | S | V | S | V |
| Y | S | R | K | A | T | E | S | V | S | V |
| S | P | R | K | A | T | E | S | V | S | V |
| Y | P | R | K | A | T | E | S | V | S | V |
| S | S | S | K | A | T | E | S | V | S | V |
| Y | S | S | K | A | T | E | S | V | S | V |
| S | P | S | K | A | T | E | S | V | S | V |
| Y | P | S | K | A | T | E | S | V | S | V |
| S | S | R | V | V | P | E | S | V | S | V |
| Y | S | R | V | V | P | E | S | V | S | V |
| S | P | R | V | V | P | E | S | V | S | V |
| Y | P | R | V | V | P | E | S | V | S | V |
| S | S | S | V | V | P | E | S | V | S | V |
| Y | S | S | V | V | P | E | S | V | S | V |
| S | P | S | V | V | P | E | S | V | S | V |
| Y | P | S | V | V | P | E | S | V | S | V |
| S | S | R | K | V | P | E | S | V | S | V |
| Y | S | R | K | V | P | E | S | V | S | V |
| S | P | R | K | V | P | E | S | V | S | V |
| Y | P | R | K | V | P | E | S | V | S | V |
| S | S | S | K | V | P | E | S | V | S | V |
| Y | S | S | K | V | P | E | S | V | S | V |
| S | P | S | K | V | P | E | S | V | S | V |
| Y | P | S | K | V | P | E | S | V | S | V |
| S | S | R | V | A | P | E | S | V | S | V |
| Y | S | R | V | A | P | E | S | V | S | V |
| S | P | R | V | A | P | E | S | V | S | V |
| Y | P | R | V | A | P | E | S | V | S | V |
| S | S | S | V | A | P | E | S | V | S | V |
| Y | S | S | V | A | P | E | S | V | S | V |
| S | P | S | V | A | P | E | S | V | S | V |
| Y | P | S | V | A | P | E | S | V | S | V |
| S | S | R | K | A | P | E | S | V | S | V |
| Y | S | R | K | A | P | E | S | V | S | V |
| S | P | R | K | A | P | E | S | V | S | V |
| Y | P | R | K | A | P | E | S | V | S | V |
| S | S | S | K | A | P | E | S | V | S | V |
| Y | S | S | K | A | P | E | S | V | S | V |
| S | P | S | K | A | P | E | S | V | S | V |
| Y | P | S | K | A | P | E | S | V | S | V |
| S | S | R | V | V | T | Q | S | V | S | V |
| Y | S | R | V | V | T | Q | S | V | S | V |
| S | P | R | V | V | T | Q | S | V | S | V |
| Y | P | R | V | V | T | Q | S | V | S | V |
| S | S | S | V | V | T | Q | S | V | S | V |
| Y | S | S | V | V | T | Q | S | V | S | V |
| S | P | S | V | V | T | Q | S | V | S | V |
| Y | P | S | V | V | T | Q | S | V | S | V |
| S | S | R | K | V | T | Q | S | V | S | V |
| Y | S | R | K | V | T | Q | S | V | S | V |
| S | P | R | K | V | T | Q | S | V | S | V |
| Y | P | R | K | V | T | Q | S | V | S | V |
| S | S | S | K | V | T | Q | S | V | S | V |
| Y | S | S | K | V | T | Q | S | V | S | V |
| S | P | S | K | V | T | Q | S | V | S | V |
| Y | P | S | K | V | T | Q | S | V | S | V |
| S | S | R | V | A | T | Q | S | V | S | V |
| Y | S | R | V | A | T | Q | S | V | S | V |
| S | P | R | V | A | T | Q | S | V | S | V |
| Y | P | R | V | A | T | Q | S | V | S | V |
| S | S | S | V | A | T | Q | S | V | S | V |
| Y | S | S | V | A | T | Q | S | V | S | V |
| S | P | S | V | A | T | Q | S | V | S | V |
| Y | P | S | V | A | T | Q | S | V | S | V |
| S | S | R | K | A | T | Q | S | V | S | V |
| Y | S | R | K | A | T | Q | S | V | S | V |
| S | P | R | K | A | T | Q | S | V | S | V |
| Y | P | R | K | A | T | Q | S | V | S | V |
| S | S | S | K | A | T | Q | S | V | S | V |

TABLE 12-continued

Exemplary Mutations of 9G8 Light Chain (SEQ ID NO: 24) to Germline at the Indicated Residue Number

| 2 | 7 | 19 | 30 | 32 | 39 | 49 | 51 | 79 | 94 | 97 |
|---|---|----|----|----|----|----|----|----|----|----|
| Y | S | S | K | A | T | Q | S | V | S | V |
| S | P | S | K | A | T | Q | S | V | S | V |
| Y | P | S | K | A | T | Q | S | V | S | V |
| S | S | R | V | V | P | Q | S | V | S | V |
| Y | S | R | V | V | P | Q | S | V | S | V |
| S | P | R | V | V | P | Q | S | V | S | V |
| Y | P | R | V | V | P | Q | S | V | S | V |
| S | S | S | V | V | P | Q | S | V | S | V |
| Y | S | S | V | V | P | Q | S | V | S | V |
| S | P | S | V | V | P | Q | S | V | S | V |
| Y | P | S | V | V | P | Q | S | V | S | V |
| S | S | R | K | V | P | Q | S | V | S | V |
| Y | S | R | K | V | P | Q | S | V | S | V |
| S | P | R | K | V | P | Q | S | V | S | V |
| Y | P | R | K | V | P | Q | S | V | S | V |
| S | S | S | K | V | P | Q | S | V | S | V |
| Y | S | S | K | V | P | Q | S | V | S | V |
| S | P | S | K | V | P | Q | S | V | S | V |
| Y | P | S | K | V | P | Q | S | V | S | V |
| S | S | R | V | A | P | Q | S | V | S | V |
| Y | S | R | V | A | P | Q | S | V | S | V |
| S | P | R | V | A | P | Q | S | V | S | V |
| Y | P | R | V | A | P | Q | S | V | S | V |
| S | S | S | V | A | P | Q | S | V | S | V |
| Y | S | S | V | A | P | Q | S | V | S | V |
| S | P | S | V | A | P | Q | S | V | S | V |
| Y | P | S | V | A | P | Q | S | V | S | V |
| S | S | R | K | A | P | Q | S | V | S | V |
| Y | S | R | K | A | P | Q | S | V | S | V |
| S | P | R | K | A | P | Q | S | V | S | V |
| Y | P | R | K | A | P | Q | S | V | S | V |
| S | S | S | K | A | P | Q | S | V | S | V |
| Y | S | S | K | A | P | Q | S | V | S | V |
| S | P | S | K | A | P | Q | S | V | S | V |
| Y | P | S | K | A | P | Q | S | V | S | V |
| S | S | R | V | V | T | E | T | A | S | V |
| Y | S | R | V | V | T | E | T | A | S | V |
| S | P | R | V | V | T | E | T | A | S | V |
| Y | P | R | V | V | T | E | T | A | S | V |
| S | S | S | V | V | T | E | T | A | S | V |
| Y | S | S | V | V | T | E | T | A | S | V |
| S | P | S | V | V | T | E | T | A | S | V |
| Y | P | S | V | V | T | E | T | A | S | V |
| S | S | R | K | V | T | E | T | A | S | V |
| Y | S | R | K | V | T | E | T | A | S | V |
| S | P | R | K | V | T | E | T | A | S | V |
| Y | P | R | K | V | T | E | T | A | S | V |
| S | S | S | K | V | T | E | T | A | S | V |
| Y | S | S | K | V | T | E | T | A | S | V |
| S | P | S | K | V | T | E | T | A | S | V |
| Y | P | S | K | V | T | E | T | A | S | V |
| S | S | R | V | A | T | E | T | A | S | V |
| Y | S | R | V | A | T | E | T | A | S | V |
| S | P | R | V | A | T | E | T | A | S | V |
| Y | P | R | V | A | T | E | T | A | S | V |
| S | S | S | V | A | T | E | T | A | S | V |
| Y | S | S | V | A | T | E | T | A | S | V |
| S | P | S | V | A | T | E | T | A | S | V |
| Y | P | S | V | A | T | E | T | A | S | V |
| S | S | R | K | A | T | E | T | A | S | V |
| Y | S | R | K | A | T | E | T | A | S | V |
| S | P | R | K | A | T | E | T | A | S | V |
| Y | P | R | K | A | T | E | T | A | S | V |
| S | S | S | K | A | T | E | T | A | S | V |
| Y | S | S | K | A | T | E | T | A | S | V |
| S | P | S | K | A | T | E | T | A | S | V |
| Y | P | S | K | A | T | E | T | A | S | V |
| S | S | R | V | V | P | E | T | A | S | V |
| Y | S | R | V | V | P | E | T | A | S | V |
| S | P | R | V | V | P | E | T | A | S | V |
| Y | P | R | V | V | P | E | T | A | S | V |
| S | S | S | V | V | P | E | T | A | S | V |
| Y | S | S | V | V | P | E | T | A | S | V |
| S | P | S | V | V | P | E | T | A | S | V |
| Y | P | S | V | V | P | E | T | A | S | V |
| S | S | R | K | V | P | E | T | A | S | V |
| Y | S | R | K | V | P | E | T | A | S | V |
| S | P | R | K | V | P | E | T | A | S | V |
| Y | P | R | K | V | P | E | T | A | S | V |
| S | S | S | K | V | P | E | T | A | S | V |
| Y | S | S | K | V | P | E | T | A | S | V |
| S | P | S | K | V | P | E | T | A | S | V |
| Y | P | S | K | V | P | E | T | A | S | V |
| S | S | R | V | A | P | E | T | A | S | V |
| Y | S | R | V | A | P | E | T | A | S | V |
| S | P | R | V | A | P | E | T | A | S | V |
| Y | P | R | V | A | P | E | T | A | S | V |
| S | S | S | V | A | P | E | T | A | S | V |
| Y | S | S | V | A | P | E | T | A | S | V |
| S | P | S | V | A | P | E | T | A | S | V |
| Y | P | S | V | A | P | E | T | A | S | V |
| S | S | R | K | A | P | E | T | A | S | V |
| Y | S | R | K | A | P | E | T | A | S | V |
| S | P | R | K | A | P | E | T | A | S | V |
| Y | P | R | K | A | P | E | T | A | S | V |
| S | S | S | K | A | P | E | T | A | S | V |
| Y | S | S | K | A | P | E | T | A | S | V |
| S | P | S | K | A | P | E | T | A | S | V |
| Y | P | S | K | A | P | E | T | A | S | V |
| S | S | R | V | V | T | Q | T | A | S | V |
| Y | S | R | V | V | T | Q | T | A | S | V |
| S | P | R | V | V | T | Q | T | A | S | V |
| Y | P | R | V | V | T | Q | T | A | S | V |
| S | S | S | V | V | T | Q | T | A | S | V |
| Y | S | S | V | V | T | Q | T | A | S | V |
| S | P | S | V | V | T | Q | T | A | S | V |
| Y | P | S | V | V | T | Q | T | A | S | V |
| S | S | R | K | V | T | Q | T | A | S | V |
| Y | S | R | K | V | T | Q | T | A | S | V |
| S | P | R | K | V | T | Q | T | A | S | V |
| Y | P | R | K | V | T | Q | T | A | S | V |
| S | S | S | K | V | T | Q | T | A | S | V |
| Y | S | S | K | V | T | Q | T | A | S | V |
| S | P | S | K | V | T | Q | T | A | S | V |
| Y | P | S | K | V | T | Q | T | A | S | V |
| S | S | R | V | A | T | Q | T | A | S | V |
| Y | S | R | V | A | T | Q | T | A | S | V |
| S | P | R | V | A | T | Q | T | A | S | V |
| Y | P | R | V | A | T | Q | T | A | S | V |
| S | S | S | V | A | T | Q | T | A | S | V |
| Y | S | S | V | A | T | Q | T | A | S | V |
| S | P | S | V | A | T | Q | T | A | S | V |
| Y | P | S | V | A | T | Q | T | A | S | V |
| S | S | R | K | A | T | Q | T | A | S | V |
| Y | S | R | K | A | T | Q | T | A | S | V |
| S | P | R | K | A | T | Q | T | A | S | V |
| Y | P | R | K | A | T | Q | T | A | S | V |
| S | S | S | K | A | T | Q | T | A | S | V |
| Y | S | S | K | A | T | Q | T | A | S | V |
| S | P | S | K | A | T | Q | T | A | S | V |
| Y | P | S | K | A | T | Q | T | A | S | V |
| S | S | R | V | V | P | Q | T | A | S | V |
| Y | S | R | V | V | P | Q | T | A | S | V |
| S | P | R | V | V | P | Q | T | A | S | V |
| Y | P | R | V | V | P | Q | T | A | S | V |
| S | S | S | V | V | P | Q | T | A | S | V |
| Y | S | S | V | V | P | Q | T | A | S | V |
| S | P | S | V | V | P | Q | T | A | S | V |
| Y | P | S | V | V | P | Q | T | A | S | V |
| S | S | R | K | V | P | Q | T | A | S | V |
| Y | S | R | K | V | P | Q | T | A | S | V |
| S | P | R | K | V | P | Q | T | A | S | V |
| Y | P | R | K | V | P | Q | T | A | S | V |
| S | S | S | K | V | P | Q | T | A | S | V |
| Y | S | S | K | V | P | Q | T | A | S | V |
| S | P | S | K | V | P | Q | T | A | S | V |
| Y | P | S | K | V | P | Q | T | A | S | V |
| S | S | R | V | A | P | Q | T | A | S | V |
| Y | S | R | V | A | P | Q | T | A | S | V |
| S | P | R | V | A | P | Q | T | A | S | V |

TABLE 12-continued

Exemplary Mutations of 9G8 Light Chain (SEQ ID NO: 24) to Germline at the Indicated Residue Number

| 2 | 7 | 19 | 30 | 32 | 39 | 49 | 51 | 79 | 94 | 97 |
|---|---|----|----|----|----|----|----|----|----|----|
| Y | P | R  | V  | A  | P  | Q  | T  | A  | S  | V  |
| S | S | S  | V  | A  | P  | Q  | T  | A  | S  | V  |
| Y | S | S  | V  | A  | P  | Q  | T  | A  | S  | V  |
| S | P | S  | V  | A  | P  | Q  | T  | A  | S  | V  |
| Y | P | S  | V  | A  | P  | Q  | T  | A  | S  | V  |
| S | S | R  | K  | A  | P  | Q  | T  | A  | S  | V  |
| Y | S | R  | K  | A  | P  | Q  | T  | A  | S  | V  |
| S | P | R  | K  | A  | P  | Q  | T  | A  | S  | V  |
| Y | P | R  | K  | A  | P  | Q  | T  | A  | S  | V  |
| S | S | S  | K  | A  | P  | Q  | T  | A  | S  | V  |
| Y | S | S  | K  | A  | P  | Q  | T  | A  | S  | V  |
| S | P | S  | K  | A  | P  | Q  | T  | A  | S  | V  |
| Y | P | S  | K  | A  | P  | Q  | T  | A  | S  | V  |
| S | S | R  | V  | V  | T  | E  | S  | A  | S  | V  |
| Y | S | R  | V  | V  | T  | E  | S  | A  | S  | V  |
| S | P | R  | V  | V  | T  | E  | S  | A  | S  | V  |
| Y | P | R  | V  | V  | T  | E  | S  | A  | S  | V  |
| S | S | S  | V  | V  | T  | E  | S  | A  | S  | V  |
| Y | S | S  | V  | V  | T  | E  | S  | A  | S  | V  |
| S | P | S  | V  | V  | T  | E  | S  | A  | S  | V  |
| Y | P | S  | V  | V  | T  | E  | S  | A  | S  | V  |
| S | S | R  | K  | V  | T  | E  | S  | A  | S  | V  |
| Y | S | R  | K  | V  | T  | E  | S  | A  | S  | V  |
| S | P | R  | K  | V  | T  | E  | S  | A  | S  | V  |
| Y | P | R  | K  | V  | T  | E  | S  | A  | S  | V  |
| S | S | S  | K  | V  | T  | E  | S  | A  | S  | V  |
| S | P | S  | K  | V  | T  | E  | S  | A  | S  | V  |
| Y | P | S  | K  | V  | T  | E  | S  | A  | S  | V  |
| S | S | R  | V  | A  | T  | E  | S  | A  | S  | V  |
| Y | S | R  | V  | A  | T  | E  | S  | A  | S  | V  |
| S | P | R  | V  | A  | T  | E  | S  | A  | S  | V  |
| Y | P | R  | V  | A  | T  | E  | S  | A  | S  | V  |
| S | S | S  | V  | A  | T  | E  | S  | A  | S  | V  |
| Y | S | S  | V  | A  | T  | E  | S  | A  | S  | V  |
| S | P | S  | V  | A  | T  | E  | S  | A  | S  | V  |
| Y | P | S  | V  | A  | T  | E  | S  | A  | S  | V  |
| S | S | R  | K  | A  | T  | E  | S  | A  | S  | V  |
| Y | S | R  | K  | A  | T  | E  | S  | A  | S  | V  |
| S | P | R  | K  | A  | T  | E  | S  | A  | S  | V  |
| Y | P | R  | K  | A  | T  | E  | S  | A  | S  | V  |
| S | S | S  | K  | A  | T  | E  | S  | A  | S  | V  |
| Y | S | S  | K  | A  | T  | E  | S  | A  | S  | V  |
| S | P | S  | K  | A  | T  | E  | S  | A  | S  | V  |
| Y | P | S  | K  | A  | T  | E  | S  | A  | S  | V  |
| S | S | R  | V  | V  | P  | E  | S  | A  | S  | V  |
| Y | S | R  | V  | V  | P  | E  | S  | A  | S  | V  |
| S | P | R  | V  | V  | P  | E  | S  | A  | S  | V  |
| Y | P | R  | V  | V  | P  | E  | S  | A  | S  | V  |
| S | S | S  | V  | V  | P  | E  | S  | A  | S  | V  |
| Y | S | S  | V  | V  | P  | E  | S  | A  | S  | V  |
| S | P | S  | V  | V  | P  | E  | S  | A  | S  | V  |
| Y | P | S  | V  | V  | P  | E  | S  | A  | S  | V  |
| S | S | R  | K  | V  | P  | E  | S  | A  | S  | V  |
| Y | S | R  | K  | V  | P  | E  | S  | A  | S  | V  |
| S | P | R  | K  | V  | P  | E  | S  | A  | S  | V  |
| Y | P | R  | K  | V  | P  | E  | S  | A  | S  | V  |
| S | S | S  | K  | V  | P  | E  | S  | A  | S  | V  |
| Y | S | S  | K  | V  | P  | E  | S  | A  | S  | V  |
| S | P | S  | K  | V  | P  | E  | S  | A  | S  | V  |
| Y | P | S  | K  | V  | P  | E  | S  | A  | S  | V  |
| S | S | R  | V  | A  | P  | E  | S  | A  | S  | V  |
| Y | S | R  | V  | A  | P  | E  | S  | A  | S  | V  |
| S | P | R  | V  | A  | P  | E  | S  | A  | S  | V  |
| Y | P | R  | V  | A  | P  | E  | S  | A  | S  | V  |
| S | S | S  | V  | A  | P  | E  | S  | A  | S  | V  |
| Y | S | S  | V  | A  | P  | E  | S  | A  | S  | V  |
| S | P | S  | V  | A  | P  | E  | S  | A  | S  | V  |
| Y | P | S  | V  | A  | P  | E  | S  | A  | S  | V  |
| S | S | R  | K  | A  | P  | E  | S  | A  | S  | V  |
| Y | S | R  | K  | A  | P  | E  | S  | A  | S  | V  |
| S | P | R  | K  | A  | P  | E  | S  | A  | S  | V  |
| Y | P | R  | K  | A  | P  | E  | S  | A  | S  | V  |
| S | S | S  | K  | A  | P  | E  | S  | A  | S  | V  |
| Y | S | S  | K  | A  | P  | E  | S  | A  | S  | V  |
| S | P | S  | K  | A  | P  | E  | S  | A  | S  | V  |
| Y | P | S  | K  | A  | P  | E  | S  | A  | S  | V  |
| S | S | R  | V  | V  | T  | Q  | S  | A  | S  | V  |
| S | P | R  | V  | V  | T  | Q  | S  | A  | S  | V  |
| Y | P | R  | V  | V  | T  | Q  | S  | A  | S  | V  |
| S | S | S  | V  | V  | T  | Q  | S  | A  | S  | V  |
| Y | S | S  | V  | V  | T  | Q  | S  | A  | S  | V  |
| S | P | S  | V  | V  | T  | Q  | S  | A  | S  | V  |
| Y | P | S  | V  | V  | T  | Q  | S  | A  | S  | V  |
| S | S | R  | K  | V  | T  | Q  | S  | A  | S  | V  |
| Y | S | R  | K  | V  | T  | Q  | S  | A  | S  | V  |
| S | P | R  | K  | V  | T  | Q  | S  | A  | S  | V  |
| Y | P | R  | K  | V  | T  | Q  | S  | A  | S  | V  |
| S | S | S  | K  | V  | T  | Q  | S  | A  | S  | V  |
| Y | S | S  | K  | V  | T  | Q  | S  | A  | S  | V  |
| S | P | S  | K  | V  | T  | Q  | S  | A  | S  | V  |
| Y | P | S  | K  | V  | T  | Q  | S  | A  | S  | V  |
| S | S | R  | V  | A  | T  | Q  | S  | A  | S  | V  |
| Y | S | R  | V  | A  | T  | Q  | S  | A  | S  | V  |
| S | P | R  | V  | A  | T  | Q  | S  | A  | S  | V  |
| Y | P | R  | V  | A  | T  | Q  | S  | A  | S  | V  |
| S | S | S  | V  | A  | T  | Q  | S  | A  | S  | V  |
| Y | S | S  | V  | A  | T  | Q  | S  | A  | S  | V  |
| S | P | S  | V  | A  | T  | Q  | S  | A  | S  | V  |
| Y | P | S  | V  | A  | T  | Q  | S  | A  | S  | V  |
| S | S | R  | K  | A  | T  | Q  | S  | A  | S  | V  |
| Y | S | R  | K  | A  | T  | Q  | S  | A  | S  | V  |
| S | P | R  | K  | A  | T  | Q  | S  | A  | S  | V  |
| Y | P | R  | K  | A  | T  | Q  | S  | A  | S  | V  |
| S | S | S  | K  | A  | T  | Q  | S  | A  | S  | V  |
| Y | S | S  | K  | A  | T  | Q  | S  | A  | S  | V  |
| S | P | S  | K  | A  | T  | Q  | S  | A  | S  | V  |
| Y | P | S  | K  | A  | T  | Q  | S  | A  | S  | V  |
| S | S | R  | V  | V  | P  | Q  | S  | A  | S  | V  |
| Y | S | R  | V  | V  | P  | Q  | S  | A  | S  | V  |
| S | P | R  | V  | V  | P  | Q  | S  | A  | S  | V  |
| Y | P | R  | V  | V  | P  | Q  | S  | A  | S  | V  |
| S | S | S  | V  | V  | P  | Q  | S  | A  | S  | V  |
| Y | S | S  | V  | V  | P  | Q  | S  | A  | S  | V  |
| S | P | S  | V  | V  | P  | Q  | S  | A  | S  | V  |
| Y | P | S  | V  | V  | P  | Q  | S  | A  | S  | V  |
| S | S | R  | K  | V  | P  | Q  | S  | A  | S  | V  |
| Y | S | R  | K  | V  | P  | Q  | S  | A  | S  | V  |
| S | P | R  | K  | V  | P  | Q  | S  | A  | S  | V  |
| Y | P | R  | K  | V  | P  | Q  | S  | A  | S  | V  |
| S | S | S  | K  | V  | P  | Q  | S  | A  | S  | V  |
| Y | S | S  | K  | V  | P  | Q  | S  | A  | S  | V  |
| S | P | S  | K  | V  | P  | Q  | S  | A  | S  | V  |
| Y | P | S  | K  | V  | P  | Q  | S  | A  | S  | V  |
| S | S | R  | V  | A  | P  | Q  | S  | A  | S  | V  |
| Y | S | R  | V  | A  | P  | Q  | S  | A  | S  | V  |
| S | P | R  | V  | A  | P  | Q  | S  | A  | S  | V  |
| Y | P | R  | V  | A  | P  | Q  | S  | A  | S  | V  |
| S | S | S  | V  | A  | P  | Q  | S  | A  | S  | V  |
| Y | S | S  | V  | A  | P  | Q  | S  | A  | S  | V  |
| S | P | S  | V  | A  | P  | Q  | S  | A  | S  | V  |
| Y | P | S  | V  | A  | P  | Q  | S  | A  | S  | V  |
| S | S | R  | K  | A  | P  | Q  | S  | A  | S  | V  |
| Y | S | R  | K  | A  | P  | Q  | S  | A  | S  | V  |
| S | P | R  | K  | A  | P  | Q  | S  | A  | S  | V  |
| Y | P | R  | K  | A  | P  | Q  | S  | A  | S  | V  |
| S | S | S  | K  | A  | P  | Q  | S  | A  | S  | V  |
| Y | S | S  | K  | A  | P  | Q  | S  | A  | S  | V  |
| S | P | S  | K  | A  | P  | Q  | S  | A  | S  | V  |
| Y | P | S  | K  | A  | P  | Q  | S  | A  | S  | V  |

A further embodiment In some embodiments of the invention, the targeted binding agent or antibody comprises a sequence comprising SEQ ID NO.: 8. In certain embodiments, SEQ ID NO.: 24 comprises any one of the combinations of germline and non-germline residues indicated by each row of Table 12. In some embodiments, SEQ ID NO: 24 comprises any one, any two, any three, any four, any five, any six, any seven, any eight, any nine, any ten, any eleven, or all eleven of the germline residues as indicated in Table 12. In certain embodiments, SEQ ID NO.: 24 comprises any one of the unique combinations of germline and non-germline residues indicated by each row of Table 12. In other embodiments, the targeted binding agent or antibody is derived from a germline sequence with VL, 3r and JL2 domains, wherein one or more residues has been mutated to yield the corresponding germline residue at that position. In certain embodiments, SEQ ID NO.: 24 can comprise further modifications that include removing structural liabilities. For example, SEQ ID NO.: 24 can comprise any one of the unique combinations of germline and non-germline residues indicated by each row of Table 12 and further include the mutation of C33 to a S. An example is 9G8 VLOP1 where the light chain has been mutated to remove the structural liability at C33 and further mutated back to the germline sequence at position 7 where the S has been mutated to a P and V at position 79 has been mutated to an A. Another example is 968 VLOP2 where C33 has been mutated to S, S at position 2 has been mutated to an Y, S at position 7 has been mutated to a P, R at position 19 has been mutated to an S, T at position 39 has been mutated to an P, and V at position 79 has been mutated to an A. See specifically Table 13.

The skilled person will be aware that there are alternative methods of defining CDR boundaries. All CDR boundaries in Table 2 and 13 are defined according to the Kabat definition.

Costar, catalog #3712). Subsequently, 30 μl of purified antibodies, serial diluted from 5 μg/ml hybridoma supernatant was added and plates were incubated at 4° C. for 1 h, at which time 20 μl of 100 ng/ml Alexa-647 labeled human Notch1/Fc was added. After a further 3 h incubation at 4 the amount of hound Notch1/Fc was determined by reading the fluorescence in each well using an FMAT 8200 instrument (Applied Biosystems). Data for 12 purified antibodies is shown in Table 14, which shows the ability of purified antibodies to inhibit interactions between recombinant full-length human DLL4 and Notch1/Fc chimera.

In addition similar experiments were performed and quantified using a FACSCalibur (BD Biosciences) instrument. For these experiments, parental 293T cells or cells transiently transfected with human DLL4 were reconstituted in PBS containing 2% FCS and added at a concentration of 25000 cells/well to wells containing purified antibodies at a final concentration of 10 μg/ml, 1 μg/ml or 0.1 μg/ml. After incubation for 1 h at 4° C., Alexa-647 labeled human Notch1/Fc was added at a final concentration of 227 ng/ml and plates were incubated for 2 h at 4 T. Following washing with PBS containing 2% FCS, the amount of bound Notch1/Fc was determined by reading the fluorescence in each well using a FACSCalibur instrument. Under these conditions, the ability of the 20 purified antibodies to inhibit DLL4-Notch1 interactions was similar to that observed using the MAT instrument (data not shown). Similar results were also obtained when

TABLE 13

| SEQ ID NO | Chain | FR1 | CDR1 | FR2 | CDR2 | FR3 | CDR3 | FR4 |
|---|---|---|---|---|---|---|---|---|
| 75 | 21H3 VHOP | QVQLVQSGAEVKKP GASVKVSCKASGYT FT | NYGIT | WVRQAPGQ GLEWMG | WISAYNGNTNRVTMTTDTSTSTAYMEL YAQKLQD RSLRSDDTAVYYCAR | | DRVPRIPVTTWGQGTMVTVSS EAFDI | |
| 50 | 21H3 VLOP1 (corresponding to 21H3RK VL) | QSVLTQPPSASGTP GQRVTISC | SGSSSNIGSYF VY | WYQQLPGT APKLLIY | RNNQRPS | GVPDRFSGSESGTSASL AISGLRSEDEADYYC | AAWDDSLSGHFGGGTKLTVL WV | |
| 76 | 21H3 VLOP2 | QSVLTQPPSASGTP GQPVTISC | SGSSSNIGSYF VY | WYQQLPGT APKLLIY | RNNQRPS | GVPDRFSGSKSGTSASL AISGLPSEDEADYYC | AAWDDSLSGHFGGFTKLTVL WV | |
| 77 | 2H10 VHOP | QVQLVESGGGVVQP GRSLRLSCAASGFT FS | RHGMH | WVRQAPGK GLEWVA | VVWFDGSNIYRFTISRDNSKNTLYLQM YADSVKC NSLRAEDTAVYYCAR | | DSRIAAADY WGQGTLVTVSS | |
| 78 | 2H10 VLOP1 | SYELTQPPSVSVSP GQTVSITC | SGDKLGDKYVS | WYQQKPGQ SPVLVIY | QESKRPS | GIPERFSGSSSGNTATL TISGTQAMDEADYYC | QTWDSSLVV EGCGTKLTVL | |
| 79 | 2H10 VLOP2 | SYELTQPPSVSVSP GQTASITC | SGDKLGDKYVS | WYQQFPGQ SPVLVIY | QESKRPS | GIPERFSGSNSGNTATL TISGTQAMDEADYYC | QTWDSSLVV GFFFTKLTVL | |
| 80 | 9G8 VHOP1 | QLQLQESGPGLVKP SETLSLSCTVSGGS | SSSSY | WGWIRQPP GKGLEWIG | SIYYSGSTYYRVSISVDTSKNQFSLKL SPSLKS SSVTAADTAVYFCAP | | QGYGGHPDVFWGQGTMVTVSS DI | |
| 81 | 9G8 VHOP2 | QLQLQESGPGLVKP SETLSLSCTVSGGS IS | SSSSY | WGWIRQPP GKGLEWIG | SIYYSGSTYYRVTISVDTSKNQFSLKL SPSLKS SSVTAADTAVYCAR | | QGYGGHPDVFWGQGTMVTVSS DI | |
| 82 | 9G8 VLOP1 | SSELTQPPSVSVSP GQTARITC | SGDKLGDVYVS | WYQQKTGQ SPVLVIY | EDTEEPS | GIPEPFSCSNSCNTATL TISGTQAMDEADYYC | QAWDSTTAVIFGGGTKLTVL | |
| 83 | 9G8 VLOP2 | SYELTQSPSVSVSP GQTASITC | SGDKLGDVYVA S | WYQQKPGQ SPVLVIY | EDTKRPS | GIPERFSGSNSGNTATL TISGTQAMDEADYYC | QAWDSTTAVIFGGGTKLTVL | |

Example 6

Potency Determination of DLL4 Antibodies to Inhibit, Notch1-DLL4 Receptor-Ligand Binding To discriminate between the purified antibodies based upon their ability to prevent the interaction between full-length recombinant DLL4 and soluble Notch1/Fc, the following assays were performed, Transfected and untransfected 239T cells were reconstituted in PBS containing 2% FCS and 5000 transfected and 17500 non-transfected cells were plated in 30 μl into wells of a 384-well tissue culture plate (Corning experiments were performed in an ELISA format using soluble human DLL4 and soluble human Notch1 (data not shown).

Further experiments were performed on selected antibodies using HEK293 cells that were stably transfected with either human, mouse or cynomolgus monkey DLL4 using retroviral constructs. In these experiments, anti-DLL4 antibodies (final concentration: 10-0.01 μg/1 ml) diluted in PBS containing 2% FCS were added to DLL4-expressing HEK 293 cells (50000 cells/well diluted in PBS containing 2% FCS) and incubated for 1 h at 4° C. Subsequently, Alexa-647 labeled human, rat or APC labeled mouse Notch1/Fc (e.g.

R&D Systems, catalog #3647-TK-050, 1057-TK-050, 5267-TK-050, respectively) was added at a final concentration of 0.01-0.5 µg/ml and plates were incubated for a further 2 h at 4° C. prior to washing and reading on a FACSCalibur instrument. Table 15 shows the ability of purified antibodies of 5 different isotypes to inhibit interactions between recombinant full length human, cynomolgus monkey and mouse DLL4 and 0.1 or 0.25 µg/ml human, rat or 0.5 µg/ml mouse Notch1/Fc chimera as determined by FACS analysis.

TABLE 14

| Antibody | IC$_{50}$ (nM) | % inhibition 16.7 nM | % inhibition 5.6 nM | % inhibition 1.9 nM | % inhibition 0.62 nM | % inhibition 0.21 nM | % inhibition 0.070 nM | % inhibition 0.020 nM |
|---|---|---|---|---|---|---|---|---|
| 1D4 | 2.00 | 123 | 124 | 58 | 13 | 5 | −2 | 7 |
| 1E4 | 0.99 | 120 | 129 | 91 | 46 | 21 | 24 | −7 |
| 4B4 | 0.72 | 136 | 127 | 95 | 65 | 23 | 21 | 14 |
| 2H10 | 2.05 | 111 | 119 | 45 | 27 | 14 | −3 | 6 |
| 3A7 | 2.94 | 104 | 82 | 39 | 19 | −1 | 7 | −1 |
| 4B3 | 3.33 | 117 | 89 | 40 | 20 | −3 | 5 | −1 |
| 9G8 | 1.88 | 121 | 125 | 68 | 22 | 33 | 14 | 10 |
| 12A1 | 1.48 | 101 | 119 | 88 | 15 | 9 | −18 | 6 |
| 17F3 | 1.81 | 115 | 121 | 69 | 29 | 14 | 15 | 14 |
| 21F7 | 1.95 | 104 | 116 | 35 | −22 | 7 | 17 | 11 |
| 20G8 | 2.02 | 115 | 114 | 29 | −14 | −4 | 3 | −5 |
| 21H3 | 1.73 | 124 | 115 | 68 | 9 | 25 | −2 | −17 |

TABLE 15

| | | Species | | |
|---|---|---|---|---|
| Antibody | Isotype | Human IC$_{50}$ ± S.D. (nM) | Cyno IC$_{50}$ ± S.D. (nM) | Mouse (rat Notch1 unless otherwise stated) IC$_{50}$ ± S.D. (nM) |
| 21H3 | IgG1 | 0.57 ± 0.24 | 0.46 | N.T. |
| | IgG2 | 0.73 ± 0.21 | N.T. | 13.53 |
| | IgG4 | 1.59 ± 0.62* | N.T. | N.T. |
| 21H3RK | IgG1 | 0.58 ± 0.26 | 0.44 ± 0.10 | 42 (mouse Notch1) |
| | IgG2 | 0.75 ± 0.12 | N.T. | 15.61 |
| 4B4 | IgG1 | 0.85 ± 0.21 | 0.50 | N.T. |
| | IgG2 | 1.19 ± 0.23 | N.T. | >67 |
| | IgG4 | 1.62 ± 0.64* | N.T. | N.T. |

*concentration of human Notch1/Fc 0.25 µg/ml.
N.T. = not tested

Example 7

Cross Reactivity of DLL4 Antibodies to Human Jagged1 and DLL1

The ability of the purified antibodies to bind to human Jagged1 and Dll1 as determined by FACS analysis. Briefly, 293T cells were either mock-transfected or transiently transfected with either human Jagged1 (accession #: NM_000214) or Dll1 (accession #: NM_005618) using Lipofectamine 2000. Cells were resuspended in PBS containing 2% FCS and seeded at 50000 cells/well into V-bottomed plates. Anti-DLL4 antibodies diluted in PBS containing 2% FCS were added at a final concentration of 5 or 15 µg/ml and plates were incubated for 1 h at 4° C. After washing with PBS containing 2% FCS, secondary antibody (Goat anti-human Fc Cy5, Jackson Immunoresearch, catalog #109-175-098, 5 µg/ml) and 7-AAD (5 µg/ml) were added and plates were incubated for 15 min at 4° C. before being washed again with PBS containing 2% FCS and being read on a FACSCalibur instrument. Mouse anti-human Jagged 1 antibody (R&D systems, catalog if mAB1277, detected with anti-mouse Fc Cy5 secondary antibody (5 µg/ml), Jackson Immunoresearch catalog #115-175-164), human Notch3/Fc chimera (R&D systems, catalog #1559-NT-050, detected with Goat anti-human Fc Cy5 antibody described above)) or Goat anti-human Dll11 antibody (R&D systems cat #AF1818, detected with anti-goat Fc Cy5, Jackson Immunoresearch, catalog if 305-175-046 (5 µg/ml)) were used as controls to confirm transfection. Data was analysed by comparing the shift in geometric mean fluorescence in the mock-transfected cells to that observed in the Jagged1- or Dll1-transfected cells and is shown in Tables 16 and 17. Table 16 shows ability: of purified antibodies (5 µg/ml) to bind to 293T cells transiently transfected with human Jagged1. Table 17 shows the ability of purified antibodies (15 µg/ml) to bind to 293T cells transiently transfected with human Dll1. Additional FACS binding studies using 21H3RK, 4B4, 9G8 or 2H10 at concentrations up to 300 µg/ml demonstrated minimal (<2.5-fold over background) binding to HEK-293 cells that stably overexpressed either human Jagged1 or human Dll1.

TABLE 16

| Antibody | Jagged1/293T X Geo mean | Mock/293T X Geo mean | Jagged1/mock ratio |
|---|---|---|---|
| 1D4 | 16.8 | 15.8 | 1.01 |
| 1E4 | 16.9 | 14.9 | 1.13 |
| 4B4 | 16.8 | 15.4 | 1.09 |
| 2H10 | 9.28 | 7.36 | 1.26 |
| 3A7 | 16.4 | 15.0 | 1.10 |
| 4B3 | 18.7 | 18.1 | 1.04 |
| 9G8 | 17.4 | 16.2 | 1.07 |
| 12A1 | 14.4 | 12.9 | 1.11 |
| 17F3 | 16.3 | 15.2 | 1.08 |
| 21F7 | 13.8 | 13.7 | 1.01 |
| 20G8 | 16.0 | 14.3 | 1.12 |
| 21H3 | 15.5 | 13.8 | 1.12 |
| N3 Fc 5 µg/ml | 51.0 | 13.2 | 3.87 |
| N3 Fc 1 µg/ml | 17.9 | 6.23 | 2.88 |
| N3 Fc 0.2 µg/ml | 8.60 | 4.39 | 1.96 |
| N3 Fc 0 µg/ml | 4.13 | 3.78 | 1.09 |
| Jagged1 Ab 5 µg/ml | 196 | 45.6 | 4.29 |
| Jagged1 Ab 1 µg/ml | 119 | 30.2 | 3.94 |
| Jagged1 Ab 0.2 µg/ml | 50.7 | 15.0 | 3.38 |
| Jagged 1 Ab 0 µg/ml | 4.61 | 4.13 | 1.12 |

TABLE 17

| Antibody | Dll1/293T X Geo mean | Mock/293T X Geo mean | Dll1/mock ratio |
|---|---|---|---|
| 1D4 | 35.3 | 32.2 | 1.09 |
| 1E4 | 31.7 | 27.7 | 1.15 |
| 4B4 | 25.9 | 21.1 | 1.23 |
| 2H10 | 44.1 | 40.1 | 1.10 |
| 3A7 | 36.8 | 34.6 | 1.06 |
| 4B3 | 30.6 | 26.0 | 1.17 |
| 9G8 | 32.3 | 26.3 | 1.23 |
| 12A1 | 47.0 | 42.1 | 1.12 |
| 17F3 | 47.0 | 41.3 | 1.14 |
| 21F7 | 30.2 | 26.8 | 1.13 |
| 20G8 | 40.0 | 30.0 | 1.34 |
| 21H3 | 32.4 | 27.9 | 1.16 |
| Dll1 Ab 5 µg/ml | 1840 | 239 | 7.68 |
| Dll1 Ab 1 µg/ml | 1240 | 197 | 6.33 |
| Dll1 Ab 0.2 µg/ml | 565 | 81.4 | 6.94 |

Example 8

Determination of the Effects of DLL4 Antibodies on DLL4 Mediated HUVEC Proliferation The ability of DLL4 antibodies to block DLL4-stimulated inhibition of HUVEC proliferation was evaluated. DLL4, extracellular domain (R&D systems, catalog #1506D4/CF) was prepared as a 50 µg/ml stock in PBS containing 0.1 BSA. Following dilution to 1 µg/ml in bicarbonate buffer (Sigma #C3041-50CAP), 100 µl/well was added to black walled 96 well plates (Perkin Elmer, catalog #6005182) and plates were incubated overnight at 4° C. Control wells were also mock coated with PBS containing 0.1% BSA. After washing with PBS, 100 µl HUVEC cells at a concentration of 4E4 cells/ml in MCDB 113 (Gibco catalog #10372) containing 10% FCS and 2 mM glutamine was added to each well. Immediately afterwards, serially diluted anti-DLL4 antibodies (20-0.027 µg/ml) were added to DLL4/mock coated wells in triplicate and cells were incubated for 96 h at 37° C./5% $CO_2$. After this incubation, 15 µl of Cell Counting Kit 8 (CCK8, NBS, catalog #CK-04-11) was added to each well and plates were incubated for 4 h at 37° C./5% $CO_2$. To determine relative cell number in each well, absorbance at 450 nm was measured on a platereader (Tecan Ultra). The effects of the anti-DLL4 antibodies are detailed in Table 18. In addition, 4B4, 21H3 and 21H3RK were also effective inhibitors of the DLL4 mediated effects when formatted as IgG1 antibodies (FIG. 1).

In addition, the abilities of the anti-DLL4 antibodies (10 µg/ml) to inhibit Notch signaling were evaluated via Western blot. Briefly, DLL4-His (R&D systems, catalog #1506-D4-050/CF) was diluted to 50 µg/ml in PBS containing 0.1% BSA. This solution was then further diluted to 1 µg/ml in 50 mM bicarbonate buffer, pH 9.6 (Sigma catalog #C-3041) and 1 ml per well added to 12 well plates and incubated overnight at 4 T. Additional wells not containing DLL4 were mock-coated using the same procedure. After washing with PBS, HUVEC cells prepared in MCDB131 medium were seeded at 12000 cells/well. Immediately after seeding, the appropriate treatment (e.g. anti-DLL4 antibodies, 10 µg/ml) was added and plates were incubated for 24 h at 37° C./5% $CO_2$. After the incubation was completed, cells were harvested in RIPA buffer. 4× sample buffer containing B-mercaptoethanol and bromophenol blue was then added and samples were boiled for 5 min at 70° C. prior to loading onto 4-12% NuPAGE gels in MOPS buffer (Invitrogen catalog #NP0001). Following electrophoretic transfer to nitrocellulose, blots were blocked for 1 h in PBST containing 5% milk followed by incubation with either cleaved anti-Notch1 (Cell signaling technology, catalog #2421) or GAPDH (Advanced Immunochemical, clone 6C5, catalog #2-RGM2) antibodies at 1:1000 or 1:10,000 dilutions, respectively in PBS containing 5% milk. After incubation on an orbital shaker overnight at 4° C. blots were washed with PBST and incubated with anti-mouse-HRP secondary antibody (Cell Signaling Technology, catalog #7072) at a concentration of 1:2000 in PBST containing 5% milk for 1 h at RT. After washing with PBST, blots were developed using Pierce Pico (catalog #34080; GAPDH) or Femto (catalog #34075; cleaved Notch1) substrate reagents and results analysed on a ChemiGenius instrument. The results obtained from these studies demonstrate that the anti-DLL4 antibodies can block DLL4-stimulated Notch signaling in HUVEC cells (data not shown).

TABLE 18

| | | N = 1 | | N = 2 | | AVERAGE | |
|---|---|---|---|---|---|---|---|
| Ab | Isotype | % inhibition 1 µg/ml | % inhibition 10 µg/ml | % inhibition 1 µg/ml | % inhibition 10 µg/ml | % inhibition 1 µg/ml | % inhibition 10 µg/ml |
| 1D4 | IgG4 | 43 | 73 | 46 | 71 | 45 | 72 |
| 1E4 | IgG2 | 73 | 81 | 75 | 82 | 74 | 82 |
| 4B4 | IgG4 | 101 | 102 | 84 | 92 | 93 | 97 |
| 2H10 | IgG4 | 98 | 110 | 87 | 95 | 93 | 103 |
| 3A7 | IgG4 | 50 | 74 | 80 | 106 | 65 | 90 |
| 4B3 | IgG4 | 20 | 38 | 41 | 49 | 31 | 44 |
| 9G8 | IgG4 | 52 | 72 | 71 | 82 | 62 | 77 |
| 12A1 | IgG4 | 50 | 62 | 62 | 85 | 56 | 74 |
| 17F3 | IgG2 | 24 | 48 | 35 | 56 | 30 | 52 |
| 21F7 | IgG2 | 30 | 48 | N.T. | N.T. | N/A | N/A |
| 20G8 | IgG4 | 94 | 103 | 75 | 93 | 85 | 98 |
| 21H3 | IgG4 | 86 | 88 | 99 | 89 | 93 | 89 |
| Control | IgG2 | 18 | 11 | 0 | 9 | 9 | 10 |
| Control | IgG4 | 14 | 6 | 8 | −3 | 11 | 2 |

N/A = Not applicable.
N.T. = Not tested

Example 9

Effects of DLL4 Antibodies on HUVEC Tube Formation In Vitro

DLL4 inhibitory antibodies were tested for the ability to reduce endothelial cell tube formation in an in vitro co-culture assay (e.g., ICS Cell Works Cat no. ZHA-1000), Human Umbilical Vein Endothelial Cells (HUVECs) and human diploid fibroblasts were either obtained as co-cultures in 24 well plates (TCS Cell works Cat no. ZHA-1000) or plates were prepared as follows: 24 well tissue culture plates were coated with collagen (1:10 dilution in distilled water; Sigma, catalog #C8919) at 37° C./5% $CO_2$ for 4 h. After washing with PBS, fibroblasts (e.g. Promocell #C-12300) were added at 15000 cells/well in FGM (Promocell #C-23010). After incubating for 3 days at 37° C./5% $CO_2$, the media was removed from the plate and HUVEC cells at 30,000 cells/well in EGM2 (Promocell #C-22111) were added. After incubating for a further 4 days at 37° C./5% $CO_2$, plates were considered ready for use and this was considered day 1 for the assay. DLL4 blocking antibodies were introduced to the cultures on day 1 and at regular intervals over an 11-day period at concentrations ranging from 20 to 0.027 µg/ml. Media was replenished on days 4, 7 and 9. The co-culture model was maintained in either TCS Optimised medium (supplied with the co-culture assay) or in MCDB131 medium supplemented with 2% foetal calf serum (FCS), 1% glutamine and 1% penicillin/streptomycin (hereafter referred to as 2% FS MCDB131 medium). The co-culture model was maintained at 37° C. in a humidified 5% $CO_2$/95% air atmosphere. Tubule formation was examined at day 11 following fixing and staining of tubules for CD31 using a tubule staining kit according to the manufacturers instructions (TCS Cell Works catalog #ZHA-1225). Briefly, cells were fixed with ice-cold 70% ethanol for 30 minutes at room temperature (RT). Cells were blocked after which they were treated with anti-human CD31 for 60 minutes at RT. Plates were washed and treated with goat anti-mouse IgG conjugated with alkaline phosphatase (AP) for 60 minutes at RT. After incubation with the AP-conjugated secondary antibody, the plates were washed and 5-bromo-4-chloro-3-indolyl phosphate/nitro blue tetrazolium (BCIP/NBT) substrate was added for approximately 10 minutes. The development of a dark purple colour within 10 minutes reflected tubule so formation. Plates were subsequently washed and left to air dry. Quantification of tubule growth was conducted by whole-well image analysis methodology using a Zeiss KS400 3.0 Image Analyser. The morphological parameter measured in the quantification methodology was total tubule length. In some experiments, the number of bifurcations in the tubes was also assessed. All tubule formations within each of the 24 wells were measured excluding a rim of 100 µm depth to avoid edge retraction artifact.

Figure 2:
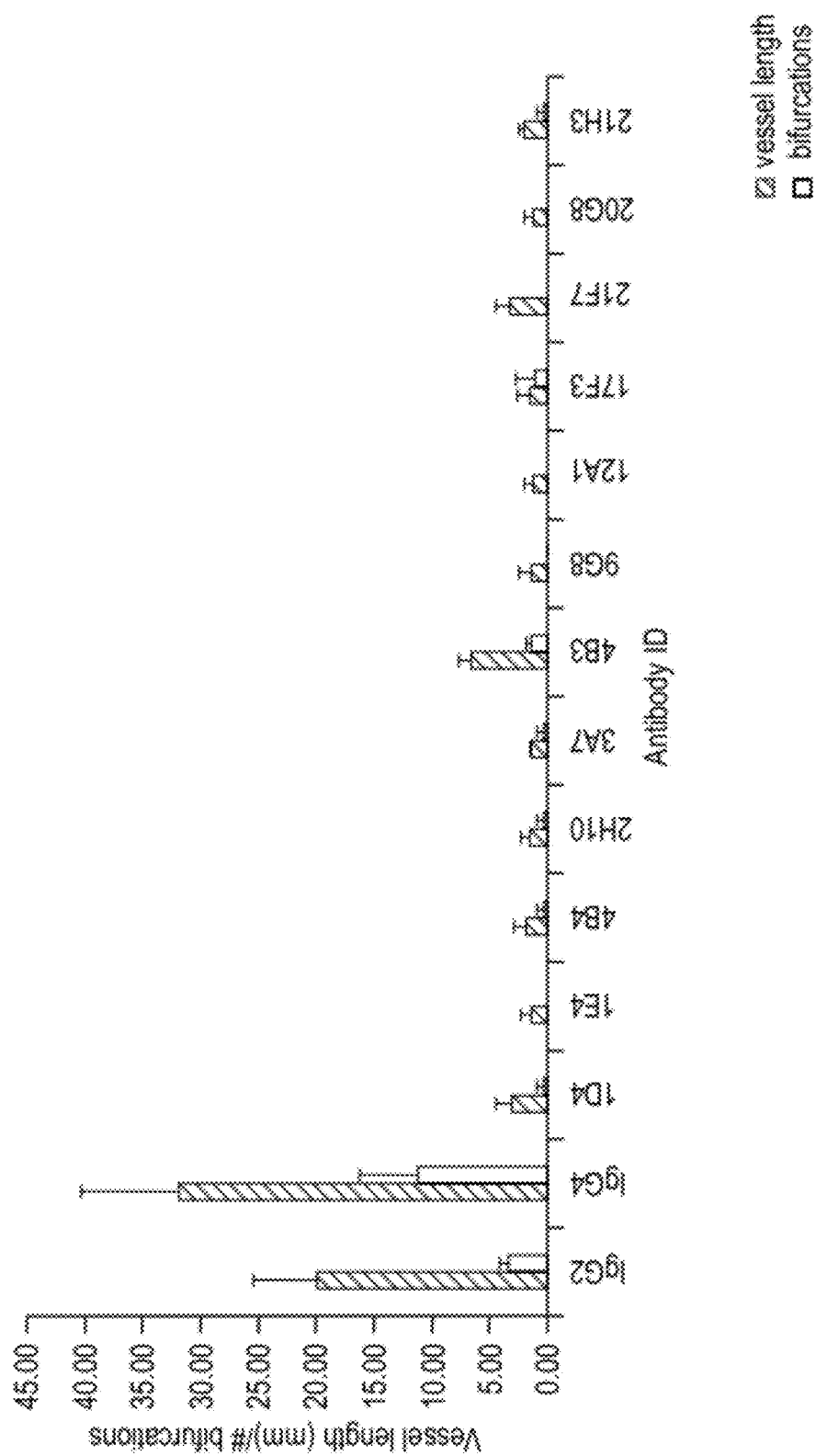
FIG. 2 depicts a bar graph showing the effects of IgG2/4 DLL4 antibodies on HUVEC tube formation in vitro as assessed by measurement of vessel length (mm) and # bifurcations.

As illustrated in FIG. 2, it was observed that the antibodies are effective in inhibiting endothelial cell tube formation in vitro. Furthermore, the potency of several of the antibodies in this assay was determined. These data are summarized in Table 19. Taken together, the data indicate that the antibodies are active in a functional assay that models the angiogenic process.

TABLE 19

| Antibody | Isotype | $IC_{50}$ (µg/ml) Vessel length | # bifurcations |
|---|---|---|---|
| 4B4 | IgG4 | 0.244 | 0.247 |
|  | IgG1 | 0.135 | 0.152 |
| 21H3 | IgG4 | 0.201 | 0.0740 |
|  | IgG1 | 0.0468 | 0.0727 |
| 21H3RK | IgG1 | 0.0507 | 0.0921 |
| 9G8 | IgG4 | 0.656 | 0.363 |
| 2H10 | IgG4 | 0.514 | 0.446 |

Example 10

Determination of Binding Affinity of Purified Antibodies

The binding affinities of the purified antibodies for DLL4 was estimated using both FACS and BIAcore techniques. For FACS affinity determination, HEK293 cells overexpressing either human or cynomolgus monkey DLL4 were seeded at approximately 85,000-104,000 cells/well and incubated with titrations of purified antibody for 5 hours at 4° C. The cells were then washed and incubated with goat anti-human IgG-Fc-Cy5+5 µg/mL 7-Amino-Actinomycin (AAD) for 30 minutes at 4° C. Bound DLL4 was detected using FACS analysis and data was fitted to the following equation (see Drake & Klakamp, 2007, J. Immunol. Methods, 318, 157-162 for derivation):

$$F = P' \frac{(K_D + L_T + n \cdot M) - \sqrt{(K_D + L_T + n \cdot M)^2 - 4n \cdot M \cdot L_T}}{2} + B$$

In this equation, F=mean fluorescence, $L_T$=total molecular mAb concentration, P'=proportionality constant that relates arbitrary fluorescence units to bound mAb, M=cellular concentration in molarity, n=number of receptors per cell, B=background signal, and $K_D$=equilibrium dissociation constant. For each mAb titration curve an estimate for $K_D$ is obtained as P', n, B, and $K_D$ are allowed to float freely in the nonlinear analysis. Table 20 summarizes the affinity estimates for the anti-DLL4 antibodies for human and cynomolgus monkey DLL4 derived using the methodology described above For Biacore analysis, each purified anti-DLL4 antibody was immobilized on a CM5 sensor chip within a T100 using standard amine coupling. Immobilization levels were kept below 200 RU. The concentration of DLL4 was determined by UV-VIS spectroscopy using a molar absorptivity at 280 nm of 110, 440 $M^{-1} cm^{-1}$, which was calculated from the sequence of the protein using a method developed by Pace et al, (G. R. Grimsley and C. N. Pace (2003) in Current Protocols in Protein Science (John Wiley & Sons, Inc.), 3.1.1-3.1.9). The antigen DLL4 (R&D systems; human catalog #1056-D4-050 or mouse, catalog #1389-D4-050) was diluted to a starting concentration of 32-64 nM and tested in a 3-fold dilution series in triplicate. The running buffer contained HBS-P with 0.1 mg/ml BSA and binding responses were collected at 23° C. Bound complexes were regenerated with a 15 s pulse of 10 mM of sodium hydroxide. The response data were globally fitted with a simple 1:1 interaction model and Table 20 summarizes the $k_a$, $k_d$ and $K_D$ estimates obtained for the anti-DLL4 antibodies when binding to human soluble DLL4 was assessed. In addition, affinity estimates to soluble mouse DLL4 were also generated for 21H3, 21H3RK and 4B4 using BIAcore: all of the antibodies in IgG format had an affinity of 360 nM or less for soluble mouse DLL4.

TABLE 20

| Antibody ID | Isotype | Human FACS $K_D$ (pM) | Cyno FACS $K_D$ (pM) |
|---|---|---|---|
| 21H3RK | IgG1 | 155 | 66.7 |
| 21H3RK | IgG2 | 225 | N.T. |
| 21H3 | IgG1 | 103 | 78.1 |
| 21H3 | IgG2 | 320 | N.T. |
| 21H3 | IgG4 | 359 | N.T. |

TABLE 20-continued

| Antibody ID | Isotype | Human FACS $K_D$ (pM) | Cyno FACS $K_D$ (pM) |
|---|---|---|---|
| 4B4 | IgG1 | 157 | 81.0 |
| 4B4 | IgG2 | 232 | N.T. |
| 4B4 | IgG4 | 516 | N.T. |
| 9G8 | IgG4 | 999 | N.T. |
| 2H10 | IgG4 | 882 | N.T. |

N.T. = not tested.

TABLE 21

| Antibody ID | Isotype | $K_a$ (M$^{-1}$ s$^{-1}$) | $K_d$ (s$^{-1}$) | $K_D$ (pM) |
|---|---|---|---|---|
| 21H3RK | IgG1 | $3.37 \times 10^5$ | $1.66 \times 10^{-4}$ | 493 |
| 21H3RK | IgG2 | $2.22 \times 10^5$ | $1.60 \times 10^{-4}$ | 721 |
| 21H3 | IgG1 | $2.88 \times 10^5$ | $1.71 \times 10^{-4}$ | 594 |
| 21H3 | IgG2 | $2.59 \times 10^5$ | $1.55 \times 10^{-4}$ | 598 |
| 21H3 | IgG4 | $3.17 \times 10^5$ | $1.52 \times 10^{-4}$ | 481 |
| 4B4 | IgG1 | $1.18 \times 10^5$ | $2.01 \times 10^{-5}$ | 170 |
| 4B4 | IgG2 | $1.07 \times 10^5$ | $3.60 \times 10^{-5}$ | 336 |
| 4B4 | IgG4 | $1.18 \times 10^5$ | $3.33 \times 10^{-5}$ | 283 |
| 9G8 | IgG4 | $1.03 \times 10^5$ | $1.36 \times 10^{-5}$ | 132 |
| 2H10 | IgG4 | $4.09 \times 10^4$ | $4.02 \times 10^{-5}$ | 981 |

Example 11

Determination of Cross-Competition For DLL4 by FACS Analysis

Figure 3:
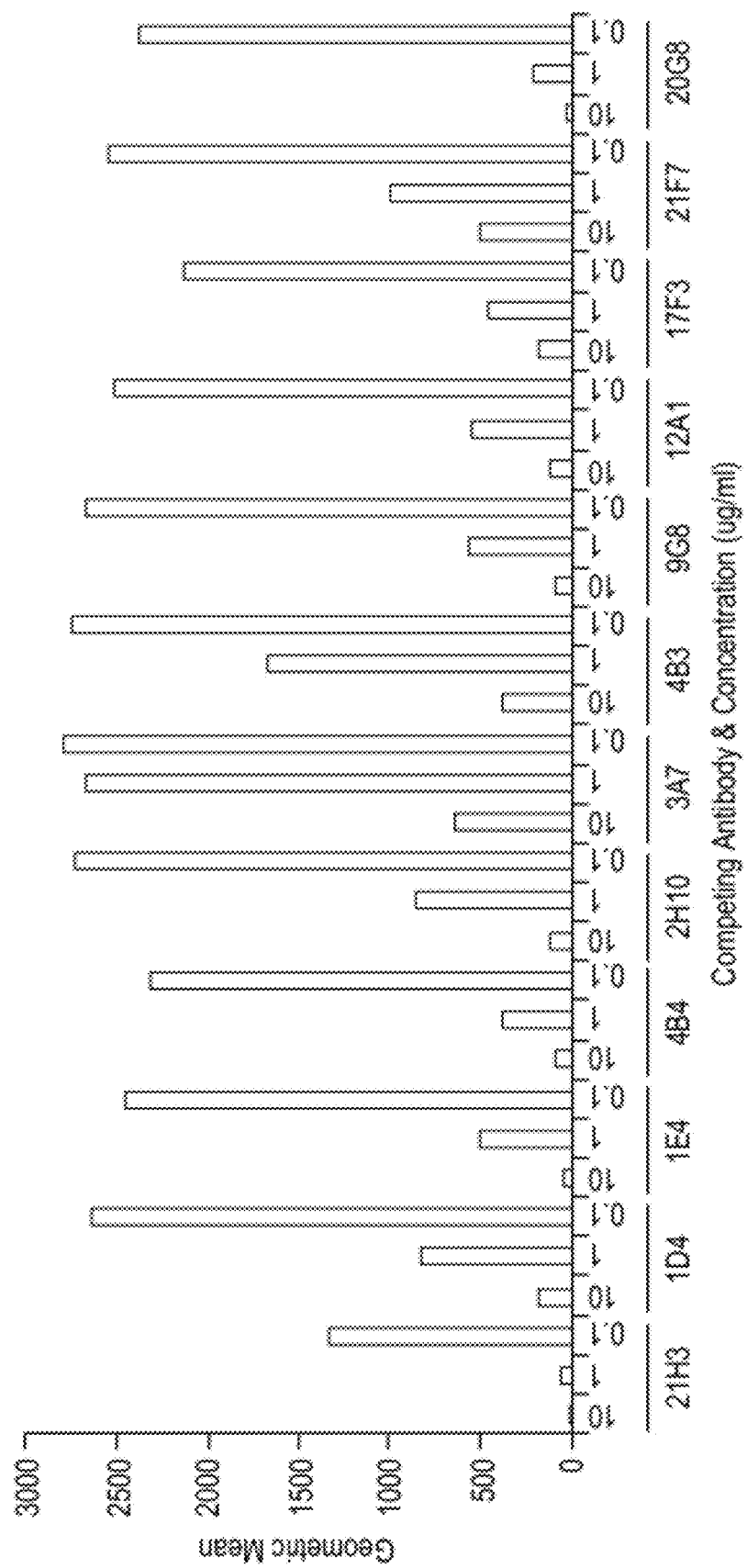
FIG. 3 depicts a bar graph showing the effects of unlabeled anti-DLL4 antibodies to displace the binding of Alexa-647 labeled 21H3RK at 0.1 μg/ml as determined by FACS analysis FIG. 4. depicts a graphic linear representation of twelve chimeric DLL4/DLL1 variants. All variants encode the extracellular domains of DLL4 with human DLL1 replacing individual sub domains or combined domain segments as depicted.

The ability of the purified DLL4 antibodies to inhibit the binding of other DLL4 antibodies to human DLL4 was assessed using a FACS assay. Briefly, antibodies were directly labelled with Alexa-647 using a commercially available labelling kit (e.g. Molecular Probes catalog #A30009, A-20186) as per the manufacturer's instructions. To determine the level of cross-competition, unlabelled anti-DLL4 antibodies (final concentration: 10-0.01 μg/ml) diluted in PBS containing 2% FCS were added to DLL4-expressing HEK 293 cells (as described in example 6; 50000 cells/well diluted in PBS containing 2% FCS) and incubated for 1 h at 4° C. Subsequently, Alexa-647 labeled anti-DLL4 antibodies were added at a final concentration of 0.1 μg/ml and plates were incubated for a further 1 h at 4° C. prior to washing and reading on a FACSCalibur instrument. Data that summarizes the ability of unlabeled antibodies (10, 1, 0.1 μg/ml) to compete with labeled 21H3RK, for binding to human DLL4 is included in FIG. 3. Additional data that summarizes the ability of unlabeled antibodies to compete with labeled 21H3RK and 4B4 for binding to human DLL4 is included in Table 22.

In addition, the ability of the antibodies to detect recombinant DLL4 (R&D systems, catalog #1506-D4-050/CF) and native DLL4 expressed in 11E1(293 cells (see example 3) was also determined via Western blot using standard techniques. Briefly, DLL4 expressing HEK293 cells were harvested in RIPA buffer (Thermo, catalog #89900 containing 1 protease inhibitor cocktail tablet (Roche, catalog #11873580001) and protein quantified using a BCA protein assay (Pierce, catalog #23227) according to the manufacturer's instructions. For Western blotting, protein samples were thawed on ice and incubated at 100° C. for 2 min prior to the addition of 10× Nupage sample reducing agent (Invitrogen, catalog #NP0004) and 4× sample buffer prior to loading into pre-cast 4-12% NuPage BisTris gels (Invitrogen, catalog #NP0321B0X) in MES buffer (Invitrogen, catalog #NP0002). Following electrophoretic transfer to nitrocellulose, blots were blocked for 1 h in Tris-buffered saline (100 mM Tris-HCl, 150 mM NaCl, pH17.5) containing 0.05% Tween 20 (TBST) containing 5% milk followed by incubation with either 9G8, 2H10, 21H3, 4B4 or 20G8 (all 2 μg/ml) or commercially available anti-DLL4 antibodies (R&D Systems, catalog #MAB1389; Abeam, catalog #ab7280, both at 1 μg/ml) in TBST containing 5% milk. After incubation on an orbital shaker overnight at 4° C., blots were washed with TBST and incubated with either anti-rat, anti-rabbit or anti-human-HRP-conjugated secondary antibodies (Jackson Immunochemicals, catalog #112-035-003 and 111-035-003, 1:20,000 dilution or KPL, catalog #074-1006, 1:10,000 dilution) TBST containing 5% milk for 1 h at RT. Excess antibody was removed by washing as above and immunocomplexes were visualized via enhanced chemiluminescence detection according to the manufacturer's instructions (Pierce, catalog #34076) and detected on Hyperfilm ECL (Amersham, catalog #28906839) or Biomax MR (Kodak, catalog #8952855) film. The results demonstrate that under these conditions, both recombinant and native DLL4 can be detected by the commercial antibodies and 9G8/2H10, but not by 21H3/20G8 or 4B4, suggesting that these antibodies may interact with different epitopes on DLL4 (data not shown).

TABLE 22

| | | Competing antibody IC$_{50}$ (μg/ml) | | | | |
|---|---|---|---|---|---|---|
| | | 21H3RK | 21H3 | 4B4 | 9G8 | 2H10 |
| Labeled antibody | 4B4 | 0.223 | 0.274 | 0.348 | 0.856 | 1.15 |
| | 21H3RK | 0.214 | 0.248 | 0.379 | 0.596 | 0.723 |

Example 12

Sequence Modifications to 9G8 and 2H10

Immunoglobulin genes undergo various modifications during maturation of the immune response, including recombination between V, D and J gene segments, isotype switching, and hypermutation in the variable regions. Recombination and somatic hypermutation are the foundation for generation of antibody diversity and affinity maturation, but they can also generate sequence liabilities that may make commercial production of such immunoglobulins as therapeutic agents difficult, or increase the immunogenicity risk of the antibody. In general, mutations in CDR regions are likely to contribute to improved affinity and function, while mutations in framework regions may increase the risk of immunogenicity. This risk can be reduced by reverting framework mutations to germline, while ensuring that activity of the antibody is not adversely impacted. Some structural liabilities may be generated by the diversification processes, or they may exist within germline sequences contributing to the heavy and light chain variable domains. Regardless of the source, it may be desirable to remove potential structural liabilities that may result in instability, aggregation, heterogeneity of product, or increased immunogenicity. Examples of undesirable liabilities include unpaired cysteines (which may lead to disulfide bond scrambling, or variable sulfhydryl adduct formation), N-linked glycosylation sites (resulting in heterogeneity of structure and activity), as well as deamidation (e.g. NG, NS), isomerization (DG), oxidation (exposed methionine), and hydrolysis (DP) sites. In an effort to reduce the risk of immunogenicity, and improve pharmaceutical properties of lead antibodies, certain variants were generated and tested for binding and activity. Site directed mutagenesis was carried out using the Stratagene Quick Change II kit, as described by the manufacturer. Variant sequences were expressed in the InVitrogen Freestyle system by transient transfection (following manufacturer recommended protocols), and purified by Protein A affinity chromatography.

The activity of the mutated antibodies was assessed in two ways: firstly, the ability of the antibodies to block the binding of soluble Notch1/Fc to full length human DLL4 stably expressed in HEK293 cells as described in Example 3 was determined and, secondly, the binding of the antibodies to the same cell line used in the receptor-ligand competition studies was determined. For the binding studies, HEK293 cells stably overexpressing human DLL4 were resuspended in PBS containing 2% FCS at a concentration of 50,000 cells/well and incubated with titrations of antibody (final concentrations 0.01-10 μg/ml) for 1 h at 4° C. The cells were then washed and incubated with 0.31 μg/ml anti-human IgG-Fc-FITC (BD Pharmingen, cat#555786) for 30 minutes at 4° C. Bound DLL4 was detected using FACS analysis. Results of these studies are summarized in Table 23, which show the effects of specific mutations to sequences of 9G8 and 2H10 on the ability of the antibodies to compete with Notch1 for binding to human DLL4 or to bind to human DLL4 relative to unmutated antibodies.

TABLE 23

| Clone | Variant | RL comp Activity ($IC_{50}$ μg/ml) | Binding Activity ($EC_{50}$ μg/ml) |
|---|---|---|---|
| 9G8 IgG2 | VH wt/VL wt | 0.170 | 0.071 |
| | VH L38W/VL wt | 0.133 | 0.070 |
| | VH wt/VL S7P | 0.181 | 0.082 |
| | VH wt/VL C33S | 0.136 | 0.067 |
| | VH wt/VL C33A | 0.302 | N.T. |
| | VH wt/VL C33G | 0.358 | N.T. |
| | VH wt/VL C33D | 0.345 | N.T. |
| | VH wt/VL C33R | 0.201 | N.T. |
| | VH wt/VL C33Y | 0.320 | N.T. |
| | VH wt/VL V79A | 0.211 | 0.095 |
| | VH L38W/VL S7P | 0.155 | 0.074 |
| | VH L38W/VL C33S | 0.107 | 0.051 |
| | VH L38W/VL V98A | 0.240 | N.T. |
| 2H10 IgG2 | VH wt/VL wt | 0.224 | 0.043 |
| | VH M93V/VL wt | 0.264 | N.T. |
| | VH wt/VL C33S | 0.084 | 0.031 |
| | VH wt/VL C33A | 0.174 | N.T. |
| | VH wt/VL C33G | 0.314 | N.T. |
| | VH wt/VL C33D | 0.178 | N.T. |
| | VH wt/VL C33R | 2.97 | N.T. |
| | VH wt/VL C33Y | >3.00 | N.T. |
| | VH M93V/VL C33S | 0.138 | N.T. |

Example 13

Evaluation of the Antiangiogenic Efficacy in a Spheroid-Based In Vivo Angiogenesis Assay Human umbilical vein endothelial cell (HUVEC) spheroids were prepared as described earlier (Korff and Augustin: J. Cell. Biol. 143: 1341-52, 1998) by pipetting 100 endothelial cells (EC) in a hanging drop on plastic dishes to allow overnight spheroid formation. The following day, using the method previously described (Alajati et al., Nature Methods 5:439-445, 2008), EC spheroids were harvested and mixed in a Matrigel/fibrin solution with single HUVECs to reach a final number of 100,000 ECs as spheroids and 200,000 single ECs per injected plug. VEGF-A and FGF-2 were added at a final concentration of 1000 ng/ml, Male SOD mice (5-8 weeks old) were subcutaneously, injected with 500 μl of the cell/matrix suspension. The following day (day 1) treatment commenced. At day 21 the study was terminated. The matrix plugs were removed and fixed in 4% PFA. All matrix plugs were paraffin embedded and cut to a thickness of 8-10 μm for histological examination. Blood vessels were visualized by staining for human CD34 and smooth muscle actin (SMA) and the vessel density and pericyte coverage was determined. Both IgG1 and IgG2 antibodies are effective in modulating vessel formation and inhibiting pericyte recruitment in viva. The data obtained suggest that treatment with anti-DLL4 antibodies (21H3RK or 4B4) induces an increase in human vessel formation of at least 100% over untreated control at antibody concentrations as low as 1 mg/kg. In addition, these increases in human vessel formation were associated with a decrease in pericyte coverage (as assessed by the percentage of human CD34 positive vessels that were also associated with cells positive for αSMA expression) of at least 50% at antibody doses of 5 mg/kg, Data summarizing the effect of 21H3RK IgG1 dosed twice weekly i.p. at 1, 0.2 and 0.04 mg/kg is shown in Table 24. Taken together, the data indicate that the antibodies are active in an in vivo assay of angiogenesis,

| Treatment (2× weekly) | Number of CD34+ve vessels | | Vessel coverage (CD34+ve/αSMA+ve vessels) | |
|---|---|---|---|---|
| | Mean | s.e.m. | Mean | s.e.m. |
| Vehicle | 235 | 37.3 | 49.9 | 2.64 |
| 21H3RK (1 mg/kg) | 645 | 78.6 | 15.9 | 2.38 |
| 21H3RK (0.2 mg/kg) | 587 | 74.7 | 17.2 | 2.8 |
| 21H3RK (0.04 mg/kg) | 478 | 61.8 | 27.1 | 3.66 |

Example 14

Epitope Mapping of 21H3RK

Monoclonal 21H3RK binds specifically to human DLL4 but does not recognize human DLL1. This specificity is employed to deduce the binding epitope of Mab 21H3RK to human DLL4. Chimeric variants were engineered with portions of the extracellular domain of DLL4 replaced with the corresponding segments of DLL1. Human DLL4 (Yoneya et al., 2001, J. Biochem., 129, 27-34, cloned in-house) and human DLL1 (accession #NM_005618, Origene, Md.) were used as templates in overlapping extension PCR to construct a series of variants which include the DLL4 transmembrane domain for surface expression of the recombinant proteins. The resulting variants were cloned into a mammalian expression vector encoding a human cytomegalovirus major immediate early (hCMVie) enhancer, promoter and 5'-untranslated region for transient mammalian expression. The chimeric variants were transiently expressed in HEK293F cells as membrane-bound proteins for flow cytometric characterization with Mab 21H3RK. 48 h post-transfection, HEK293F transfectants were incubated with 1 μg/ml of Mab 21H3RK for 1 h on ice in PBS, washed, then incubated with goat anti-human IgG-FITC (Jackson ImmunoResearch Laboratories, PA) and analyzed with a LSRII flow cytometer (BD Biosciences, CA). The expression levels of all chimeric variants were monitored by incubating with a mixture of both goat anti-mouse DLL4 (which also recognizes human DLL4)

and goat anti-human DLL1 polyclonal antibodies (both from R&D Systems., MN), then detected with porcine anti-goat IgG-PE (Invitrogen, CA).

Figure 4:
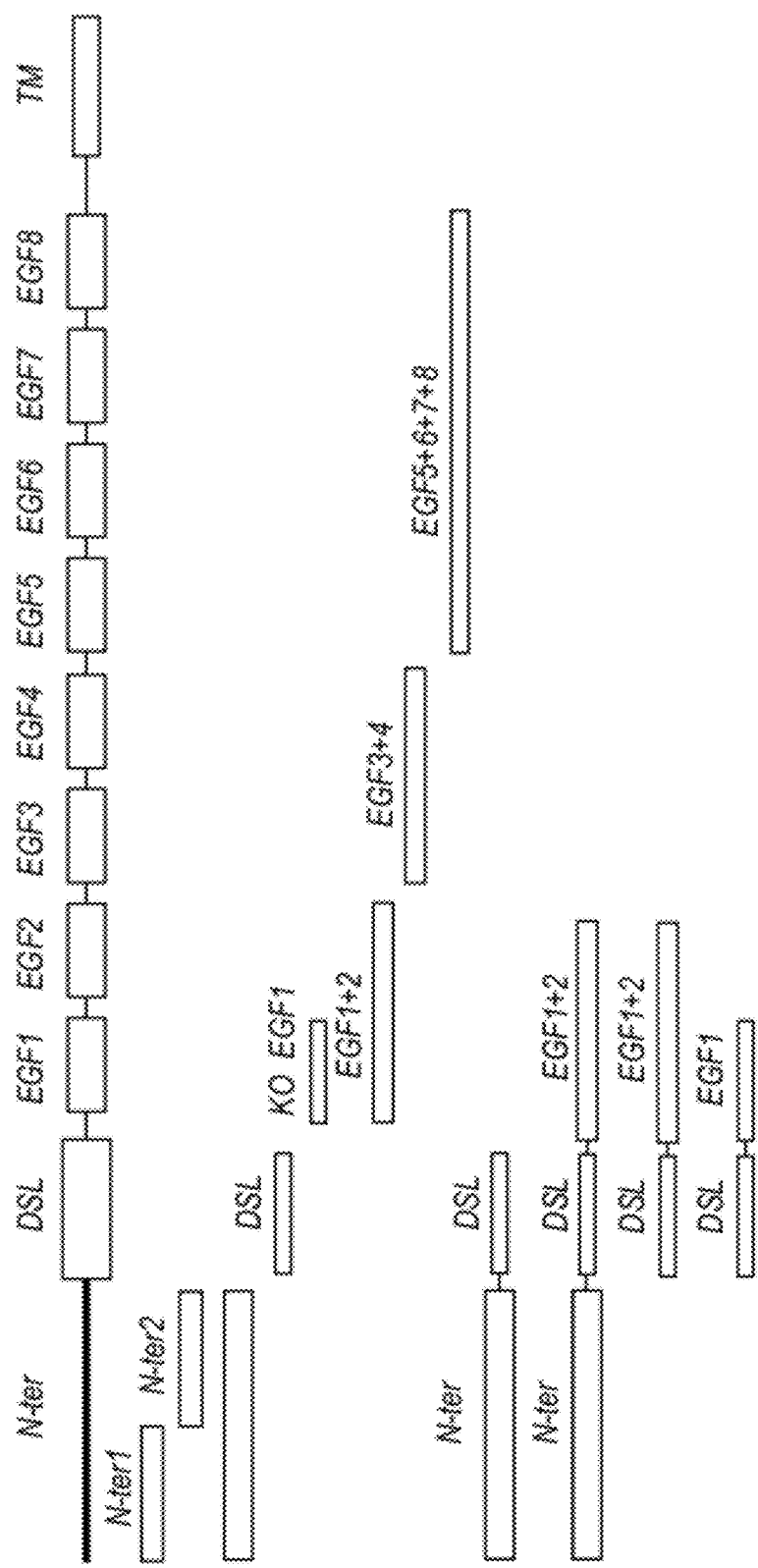
Figure 5A:
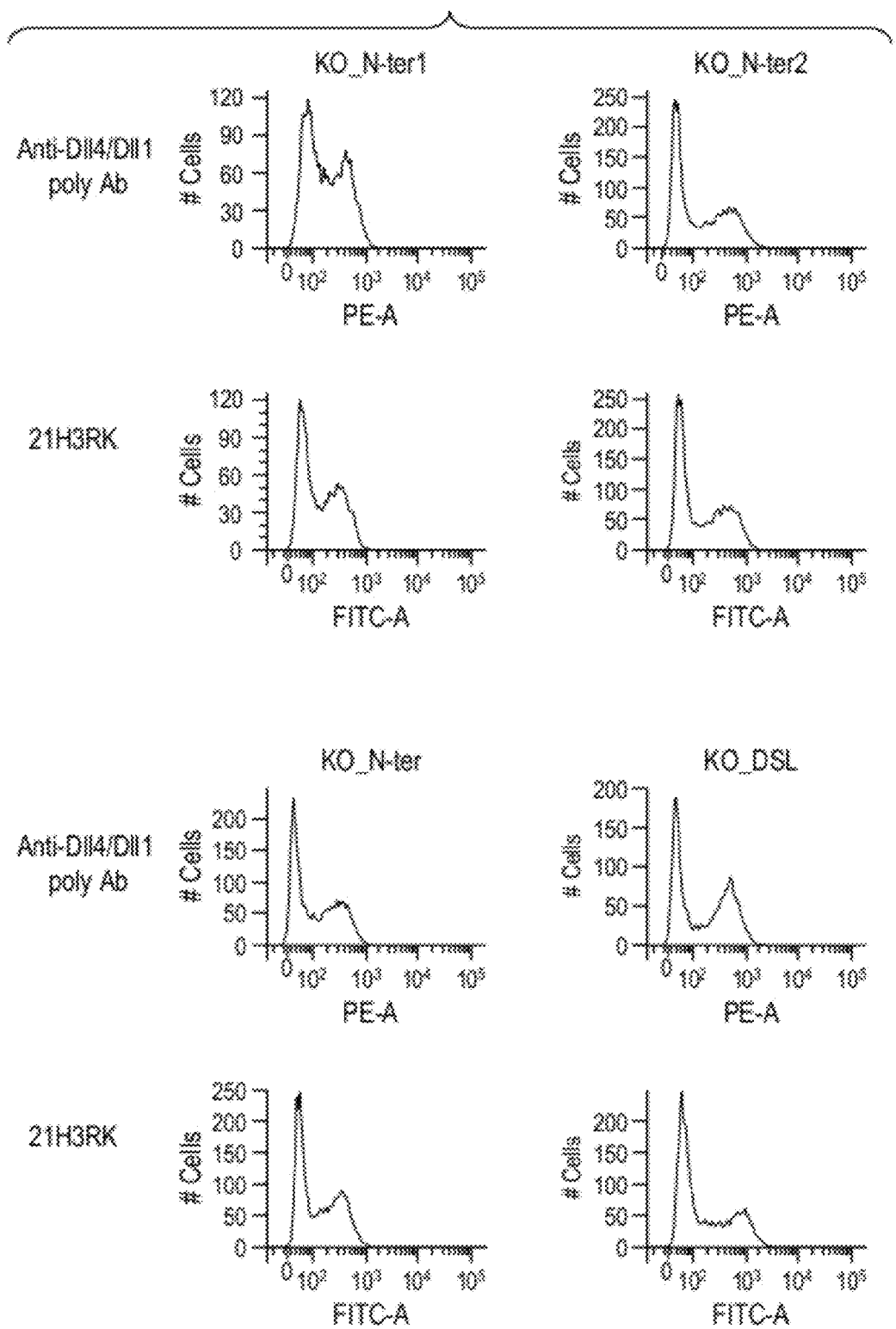
FIGS. 5A-5D depicts line graphs showing binding of 21H3RK to chimeric knock out ("KO") variants encoding DLL4 with segments of the extracellular domain substituted with the corresponding DLL1 domains.
Figure 5B:
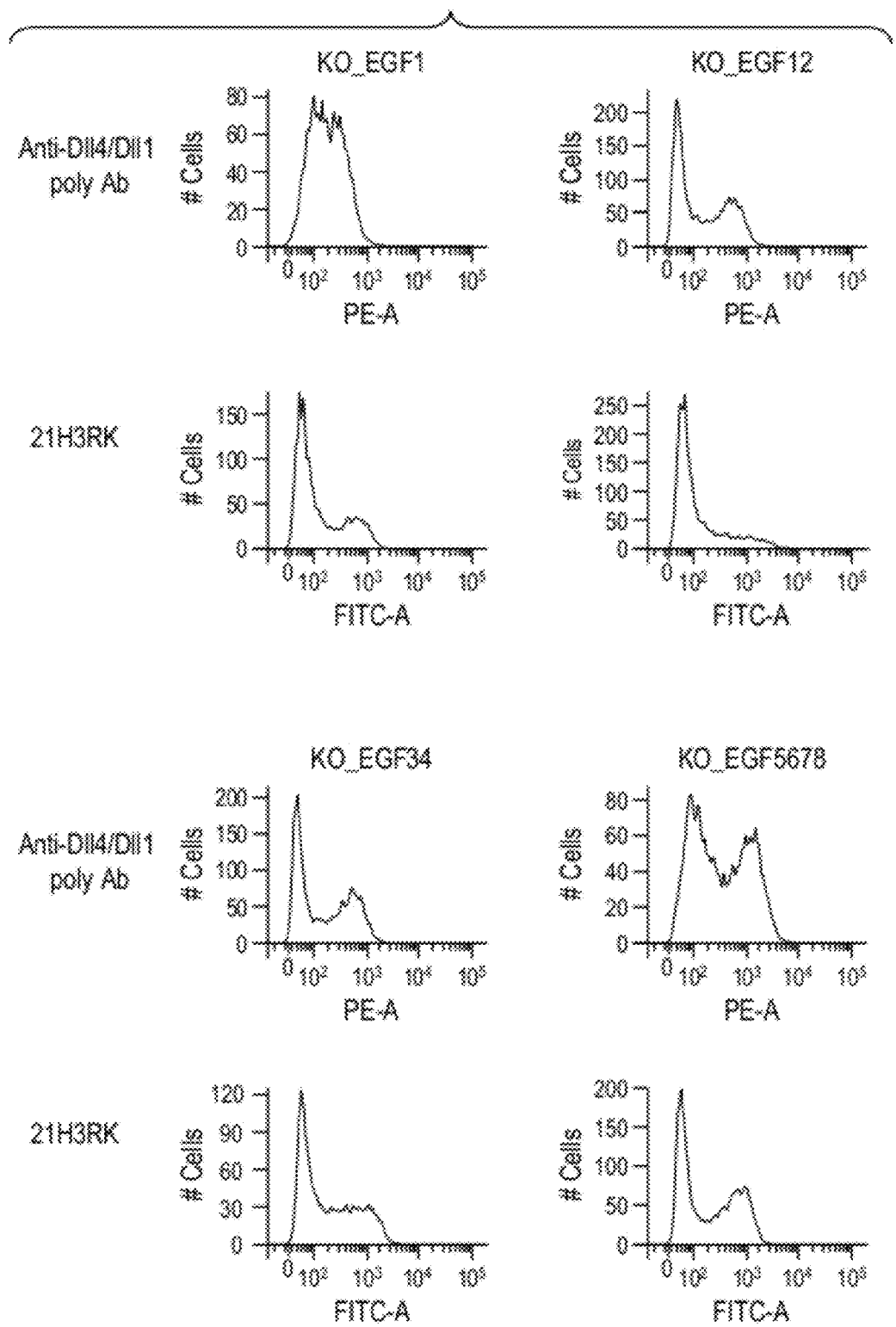
Figure 5C:
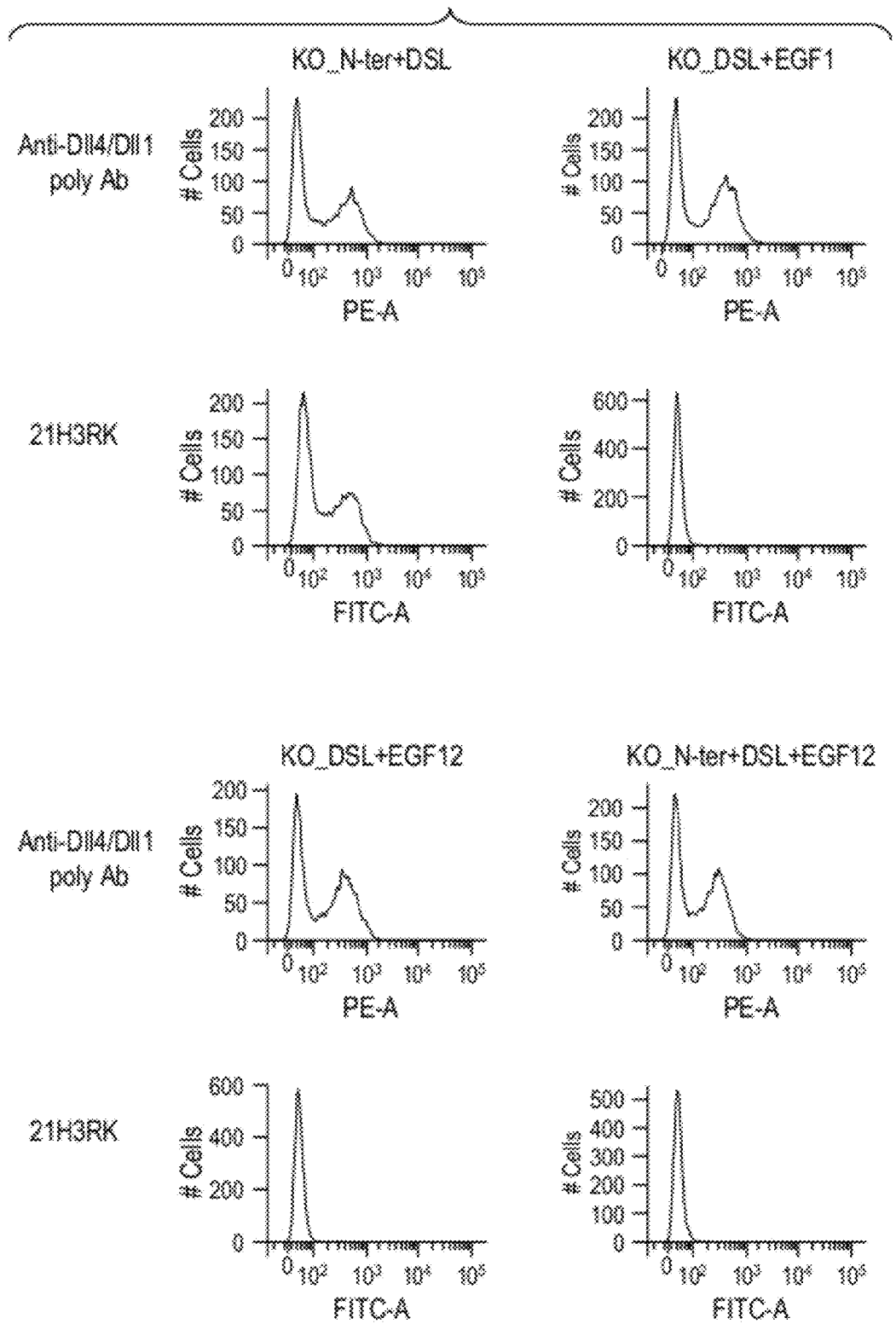
Figure 5D:
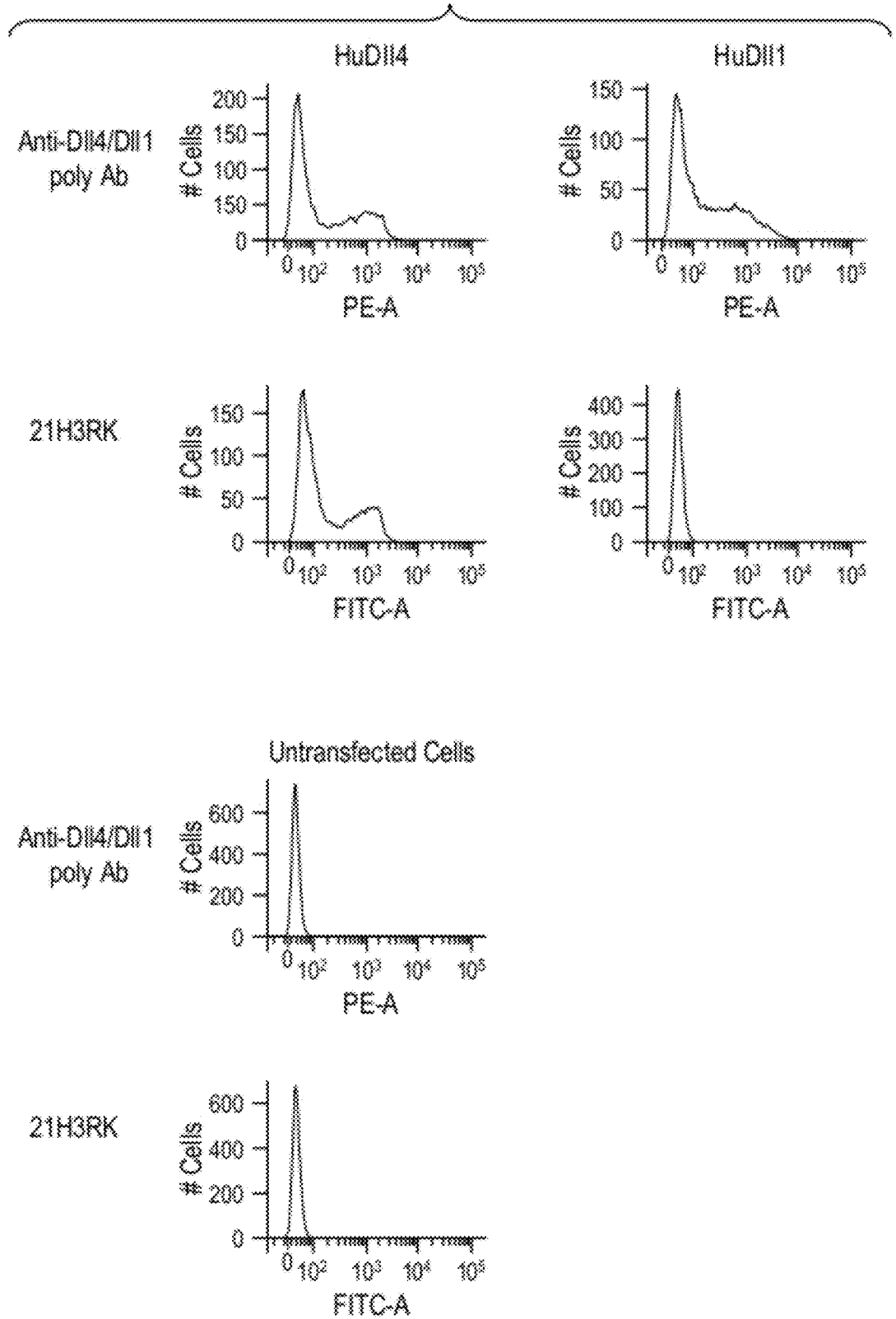
Figure 6A:
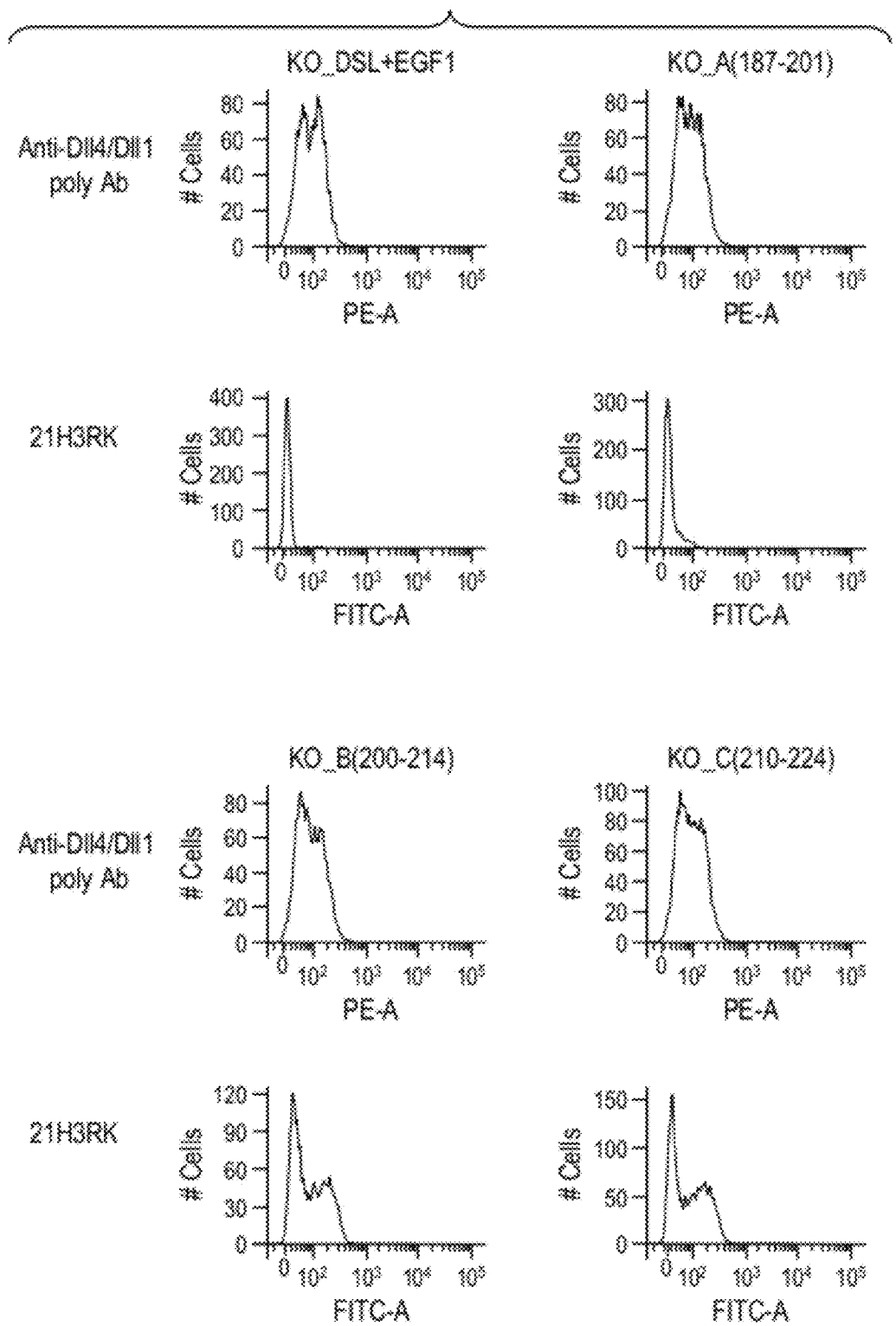
FIGS. 6A-6C depicts line graphs showing binding of 21H3RK to chimeric knock out ("KO") variants encoding DLL4 with segments of the extracellular domain substituted with the corresponding DLL1 domains and chimeric knock in ("KI") variants encoding DLL1 with regions substituted with DLL4 counterparts.
Figure 6B:
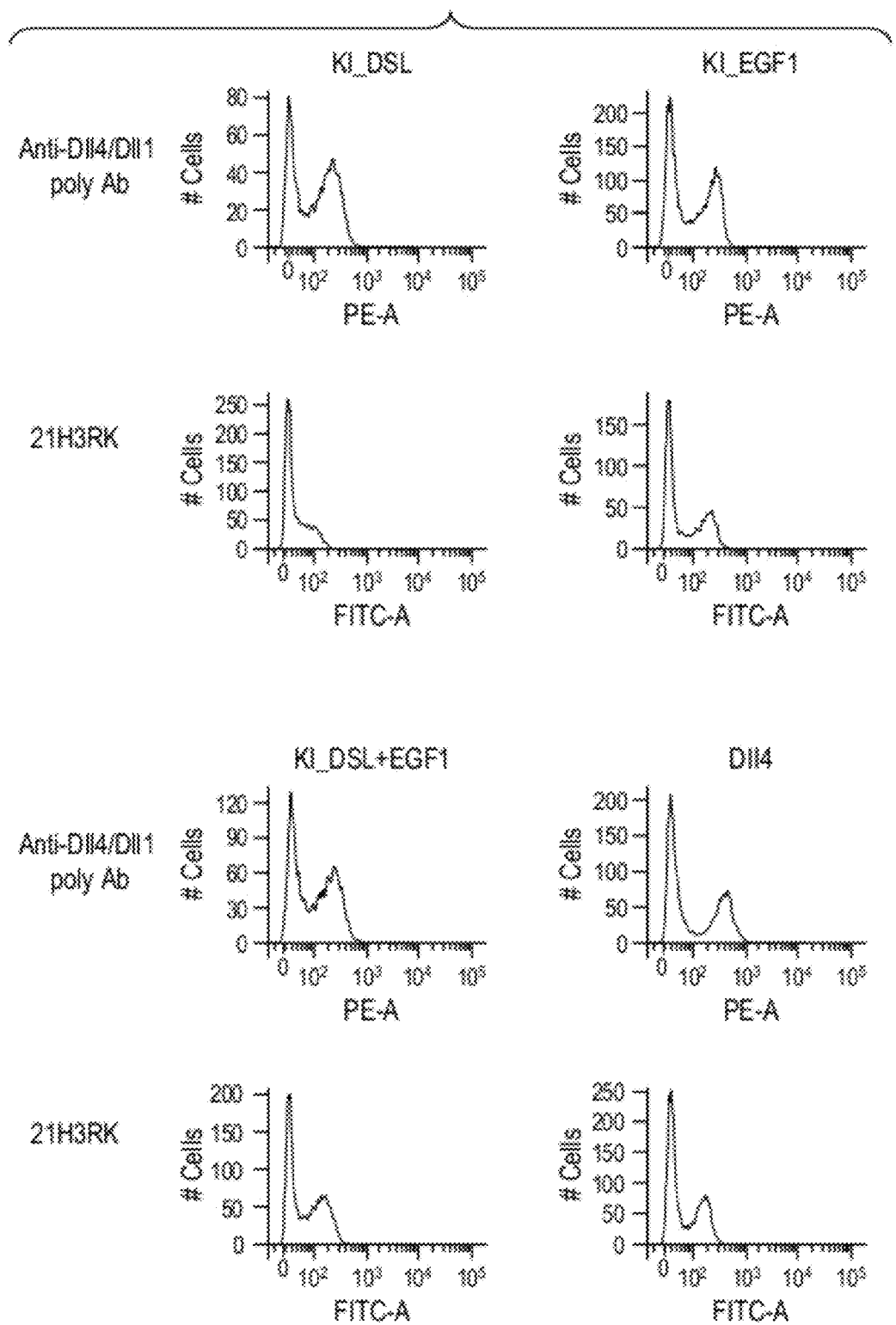
Figure 6C:
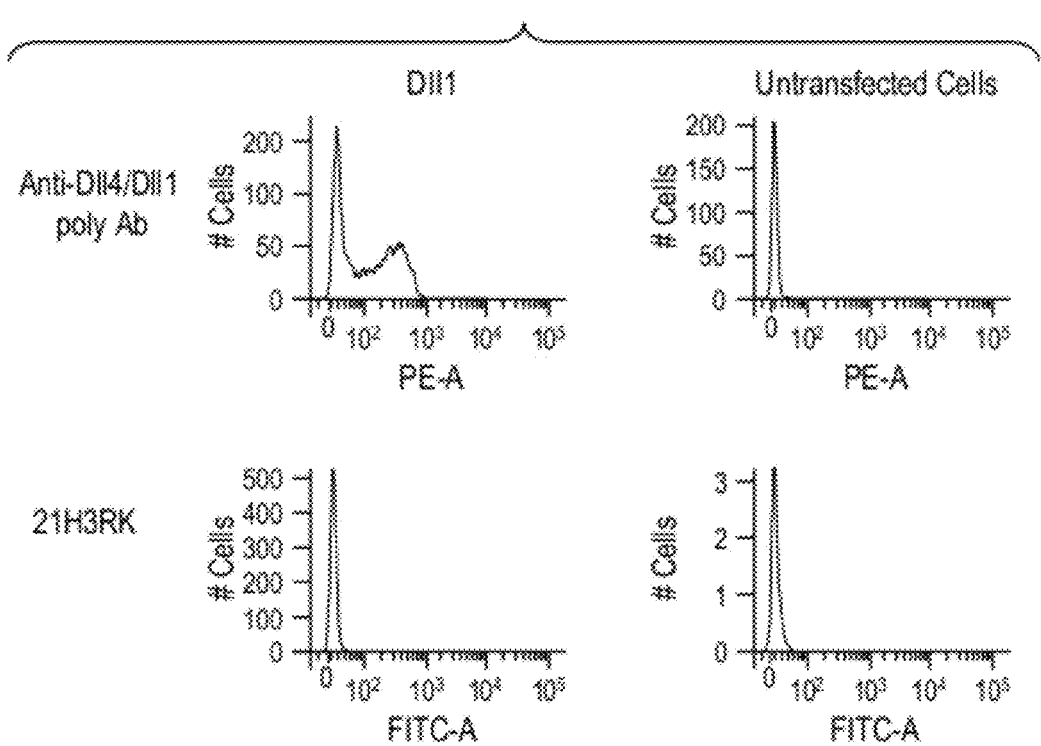

Although human Dll1 and Dll4 share 53% identity at the amino acid level, Mab 21H3RK binds specifically to Dll4 but does not recognize Dll1. Chimeric variants of human Dll4 encoding small portions of human Dll1 were constructed to identify the region responsible for this specificity. Twelve chimeric knock-out variants were constructed by substituting subdomains of human Dll4 with the corresponding residues of human Dll1. FIG. 4 illustrates how the extracellular portion of DLL4 was divided into structurally defined sub domains. The large amino-terminus (N-ter) of the mature DLL4 protein was divided into two smaller segments. KO variant N-ter 1 replaces the first 86 amino acids (AA) of the mature DLL4 protein with human DLL1, and KO variant N-ter 2 replaces amino acids 87-146 with human DLL1. Other knockout variants represented in the figure include the Dll1 substitution of: the entire N-terminal domain (AA 1-146), the DSL, domain (AA 147-191), the EGF1 domain (AA 192-224), both the EGF1 and 2 domains (AA 1.92-255), both the EGF3 and 4 domains (AA 256-333), and the four EGF5-8 domains (AA 334-503). Additionally, combined domain substitution variants were engineered: both the N-terminal and DSL domains (AA 1-191), the N-terminal plus the DSL and EGF1-2 domains (AA1-255), the DSL and EGF1-2 domains (AA 147-255), and the DSL and EGF1 domains (AA 147-224). All recombinant proteins were expressed well on the cell surface as monitored with anti-Dll4 and Dll1 polyclonal antibodies (FIG. 5, upper panels of both rows), however Mab 21H3RK did not recognize any of the constructs comprised of both DSL and EGF1 human Dll1 domains (FIG. 5, bottom panel). Additionally, the Dll1 construct encoded with Dll4 DSL and EGF1 domains (knock-in mutants) conferred Mab 21H3RK binding to Dll1 (FIG. 6). Therefore, the binding epitope of 21H3RK is localized within the DSL and EGF1 domains.

To further refine the binding epitope within this segment of the protein and identify the critical residues responsible for the Mab 21H3RK binding specificity, three additional variants were engineered. Three, fifteen amino acid segments within the DSL and/or the EGF1 domains of Dll4 were substituted with the corresponding Dll1 residues: is fragment A (AA 187-201), fragment B (AA 200-214), and fragment C (AA 210-224) encode only a few amino acid substitutions where Dll1 and Dll4 sequences are not conserved. Fragment A spans the last five amino acids of the DSL domain, the four amino acid linker between the DSL and EGF1 domain, and six amino acids of the EGF1 domain. Substituting these 15 amino acids with Dll1 residues resulted in the loss of Mab 21H3RK binding. No effect was observed when Dll4 residues in fragments B and C were replaced with Dll1. These data identifies the 15 amino acids (AA 187-201) including C-terminus of DSL and N-terminus of EGF1 are important for binding, the epitope to 21H3RK has been mapped to DSL and EGF1 domains (AA 147-224) with the critical region localizing at C-terminus of DSL and N-terminus of EGF1 (AA187-201).

Example 15

Determination of DLL4 Antibodies to Cause Internalization of DLL4 by FACS Analysis The ability of the purified antibodies to induce internalization of DLL4 was investigated by FACS analysis. HEK293 cells stably overexpressing DLL4 were dissociated and washed in FACS buffer (PBS 2% FCS) prior to plating at 50,000-100,000 cells per well in V-bottom plates. Primary antibodies (anti-DLL4 or appropriate isotype control) were diluted to a final concentration of 10 μg/ml in warm 37° C. FACS buffer and added to the cells for 30, 60, 120 or 240 min in a tissue culture incubator (37° C./5% $CO_2$). At the appropriate time point, cells were spun at 500 g in a centrifuge prechilled to 4° C. and washed in cold FACS buffer, prior to incubation with a FITC labelled anti-human IgG secondary antibody (1 μg/ml, Jackson Labs, cat #109-096-098) for 10 min on ice. After incubation, cells were respun at 500 g in a pre-chilled centrifuge, washed with cold FACS buffer and fixed with 2% paraformaldehye for 20 min. Internalization was assessed by reading on a FACSCalibur. Under these assay conditions, <10% internalization of 21H3RK occurred at the above time points. Internalization can also be determined by incubating with a non-cross-competing antibody to DLL4 instead of a secondary anti-human IgG antibody. In some experiments, primary antibody (10 μg/ml) diluted in FACS buffer was pre-incubated with DLL4 overexpressing cells as described above for 30 min on ice prior to washing in warm 37° C. FACS buffer and incubating cells in a tissue culture incubator (37° C./5% $CO_2$) for 30, 60, 120 or 240 min. After these incubations, cells were washed and incubated with secondary antibody and fixed as described above prior to reading on a FACSCalibur. Under these conditions. <15% and <35% internalization relative to t=0 control was observed for 21H3RK and 4B4 at t=60 and 240 min, respectively. Internalization under the above assay conditions can also be determined by incubating with a non-cross-competing antibody to DLL4 instead of a secondary anti-human IgG antibody Example 16

Activity of Anti-DLL4 Antibodies in a Mouse Matrigel Plug Model of Angiogenesis

The ability of anti-DLL4 antibodies to modulate angiogenesis can be assessed using a Matrigel plug assay. In this assay, angiogenesis-inducing compounds such as bFGF, VEGF or tumor cells can be introduced into liquid Matrigel which, after subcutaneous injection, solidifies and permits infiltration by endothelial and vascular smooth muscle cells and allows the formation of new blood vessels. Briefly, Matrigel in liquid form at 4° C. can be mixed with vehicle (e.g. PBS) or growth factors/tumor cells (e.g. LL2, MCF7, A431, Colo205, KNRK, Calu-6, SW620, Panc1) and 0.5 ml injected subcutaneously into the lower abdominal area of female 129s1/SvlmJ mice (6-8 weeks old, n=5 per group). Anti-DLL4 antibodies can be administered twice weekly via intraperitoneal injection. After 5-10 days, animals can be euthanized humanely and plugs can be recovered for assessment of angiogenesis, which can be determined by histological scoring of vessel density and mural cell coverage by for example, assessment of CD31 and alpha smooth muscle actin (αSMA) immunostaining, measurement of haemoglobin content, and measurement of vessel perfusion using, for example, FITC-Dextran. The ability of anti-DLL4 antibodies to modulate angiogenesis is thus determined.

Example 17

Activity of Anti-DLL4 Antibodies in Human Tumor Xenograft Models from Primary Patient Tumor Samples This example describes the use of anti-DLL4 antibodies to inhibit or prevent the growth of tumors derived from primary patient samples when grown as xenografts in mice. Briefly, the recipient mouse can be anesthetized by isoflurane inhalation until it has reached a surgical level of anesthesia. The primary tumor can then be rinsed with RPMI supplemented with antibiotics and 10% FCSi before being minced to produce a "slushy mixture" with scalpels and divided into appropriate volumes for implantation (e.g., a 300 mg tumor can be implanted into 4 mice). Tumor mixtures can be loaded into 13-gauge cancer implant trocars. The shaft of the trocars can be completely filled with tumor mixtures and inserted subcutaneously into the right flank and the contents dispensed under the dorsal fat pad. The mouse can then be returned to its cage and monitored for recovery.

In the first passage, usually 3-5 mice are implanted with primary tumor mixture. When the tumors reach 800-1000 mm$^3$, they are sliced into approximately 3×3×3 mm fragments and subpassaged into 5 mice with 1 fragment into each mouse. The remaining tumor material is archived in Recovery™ Cell Culture Freezing medium (Gibco, catalog #12648-010) in addition to H&E staining and DNA/RNA extraction. Tumors beyond passage 2 can be used for implant for efficacy studies. In efficacy experiments, 1 tumor fragment is implanted into each animal.

Tumor growth is followed by measuring 2 perpendicular diameters. Tumor measurements and body weights can be recorded twice a week for 2 weeks after the initiation of treatment. The formula for tumor volume calculation is as following: $(L \times W^2)/2$.

DLL4 antagonistic antibodies can be dosed as a solution. Treatments can be initiated when the average tumor volume reached approximately 100-200 mm$^3$ or at the same time as tumor implantation. The treatment period can consist of a total of 28 days. DLL4 antagonistic antibodies can be administered at for example, 5, 10 or 20 mg/kg/day (ip, qd, 2×/wk) as a single agent or in combination with other agents. Tumor measurements and body weights are recorded twice a week for 4 weeks after the initiation of treatment. The ability of DLL4 antibodies to inhibit the growth of tumor xenografts derived from patient samples either alone or in combination is thus is determined.

What is claimed is:

1. A method of treating a malignant tumor in an animal in need thereof, comprising: administering to said animal a therapeutically effective dose of an antibody or antigen-binding fragment thereof that specifically binds to Delta-like ligand 4 (DLL4), wherein the antibody or antigen-binding fragment thereof comprises: (a) a heavy chain variable region (VH) comprising CDR1, CDR2, and CDR3 of SEQ ID NO: 30; and (b) a light chain variable region (VL) comprising CDR1, CDR2 and CDR3 of SEQ ID NO: 32 or a VL comprising CDR1, CDR2 and CDR3 of SEQ ID NO: 50.

2. The method of claim 1, wherein said animal is a human.

3. The method of claim 1, wherein said malignant tumor is selected from the group consisting of: melanoma, small cell lung cancer, non-small cell lung cancer, glioma, hepatocellular (liver) carcinoma, thyroid tumor, gastric (stomach) cancer, prostate cancer, breast cancer, ovarian cancer, bladder cancer, lung cancer, glioblastoma, endometrial cancer, kidney cancer, colon cancer, pancreatic cancer, esophageal carcinoma, head and neck cancers, mesothelioma, sarcomas, biliary (cholangiocarcinoma), small bowel adenocarcinoma, pediatric malignancies and epidermoid carcinoma.

4. The method of claim 1, wherein said antibody or antigen-binding fragment thereof comprises (a) a VH comprising CDR1, CDR2 and CDR3 of SEQ ID NO: 30; and (b) a VL comprising CDR1, CDR2 and CDR3 of SEQ ID NO: 32.

5. The method of claim 1, wherein said antibody or antigen-binding fragment thereof comprises (a) a VH comprising CDR1, CDR2 and CDR3 of SEQ ID NO: 30; and (b) a VL comprising CDR1, CDR2 and CDR3 of SEQ ID NO: 50.

* * * * *

UNITED STATES PATENT AND TRADEMARK OFFICE
CERTIFICATE OF CORRECTION

PATENT NO. : 8,663,636 B2  
APPLICATION NO. : 13/446637  
DATED : March 4, 2014  
INVENTOR(S) : Foltz et al.

Page 1 of 1

It is certified that error appears in the above-identified patent and that said Letters Patent is hereby corrected as shown below:

On the Title Page, item (73), under "Assignee", in Column 1, Line 1, delete "Gaichersburg," and insert -- Gaithersburg, --.

Signed and Sealed this  
Twenty-fourth Day of June, 2014

Michelle K. Lee  
*Deputy Director of the United States Patent and Trademark Office*

SEQUENCE LISTING

```
<160> NUMBER OF SEQ ID NOS: 93

<210> SEQ ID NO 1
<211> LENGTH: 351
<212> TYPE: DNA
<213> ORGANISM: Homo sapiens

<400> SEQUENCE: 1
caggtgctgc tgatccagtc tggcgccgag gtgaagaagc ctggcgcctc cgtccaggtg      60
tcctgcaagg cctccggcta caccttcacc aactacggcg tgatctgggt gcggcaggcc     120
cccggccagg gctggagta catgggctgg atctccgcct acaacggcaa caccaattac     180
gcccagaagc tgcaggacag agtcaccatg acctccgaca cctccaccac caccgcctac     240
atggaactgc ggtccctgcg gagcgacgac accgccgtgt actactgcgc cagagagctg     300
ggctcctcct tcgactactg gggccagggc accctggtca ccgtctcctc a             351

<210> SEQ ID NO 2
<211> LENGTH: 117
<212> TYPE: PRT
<213> ORGANISM: Homo sapiens

<400> SEQUENCE: 2

Gln Val Leu Leu Ile Gln Ser Gly Ala Glu Val Lys Lys Pro Gly Ala
1               5                   10                  15

Ser Val Gln Val Ser Cys Lys Ala Ser Gly Tyr Thr Phe Thr Asn Tyr
                20                  25                  30

Gly Val Ile Trp Val Arg Gln Ala Pro Gly Gln Gly Leu Glu Tyr Met
            35                  40                  45

Gly Trp Ile Ser Ala Tyr Asn Gly Asn Thr Asn Tyr Ala Gln Lys Leu
        50                  55                  60

Gln Asp Arg Val Thr Met Thr Ser Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Leu Gly Ser Ser Phe Asp Tyr Trp Gly Gln Gly Thr Leu
            100                 105                 110

Val Thr Val Ser Ser
        115
```

<210> SEQ ID NO 3
<211> LENGTH: 327
<212> TYPE: DNA
<213> ORGANISM: Homo sapiens

<400> SEQUENCE: 3

```
tcctacgagc tgacccagcc tccttccgtg tccgtgtccc ctggccagac cgccggatc      60 acctgctccg gcgacgccct gcctaagaag tacgcctact ggtatcagca gaagtccggc    120
caggcccctg tgctggtgat ctacgaggac atcaagcggc cttccggcat ccctgagcgg    180
ttctccggct cctcctccgg caccatggcc accctgacca tctctggcgc ccaggtggag    240
gacgaggccg actactactg cttctccacc gacaactccg gcgaccactc cgtgtttggc    300
ggcggaacaa agctgaccgt gctgggc                                        327
```

<210> SEQ ID NO 4
<211> LENGTH: 108
<212> TYPE: PRT
<213> ORGANISM: Homo sapiens

<400> SEQUENCE: 4

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Ile Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Phe Ser Thr Asp Asn Ser Gly Asp His
                85                  90                  95

Ser Val Phe Gly Gly Thr Lys Leu Thr Val Leu
            100                 105

<210> SEQ ID NO 5
<211> LENGTH: 354
<212> TYPE: DNA
<213> ORGANISM: Homo sapiens

<400> SEQUENCE: 5

```
caggtgcagc tggtggagtc tgggggaggc gtggtccagc ctggggaggtc cctgagactc     60 tcctgtgcag cgtctggatt caccttcagt aggcatggca tgcactgggt ccgccaggct    120
ccaggcaagg gctggagtg gtggcagtt gtgtggtttg atggaagtaa tatatactat     180
gcagactccg tgaagggccg attcaccatc tccagagaca ttccaagaa cacgctgtat    240 ctgcaaatga acagcctgag agccgaggac acggctatgt attactgtgc gagagattct    300
cgtatagcag ctgctgacta ctggggccag ggaaccctgg tcaccgtctc ctca         354
```

<210> SEQ ID NO 6
<211> LENGTH: 118
<212> TYPE: PRT
<213> ORGANISM: Homo sapiens

<400> SEQUENCE: 6

Gln Val Gln Leu Val Glu Ser Gly Gly Gly Val Val Gln Pro Gly Arg

```
1               5                   10                  15
Ser Leu Arg Leu Ser Cys Ala Ala Ser Gly Phe Thr Phe Ser Arg His
            20                  25                  30

Gly Met His Trp Val Arg Gln Ala Pro Gly Lys Gly Leu Glu Trp Val
        35                  40                  45

Ala Val Val Trp Phe Asp Gly Ser Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Asp Ser Arg Ile Ala Ala Asp Tyr Trp Gly Gln Gly Thr
            100                 105                 110

Leu Val Thr Val Ser Ser
        115
```

```
<210> SEQ ID NO 7
<211> LENGTH: 318
<212> TYPE: DNA
<213> ORGANISM: Homo sapiens

<400> SEQUENCE: 7
tcctatgaac tgactcagcc accctcagtg tccgtgtccc caggacagac agtcagcatc     60
acctgctctg gagataaatt gggggataaa tatgtttgct ggtatcagca gaagccaggc    120
cagtcccctg tgctggtcat ctatcaagaa agcaagcggc cctcagggat ccctgagcga    180
ttctctggct ccagctctgg gaacacagcc actctgacca tcagcgggac ccaggctatg    240
gatgaggctg actattactg tcagacgtgg gacagtagtc ttgtggtatt cggcggaggg    300
accaagctga ccgtccta                                                  318

<210> SEQ ID NO 8
<211> LENGTH: 106
<212> TYPE: PRT
<213> ORGANISM: Homo sapiens

<400> SEQUENCE: 8
```

```
Ser Tyr Glu Leu Thr Gln Pro Pro Ser Val Ser Val Ser Pro Gly Gln
1               5                   10                  15

Thr Val Ser Ile Thr Cys Ser Gly Asp Lys Leu Gly Asp Lys Tyr Val
            20                  25                  30

Cys Trp Tyr Gln Gln Lys Pro Gly Gln Ser Pro Val Leu Val Ile Tyr
        35                  40                  45

Gln Glu Ser Lys Arg Pro Ser Gly Ile Pro Glu Arg Phe Ser Gly Ser
    50                  55                  60

Ser Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Ser Ser Leu Val Val
                85                  90                  95

Phe Gly Gly Gly Thr Lys Leu Thr Val Leu
            100                 105
```

```
<210> SEQ ID NO 9
<211> LENGTH: 354
<212> TYPE: DNA
<213> ORGANISM: Homo sapiens

<400> SEQUENCE: 9
```

-continued

```
caggttcagc tggtgcaatc tggagctgag gtgaagaagc ctggggcctc agtgaaggtc      60
tcctgccagg cttctggtta caccttacc aactatggta tcagctgggt gcgacaggcc     120
cctggacaag gcttgagtg gatgggatgg atcaacgctt acaatggtaa cacaaactat     180
gcacagaacc tccagggcag agtcaccatg accacagaca catccacgaa cacagcctac     240
atggaactga ggagcctgag atctgacgac acggccgtgt attactgtgc gcgagtggca     300
gcagctgctt tctttgacta ttgggaccag ggaaccctgg tcaccgtctc ctca           354
```

<210> SEQ ID NO 10
<211> LENGTH: 118
<212> TYPE: PRT
<213> ORGANISM: Homo sapiens

<400> SEQUENCE: 10

```
Gln Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Thr Asn Tyr
                20                  25                  30

Gly Ile Ser Trp Val Arg Gln Ala Pro Gly Gln Gly Leu Glu Trp Met
            35                  40                  45

Gly Trp Ile Asn Ala Tyr Asn Gly Asn Thr Asn Tyr Ala Gln Asn Leu
        50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ala Ala Ala Ala Phe Phe Asp Tyr Trp Asp Gln Gly Thr
                100                 105                 110

Leu Val Thr Val Ser Ser
                115
```

<210> SEQ ID NO 11
<211> LENGTH: 315
<212> TYPE: DNA
<213> ORGANISM: Homo sapiens

<400> SEQUENCE: 11

```
tcctatgagt tgactcagcc accctcagtg tccgtgtccc caggacagac agccagcatc      60
acctgctctg gagataaaatt ggggataaa tatgtttgct ggtatcaaca gaagccaggc     120
cagtcccctg tattggtcat ctatcaagat agtaagcggc cctcagggat ccctgagcga     180
ttctctggct ccaactctgg gaacacagcc actctgacca tcagcgggac ccaggctatg     240
gatgaggctg actattactg tcaggcgtgg gacagcagca ctgttttcgg cggagggacc     300
aagttgaccg tccta                                                     315
```

<210> SEQ ID NO 12
<211> LENGTH: 105
<212> TYPE: PRT
<213> ORGANISM: Homo sapiens

<400> SEQUENCE: 12

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Val
                20                  25                  30

Cys Trp Tyr Gln Gln Lys Pro Gly Gln Ser Pro Val Leu Val Ile Tyr
            35                  40                  45
```

```
Gln Asp Ser Lys Arg Pro Ser Gly Ile Pro Glu Arg Phe Ser Gly Ser
         50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Thr Val Phe
                 85                  90                  95

Gly Gly Gly Thr Lys Leu Thr Val Leu
            100                 105

<210> SEQ ID NO 13
<211> LENGTH: 351
<212> TYPE: DNA
<213> ORGANISM: Homo sapiens

<400> SEQUENCE: 13
caggttcagc tggtgcagtc tggagctgag gtgaagaggc ctggggcctc agtgaaggtc      60
tcctgcaagg cttccggtta cacctttacc agctatggta tcacctgggt gcgacaggcc    120
cctggacaag gcttgagta catgggatgg atcagcactt acaatggtaa cacagactat     180
gcacagaagt tccagggcag agtcaccatg accgcagaca tatctacgag cacagcctac    240
atggagctga ggagcctgag atctgacgac acggccgtgt attattgtgc gcgagaacgg    300
ggctcctact ttgactactg gggccaggga accctggtca ccgtctcctc t             351

<210> SEQ ID NO 14
<211> LENGTH: 117
<212> TYPE: PRT
<213> ORGANISM: Homo sapiens

<400> SEQUENCE: 14

Gln Val Gln Leu Val Gln Ser Gly Ala Glu Val Lys Arg Pro Gly Ala
 1               5                  10                  15

Ser Val Lys Val Ser Cys Lys Ala Ser Gly Tyr Thr Phe Thr Ser Tyr
                 20                  25                  30

Gly Ile Thr Trp Val Arg Gln Ala Pro Gly Gln Gly Leu Glu Tyr Met
             35                  40                  45

Gly Trp Ile Ser Thr Tyr Asn Gly Asn Thr Asp Tyr Ala Gln Lys Phe
     50                  55                  60

Gln Gly Arg Val Thr Met Thr Ala Asp Ile Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Glu Arg Gly Ser Tyr Phe Asp Tyr Trp Gly Gln Gly Thr Leu
                100                 105                 110

Val Thr Val Ser Ser
            115

<210> SEQ ID NO 15
<211> LENGTH: 321
<212> TYPE: DNA
<213> ORGANISM: Homo sapiens

<400> SEQUENCE: 15
tcctatgagc tgacacagcc accctcggtg tcagtgtccc caggacaaac ggccaggatc      60
acctgctctg gagatacatt gccaaaaaaa tatgcttatt ggtaccagca gaagtcaggc    120
caggcccctg tgctggtcat ctatgaggac atcaaacgac cctccgggat ccctgagaga    180
ttctctggct ccagctcagg gacaatggcc accttgacta tcagtggggc ccaggtggag    240
```

```
gatgaagctg actactactg tttctcaaca gacagcggtg gtaatcataa attcggcgga      300
gggaccaagc tgaccgtcct a                                                321
```

<210> SEQ ID NO 16
<211> LENGTH: 107
<212> TYPE: PRT
<213> ORGANISM: Homo sapiens

<400> SEQUENCE: 16

```
Ser Tyr Glu Leu Thr Gln Pro Pro Ser Val Ser Val Ser Pro Gly Gln
1               5                   10                  15

Thr Ala Arg Ile Thr Cys Ser Gly Asp Thr Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Ile Lys Arg Pro Ser Gly Ile Pro Glu Arg Phe Ser Gly Ser
50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Phe Ser Thr Asp Ser Gly Gly Asn His
                85                  90                  95

Lys Phe Gly Gly Gly Thr Lys Leu Thr Val Leu
            100                 105
```

<210> SEQ ID NO 17
<211> LENGTH: 354
<212> TYPE: DNA
<213> ORGANISM: Homo sapiens

<400> SEQUENCE: 17

```
caggttcagc tggtgcaatc tggagctgag gtgaagaagc ctggggcctc agtgaaggtc       60
tcctgcaagg cttctggtta cacctttacc aactatggta tcagctgggt gcgacaggcc      120
cctggacaag gcttgagtg gatgggatgg atcaacgctt acaatggtaa cacaaactat       180
gcacagaacc tccagggcag agtcaccatg accacagaca catccacgaa cacagcctac      240
atggaactga ggagcctgag atctgacgac acggccgtgt attactgtgc gcgagtggca      300
ccagctgctt tctttgacta ctgggaccag ggaaccctgg tcaccgtctc ctca            354
```

<210> SEQ ID NO 18
<211> LENGTH: 118
<212> TYPE: PRT
<213> ORGANISM: Homo sapiens

<400> SEQUENCE: 18

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Asn Ala Tyr Asn Gly Asn Thr Asn Tyr Ala Gln Asn Leu
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95
```

```
Ala Arg Val Ala Pro Ala Ala Phe Phe Asp Tyr Trp Asp Gln Gly Thr
            100                 105                 110

Leu Val Thr Val Ser Ser
        115

<210> SEQ ID NO 19
<211> LENGTH: 315
<212> TYPE: DNA
<213> ORGANISM: Homo sapiens

<400> SEQUENCE: 19
tcctatgagt tgactcagcc accctcagtg tccgtgtccc caggacagac agccagcatc      60
acctgctctg gagataaatt gggggataaa tatgtttgct ggtatcaaca gaagccaggc     120
cagtcccctg tattggtcat ctatcaagat aataagcggc cctcagggat ccctgagcga     180
ttctctggct ccaactctgg gaacacagcc actctgatca tcagcgggac ccaggctatg     240
gatgaggctg actattactg tcaggcgtgg gacagcagca ctgttttcgg cggagggacc     300
aagctgaccg tccta                                                     315

<210> SEQ ID NO 20
<211> LENGTH: 105
<212> TYPE: PRT
<213> ORGANISM: Homo sapiens

<400> SEQUENCE: 20

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Val
            20                  25                  30

Cys Trp Tyr Gln Gln Lys Pro Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Ile Ile Ser Gly Thr Gln Ala Met
65                  70                  75                  80

Asp Glu Ala Asp Tyr Tyr Cys Gln Ala Trp Asp Ser Ser Thr Val Phe
                85                  90                  95

Gly Gly Gly Thr Lys Leu Thr Val Leu
            100                 105

<210> SEQ ID NO 21
<211> LENGTH: 366
<212> TYPE: DNA
<213> ORGANISM: Homo sapiens

<400> SEQUENCE: 21
cagctgcagc tgcaggagtc gggcccagga ctggtgaagc cttcggagac cctgtccctc      60
tcctgcactg tctctggtgg ctccatcagc agtagtagtt cctactgggg cttgatccgc     120
cagcccccag ggaaggggct ggagtggatt gggagtatct attatagtgg gagtacgtac     180
tacagtccgt ccctcaagag tcgagtcagc atatccgtag acacgtccaa gaaccagttc     240
tccctgaagc tgagctctgt gaccgccgca gacacggctg tgtattttg tgcgagacag      300 ggctacggtg gtcaccctga tgttttttgac atctggggcc aagggacaat ggtcaccgtc     360
tcttca                                                               366

<210> SEQ ID NO 22
<211> LENGTH: 122
```

```
<212> TYPE: PRT
<213> ORGANISM: Homo sapiens

<400> SEQUENCE: 22

Gln Leu Gln Leu Gln Glu Ser Gly Pro Gly Leu Val Lys Pro Ser Glu
1               5                  10                  15

Thr Leu Ser Leu Ser Cys Thr Val Ser Gly Gly Ser Ile Ser Ser Ser
            20                  25                  30

Ser Ser Tyr Trp Gly Leu Ile Arg Gln Pro Pro Gly Lys Gly Leu Glu
        35                  40                  45

Trp Ile Gly Ser Ile Tyr Tyr Ser Gly Ser Thr Tyr Tyr Ser Pro Ser
    50                  55                  60

Leu Lys Ser Arg Val Ser Ile Ser Val Asp Thr Ser Lys Asn Gln Phe
65                  70                  75                  80

Ser Leu Lys Leu Ser Ser Val Thr Ala Ala Asp Thr Ala Val Tyr Phe
                85                  90                  95

Cys Ala Arg Gln Gly Tyr Gly Gly His Pro Asp Val Phe Asp Ile Trp
            100                 105                 110

Gly Gln Gly Thr Met Val Thr Val Ser Ser
        115                 120

<210> SEQ ID NO 23
<211> LENGTH: 321
<212> TYPE: DNA
<213> ORGANISM: Homo sapiens

<400> SEQUENCE: 23
tcctctgaac tgactcagtc accctcagtg tccgtgtccc caggacagac agcccgcatc    60
acctgctctg gagataagtt gggggatgta tatgtttgct ggtatcagca aaagacaggc   120 cagtccccctg ttctggtcat ctatgaagat accaagcggc cctcagggat ccctgagcga   180
ttctctggct ccaactctgg gaacacagcc actctgacca tcagcgggac ccaggttatg   240
gatgaggctg actattactg tcaggcgtgg acagcacca ctgctgtgat ttttggcgga   300
gggaccaagc tgaccgtcct a                                              321

<210> SEQ ID NO 24
<211> LENGTH: 107
<212> TYPE: PRT
<213> ORGANISM: Homo sapiens

<400> SEQUENCE: 24

Ser Ser Glu Leu Thr Gln Ser Pro Ser Val Ser Val Ser Pro Gly Gln
1               5                  10                  15

Thr Ala Arg Ile Thr Cys Ser Gly Asp Lys Leu Gly Asp Val Tyr Val
            20                  25                  30

Cys Trp Tyr Gln Gln Lys Thr Gly Gln Ser Pro Val Leu Val Ile Tyr
        35                  40                  45

Glu Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Val Met
65                  70                  75                  80

Asp Glu Ala Asp Tyr Tyr Cys Gln Ala Trp Asp Ser Thr Thr Ala Val
                85                  90                  95

Ile Phe Gly Gly Gly Thr Lys Leu Thr Val Leu
            100                 105

<210> SEQ ID NO 25
```

```
<211> LENGTH: 372
<212> TYPE: DNA
<213> ORGANISM: Homo sapiens

<400> SEQUENCE: 25
caggttcagc tggtgcagtc tggagctgag gtgaagaagc ctggggcctc agtgaaggtc      60
tcctgcaagg cttctgggta cacctttacc agttatggta tcagctgggt gcgacaggcc     120
cctggacaag gcttgagtg gatgggatgg atcagcgttt acaatggtaa tacaaactat     180
gcacagaagc tccagggcag agtcaccatg accacagaca catccacgag cacagcgtac     240
atggaggtga ggagcctgag atctgacgac acggccgtct attattgtgc gagagatcga     300
gtaccccgta tacctagaac tacggaggct tttgatatct ggggccgagg gacaatggtc     360
accgtttgtt ca                                                          372

<210> SEQ ID NO 26
<211> LENGTH: 124
<212> TYPE: PRT
<213> ORGANISM: Homo sapiens

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Val Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Val Arg Ser Leu Arg Ser Asp Asp Thr Ala Val Tyr Tyr Cys
                85                  90                  95

Ala Arg Asp Arg Val Pro Arg Ile Pro Arg Thr Thr Glu Ala Phe Asp
            100                 105                 110

Ile Trp Gly Arg Gly Thr Met Val Thr Val Cys Ser
        115                 120

<210> SEQ ID NO 27
<211> LENGTH: 333
<212> TYPE: DNA
<213> ORGANISM: Homo sapiens

<400> SEQUENCE: 27
cagtctgtgc tgactcagcc accctcagcg tctgggaccc ccgggcagag ggtcaccatc      60
tcttgttctg gaagcagctc caacatcgga agttattatg tttactggta ccagcagctc     120
ccaggaacgg cccccaaact cctcatctat gggataatc agcggccctc aggggtccct     180
gaccgattct ctggctccaa gtctggcacc tcagcctccc tggccatcag ggggctccgg     240
tccgatgatg aggctgacta ttactgtgca gcatgggatg cagcctgag tggtcattgg     300 gtgttcggcg gagggaccaa gctgaccgtc cta                                   333

<210> SEQ ID NO 28
<211> LENGTH: 111
<212> TYPE: PRT
<213> ORGANISM: Homo sapiens

<400> SEQUENCE: 28
```

-continued

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Tyr
            20                  25                  30

Tyr Val Tyr Trp Tyr Gln Gln Leu Pro Gly Thr Ala Pro Lys Leu Leu
        35                  40                  45

Ile Tyr Arg Asp Asn Gln Arg Pro Ser Gly Val Pro Asp Arg Phe Ser
    50                  55                  60

Gly Ser Lys Ser Gly Thr Ser Ala Ser Leu Ala Ile Arg Gly Leu Arg
65                  70                  75                  80

Ser Asp Asp Glu Ala Asp Tyr Tyr Cys Ala Ala Trp Asp Ser Leu
                85                  90                  95

Ser Gly His Trp Val Phe Gly Gly Gly Thr Lys Leu Thr Val Leu
            100                 105                 110
```

<210> SEQ ID NO 29
<211> LENGTH: 372
<212> TYPE: DNA
<213> ORGANISM: Homo sapiens

<400> SEQUENCE: 29

```
caggtgcagc tggtgcagtc tggcgccgag gtgaagaagc ctggcgcctc cgtcaaggtg    60
tcctgcaagg cctccggcta caccttcacc aactacggca tcacctgggt gcggcaggct   120
cccggccagg gccccgagtg gatgggctgg atctccgcct acaacggcaa caccaattac   180
gcccagaagc tgcaggacag agtcaccgtg accaccgaca cctccacctc caccgcctac   240
atggaactgc ggtccctgcg gagcgacgac accgccgtgt actactgcgc caggacagg   300
gtgcccagaa tccctgtgac cacagaggcc ttcgacatct ggggccaggg caccatggtc   360
accgtctctt ca                                                       372
```

<210> SEQ ID NO 30
<211> LENGTH: 124
<212> TYPE: PRT
<213> ORGANISM: Homo sapiens

<400> SEQUENCE: 30

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Thr Trp Val Arg Gln Ala Pro Gly Gln Gly Pro Glu Trp Met
        35                  40                  45

Gly Trp Ile Ser Ala Tyr Asn Gly Asn Thr Asn Tyr Ala Gln Lys Leu
    50                  55                  60

Gln Asp Arg Val Thr Val Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Val Pro Arg Ile Pro Val Thr Thr Glu Ala Phe Asp
            100                 105                 110

Ile Trp Gly Gln Gly Thr Met Val Thr Val Ser Ser
        115                 120
```

<210> SEQ ID NO 31
<211> LENGTH: 333
<212> TYPE: DNA
<213> ORGANISM: Homo sapiens

<400> SEQUENCE: 31

```
cagtctgtgc tgactcagcc accctcagcg tctgggaccc ccgggcagag ggtcaccatc      60
tcttgttctg gaagcagctc aacatcgga agttattttg tatactgta ccaacagctc      120 ccaggaacgg cccccaaact cctcatctat aggaataatc agcggccctc aggggtccct     180
gaccgattct ctggctccga gtctggcacc tcagcctccc tggccatcag tggactccgg     240
tccgaggatg aggctgatta ttactgtgca gcatgggatg acagcctgag tggtcattgg     300
gtgttcggcg agggaccag actgaccgtc cta                                   333
```

<210> SEQ ID NO 32
<211> LENGTH: 111
<212> TYPE: PRT
<213> ORGANISM: Homo sapiens

<400> SEQUENCE: 32

```
Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Tyr
             20                  25                  30

Phe Val Tyr Trp Tyr Gln Gln Leu Pro Gly Thr Ala Pro Lys Leu Leu
         35                  40                  45

Ile Tyr Arg Asn Asn Gln Arg Pro Ser Gly Val Pro Asp Arg Phe Ser
     50                  55                  60

Gly Ser Glu Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly His Trp Val Phe Gly Gly Gly Thr Arg Leu Thr Val Leu
            100                 105                 110
```

<210> SEQ ID NO 33
<211> LENGTH: 390
<212> TYPE: DNA
<213> ORGANISM: Homo sapiens

<400> SEQUENCE: 33

```
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg gctggagtg gtggcagtt acatggtatg atggaagtaa taaatactat      180
gcagactccg tgaagggccg attcaccatc tccagagaca attccaagaa tacgctgtat     240
ctgcaaatga acagcctgag agccgaggac acggctgtgt attactgtgc gagagagaat     300
tgtagtagta ccagctgcta ttatacagta actacggact actacgggat ggacgtctgg     360
ggccaaggga ccacggtcac cgtctcctca                                      390
```

<210> SEQ ID NO 34
<211> LENGTH: 130
<212> TYPE: PRT
<213> ORGANISM: Homo sapiens

<400> SEQUENCE: 34

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30
```

-continued

```
Gly Met His Trp Val Arg Gln Ala Pro Gly Lys Gly Leu Glu Trp Val
         35                  40                  45

Ala Val Thr Trp Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Asn Cys Ser Ser Thr Ser Cys Tyr Tyr Thr Val Thr Thr
            100                 105                 110

Asp Tyr Tyr Gly Met Asp Val Trp Gly Gln Gly Thr Thr Val Thr Val
            115                 120                 125

Ser Ser
130
```

<210> SEQ ID NO 35
<211> LENGTH: 324
<212> TYPE: DNA
<213> ORGANISM: Homo sapiens

<400> SEQUENCE: 35

```
gaaattgtgt tgacgcagtc tccaggcacc ctgtctttgt ctccagggga aagagccacc      60
ctctcctgca gggccagtca gcgtgttagc agcagctact taacctggta ccagcagaaa     120
cctggccagg cacccaggct cctcatctat ggtgcatcca tcagggccac tggcatccca     180
gacaggttca gtggcagtgg gtctgggaca gacttcactc tcaccatcac cagactggag     240
cctgaagatt ttgcagtgta tttctgtcag cagtgttata cctcaccgat caccttcggc     300
caagggacac gactggacat taaa                                            324
```

<210> SEQ ID NO 36
<211> LENGTH: 108
<212> TYPE: PRT
<213> ORGANISM: Homo sapiens

<400> SEQUENCE: 36

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Arg Val Ser Ser Ser
             20                  25                  30

Tyr Leu Thr Trp Tyr Gln Gln Lys Pro Gly Gln Ala Pro Arg Leu Leu
         35                  40                  45

Ile Tyr Gly Ala Ser Ile Arg Ala Thr Gly Ile Pro Asp Arg Phe Ser
     50                  55                  60

Gly Ser Gly Ser Gly Thr Asp Phe Thr Leu Thr Ile Thr Arg Leu Glu
 65                  70                  75                  80

Pro Glu Asp Phe Ala Val Tyr Phe Cys Gln Gln Cys Tyr Thr Ser Pro
                 85                  90                  95

Ile Thr Phe Gly Gln Gly Thr Arg Leu Asp Ile Lys
            100                 105
```

<210> SEQ ID NO 37
<211> LENGTH: 372
<212> TYPE: DNA
<213> ORGANISM: Homo sapiens

<400> SEQUENCE: 37

```
gaggtgcagg tggtggagtc tgggggaggc ttggtccagc ctggggggtc cctgagactc      60
```

```
tcctgtgaag cctctggatt cacctttagt aactattgga tgatctgggt ccgccaggct    120
ccagggaagg ggctggagtg ggtggccagt ataaaggaag atggcagtga aaatactat    180 gtggactctg tgaagggccg attcaccatc tccagagaca acgccaagag ctcactgtat    240
ctgcaaatga acagtctgag agccgaggac acggctgtgt attactgtgt gagagactgg    300
gagctaagag gtcactatta ctaccacggt atggacgtct ggggccaagg gaccacggtc    360
accgtctcct ca                                                        372
```

<210> SEQ ID NO 38
<211> LENGTH: 124
<212> TYPE: PRT
<213> ORGANISM: Homo sapiens

<400> SEQUENCE: 38

```
Glu Val Gln Val Val Glu Ser Gly Gly Gly Leu Val Gln Pro Gly Gly
1               5                   10                  15

Ser Leu Arg Leu Ser Cys Glu Ala Ser Gly Phe Thr Phe Ser Asn Tyr
            20                  25                  30

Trp Met Ile Trp Val Arg Gln Ala Pro Gly Lys Gly Leu Glu Trp Val
        35                  40                  45

Ala Ser Ile Lys Glu Asp Gly Ser Glu Lys Tyr Tyr Val Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Val Arg Asp Trp Glu Leu Arg Gly His Tyr Tyr Tyr His Gly Met Asp
            100                 105                 110

Val Trp Gly Gln Gly Thr Thr Val Thr Val Ser Ser
        115                 120
```

<210> SEQ ID NO 39
<211> LENGTH: 321
<212> TYPE: DNA
<213> ORGANISM: Homo sapiens

<400> SEQUENCE: 39

```
gacatacaga tgacccagtc tccatcctcc ctgtctgcat ctgtgggaga cagagtcacc     60
atcacttgcc gggcaagtct ggacattaga aatgatttag ctggtttctg cagaaaccca    120
gggaaagccc ctaagcgcct gatctatgct gcatccagtt tgcaaagtgg ggtcccatca    180
aggttcagcg gcagtggatc tgggacagaa ttcactctca caatcaacag cctgcagcct    240
gaagattttg caacttatta ctgtctacaa catcgtaatt acccattcac tttcggccct    300
gggactaaag tggatttcaa a                                               321
```

<210> SEQ ID NO 40
<211> LENGTH: 107
<212> TYPE: PRT
<213> ORGANISM: Homo sapiens

<400> SEQUENCE: 40

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Leu Asp Ile Arg Asn Asp
            20                  25                  30

Leu Gly Trp Phe Leu Gln Lys Pro Gly Lys Ala Pro Lys Arg Leu Ile
        35                  40                  45
```

```
Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Asn Ser Leu Gln Pro
65              70                  75                  80

Glu Asp Phe Ala Thr Tyr Tyr Cys Leu Gln His Arg Asn Tyr Pro Phe
                85                  90                  95

Thr Phe Gly Pro Gly Thr Lys Val Asp Phe Lys
            100                 105

<210> SEQ ID NO 41
<211> LENGTH: 369
<212> TYPE: DNA
<213> ORGANISM: Homo sapiens

<400> SEQUENCE: 41
caggtgcagc tggtgcagtc tggggctgag gtgaggaagt ctggggcctc agtgaaggtc      60
tcctgcaagg cttctggata ctccttcacc acttatgata tcaactgggt gcgacaggcc    120
actggacaag gcttgagtg atgggatgg atgaaccta acagtggtta cacagactat       180
gcacagaagt tccagggcag agtcaccctg accaggaaca tgtccataga cacagcctac    240
atggaactga gcagcctgag atctgaggac acggccgtct attactgtgc gagagcatat    300
tactatgata gtagtgctta ttaccctcttt gactattggg gccagggaac cctggtcacc    360
gtctcctca                                                             369

<210> SEQ ID NO 42
<211> LENGTH: 123
<212> TYPE: PRT
<213> ORGANISM: Homo sapiens

<400> SEQUENCE: 42

Gln Val Gln Leu Val Gln Ser Gly Ala Glu Val Arg Lys Ser Gly Ala
1               5                   10                  15

Ser Val Lys Val Ser Cys Lys Ala Ser Gly Tyr Ser Phe Thr Thr Tyr
                20                  25                  30

Asp Ile Asn Trp Val Arg Gln Ala Thr Gly Gln Gly Leu Glu Trp Met
            35                  40                  45

Gly Trp Met Asn Pro Asn Ser Gly Tyr Thr Asp Tyr Ala Gln Lys Phe
    50                  55                  60

Gln Gly Arg Val Thr Leu Thr Arg Asn Met Ser Ile Asp Thr Ala Tyr
65              70                  75                  80

Met Glu Leu Ser Ser Leu Arg Ser Glu Asp Thr Ala Val Tyr Tyr Cys
                85                  90                  95

Ala Arg Ala Tyr Tyr Tyr Asp Ser Ser Ala Tyr Tyr Leu Phe Asp Tyr
                100                 105                 110

Trp Gly Gln Gly Thr Leu Val Thr Val Ser Ser
            115                 120

<210> SEQ ID NO 43
<211> LENGTH: 321
<212> TYPE: DNA
<213> ORGANISM: Homo sapiens

<400> SEQUENCE: 43
gacatccaga tgacccagtc tccatcctca ctgtctgcat ctgtaggaga cagagtcacc      60
atcacttgtc gggcgagtca gggcattagc aattatttag cctggtttca gcagaaacca    120
gggaaagccc ctaagtccct aatctatgct gcatccagtt tgcaaagtgg ggtcccatca    180
```

```
aagttcagcg gcagtggatc cgggacagat ttcactctca ccatcagcag cctgcagcct    240
gaagattttg caacttattt ctgccaacag tatattagtt accctctcac tttcggcgga    300
gggaccaagg tggagatcaa a                                              321
```

<210> SEQ ID NO 44
<211> LENGTH: 106
<212> TYPE: PRT
<213> ORGANISM: Homo sapiens

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Ile Ser Tyr Pro Leu
                85                  90                  95

Thr Phe Gly Gly Gly Thr Lys Val Glu Ile
            100                 105
```

<210> SEQ ID NO 45
<211> LENGTH: 363
<212> TYPE: DNA
<213> ORGANISM: Homo sapiens

<400> SEQUENCE: 45

```
cagctgcagc tgcaggagtc gggcccagga ctggtgaagc cttcggagac cctgtccctc     60
acctgcactg tctctggtgg ctccatcagc agtagtagtt attactgggg ctggatccgc    120
cagcccccag ggaagggact ggagtggatt gggagtttct attatagtcg agcacctac     180 tacaacccgt ccctcaagag tcgagtcacc atatccgtag acacgtccaa gaaccagttc    240
tccctgaagc tgagctctgt gaccgccgca gacacggctg tgcattactg tgcgaggggg    300
agtatagcag tgcctgatgc ttttgatatc tggggccaag gacaatggt caccgtctct    360 tca                                                                  363
```

<210> SEQ ID NO 46
<211> LENGTH: 121
<212> TYPE: PRT
<213> ORGANISM: Homo sapiens

<400> SEQUENCE: 46

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Phe Tyr Tyr Ser Arg Ser Tyr Tyr Asn Pro Ser
    50                  55                  60

Leu Lys Ser Arg Val Thr Ile Ser Val Asp Thr Ser Lys Asn Gln Phe
65                  70                  75                  80
```

```
Ser Leu Lys Leu Ser Ser Val Thr Ala Ala Asp Thr Ala Val His Tyr
                85                  90                  95
Cys Ala Arg Gly Ser Ile Ala Val Pro Asp Ala Phe Asp Ile Trp Gly
            100                 105                 110
Gln Gly Thr Met Val Thr Val Ser Ser
        115                 120

<210> SEQ ID NO 47
<211> LENGTH: 318
<212> TYPE: DNA
<213> ORGANISM: Homo sapiens

<400> SEQUENCE: 47
tcctatgagc tgactcagcc accctcagtg tccgtgtccc caggacagac agccagcatc      60
acctgctctg gagataaatt gggagataaa tttgcttgct ggtatcagca gaaaccaggc     120
cactcccctg tgttggtcgt ctatcaagat aacaagcggc cctcaggat ccctgagcga      180 ttctctggct ccaactctgg gaactcagcc actctgacca tcagcgggac ccaggctatg     240
gatgaggctg actattactg tcaggcgtgg gacagcaaca ctgcggtatt cggcggaggg     300
accaagctga ccgtccta                                                   318

<210> SEQ ID NO 48
<211> LENGTH: 106
<212> TYPE: PRT
<213> ORGANISM: Homo sapiens

<400> SEQUENCE: 48

Ser Tyr Glu Leu Thr Gln Pro Pro Ser Val Ser Val Ser Pro Gly Gln
1               5                   10                  15
Thr Ala Ser Ile Thr Cys Ser Gly Asp Lys Leu Gly Asp Lys Phe Ala
            20                  25                  30
Cys Trp Tyr Gln Gln Lys Pro Gly His Ser Pro Val Leu Val Val Tyr
        35                  40                  45
Gln Asp Asn Lys Arg Pro Ser Gly Ile Pro Glu Arg Phe Ser Gly Ser
    50                  55                  60
Asn Ser Gly Asn Ser Ala Thr Leu Thr Ile Ser Gly Thr Gln Ala Met
65                  70                  75                  80
Asp Glu Ala Asp Tyr Tyr Cys Gln Ala Trp Asp Ser Asn Thr Ala Val
                85                  90                  95
Phe Gly Gly Gly Thr Lys Leu Thr Val Leu
            100                 105

<210> SEQ ID NO 49
<211> LENGTH: 336
<212> TYPE: DNA
<213> ORGANISM: Homo sapiens

<400> SEQUENCE: 49
cagtccgtgc tgacccagcc tccttccgcc tccggcaccc ctggccagag agtgaccatc      60
tcctgctccg gctcctcctc caacatcggc tcctacttcg tgtactggta tcagcagctg     120
cctggcaccg cccctaagct gctgatctac cggaacaacc agcggccttc cggcgtgcct     180
gaccggttct ccggctccga gtccggcacc agcgccagct ggccatctc cggcctgaga     240 tccgaggacg aggccgacta ctactgcgcc gcctgggacg actccctgtc cggccactgg     300
gtgttcggcg gaggaacaaa gctgaccgtg ctgggc                               336
```

-continued

```
<210> SEQ ID NO 50
<211> LENGTH: 111
<212> TYPE: PRT
<213> ORGANISM: Homo sapiens

<400> SEQUENCE: 50

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Tyr
            20                  25                  30

Phe Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Glu Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly His Trp Val Phe Gly Gly Gly Thr Lys Leu Thr Val Leu
            100                 105                 110

<210> SEQ ID NO 51
<211> LENGTH: 115
<212> TYPE: PRT
<213> ORGANISM: Homo sapiens

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Leu Gly Tyr Phe Asp Tyr Trp Gly Gln Gly Thr Leu Val Thr
            100                 105                 110

Val Ser Ser
        115

<210> SEQ ID NO 52
<211> LENGTH: 108
<212> TYPE: PRT
<213> ORGANISM: Homo sapiens

<400> SEQUENCE: 52

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
            35                  40                  45

Glu Asp Ser Lys Arg Pro Ser Gly Ile Pro Glu Arg Phe Ser Gly Ser
        50                  55                  60
```

```
Ser Ser Gly Thr Met Ala Thr Leu Thr Ile Ser Gly Ala Gln Val Glu
 65                  70                  75                  80

Asp Glu Ala Asp Tyr Tyr Cys Tyr Ser Thr Asp Ser Ser Gly Asn His
                 85                  90                  95

Val Val Phe Gly Gly Gly Thr Lys Leu Thr Val Leu
            100                 105

<210> SEQ ID NO 53
<211> LENGTH: 115
<212> TYPE: PRT
<213> ORGANISM: Homo sapiens

<400> SEQUENCE: 53

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ile Ala Ala Ala Asp Tyr Trp Gly Gln Gly Thr Leu Val Thr
            100                 105                 110

Val Ser Ser
        115

<210> SEQ ID NO 54
<211> LENGTH: 107
<212> TYPE: PRT
<213> ORGANISM: Homo sapiens

<400> SEQUENCE: 54

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Ala Val
                 85                  90                  95

Val Phe Gly Gly Gly Thr Lys Leu Thr Val Leu
            100                 105

<210> SEQ ID NO 55
<211> LENGTH: 116
<212> TYPE: PRT
<213> ORGANISM: Homo sapiens

<400> SEQUENCE: 55

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Ala Ala Tyr Phe Asp Tyr Trp Gly Gln Gly Thr Leu Val
            100                 105                 110

Thr Val Ser Ser
            115

<210> SEQ ID NO 56
<211> LENGTH: 107
<212> TYPE: PRT
<213> ORGANISM: Homo sapiens

<400> SEQUENCE: 56

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Val Phe Gly Gly Gly Thr Lys Leu Thr Val Leu
            100                 105

<210> SEQ ID NO 57
<211> LENGTH: 115
<212> TYPE: PRT
<213> ORGANISM: Homo sapiens

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Arg Tyr Phe Asp Tyr Trp Gly Gln Gly Thr Leu Val Thr
            100                 105                 110

```
Val Ser Ser
        115

<210> SEQ ID NO 58
<211> LENGTH: 108
<212> TYPE: PRT
<213> ORGANISM: Homo sapiens

<400> SEQUENCE: 58

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Gly Asn His
                85                  90                  95

Val Val Phe Gly Gly Gly Thr Lys Leu Thr Val Leu
            100                 105

<210> SEQ ID NO 59
<211> LENGTH: 118
<212> TYPE: PRT
<213> ORGANISM: Homo sapiens

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Val Pro Ala Ala Tyr Phe Asp Tyr Trp Gly Gln Gly Thr
            100                 105                 110

Leu Val Thr Val Ser Ser
        115

<210> SEQ ID NO 60
<211> LENGTH: 107
<212> TYPE: PRT
<213> ORGANISM: Homo sapiens

<400> SEQUENCE: 60

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45
```

Gln Asp Ser Lys Arg Pro Ser Gly Ile Pro Glu Arg Phe Ser Gly Ser
            50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Ala Val
                85                  90                  95

Val Phe Gly Gly Gly Thr Lys Leu Thr Val Leu
            100                 105

<210> SEQ ID NO 61
<211> LENGTH: 117
<212> TYPE: PRT
<213> ORGANISM: Homo sapiens

<400> SEQUENCE: 61

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Tyr Gly Gly Ala Phe Asp Ile Trp Gly Gln Gly Thr Met
            100                 105                 110

Val Thr Val Ser Ser
        115

<210> SEQ ID NO 62
<211> LENGTH: 107
<212> TYPE: PRT
<213> ORGANISM: Homo sapiens

<400> SEQUENCE: 62

Ser Tyr Glu Leu Thr Gln Pro Pro Ser Val Ser Val Ser Pro Gly Gln
 1               5                  10                  15

Thr Ala Ser Ile Thr Cys Ser Gly Asp Lys Leu Gly Asp Lys Tyr Ala
                20                  25                  30

Cys Trp Tyr Gln Gln Lys Pro Gly Gln Ser Pro Val Leu Val Ile Tyr
            35                  40                  45

Gln Asp Ser Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Ala Val
                85                  90                  95

Val Phe Gly Gly Gly Thr Lys Leu Thr Val Leu
            100                 105

<210> SEQ ID NO 63
<211> LENGTH: 122
<212> TYPE: PRT
<213> ORGANISM: Homo sapiens -continued

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ile Val Val Val Ala Ala Thr Ala Phe Asp Ile Trp
            100                 105                 110

Gly Gln Gly Thr Met Val Thr Val Ser Ser
        115                 120

<210> SEQ ID NO 64
<211> LENGTH: 110
<212> TYPE: PRT
<213> ORGANISM: Homo sapiens

<400> SEQUENCE: 64

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Val Val Phe Gly Gly Gly Thr Lys Leu Thr Val Leu
            100                 105                 110

<210> SEQ ID NO 65
<211> LENGTH: 122
<212> TYPE: PRT
<213> ORGANISM: Homo sapiens

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ile Val Val Val Ala Ala Thr Ala Phe Asp Ile Trp
            100                 105                 110

Gly Gln Gly Thr Met Val Thr Val Ser Ser
        115                 120

<210> SEQ ID NO 66
<211> LENGTH: 110
<212> TYPE: PRT
<213> ORGANISM: Homo sapiens

<400> SEQUENCE: 66

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Val Val Phe Gly Gly Gly Thr Lys Leu Thr Val Leu
            100                 105                 110

<210> SEQ ID NO 67
<211> LENGTH: 122
<212> TYPE: PRT
<213> ORGANISM: Homo sapiens

<400> SEQUENCE: 67

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Cys Ser Ser Thr Ser Cys Tyr Tyr Tyr Gly Met Asp Val Trp
            100                 105                 110

Gly Gln Gly Thr Thr Val Thr Val Ser Ser
        115                 120

<210> SEQ ID NO 68
<211> LENGTH: 108
<212> TYPE: PRT
<213> ORGANISM: Homo sapiens

<400> SEQUENCE: 68

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser

-continued

```
                    20                  25                  30
Tyr Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys
            100                 105

<210> SEQ ID NO 69
<211> LENGTH: 121
<212> TYPE: PRT
<213> ORGANISM: Homo sapiens

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Glu Leu Tyr Tyr Tyr Tyr Gly Met Asp Val Trp Gly
            100                 105                 110

Gln Gly Thr Thr Val Thr Val Ser Ser
        115                 120

<210> SEQ ID NO 70
<211> LENGTH: 107
<212> TYPE: PRT
<213> ORGANISM: Homo sapiens

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Phe
                85                  90                  95

Thr Phe Gly Pro Gly Thr Lys Val Asp Ile Lys
            100                 105

<210> SEQ ID NO 71
```

```
<211> LENGTH: 122
<212> TYPE: PRT
<213> ORGANISM: Homo sapiens

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
            35                  40                  45

Gly Trp Met Asn Pro Asn Ser Gly Asn Thr Gly Tyr Ala Gln Lys Phe
50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Tyr Asp Ser Ser Gly Tyr Tyr Phe Asp Tyr Trp
            100                 105                 110

Gly Gln Gly Thr Leu Val Thr Val Ser Ser
            115                 120

<210> SEQ ID NO 72
<211> LENGTH: 107
<212> TYPE: PRT
<213> ORGANISM: Homo sapiens

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Phe Gln Gln Lys Pro Gly Lys Ala Pro Lys Ser Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 73
<211> LENGTH: 117
<212> TYPE: PRT
<213> ORGANISM: Homo sapiens

<400> SEQUENCE: 73

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
```

```
                  65                  70                  75                  80
Ser Leu Lys Leu Ser Ser Val Thr Ala Ala Asp Thr Ala Val Tyr Tyr
                        85                  90                  95

Cys Ala Arg Ile Ala Val Ala Phe Asp Ile Trp Gly Gln Gly Thr Met
                100                 105                 110

Val Thr Val Ser Ser
                115

<210> SEQ ID NO 74
<211> LENGTH: 107
<212> TYPE: PRT
<213> ORGANISM: Homo sapiens

<400> SEQUENCE: 74

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Val Phe Gly Gly Gly Thr Lys Leu Thr Val Leu
                100                 105

<210> SEQ ID NO 75
<211> LENGTH: 124
<212> TYPE: PRT
<213> ORGANISM: Homo sapiens

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Thr Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Val Pro Arg Ile Pro Val Thr Thr Glu Ala Phe Asp
                100                 105                 110

Ile Trp Gly Gln Gly Thr Met Val Thr Val Ser Ser
                115                 120

<210> SEQ ID NO 76
<211> LENGTH: 111
<212> TYPE: PRT
<213> ORGANISM: Homo sapiens

<400> SEQUENCE: 76
```

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Tyr
            20                  25                  30

Phe Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly His Trp Val Phe Gly Gly Thr Lys Leu Thr Val Leu
            100                 105                 110

<210> SEQ ID NO 77
<211> LENGTH: 118
<212> TYPE: PRT
<213> ORGANISM: Homo sapiens

<400> SEQUENCE: 77

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Arg His
            20                  25                  30

Gly Met His Trp Val Arg Gln Ala Pro Gly Lys Gly Leu Glu Trp Val
            35                  40                  45

Ala Val Val Trp Phe Asp Gly Ser Asn Ile Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Arg Ile Ala Ala Asp Tyr Trp Gly Gln Gly Thr
            100                 105                 110

Leu Val Thr Val Ser Ser
        115

<210> SEQ ID NO 78
<211> LENGTH: 106
<212> TYPE: PRT
<213> ORGANISM: Homo sapiens

<400> SEQUENCE: 78

Ser Tyr Glu Leu Thr Gln Pro Pro Ser Val Ser Val Ser Pro Gly Gln
1               5                   10                  15

Thr Val Ser Ile Thr Cys Ser Gly Asp Lys Leu Gly Asp Lys Tyr Val
            20                  25                  30

Ser Trp Tyr Gln Gln Lys Pro Gly Gln Ser Pro Val Leu Val Ile Tyr
            35                  40                  45

Gln Glu Ser Lys Arg Pro Ser Gly Ile Pro Glu Arg Phe Ser Gly Ser
50                  55                  60

Ser Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Ser Ser Leu Val Val
                85                  90                  95

Phe Gly Gly Gly Thr Lys Leu Thr Val Leu

-continued

<210> SEQ ID NO 79
<211> LENGTH: 106
<212> TYPE: PRT
<213> ORGANISM: Homo sapiens

<400> SEQUENCE: 79

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Val
            20                  25                  30

Ser Trp Tyr Gln Gln Lys Pro Gly Gln Ser Pro Val Leu Val Ile Tyr
        35                  40                  45

Gln Glu Ser Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Ser Ser Leu Val Val
                85                  90                  95

Phe Gly Gly Gly Thr Lys Leu Thr Val Leu
            100                 105

<210> SEQ ID NO 80
<211> LENGTH: 122
<212> TYPE: PRT
<213> ORGANISM: Homo sapiens

<400> SEQUENCE: 80

Gln Leu Gln Leu Gln Glu Ser Gly Pro Gly Leu Val Lys Pro Ser Glu
1               5                   10                  15

Thr Leu Ser Leu Ser Cys Thr Val Ser Gly Gly Ser Ile Ser Ser Ser
            20                  25                  30

Ser Ser Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Ser Pro Ser
50                  55                  60

Leu Lys Ser Arg Val Ser Ile Ser Val Asp Thr Ser Lys Asn Gln Phe
65                  70                  75                  80

Ser Leu Lys Leu Ser Ser Val Thr Ala Ala Asp Thr Ala Val Tyr Phe
                85                  90                  95

Cys Ala Arg Gln Gly Tyr Gly Gly His Pro Asp Val Phe Asp Ile Trp
            100                 105                 110

Gly Gln Gly Thr Met Val Thr Val Ser Ser
        115                 120

<210> SEQ ID NO 81
<211> LENGTH: 122
<212> TYPE: PRT
<213> ORGANISM: Homo sapiens

<400> SEQUENCE: 81

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Ser Tyr Trp Gly Trp Ile Arg Gln Pro Pro Gly Lys Gly Leu Glu
        35                  40                  45

-continued

Trp Ile Gly Ser Ile Tyr Tyr Ser Gly Ser Thr Tyr Tyr Ser Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Gly Tyr Gly Gly His Pro Asp Val Phe Asp Ile Trp
            100                 105                 110

Gly Gln Gly Thr Met Val Thr Val Ser Ser
            115                 120

<210> SEQ ID NO 82
<211> LENGTH: 107
<212> TYPE: PRT
<213> ORGANISM: Homo sapiens

<400> SEQUENCE: 82

Ser Ser Glu Leu Thr Gln Pro Pro Ser Val Ser Val Ser Pro Gly Gln
1               5                   10                  15

Thr Ala Arg Ile Thr Cys Ser Gly Asp Lys Leu Gly Asp Val Tyr Val
            20                  25                  30

Ser Trp Tyr Gln Gln Lys Thr Gly Gln Ser Pro Val Leu Val Ile Tyr
        35                  40                  45

Glu Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Thr Thr Ala Val
                85                  90                  95

Ile Phe Gly Gly Gly Thr Lys Leu Thr Val Leu
            100                 105

<210> SEQ ID NO 83
<211> LENGTH: 108
<212> TYPE: PRT
<213> ORGANISM: Homo sapiens

<400> SEQUENCE: 83

Ser Tyr Glu Leu Thr Gln Ser Pro Ser Val Ser Val Ser Pro Gly Gln
1               5                   10                  15

Thr Ala Ser Ile Thr Cys Ser Gly Asp Lys Leu Gly Asp Val Tyr Val
            20                  25                  30

Ala Ser Trp Tyr Gln Gln Lys Pro Gly Gln Ser Pro Val Leu Val Ile
        35                  40                  45

Tyr Glu Asp Thr Lys Arg Pro Ser Gly Ile Pro Glu Arg Phe Ser Gly
    50                  55                  60

Ser Asn Ser Gly Asn Thr Ala Thr Leu Thr Ile Ser Gly Thr Gln Ala
65                  70                  75                  80

Met Asp Glu Ala Asp Tyr Tyr Cys Gln Ala Trp Asp Ser Thr Thr Ala
                85                  90                  95

Val Ile Phe Gly Gly Gly Thr Lys Leu Thr Val Leu
            100                 105

<210> SEQ ID NO 84
<211> LENGTH: 124
<212> TYPE: PRT
<213> ORGANISM: Mus musculus

<400> SEQUENCE: 84

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Gly Ile Thr Trp Val Arg Gln Ala Pro Gly Gln Gly Pro Glu Trp Met
        35                  40                  45

Gly Trp Ile Ser Pro Tyr Asn Gly Asn Thr Asn Tyr Ala Gln Lys Leu
    50                  55                  60

Gln Asp Arg Val Thr Val Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Thr Pro Arg Ile Pro Trp Thr Ala Ala Phe Asp
                100                 105                 110

Ile Trp Gly Gln Gly Thr Met Val Thr Val Ser Ser
            115                 120
```

<210> SEQ ID NO 85
<211> LENGTH: 111
<212> TYPE: PRT
<213> ORGANISM: Mus musculus

<400> SEQUENCE: 85

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Tyr
            20                  25                  30

Phe Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Glu Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ser Ser Leu
                85                  90                  95

Ser Gly His Trp Val Phe Gly Gly Gly Thr Lys Leu Thr Val Leu
                100                 105                 110
```

<210> SEQ ID NO 86
<211> LENGTH: 124
<212> TYPE: PRT
<213> ORGANISM: Mus musculus

<400> SEQUENCE: 86

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Met Tyr
            20                  25                  30

Gly Ile Thr Trp Val Arg Gln Ala Pro Gly Gln Gly Pro Glu Trp Met
        35                  40                  45

Gly Trp Ile Ser Pro Tyr Asn Gly Asn Thr Asn Tyr Ala Gln Lys Leu
    50                  55                  60

Gln Asp Arg Val Thr Val Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95
```

```
Ala Arg Asp Arg Val Pro Arg Ile Pro Trp Thr Thr Ala Ala Phe Asp
            100                 105                 110

Ile Trp Gly Gln Gly Thr Met Val Thr Val Ser Ser
            115                 120
```

<210> SEQ ID NO 87
<211> LENGTH: 111
<212> TYPE: PRT
<213> ORGANISM: Mus musculus

<400> SEQUENCE: 87

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Tyr
            20                  25                  30

Phe Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Glu Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ser Ser Leu
                85                  90                  95

Ser Gly His Trp Val Phe Gly Gly Gly Thr Lys Leu Thr Val Leu
            100                 105                 110
```

<210> SEQ ID NO 88
<211> LENGTH: 124
<212> TYPE: PRT
<213> ORGANISM: Mus musculus

<400> SEQUENCE: 88

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile His Tyr
            20                  25                  30

Gly Ile Thr Trp Val Arg Gln Ala Pro Gly Gln Gly Pro Glu Trp Met
            35                  40                  45

Gly Trp Ile Ser Ala Tyr Asn Gly Asn Thr Asn Tyr Ala Gln Lys Leu
        50                  55                  60

Gln Asp Arg Val Thr Val Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Val Pro Arg Ile Pro Trp Thr Thr Ala Ala Phe Asp
            100                 105                 110

Ile Trp Gly Gln Gly Thr Met Val Thr Val Ser Ser
            115                 120
```

<210> SEQ ID NO 89
<211> LENGTH: 111
<212> TYPE: PRT
<213> ORGANISM: Mus musculus

<400> SEQUENCE: 89

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Tyr
            20                  25                  30
```

Phe Val Tyr Trp Tyr Gln Gln Leu Pro Gly Thr Ala Pro Lys Leu Leu
                35                  40                  45

Ile Tyr Arg Asn Asn Gln Arg Pro Ser Gly Val Pro Asp Arg Phe Ser
     50                  55                  60

Gly Ser Glu Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Ser Ser Leu
                 85                  90                  95

Ser Gly His Trp Val Phe Gly Gly Gly Thr Lys Leu Thr Val Leu
            100                 105                 110

<210> SEQ ID NO 90
<211> LENGTH: 78
<212> TYPE: PRT
<213> ORGANISM: Homo sapiens

<400> SEQUENCE: 90

Val Ile Cys Ser Asp Asn Tyr Tyr Gly Asp Asn Cys Ser Arg Leu Cys
 1               5                  10                  15

Lys Lys Arg Asn Asp His Phe Gly His Tyr Val Cys Gln Pro Asp Gly
             20                  25                  30

Asn Leu Ser Cys Leu Pro Gly Trp Thr Gly Glu Tyr Cys Gln Gln Pro
         35                  40                  45

Ile Cys Leu Ser Gly Cys His Glu Gln Asn Gly Tyr Cys Ser Lys Pro
     50                  55                  60

Ala Glu Cys Leu Cys Arg Pro Gly Trp Gln Gly Arg Leu Cys
 65                  70                  75

<210> SEQ ID NO 91
<211> LENGTH: 15
<212> TYPE: PRT
<213> ORGANISM: Homo sapiens

<400> SEQUENCE: 91

Thr Gly Glu Tyr Cys Gln Gln Pro Ile Cys Leu Ser Gly Cys His
 1               5                  10                  15

<210> SEQ ID NO 92
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
aagctggcta gcgcgaatgg cggcagcgtc ccggag                             36

<210> SEQ ID NO 93
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
cagcctcgag cggccgccca ggggaagctg ggcggcaagc                         40